US006750015B2

(12) United States Patent
Horwitz et al.

(10) Patent No.: US 6,750,015 B2
(45) Date of Patent: Jun. 15, 2004

(54) PROGESTERONE RECEPTOR-REGULATED GENE EXPRESSION AND METHODS RELATED THERETO

(76) Inventors: Kathryn B. Horwitz, 9853 E. Ida Ave., Greenwood Village, CO (US) 80111; Jennifer Richer, 1165 S. Williams St., Denver, CO (US) 80246

( * ) Notice: Subject to any disclaimer, the term of this patent is extended or adjusted under 35 U.S.C. 154(b) by 0 days.

(21) Appl. No.: 09/814,915

(22) Filed: Mar. 21, 2001

(65) Prior Publication Data

US 2003/0027208 A1 Feb. 6, 2003

Related U.S. Application Data

(60) Provisional application No. 60/214,870, filed on Jun. 28, 2000.

(51) Int. Cl.$^7$ .......................... C12Q 1/68; G01N 33/53

(52) U.S. Cl. ............................. 435/6; 435/7.1; 435/7.2

(58) Field of Search ............................ 435/6, 7.1, 7.2; 530/350

(56) References Cited

U.S. PATENT DOCUMENTS

| | | | |
|---|---|---|---|
| 5,364,791 A | 11/1994 | Vegeto et al. | 435/320.1 |
| 5,506,102 A | 4/1996 | McDonnell | 435/6 |
| 5,683,885 A | 11/1997 | Kieback | 435/7.1 |
| 5,759,785 A | 6/1998 | Tsai et al. | 435/7.1 |
| 5,770,176 A | 6/1998 | Nargessi | 424/1.49 |
| 5,808,139 A | 9/1998 | Pathirana et al. | 560/138 |
| 5,935,934 A | 8/1999 | Vegeto et al. | 514/44 |
| 5,945,279 A | 8/1999 | O'Malley et al. | 435/6 |

FOREIGN PATENT DOCUMENTS

WO WO 98/05679 2/1998

OTHER PUBLICATIONS

Richer, *ENDO*, p. 341 (2000) (Abstract #1411).
Bethea et al., *Endocrinology,* 139(2):677–687 (1998).
Fujimoto et al., *J. Steroid Biochem. Molec. Biol.,* 62(5/6):449–454 (1997).
Graham et al., *Cancer Res.,* 55:5063–5068 (1995).
Graham et al., *Cancer Res.,* 52:593–602 (1992).
Groshong et al., *Mol. Endocrinol.,* 11:1593–1607 (1997).
Horwitz et al., *J. Biol. Chem.,* 253(22):8185–8191 (1978).
Kester et al., *J. Biol. Chem.,* 272(26):16637–16643 (1997).
Lydon et al., *Genes & Devel.,* 9:2266–2278 (1995).
McDonnell et al., *J. Biol. Chem.,* 269(16):11945–11949 (1994).
McGowan et al., *Mol. Endocrinol.,* 13:1657–1671 (1999).
Mote et al., *J. Clin. Endocrinol. Metab.,* 84:2963–2971 (1999).
Mulac–Jericevic et al., *Science,* 289:1751–1754 (2000).
Nishida et al., *Biochem. Biophys. Res. Comm.,* 241:258–263 (1997).
Richer et al., *J. Biol. Chem.,* 273(47):31317–31326 (1998).
Sartorius et al., *Cancer Res.,* 54:3868–3877 (1994).
Sartorius et al., *Mol. Endocrinol.,* 8:1347–1360 (1994).
Shyamala et al., *Proc. Natl. Acad. Sci. USA,* 95:696–701 (1998).
Shyamala et al., *PNAS,* 97(7):3044–3049 (2000).
Tian et al., *PNAS,* 97(26):14358–14363 (2000).
Tung et al., *Mol. Endocrinol.,* 7:1256–1265 (1993).
Vegeto et al., *Mol. Endocrinol.,* 7:1244–1255 (1993).

*Primary Examiner*—Elizabeth Kemmerer
*Assistant Examiner*—Ruixiang Li
(74) *Attorney, Agent, or Firm*—Sheridan Ross P.C.

(57) ABSTRACT

Disclosed are expression profiles of genes that are regulated by progesterone receptors, and particularly by progesterone receptor isoforms PR-A and PR-B. Methods for using such genes to identifying progesterone receptor agonist and antagonist ligands are described. Also described are methods for identifying isoform-specific progesterone receptor ligands, for identifying tissue-specific progesterone receptor ligands, and for determining the profile of genes regulated by progesterone receptors in a breast tumor sample. In addition, pluralities of polynucleotides from genes that are regulated by progesterone receptors are disclosed, as are pluralities of antibodies that selectively bind to proteins encoded by such genes.

31 Claims, No Drawings

SEQUENCE LISTING

```
<160> NUMBER OF SEQ ID NOS: 108

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1

atccagcgta ctccaaagat tc                                              22


<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2

tccttgctga aagacaagtc tg                                              22


<210> SEQ ID NO 3
<211> LENGTH: 3817
<212> TYPE: DNA
<213> ORGANISM: Homo sapiens

<400> SEQUENCE: 3

tgaattcgtg agagacttga gggaggcgct gcgactgaca agcggctctg cccgggacct      60

tctcgctttc atctagcgct gcactcaatg gaggggcggg caccgcagtg cttaatgctg     120

tcttaactag tgtaggaaaa cggctcaacc caccgctgcc gaaatgaagt ataagaatct     180

tatggcaagg gccttatatg acaatgtccc agagtgtgcc gaggaactgg cctttcgcaa     240

gggagacatc ctgaccgtca tagagcagaa cacaggggga ctggaaggat ggtggctgtg     300

ctcgttacac ggtcggcaag gcattgtccc aggcaaccgg gtgaagcttc tgattggtcc     360

catgcaggag actgcctcca gtcacgagca gcctgcctct ggactgatgc agcagacctt     420

tggccaacag aagctctatc aagtgccaaa cccacaggct gctccccgag acaccatcta     480
```

-continued

```
ccaagtgcca ccttcctacc aaaatcaggg aatttaccaa gtccccactg gccacggcac    540
ccaagaacaa gaggtatatc aggtgccacc atcagtgcag agaagcattg gggaaccag     600
tgggccccac gtgggtaaaa aggtgataac ccccgtgagg acaggccatg gctacgtata    660
cgagtaccca tccagatacc aaaaggatgt ctatgatatc cctccttctc ataccactca    720
aggggtatac gacatccctc cctcatcagc aaaaggccct gtgttttcag ttccagtggg    780
agagataaaa cctcaagggg tgtatgacat cccgcctaca aaaggggtat atgccattcc    840
gccctctgct tgccgggatg aagcagggct tagggaaaaa gactatgact tccccccctcc   900
catgagacaa gctggaaggc cggacctcag accggagggg gtttatgaca ttcctccaac    960
ctgcaccaag ccagcaggga aggaccttca tgtaaaatac aactgtgaca ttccaggagc   1020
tgcagaaccg gtggctcgaa ggcaccagag cctgtccccg aatcacccac ccccgcaact   1080
cggacagtca gtgggctctc agaacgacgc atatgatgtc ccccgaggcg ttcagtttct   1140
tgagccacca gcagaaacca gtgagaaagc aaacccccag gaaagggatg gtgtttatga   1200
tgtccctctg cataacccgc cagatgctaa aggctctcgg gacttggtgg atgggatcaa   1260
ccgattgtct ttctccagta caggcagcac ccggagtaac atgtccacgt cttccacctc   1320
ctccaaggag tcctcactgt cagcctcccc agctcaggac aaaaggctct tcctggatcc   1380
agacacagct attgagagac ttcagcggct ccagcaggcc cttgagatgg gtgtctccag   1440
cctaatggca ctggtcacta ccgactggcg gtgttacgga tatatggaaa gacacatcaa   1500
tgaaatacgc acagcagtgg acaaggtgga gctgttcctg aaggagtacc tccactttgt   1560
caagggagct gttgcaaatg ctgcctgcct cccggaactc atcctccaca acaagatgaa   1620
gcgggagctg caacgagtcg aagactccca ccagatcctg agtcaaacca gccatgactt   1680
aaatgagtgc agctggtccc tgaatatctt ggccatcaac aagccccaga acaagtgtga   1740
cgatctggac cggtttgtga tggtggcaaa gacggtgccc gatgacgcca agcagctcac   1800
cacaaccatc aacaccaacg cagaggccct cttcagaccc ggccctggca gcttgcatct   1860
gaagaatggg ccggagagca tcatgaactc aacggagtac ccacacggtg gctcccaggg   1920
acagctgctg catcctggtg accacaaggc ccaggcccac aacaaggcac tgcccccagg   1980
cctgagcaag gagcaggccc ctgactgtag cagcagtgat ggttctgaga ggagctggat   2040
ggatgactac gattacgtcc acctacaggg taaggaggag tttgagaggc aacagaaaga   2100
gctattggaa aaagagaata tcatgaaaca gaacaagatg cagctggaac atcatcagct   2160
gagccagttc cagctgttgg aacaagagat tacaaagccc gtggagaatg acatctcgaa   2220
gtggaagccc tctcagagcc tacccaccac aaacagtggc gtgagtgctc aggatcggca   2280
gttgctgtgc ttctactatg accaatgtga gacccatttc atttcccttc tcaacgccat   2340
tgacgcactc ttcagttgtg tcagctcagc ccagcccccg cgaatcttcg tggcacacag   2400
caagtttgtc atcctcagtg cacacaaact ggtgttcatt ggagacacgc tgacacggca   2460
ggtgactgcc caggacattc gcaacaaagt catgaactcc agcaaccagc tctgcgagca   2520
gctcaagact atagtcatgg caaccaagat ggccgccctc cattacccca gcaccacggc   2580
cctgcaggaa atggtgcacc aagtgacaga cctttctaga aatgcccagc tgttcaagcg   2640
ctctttgctg gagatggcaa cgttctgaga agaaaaaaaa gaggaagggg actgcgttaa   2700
cggttactaa ggaaaactgg aaatactgtc tggtttttgt aaatgttatc tatttttgta   2760
gataatttta tataaaaatg aaatatttta acattttatg ggtcagacaa ctttcagaaa   2820
```

-continued

```
ttcagggagc tggagaggga aatctttttt tccccccctga gtgttcttat gtatacacag   2880

aagtatctga gacataaact gtacagaaaa cttgtccacg tcctttttgta tgcccatgta   2940

ttcatgtttt tgtttgtaga tgtttgtctg atgcatttca ttaaaaaaaa aaccatgaat   3000

tacgaagcac cttagtaagc accttctaat gctgcatttt ttttgttgtt gttaaaaaca   3060

tccagctggt tataatattg ttctccacgt ccttgtgatg attctgagcc tggcactggg   3120

aatctgggaa gcatagttta tttgcaagtg ttcaccttcc aaatcatgag gcatagcatg   3180

acttattctt gttttgaaaa ctcttttcaa aactgaccat cttaaacaca tgatggccaa   3240

gtgccacaaa gccctcttgc ggagacattt acgaatatat atgtggatcc aagtctcgat   3300

agttaggcgt tggagggaag agagaccaga gagtttagag gccaggacca cagttaggat   3360

tgggttgttt caatactgag agacagctac aataaaagga gagcaattgc ctccctgggg   3420

ctgttcaatc ttctgcattt gtgagtggtt cagtcatgag gttttccaaa agatgttttt   3480

agagttgtaa aaaccatatt tgcagcaaag atttacaaag gcgtatcaga ctatgattgt   3540

tcaccaaaat aggggaatgg tttgatccgc cagttgcaag tagaggcctt tctgactctt   3600

aatattcact ttggtgctac taccccccatt acctgaggaa ctggccaggt ccttgatcat   3660

ggaactatag agctaccaga catatcctgc tctctaaggg aatttattgc tatcttgcac   3720

cttctttaaa actcaaaaaa catatgcaga cctgacactc aagagtggct agctacacag   3780

agtccatcta atttttgcaa cttccccccc cgaattc                             3817
```

```
<210> SEQ ID NO 4
<211> LENGTH: 2218
<212> TYPE: DNA
<213> ORGANISM: Homo sapiens

<400> SEQUENCE: 4

tcctacaagc agccggcggc gccgccgagt gaggggacgc ggcgcggtgg ggcggcgcgg     60

cccgaggagg cggcggagga ggggccgccc gcggcccccg gctcactccg gcactccggg    120

ccgctcggcc cccatgcctg cccgaccgcg ctgccggagc cccaggtgac cagcgccatg    180

tccagccagg tggtgggcat tgagcctctc tacatcaagg cagagccggc cagccctgac    240

agtccaaagg gttcctcgga gacagagacc gagcctcctg tggccctggc ccctggtcca    300

gctcccactc gctgcctccc aggccacaag gaagaggagg atggggaggg ggctgggcct    360

ggcgagcagg gcggtgggaa gctggtgctc agctccctgc ccaagcgcct ctgcctggtc    420

tgtggggacg tggcctccgg ctaccactat ggtgtggcat cctgtgaggc ctgcaaagcc    480

ttcttcaaga ggaccatcca ggggagcatc gagtacagct gtccggcctc caacgagtgt    540

gagatcacca agcggagacg caaggcctgc caggcctgcc gcttcaccaa gtgcctgcgg    600

gtgggcatgc tcaaggaggg agtgcgcctg gaccgcgtcc ggggtgggcg gcagaagtac    660

aagcggcggc cggaggtgga cccactgccc ttcccgggcc ccttccctgc tgggcccctg    720

gcagtcgctg gaggcccccg gaagacagcc ccagtgaatg cactggtgtc tcatctgctg    780

gtggttgagc ctgagaagct ctatgccatg cctgaccccg caggccctga tgggcacctc    840

ccagccgtgg ctaccctctg tgacctcttt gaccgagaga ttgtggtcac catcagctgg    900

gccaagagca tcccaggctt ctcatcgctg tcgctgtctg accagatgtc agtactgcag    960

agcgtgtgga tggaggtgct ggtgctgggt gtggcccagc gctcactgcc actgcaggat   1020

gagctggcct tcgctgagga cttagtcctg gatgaagagg gggcacgggc agctggcctg   1080

ggggaactgg gggctgccct gctgcaacta gtgcggcggc tgcaggccct gcggctggag   1140
```

-continued cgagaggagt atgttctact aaaggccttg gcccttgcca attcagactc tgtgcacatc 1200
gaagatgccg aggctgtgga gcagctgcga gaagctctgc acgaggccct gctggagtat 1260
gaagccggcc gggctggccc cggagggggt gctgagcggc ggcgggcggg caggctgctg 1320
ctcacgctac cgctcctccg ccagacagcg ggcaaagtgc tggcccattt ctatggggtg 1380
aagctggagg gcaaggtgcc catgcacaag ctgttcttgg agatgctcga ggccatgatg 1440
gactgaggca aggggtggga ctggtggggg ttctggcagg acctgcctag catggggtca 1500
gccccaaggg ctggggcgga gctggggtct gggcagtgcc acagcctgct ggcagggcca 1560
gggcaatgcc atcagcccct gggaacaggc cccacgccct ctcctccccc tcctaggggg 1620
tgtcagaagc tgggaacgtg tgtccaggct ctgggcacag tgctgcccct tgcaagccat 1680
aacgtgcccc cagagtgtag gggccttgc ggaagccata gggggctgca cgggatgcgt 1740
gggaggcaga aacctatctc agggagggaa ggggatggag gccagagtct cccagtgggt 1800
gatgcttttg ctgctgctta atcctacccc ctcttcaaag cagagtggga cttggagagc 1860
aaaggcccat gcccccttcg ctcctcctct catcatttgc attgggcatt agtgtccccc 1920
cttgaagcaa taactccaag cagactccag cccctggacc cctggggtgg ccagggcttc 1980
cccatcagct cccaacgagc ctcctcaggg ggtaggagag cactgcctct atgccctgca 2040
gagcaataac actatattta tttttgggtt tggccaggga ggcgcaggga catggggcaa 2100
gccagggccc agagcccttg gctgtacaga gactctattt taatgtatat ttgctgcaaa 2160
gagaaaccgc ttttggtttt aaacctttaa tgagaaaaaa atatataata ccgagctc 2218

<210> SEQ ID NO 5
<211> LENGTH: 606
<212> TYPE: DNA
<213> ORGANISM: Homo sapiens

<400> SEQUENCE: 5
atggcaggaa aatcttcact ttttaaagta attctccttg gagatggtgg agttgggaag 60
agttcactta tgaacagata tgtaactaat aagtttgata cccagctctt ccatacaata 120
ggtgtggaat ttttaaataa agatttggaa gtggatggac attttgttac catgcagatt 180
tgggacacgg caggtcagga gcgattccga agcctgagga caccatttta cagaggttct 240
gactgctgcc tgcttacttt tagtgtcgat gattcacaaa gcttccagaa cttaagtaac 300
tggaagaaag aattcatata ttatgcagat gtgaaagagc ctgagagctt tccttttgtg 360
attctgggta acaagattga cataagcgaa cggcaggtgt ctacagaaga agcccaagct 420
tggtgcaggg acaacggcga ctatccttat tttgaaacaa gtgcaaaaga tgccacaaat 480
gtggcagcag cctttgagga agcggttcga agagttcttg ctaccgagga taggtcagat 540
catttgattc agacagacac agtcaatctt caccgaaagc ccaagcctag ctcatcttgc 600
tgttga 606

<210> SEQ ID NO 6
<211> LENGTH: 2461
<212> TYPE: DNA
<213> ORGANISM: Homo sapiens

<400> SEQUENCE: 6
ccgcagccgc cgccgccgcc gccgccgcga tgtgaccttc agggccgcca ggacgggatg 60
accggagcct ccgccccgcg gcgcccgctc gcctcggcct cccgggcgct ctgaccgcgc 120

-continued

```
gtccccggcc cgccatggcc ccttcgctct cgcccgggcc cgccgccctg cgccgcgcgc    180
cgcagctgct gctgctgctg ctggccgcgg agtgcgcgct tgccgcgctg ttgccggcgc    240
gcgaggccac gcagttcctg cggcccaggc agcgccgcgc ctttcaggtc ttcgaggagg    300
ccaagcaggg ccacctggag agggagtgcg tggaggagct gtgcagccgc gaggaggcgc    360
gggaggtgtt cgagaacgac cccgagacgg attattttta cccaagatac ttagactgca    420
tcaacaagta tgggtctccg tacaccaaaa actcaggctt cgccacctgc gtgcaaaacc    480
tgcctgacca gtgcacgccc aacccctgcg ataggaaggg gacccaagcc tgccaggacc    540
tcatgggcaa cttcttctgc ctgtgtaaag ctggctgggg gggccggctc tgcgacaaag    600
atgtcaacga atgcagccag gagaacgggg gctgcctcca gatctgccac aacaagccgg    660
gtagcttcca ctgttcctgc cacagcggct tcgagctctc ctctgatggc aggacctgcc    720
aagacataga cgagtgcgca gactcggagg cctgcgggga ggcgcgctgc aagaacctgc    780
ccggctccta ctcctgcctc tgtgacgagg gctttgcgta cagctcccag gagaaggctt    840
gccgagatgt ggacgagtgt ctgcagggcc gctgtgagca ggtctgcgtg aactccccag    900
ggagctacac ctgccactgt gacgggcgtg gggcctcaa gctgtcccag gacatggaca    960
cctgtgagga catcttgccg tgcgtgccct tcagcgtggc caagagtgtg aagtccttgt   1020
acctgggccg gatgttcagt gggacccccg tgatccgact gcgcttcaag aggctgcagc   1080
ccaccaggct ggtagctgag tttgacttcc ggacctttga ccccgagggc atcctcctct   1140
ttgccggagg ccaccaggac agcacctgga tcgtgctggc cctgagagcc ggccggctgg   1200
agctgcagct gcgctacaac ggtgtcggcc gtgtcaccag cagcggcccg gtcatcaacc   1260
atggcatgtg gcagacaatc tctgttgagg agctggcgcg gaatctggtc atcaaggtca   1320
acagggatgc tgtcatgaaa atcgcggtgg ccggggactt gttccaaccg gagcgaggac   1380
tgtatcatct gaacctgacc gtgggaggta ttcccttcca tgagaaggac ctcgtgcagc   1440
ctataaaccc tcgtctggat ggctgcatga ggagctggaa ctggctgaac ggagaagaca   1500
ccaccatcca ggaaacggtg aaagtgaaca cgaggatgca gtgcttctcg gtgacggaga   1560
gaggctcttt ctaccccggg agcggcttcg ccttctacag cctggactac atgcggaccc   1620
ctctggacgt cgggactgaa tcaacctggg aagtagaagt cgtggctcac atccgcccag   1680
ccgcagacac aggcgtgctg tttgcgctct gggcccccga cctccgtgcc gtgcctctct   1740
ctgtggcact ggtagactat cactccacga agaaactcaa gaagcagctg gtggtcctgg   1800
ccgtggagca tacggccttg gccctaatgg agatcaaggt ctgcgacggc caagagcacg   1860
tggtcaccgt ctcgctgagg gacggtgagg ccaccctgga ggtggacggc accaggggcc   1920
agagcgaggt gagcgccgcg cagctgcagg agaggctggc cgtgctcgag aggcacctgc   1980
ggagccccgt gctcaccttt gctggcggcc tgccagatgt gccggtgact tcagcgccag   2040
tcaccgcgtt ctaccgcggc tgcatgacac tggaggtcaa ccggaggctg ctggacctgg   2100
acgaggcggc gtacaagcac agcgacatca cggcccactc ctgcccccccc gtggagcccg   2160
ccgcagccta ggcccccacg ggacgcggca ggcttctcag tctctgtccg agacagccgg   2220
gaggagcctg gggctcctc accacgtggg gccatgctga gagctgggct ttcctctgtg   2280
accatcccgg cctgtaacat atctgtaaat agtgagatgg acttggggcc tctgacgccg   2340
cgcactcagc cgtgggcccg ggcgcgggga ggccggcgca gcgcagagcg ggctcgaaga   2400
aaataattct ctattatttt tattaccaag cgcttctttc tgactctaaa atatggaaaa   2460
t                                                                     2461
```

-continued

<210> SEQ ID NO 7
<211> LENGTH: 2127
<212> TYPE: DNA
<213> ORGANISM: Homo sapiens

<400> SEQUENCE: 7

```
ctcgcactcc ctctggccgg cccagggcgc cttcagccca acctccccag ccccacgggc     60
gccacggaac ccgctcgatc tcgccgccaa ctggtagaca tggagacccc tgcctggccc    120
cgggtcccgc gccccgagac cgccgtcgct cggacgctcc tgctcggctg ggtcttcgcc    180
caggtggccg gcgcttcagg cactacaaat actgtggcag catataattt aacttggaaa    240
tcaactaatt tcaagacaat tttggagtgg gaacccaaac ccgtcaatca agtctacact    300
gttcaaataa gcactaagtc aggagattgg aaaagcaaat gcttttacac aacagacaca    360
gagtgtgacc tcaccgacga gattgtgaag gatgtgaagc agacgtactt ggcacgggtc    420
ttctcctacc cggcagggaa tgtggagagc accggttctg ctggggagcc tctgtatgag    480
aactccccag agttcacacc ttacctggag acaaacctcg gacagccaac aattcagagt    540
tttgaacagg tgggaacaaa agtgaatgtg accgtagaag atgaacggac tttagtcaga    600
aggaacaaca ctttcctaag cctccgggat gtttttggca aggacttaat ttatacactt    660
tattattgga aatcttcaag ttcaggaaag aaaacagcca aacaaacac taatgagttt    720
ttgattgatg tggataaagg agaaaactac tgtttcagtg ttcaagcagt gattccctcc    780
cgaacagtta accggaagag tacagacagc ccggtagagt gtatgggcca ggagaaaggg    840
gaattcagag aaatattcta catcattgga gctgtggtat ttgtggtcat catccttgtc    900
atcatcctgg ctatatctct acacaagtgt agaaaggcag gagtggggca gagctggaag    960
gagaactccc cactgaatgt ttcataaagg aagcactgtt ggagctactg caaatgctat   1020
attgcactgt gaccgagaac ttttaagagg atagaataca tggaaacgca aatgagtatt   1080
tcggagcatg aagaccctgg agttcaaaaa actcttgata tgacctgtta ttaccattag   1140
cattctggtt ttgacatcag cattagtcac tttgaaatgt aacgaatggt actacaacca   1200
attccaagtt ttaattttta acaccatggc accttttgca cataacatgc tttagattat   1260
atattccgca ctcaaggagt aaccaggtcg tccaagcaaa aacaaatggg aaaatgtctt   1320
aaaaaatcct gggtggactt ttgaaaagct tttttttttt tttttttttg agacggagtc   1380
ttgctctgtt gcccaggctg gagtgcagta gcacgatctc ggctcactgc accctccgtc   1440
tctcgggttc aagcaattgt ctgcctcagc ctcccgagta gctgggatta caggtgcgca   1500
ctaccacacc aagctaattt ttgtattttt tagtagagat ggggtttcac catcttggcc   1560
aggctggtct tgaattcctg acctcagttg atccacccac cttggcctcc caaagtgcta   1620
gtattatggg cgtgaaccac catgcccagc cgaaaagctt ttgaggggct gacttcaatc   1680
catgtaggaa agtaaaatgg aaggaaattg ggtgcatttc taggactttt ctaacatatg   1740
tctataatat agtgtttagg ttcttttttt tttcaggaat acatttggaa attcaaaaca   1800
attggcaaac tttgtattaa tgtgttaagt gcaggagaca ttggtattct gggcaccttc   1860
ctaatatgct ttacaatctg cactttaact gacttaagtg gcattaaaca tttgagagct   1920
aactatattt ttataagact actatacaaa ctacagagtt tatgatttaa ggtacttaaa   1980
gcttctatgg ttgacattgt atatataatt ttttaaaaag gttttctata tggggatttt   2040
ctatttatgt aggtaatatt gttctatttg tatatattga gataatttat ttaatatact   2100
```

-continued

```
ttaaataaag gtgactggga attgtta                                       2127


<210> SEQ ID NO 8
<211> LENGTH: 5426
<212> TYPE: DNA
<213> ORGANISM: Homo sapiens

<400> SEQUENCE: 8

ggggaggaag aaaggcgaag gcaaggcgaa ggggtggaga gtgatatgaa gagcgagaga     60

aaagagagga cagcggacga gcagatccgg tatctggaat cccggcgcct agaacgtgtt    120

tttcgggaga gcaaaggctg tgtctacggc aggctgggga tatagcctct ccttccgatg    180

aaaagagaaa ggaagaatgg actacagcca ccaaacgtcc ctagtcccat gtggacaaga    240

taaatacatt tccaaaaatg aacttctctt gcatctgaag acctacaact tgtactatga    300

aggccagaat ttacagctcc ggcaccggga ggaagaagac gagttcattg tggaggggct    360

cctgaacatc tcctggggcc tgcgccggcc cattcgcctg cagatgcagg atgacaacga    420

acgcattcga ccccctccat cctcctcctc ctggcactct ggctgtaacc tgggggctca    480

gggaaccact ctgaagcccc tgactgtgcc caaagttcag atctcagagg tggatgcccc    540

gccggagggt gaccagatgc caagctccac agactccagg ggcctgaagc ccctgcagga    600

ggacacccca cagctgatgc gcacacgcag tgatgttggg gtgcgtcgcc gtggcaatgt    660

gaggacgcct agtgaccagc ggcgaatcag acgccaccgc ttctccatca acggccattt    720

ctacaaccat aagacatccg tgttcacacc agcctatggc tctgtcacca acgtccgcat    780

caacagcacc atgaccaccc cacaggtcct gaagctgctg ctcaacaaat ttaagattga    840

gaattcagca gaggagtttg ccttgtacgt ggtccatacg agtggtgaga aacagaagct    900

gaaggccacc gattacccgc tgattgcccg aatcctccag ggcccatgtg agcagatctc    960

caaagtgttc ctaatggaga aggaccaggt ggaggaagtc acctacgacg tggcccagta   1020

tataaagttc gagatgccgg tacttaaaag cttcattcag aagctccagg aggaagaaga   1080

tcgggaagta aagaagctga tgcgcaagta caccgtgctc cggctaatga ttcgacagag   1140

gctggaggag atagccgaga ccccagcaac aatctgagcc atgagaacga ggggatctgg   1200

gcaccccagg aaccgccatt gcccataaga cccccaggaa gctaggcact ttctttccat   1260

ggaaacattt agacacaaac ctccccagct ccggccaagc catcatttgc tacctggagc   1320

tggatgtaga agtcagcaga cagctcccta tccctggacc cctgccctcc ttttttctgc   1380

tcacaaggac ttttgatttt agttataagg aggacccaaa atgtgtgtgt gtacatgtgt   1440

gtgcacacat ggtacgtgtc catgtgccta cctgatactt tcacatgtaa ttaaattcca   1500

ggcaaccagc acaagagccg tgagcttggc acatgtgctg ctcgtgagca ggaaaatcag   1560

aggagccact gatctgagtg gtatttaggt tgaaggaaag atttctcctc tcaagtgcca   1620

gggagcagcc acacgtctgt ctgtgtttag agagggaaga gggttctcca ggttcaccat   1680

ttgggttgtt tatatgttgg tagaaattct ccctgtatgc ctagaaggat cagtgaatgt   1740

aagagccttg gaaattaaca aaataacagc cacataacct tgcggcaagt ctgatggaaa   1800

gaaaaagata aaccatccgt ggggtagatg caataagccc acgtattttt acactggaaa   1860

cgttgattgt tttaaatgac aaagacatat gtgatgttct atgtggaaac ctgtgaagag   1920

tggattctgc ctccatctct gcctccatgg ctacctttag gagacagaga agatcctgtg   1980

tgtttctctg tacccagctg acagcctgtc tctatggcgc ttccttgagt ggaaggaaat   2040

gtctcaagaa acaaagatct cgctggtgcg tacacagtgc tgaccagcta gtgtggccag   2100
```

-continued

```
ggcctggtgg cctggtggcc aggaagtttc aggttgaagg gaaatgtcga ggctacctgc   2160
agatatgaca ggtgccttga acgcagccca tcttcatgtc atcaaaggtc ttcctgcact   2220
tgaagctggg gcgatgtttg cagtcaagac cattctttcc aacctctggg ttcttgcaag   2280
ttgccctcac cttgtgtgtg gagatgcatt ccaagaatga agcctcatct tgctactgag   2340
tgtggggttc agggaagctc tttaggccac ctggtgaagg tgcatgggga ggatggagct   2400
tctcctcagc tcctctgagc agccacctat gtgatcttta aatccaaccc caatgggaga   2460
aaagggcaag aacagtctgt gccctgggac tcctatcagg aagcttgaca ggcagctggg   2520
catcagtgca gctgatatcg tttgaggagg gagacagatg cttggacctg ggtgcctggc   2580
tatggagatt gaccaagcaa gatcaggagc tcctgatagc aggcgtcttt gagcctagct   2640
ggggtagagg cactgcccat ctcttctcca ccttctctcc acagaatgtt tgcagagctg   2700
ggcagttgag gaaaggacag cccctggttg gtgcctccaa aggaaggtgg actttttttgg   2760
tggagacgtt tctgccctgg gcaccctcct gcccccgatt catacctatg gcttcttgag   2820
aaggctcaca gctgtggtct taacgtagac tgcagaaaga tggcatgcgg cccctggcat   2880
ttcgccaagg gttttatagc aagtctcctt cctccatagg gacagcagca ccagccctgt   2940
ggggcatgga gtggaagccc agaagggctt ctgcaagctg cacagaactg gggtaagaag   3000
acaaagagta gccaccggga gaggcttcct ttgttacagc tgggaaagaa cagttctgtg   3060
aatgcaaaca cctcctgagt tttgcaattg agaaaatgat ttggagaact tctcttctgg   3120
taatttttat tttgaatgtt cagggcctta gttggcccca gtaattctcc ttggaggact   3180
tgggagaaga atttccacaa agcaaactac taaccactag ctcttactgg acagcgattt   3240
ctggcttata agagttctct ttgatttgca ctagcactac gatagtgtta gatggggaaa   3300
tactgcaaca tgtccagttg gccagatcac tttccaaggg agcgatacta aggcagactc   3360
agctttttaa agatgggagg tcaggaggtg gaagtgagag gagatcccat ctcacacaac   3420
acacttccac gtaatgcaga ccacactttt ccattttgtc ctgccctctt gagaggtcat   3480
ttctcacgtc ctaagaacct gatcagaaat tttggaaggg ttctttgaaa tagcagcagt   3540
tgaaacagag acactttgcc acagtgtgga gcagattttc tcactggtat cacatggtct   3600
tgcagttttg aactcttcga ccgatttgtg ggagtttatg taattgcgtg caatgaacct   3660
gaaattgtgt aaaggacaaa agaccagttt atagggttgg gtttttttttc caacttgtga   3720
aaagcagttt agctgcatct gtctccccac cacccccacc ccgggagggg cttatgttac   3780
aaggtgatca agtgaaggaa aaacctgagc ctatctggct gggatggtgg aattaagcac   3840
aaggtcacat tctctgtgat cacatgagag ggaaggtgat gacttaaatg gcagggggtg   3900
gggattatct tggggagagg ctgaaaagca caaaagatag tcttccctgt acgtattggt   3960
gaagaacgtg cacaaggctg gatggacttc aacttggagt tgagttgagg caagaggatt   4020
tctggatatt agtcacccat ctgcaagaaa aatgctgagg cctcgggtca agattttgat   4080
ctgagacatg ctgatgcttc aaggagaaat attttcacaa tcctctcttc cctcaccaga   4140
agagaacagt actctctcct agaaacctct aggtaaacac attttatcct aatatcggta   4200
gcatataatg cccccccaa aatatctgtt ttccatgcaa aaaagtctca acaagaagtc   4260
tgtggagttg agtggttact tcaaagtgtc aggagagtga agaaattggc cacagaagag   4320
caagaagctc tcttaagaaa agggaattct ctttaaagaa accaccacca acaacaaaac   4380
aaccaaaaac catgttttat gtcaaagctc tgtagcacag agaatgtggt gtcacagata   4440
```

-continued

```
catcgccgag agaggtttct ttctttcttt tttttttttt tgagacagag tctggttctg   4500

tttcccaggc tggagtgcag tggtgggatc tcagctcact gcaacatccg cctctggggt   4560

tcaagtgatt ctcctgtctc agcctcccaa gtagctggaa ttacagggac ccgccaccac   4620

gcccggctaa tttttttgtg tggttttagt agaggtgggg tttcaccatc ttggccaggc   4680

tggtcttgaa ctcctgacct cgtgatccac ccgcctaggc ctcccaaagt gttgggatta   4740

caggcgtgag ccactgtgcc cagccaaaag agaaatttct acatgaacaa ggcaatttca   4800

gtgtcttaca gcggccaaac catgacgtga agaatgagat aggagacagg agatcaccat   4860

aagcgtccct gatatagcag cacacatttt cacgtttcca cttaaatcgt tttgcacaaa   4920

gtcttgcttc gctcagatga gatgagatat gatttcctag agatgtaaaa ataagaatga   4980

atgtggcgcc cccttcttcc agatgtaata gaaagctctg ccctatcaca agggggggtgt   5040

tgaagcgccc cttgtgtttt aactgtattt aactgagcac aagatgcaca agctgtggtg   5100

ggaaaccctc agtttacctt tggagtcttc cctgcagatc gcagacctgt ttccaggctg   5160

atgtttctgg tgtgtaattg ctagcgtttc tgaagggttt tcccaattgt tttagccttg   5220

tgaagtattc ttaattataa cttgcctttc agcgatggta catgacttga ttcaacgttt   5280

ggttctgaac ttacacactg atgcgtttac tcatctaaca taatctgaca gggcctcagc   5340

aagggagcca tacatttttg taacattttg atatgtttta atgcatctga cttagatctt   5400

actgaaataa agcacttttc aaagag                                          5426
```

<210> SEQ ID NO 9
<211> LENGTH: 3095
<212> TYPE: DNA
<213> ORGANISM: Homo sapiens

<400> SEQUENCE: 9

```
tagcagagca atcaccacca agcctggaat aactgcaagg gctctgctga catcttcctg     60

aggtgccaag gaaatgagga tggaggaagg aatgaatgtt ctccatgact ttgggatcca    120

gtcaacacat tacctccagg tgaattacca agactcccag gactggttca tcttggtgtc    180

cgtgatcgca gacctcagga atgccttcta cgtcctcttc cccatctggt tccatcttca    240

ggaagctgtg ggcattaaac tcctttgggt agctgtgatt ggagactggc tcaacctcgt    300

ctttaagtgg attctctttg gacagcgtcc atactggtgg gttttggata ctgactacta    360

cagcaacact tccgtgcccc tgataaagca gttccctgta acctgtgaga ctggaccagg    420

gagcccctct ggccatgcca tgggcacagc aggtgtatac tacgtgatgg tcacatctac    480

tctttccatc tttcagggaa agataaagcc gacctacaga tttcggtgct tgaatgtcat    540

tttgtggttg ggattctggg ctgtgcagct gaatgtctgt ctgtcacgaa tctaccttgc    600

tgctcatttt cctcatcaag ttgttgctgg agtcctgtca ggcattgctg ttacagaaac    660

tttcagccac atccacagca tctataatgc cagcctcaag aaatattttc tcattacctt    720

cttcctgttc agcttcgcca tcggatttta tctgctgctc aagggactgg gtgtagacct    780

cctgtggact ctggagaaag cccagaggtg gtgcgagcag ccagaatggg tccacattga    840

caccacaccc tttgccagcc tcctcaagaa cctgggcacg ctctttggcc tggggctggc    900

tctcaactcc agcatgtaca gggagagctg caaggggaaa ctcagcaagt ggctcccatt    960

ccgcctcagc tctattgtag cctccctcgt cctcctgcac gtctttgact ccttgaaacc   1020

cccatcccaa gtcgagctgg tcttctacgt cttgtccttc tgcaagagtg cggtagtgcc   1080

cctggcatcc gtcagtgtca tcccctactg cctcgcccag gtcctgggcc agccgcacaa   1140
```

-continued gaagtcgttg taagagatgt ggagtcttcg gtgtttaaag tcaacaacca tgccagggat 1200
tgaggaggac tactatttga agcaatgggc actggtattt ggagcaagtg acatgccatc 1260
cattctgccg tcgtggaatt aaatcacgga tggcagattg gagggtcgcc tggcttattc 1320
ccatgtgtga ctccagcctg ccctcagcac agactctttc agatggaggt gccatatcac 1380
gtacaccata tgcaagtttc ccgccaggag gtcctcctct ctctacttga atactctcac 1440
aagtagggag ctcactccca ctggaacagc ccattttatc tttgaatggt cttctgccag 1500
cccattttga ggccagaggt gctgtcagct caggtggtcc tcttttacaa tcctaatcat 1560
attgggtaat gtttttgaaa agctaatgaa gctattgaga aagacctgtt gctagaagtt 1620
gggttgttct ggattttccc ctgaagactt acttattctt ccgtcacata tacaaaagca 1680
agacttccag gtagggccag ctcacaagcc caggctggag atcctaactg agaattttct 1740
acctgtgttc attcttaccg agaaaaggag aaaggagctc tgaatctgat aggaaaagaa 1800
ggctgcctaa ggaggagttt ttagtatgtg gcgtatcatg caagtgctat gccaagccat 1860
gtctaaatgg ctttaattat atagtaatgc actctcagta atgggggacc agcttaagta 1920
taattaatag atggttagtg gggtaattct gcttctagta tttttttttac tgtgcataca 1980 tgttcatcgt atttccttgg atttctgaat ggctgcagtg acccagatat tgcactaggt 2040
caaaacattc aggtatagct gacatctcct ctatcacatt acatcatcct ccttataagc 2100
ccagctctgc tttttccaga ttcttccact ggctccacat ccaccccact ggatcttcag 2160
aaggctagag ggcgactctg gtggtgcttt tgtatgtttc aattaggctc tgaaatcttg 2220
ggcaaaatga caaggggagg gccaggattc ctctctcagg tcactccagt gttactttta 2280
attcctagag ggtaaatatg actcctttct ctatcccaag ccaaccaaga gcacattctt 2340
aaaggaaaag tcaacatctt ctctcttttt tttttttttt gagacagggt ctcactatgt 2400
tgcccaggct gctcttgaat tcctgggctc aagcagtcct cccaccctac cacagcgtcc 2460
cgcgtagctg gcatacaggt gcaagccact atgtccagct agccaactcc tccttgcctg 2520
cttttctttt tttttctttt tttgagacgg cgcacctatc acccaggctg gagtggagtg 2580
gcacgatctt ggctcactgc aacctcttcc tcctggttca agcgattctc atgtctcagc 2640
ctcctcagta gctaggacta ccggcgtgca ccaccatgcc aggctaattt ttatattttt 2700
agaattttag aagagatggg atttcatcat gttggccagg ctggtctcga actcctgacc 2760
tcaagtgatc cacctgcctt ggcctcccaa ggtgctagga ttacaggcat gagccaccgc 2820
accgggccct ccttgcctgt ttttcaatct catctgatat gcagagtatt tctgccccac 2880
ccacctaccc cccaaaaaaa gctgaagcct atttatttga aagtccttgt ttttgctact 2940
aattatatag tataccatac attatcattc aaaacaacca tcctgctcat aacatctttg 3000
aaaagaaaaa tatatatgtg cagtatttta ttaaagcaac attttattta agaataaagt 3060
cttgttaatt actatatttt agatgcaatg tgatc 3095

<210> SEQ ID NO 10
<211> LENGTH: 4460
<212> TYPE: DNA
<213> ORGANISM: Homo sapiens

<400> SEQUENCE: 10
cggggcagca accaggagat tccctgggcc tgcaggaagc ccttccgcgg accgaaagat 60
tgttccccat tttggagatg aagaaactga gactcaaagc agctgagtga ccttcccaag 120

-continued

```
gacacacact gaactgggcg gtgatcagga tctgaatgca cagggcgggt gttcagcgat    180
tgtttactac gttgaacgtg acctccagga aagcagttct ggccgagatc cctgacaac    240
gcaaagcaag aagtaacgtg gaaggaggct ccccaagctg gctggccatt ttgctgctgt    300
gtgtggaggt gctgtcagtg gcatgcccaa acccaaagct ggaagaggaa taaattacaa    360
gtggtcaagg ttgcatcctt ttgagctcag gacctgcttg taagccgaga gggttctctg    420
gccctaatct agccaagcac catggagaga atcagtgcct tcttcagctc tatctgggac    480
accatcttga ccaaacacca agaaggcatc tacaacacca tctgcctggg agtcctcctg    540
ggcctgccac tcttggtgat catcacactc ctcttcatct gttgccattg ctgctggagc    600
ccaccaggca agaggggcca gcagccagag aagaaaaaga agaagaagaa gaagaaggat    660
gaagaagacc tctggatctc tgctcaaccc aagcttctcc agatggagaa gagaccatca    720
ctgcctgttt agttaggcag gaagcagagg tgtttccttt ctggggctaa gcctccttct    780
gaccacacac agacatttca ggaacccctg aaataatgca ctatgtccat gtccacagag    840
taactactca accaaggaac aaacctcaga ctaagtgtcc cagtggaggg cagtcccagg    900
gaccacgtgg acaattcttg gatactgtct tggcagctat gtgtccaata gcaatgctcc    960
ttactgcaga cccaggcatg cctcccacct gtctctggca taccccacat gcaaagcaca   1020
aagaacattt atccatacat ctcaatatgg ttcccaagtg tgtgcacatg cacgtaacac   1080
acacacacac aaattcaggt agcaggtacg tgggcaagta tattctgctc atcaaatggt   1140
cattggctat gtactttgtg cagggaagta cattatctac agtcacaaaa atgtctcatg   1200
ggaaagcctt gccagattca gacacatata tacaatttcc taaccagcaa ggcccccata   1260
caccatctat tccataaacc actcaggtta cagatgcatg ctttcctatt tctaactcta   1320
cacataaact tttactggaa gtactcataa ttggacattc cagcaacctg ctacagtccc   1380
cacccttgtg tgtcttgata cagacacacc aagtttctgt gcctctgacc cctcacctgt   1440
gccaagatgt ttaaagtgtg atggttcaaa attcattgaa agctcttttc ttgtaactca   1500
tgacaaagtc cgtcctcatt gccactgaga ggtgtttaat gtgatccaag acctctctgt   1560
gaaacattac ccccgcaaac cactcagcaa agtgcctttc tccaagcaag aacaaagagc   1620
tcttggtggt gactgctaga aaattatgga agcccactca tttatgtcag tggactgcaa   1680
ctgtgtacct gtgcaatgtt tacagatgga aagggtgagg agatgctaca cctgagctag   1740
gtatctccta tataaccaaa gtttccagca gggaaggaac tagacaatca tcagtgcagt   1800
ctcacagaag gcaacactgg aagtgatgtc ataaggttgt gatgtgtgca cggtacggca   1860
caggtgggat gcagaggtaa cagagtttaa atgaaagtag gatgaagcta taaagaggtt   1920
tatttatatt tatattgaag ctcaggcaag tgccttgcac acagtaggta cttataacta   1980
actgtggtta ctgttggata tgtgatgttg ttaagggtaa gcttgtaata cctcaccaat   2040
tctctgcgag tgatcttctc ttctaagtga gcccactaat tgctgcaatg gatgaaattg   2100
ggtgtttaat gctggagagc acatgtaggt gacacatgtg ccttgaggta tgtgaggaca   2160
tgtaaattag atccacagtg agctgaggag ggctttcccc gccagagtga ggttgggaag   2220
cagagttaat ccacttatag gatgaactgc ttggtatttt tattgtattg tgactgtatt   2280
acaaagatgg acaattcact ccttgggagc aagttatgct ctagaagttt atttacaaat   2340
atgctgggca gctctcttga aatattttcc caaggaagct attctacaca gtggcaaaat   2400
tgctatctaa ttaataatgt agctaaacta tgatatttat agtagcaaaa aactaaattc   2460
tataagattg cattaaagga aagatatatt ctatttgctc acttgggctg cttggtactc   2520
```

-continued

```
acctgccctc caggtgtact ttaggcctgt ggagggtggg catttagtgg tgacccttgc   2580
accagggttt tctaacagat gaccctgtga atcataattt aaacctgcat atattttata   2640
gccagtcaca tttgccctct caccctatat ggccataaac tgcctaagca ctcaggcctc   2700
ccactcatca acccctttga ccagagaaag aagcactctg gttctctatc cccttgtcac   2760
atagagagtt tgtcatgggg cctctggctg tgcccttcac ataacagaat aacttgccat   2820
ctgcctgcac caaacccagg gatgtggaag acatctcccc acaactgcca ctgctcacca   2880
ggacaagctg cccttcctgt ctccacctct cagtcccccct agaatggatg gctggggaga   2940
ggtggaggct gacagctgag acgtagtgtc agatatgatc taggagggcg gatcaccggg   3000
atccgggacc atacaagtaa catggtttcc atggcaactg cttgctcgtt tgaattaaga   3060
cagcagtcag ttgtcattgc catgacaagg cctctatctc caggcacaat gtccctgctg   3120
tctcctaatc caatggactt gctctcaccc cagggatgaa acacccagaa actcacttct   3180
cagtcacttc cacagccgat gactcagaag agccaaaccc agaatggggc ctctcttttc   3240
cccatcacag actcccctga caacctttcc tggcgtaact agaggagtcc cagtgcagga   3300
taggccctaa acgttttgtt aaataaacag gtgcatgaaa ggagcctaag gccattgttg   3360
atatccactc tcttctttcc acttccttct catctttttc tccatgtttt atgcttctct   3420
gattccctct tctgcctgca ccagaccagc cccagccctt tattcctctc cattttcact   3480
ccttccagcc tctgtccctg aactgccact ggcaacccat gggacctcag gaccagagac   3540
tgcttgactc atctggggag ggtaagttca cgggggacaa aaaaatgatt cctaaagaag   3600
aggcttccta gaccagcaca ggctccagaa agacatcccc taggcctgga cttctgagca   3660
gctttagcca ggctccggac ggcagccaga ggaggccttt ccccattgct cctttcccca   3720
ttgctcaatg gattccatgt ttctttttct tggggggagc agggagggag aaaggtagaa   3780
aaatggcagc cacctttcca agaaaaatat aaagggtcca agctgtatag tatttgtcag   3840
tatttttttc tgtaaaattc gaacacacac aaaagaaaaa tttatttaaa taaaatactt   3900
tgaaaatgaa aagtcttgat gtagtcagat ggttactttc ttaacattag gtattacccc   3960
cactcagaca tcactcagaa atgatcaatg cagggactct ttctgtgaca caaatgtccc   4020
agccctccct ggtcaccgcc ttcgccatgg tagagtcgta ggtctgagga tgaggaatgt   4080
ggctgtctca cccttgcttg caaaacagat ggccttggag accagactcc ctcaaaggtg   4140
ccagctacag gaaaaataca ctgatgttcc ttggcaacac ttacagaact ttccatcaat   4200
gagggtccat caatggcttc ttaaaggaaa agggggggaaa tagcaaaaac ctaaggaaga   4260
atggaccttt gagttaaatc cagtgtttgt tgggaaagga gggatcaaaa acctctatag   4320
tagccactag ggcaaaaact gtgtgtatgt gtgtgtgtat gtgtgtgtac actgttcaat   4380
atggttcaat atggtaccaa tagccacatg tgactattta aattcattgc aatgaaataa   4440
aattaaaggt atactagctc                                                4460

<210> SEQ ID NO 11
<211> LENGTH: 3076
<212> TYPE: DNA
<213> ORGANISM: Homo sapiens

<400> SEQUENCE: 11

gaattcaaaa tgtcttcagt tgtaaatctt accattattt tacgtacctc taagaaataa     60
aagtgcttct aattaaaata tgatgtcatt aattatgaaa tacttcttga taacagaagt    120
```

-continued

```
tttaaaatag ccatcttaga atcagtgaaa tatggtaatg tattattttc ctcctttgag    180
ttaggtcttg tgcttttttt tcctggccac taaatttcac aatttccaaa aagcaaaata    240
aacatattct gaatattttt gctgtgaaac acttgacagc agagctttcc accatgaaaa    300
gaagcttcat gagtcacaca ttacatcttt gggttgattg aatgccactg aaacattcta    360
gtagcctgga gaagttgacc tacctgtgga gatgcctgcc attaaatggc atcctgatgg    420
cttaatacac atcactcttc tgtgaagggt tttaattttc aacacagctt actctgtagc    480
atcatgttta cattgtatgt ataaagatta tacaaaggtg caattgtgta tttcttcctt    540
aaaatgtatc agtataggat ttagaatctc catgttgaaa ctctaaatgc atagaaataa    600
aaataataaa aaatttttca ttttggcttt tcagcctagt attaaaactg ataaaagcaa    660
agccatgcac aaaactacct ccctagagaa aggctagtcc cttttcttcc ccattcattt    720
cattatgaac atagtagaaa acagcatatt cttatcaaat ttgatgaaaa gcgccaacac    780
gtttgaactg aaatacgact tgtcatgtga actgtaccga atgtctacgt attccacttt    840
tcctgctggg gttcctgtct cagaaaggag tcttgctcgt gctggtttct attacactgg    900
tgtgaatgac aaggtcaaat gcttctgttg tggcctgatg ctggataact ggaaaagagg    960
agacagtcct actgaaaagc ataaaaagtt gtatcctagc tgcagattcg ttcagagtct   1020
aaattccgtt aacaacttgg aagctacctc tcagcctact tttccttctt cagtaacaaa   1080
ttccacacac tcattacttc cgggtacaga aaacagtgga tatttccgtg gctcttattc   1140
aaactctcca tcaaatcctg taaactccag agcaaatcaa gatttttctg ccttgatgag   1200
aagttcctac cactgtgcaa tgaataacga aaatgccaga ttacttactt ttcagacatg   1260
gccattgact tttctgtcgc caacagatct ggcaaaagca ggcttttact acataggacc   1320
tggagacaga gtggcttgct ttgcctgtgg tggaaaattg agcaattggg aaccgaagga   1380
taatgctatg tcagaacacc tgagacattt tcccaaatgc ccatttatag aaaatcagct   1440
tcaagacact tcaagataca cagtttctaa tctgagcatg cagacacatg cagcccgctt   1500
taaaacattc tttaactggc cctctagtgt tctagttaat cctgagcagc ttgcaagtgc   1560
gggtttttat tatgtgggta acagtgatga tgtcaaatgc ttttgctgtg atggtggact   1620
caggtgttgg gaatctggag atgatccatg ggttcaacat gccaagtggt ttccaaggtg   1680
tgagtacttg ataagaatta aaggacagga gttcatccgt caagttcaag ccagttaccc   1740
tcatctactt gaacagctgc tatccacatc agacagccca ggagatgaaa atgcagagtc   1800
atcaattatc cattttgaac ctggagaaga ccattcagaa gatgcaatca tgatgaatac   1860
tcctgtgatt aatgctgccg tggaaatggg ctttagtaga agcctggtaa aacagacagt   1920
tcaaagaaaa atcctagcaa ctggagagaa ttatagacta gtcaatgatc ttgtgttaga   1980
cttactcaat gcagaagatg aaataaggga agaggagaga gaaagagcaa ctgaggaaaa   2040
agaatcaaat gatttattat taatccggaa gaatagaatg gcactttttc aacatttgac   2100
ttgtgtaatt ccaatcctgg atagtctact aactgccgga attattaatg aacaagaaca   2160
tgatgttatt aaacagaaga cacagacgtc tttacaagca agagaactga ttgatacgat   2220
tttagtaaaa ggaaatattg cagccactgt attcagaaac tctctgcaag aagctgaagc   2280
tgtgttatat gagcatttat ttgtgcaaca ggacataaaa tatattccca cagaagatgt   2340
ttcagatcta ccagtggaag aacaattgcg gagactacaa gaagaaagaa catgtaaagt   2400
gtgtatggac aaagaagtgt ccatagtgtt tattccttgt ggtcatctag tagtatgcaa   2460
agattgtgct ccttctttaa gaaagtgtcc tatttgtagg agtacaatca agggtacagt   2520
```

-continued tcgtacattt ctttcatgaa gaagaaccaa aacatcatct aaactttaga attaatttat 2580
taaatgtatt ataactttaa cttttatcct aatttggttt ccttaaaatt tttatttatt 2640
tacaactcaa aaaacattgt tttgtgtaac atatttatat atgtatctaa accatatgaa 2700
catatatttt ttagaaacta agagaatgat aggcttttgt tcttatgaac gaaaaagagg 2760
tagcactaca aacacaatat tcaatcaaaa tttcagcatt attgaaattg taagtgaagt 2820
aaaacttaag atatttgagt taacctttaa gaattttaaa tattttggca ttgtactaat 2880
acctggtttt ttttttgttt tgttttttttg tacagacagg gcagcatact gagaccctgc 2940
ctttaaaaac aaacagaaca aaaacaaaac accagggaca catttctctg tcttttttga 3000
tcagtgtcct atacatcgaa ggtgtgcata tatgttgaat gacattttag ggacatggtg 3060
tttttataaa gaattc 3076

<210> SEQ ID NO 12
<211> LENGTH: 3056
<212> TYPE: DNA
<213> ORGANISM: Homo sapiens

<400> SEQUENCE: 12
cccagctggt gctgaagctc gtcagttcac catccgccct cggcttccgc ggggcgctgg 60
gccgccagcc tcggcaccgt cctttccttt ctccctcgcg ttaggcaggt gacagcaggg 120
acatgtctcg ggagatgcag gatgtagacc tcgctgaggt gaagcctttg gtggagaaag 180
gggagaccat caccggcctc ctgcaagagt ttgatgtcca ggagcaggac atcgagactt 240
tacatggctc tgttcacgtc acgctgtgtg ggactcccaa gggaaaccgg cctgtcatcc 300
tcacctacca tgacatcggc atgaaccaca aaacctgcta caacccccctc ttcaactacg 360 aggacatgca ggagatcacc cagcactttg ccgtctgcca cgtggacgcc cctggccagc 420
aggacggcgc agcctccttc cccgcagggt acatgtaccc ctccatggat cagctggctg 480
aaatgcttcc tggagtcctt caacagtttg ggctgaaaag cattattggc atgggaacag 540
gagcaggcgc ctacatccta actcgatttg ctctaaacaa ccctgagatg gtggagggcc 600
ttgtccttat caacgtgaac ccttgtgcgg aaggctggat ggactgggcc gcctccaaga 660
tctcaggatg gacccaagct ctgccggaca tggtggtgtc ccaccttttt gggaaggaag 720
aaatgcagag taacgtggaa gtggtccaca cctaccgcca gcacattgtg aatgacatga 780
accccggcaa cctgcacctg ttcatcaatg cctacaacag ccggcgcgac ctggagattg 840
agcgaccaat gccgggaacc cacacagtca ccctgcagtg ccctgctctg ttggtggttg 900
gggacagctc gcctgcagtg gatgccgtgg tggagtgcaa ctcaaaattg gacccaacaa 960
agaccactct cctcaagatg gcggactgtg gcggcctccc gcagatctcc cagccggcca 1020
agctcgctga ggccttcaag tacttcgtgc agggcatggg atacatgccc tcggctagca 1080
tgacccgcct gatgcggtcc cgcacagcct ctggttccag cgtcacttct ctggatggca 1140
cccgcagccg ctcccacacc agcgagggca cccgaagccg ctcccacacc agcgagggca 1200
cccgcagccg ctcgcacacc agcgaggggg cccacctgga catcaccccc aactcgggtg 1260
ctgctgggaa cagcgccggg cccaagtcca tggaggtctc ctgctaggcg gcctgcccag 1320
ctgccgcccc cggactctga tctctgtagt ggccccctcc tccccggccc cttttcgccc 1380
cctgcctgcc atactgcgcc taactcggta ttaatccaaa gcttattttg taagagtgag 1440
ctctggtgga gacaaatgag gtctattacg tgggtgccct ctccaaaggc ggggtggcgg 1500

-continued

```
tggaccaaag gaaggaagca agcatctccg catcgcatcc tcttccatta accagtggcc   1560
ggttgccact ctcctcccct ccctcagaga caccaaactg ccaaaaacaa gacgcgtagc   1620
agcacacact tcacaaagcc aagcctaggc cgccctgagc atcctggttc aaacgggtgc   1680
ctggtcagaa ggccagccgc ccacttcccg tttcctcttt aactgaggag aagctgatcc   1740
agtttccgga aacaaaatcc ttttctcatt tggggagggg ggtaatagtg acatgcaggc   1800
acctctttta aacaggcaaa acaggaaggg ggaaaaggtg ggattcatgt cgaggctaga   1860
ggcatttgga acaacaaatc tacgtagtta acttgaagaa accgattttt aaagttggtg   1920
catctagaaa gctttgaatg cagaagcaaa caagcttgat ttttctagca tcctcttaat   1980
gtgcagcaaa agcaggcaac aaaatctcct ggctttacag acaaaaatat ttcagcaaac   2040
gttgggcatc atggtttttg aaggctttag ttctgctttc tgcctctcct ccacagcccc   2100
aacctcccac ccctgataca tgagccagtg attattcttg ttcagggaga agatcattta   2160
gatttgtttt gcattcctta gaatggaggg caacattcca cagctgccct ggctgtgatg   2220
agtgtccttg caggggccgg agtaggagca ctggggtggg ggcggaattg gggttactcg   2280
atgtaaggga ttccttgttg ttgtgttgag atccagtgca gttgtgattt ctgtggatcc   2340
cagcttggtt ccaggaattt tgtgtgattg gcttaaatcc agttttcaat cttcgacagc   2400
tgggctggaa cgtgaactca gtagctgaac ctgtctgacc cggtcacgtt cttggatcct   2460
cagaactctt tgctcttgtc ggggtggggg tgggaactca cgtgggggagc ggtggctgag   2520
aaaatgtaag gattctggaa tacatattcc atgggacttt ccttccctct cctgcttcct   2580
cttttcctgc tccctaacct ttcgccgaat ggggcagcac cactgacgtt tctgggcggc   2640
cagtgcggct gccaggttcc tgtactactg ccttgtactt ttcattttgg ctcaccgtgg   2700
attttctcat aggaagtttg gtcagagtga attgaatatt gtaagtcagc cactgggacc   2760
cgaggatttc tgggaccccg cagttgggag gaggaagtag tccagccttc caggtggcgt   2820
gagaggcaat gactcgttac ctgccgccca tcaccttgga ggccttccct ggccttgagt   2880
agaaaagtcg gggatcgggg caagagaggc tgagtacgga tgggaaacta ttgtgcacaa   2940
gtctttccag aggagtttct taatgagata tttgtattta tttccagacc aataaatttg   3000
taactttgca gcggaaaaaa aaaaaaaaaa aaaaaaaaaa aaaaaaaaaa aaaaaa       3056
```

<210> SEQ ID NO 13
<211> LENGTH: 1930
<212> TYPE: DNA
<213> ORGANISM: Homo sapiens

<400> SEQUENCE: 13

```
ggagagagag aggacagaga gcaagtcact cccggctgcc tttttcacct ctgacagagc     60
ccagacacca tgaacgcaag tgaattccga aggagaggga aggagatggt ggattacgtg    120
gccaactaca tggaaggcat tgagggacgc caggtctacc ctgacgtgga gcccgggtac    180
ctgcggccgc tgatccctgc cgctgcccct caggagccag acacgtttga ggacatcatc    240
aacgacgttg agaagataat catgcctggg gtgacgcact ggcacagccc ctacttcttc    300
gcctacttcc ccactgccag ctcgtacccg gccatgcttg cggacatgct gtgcggggcc    360
attggctgca tcggcttctc ctgggcggca agcccagcat gcacagagct ggagactgtg    420
atgatggact ggctcgggaa gatgctggaa ctaccaaagg catttttgaa tgagaaagct    480
ggagaagggg gaggagtgat ccagggaagt gccagtgaag ccaccctggt ggccctgctg    540
gccgctcgga ccaaagtgat ccatcggctg caggcagcgt ccccagagct cacacaggcc    600
```

-continued

```
gctatcatgg agaagctggt ggcttactca tccgatcagg cacactcctc agtggaaaga    660

gctgggttaa ttggtggagt gaaattaaaa gccatcccct cagatggcaa cttcgccatg    720

cgtgcgtctg ccctgcagga agccctggag agagacaaag cggctggcct gattcctttc    780

tttatggttg ccaccctggg gaccacaaca tgctgctcct ttgacaatct cttagaagtc    840

ggtcctatct gcaacaagga agacatatgg ctgcacgttg atgcagccta cgcaggcagt    900

gcattcatct gccctgagtt ccggcacctt ctgaatggag tggagtttgc agattcattc    960

aactttaatc cccacaaatg gctattggtg aattttgact gttctgccat gtgggtgaaa   1020

aagagaacag acttaacggg agcctttaga ctggacccca cttacctgaa gcacagccat   1080

caggattcag ggcttatcac tgactaccgg cattggcaga taccactggg cagaagattt   1140

cgctctttga aaatgtggtt tgtatttagg atgtatggag tcaaaggact gcaggcttat   1200

atccgcaagc atgtccagct gtcccatgag tttgagtcac tggtgcgcca ggatccccgc   1260

tttgaaatct gtgtggaagt cattctgggg cttgtctgct ttcggctaaa gggttccaac   1320

aaagtgaatg aagctcttct gcaaagaata aacagtgcca aaaaaatcca cttggttcca   1380

tgtcacctca gggacaagtt tgtcctgcgc tttgccatct gttctcgcac ggtggaatct   1440

gcccatgtgc agcgggcctg ggaacacatc aaagagctgg cggccgacgt gctgcgagca   1500

gagagggagt aggagtgaag ccagctgcag gaatcaaaaa ttgaagagag atatatctga   1560

aaactggaat aagaagcaaa taaatatcat cctgccttca tggaactcag ctgtctgtgg   1620

cttcccatgt ctttctccaa agccatccag agggttgtga ttttgtctgc ttagtatctc   1680

atcaacaaag aaatattatt tgctaattaa aaagttaatc ttcatggcca tagcttttat   1740

tcattagctg tgatttttgt tgattaaaac attatagatt ttcatgttct tgcagtcatc   1800

agaagtggta ggaaagcctc actgatatat tttccagggc aatcaatgtt cacgcaactt   1860

gaaattatat ctgtggtctt caaattgtct tttgtcatgt ggctaaatgc ctaataaaca   1920

attcaagtga                                                          1930
```

<210> SEQ ID NO 14
<211> LENGTH: 512
<212> TYPE: DNA
<213> ORGANISM: Homo sapiens

<400> SEQUENCE: 14

```
gccctttctg cctctgcggg gctctggtcg ccggccaagg aaaaacgagg ctggaccctg     60

aacagcgcgg gctacctgct gggcccacat gccgttggca accacaggtc attcagcgac    120

aagaatggcc tcaccagcaa gcgggagctg cggcccgaag atgacatgaa accaggaagc    180

tttgacaggt ccatacctga aaacaatatc atgcgcacaa tcattgagtt tctgtctttc    240

ttgcatctca aagaggccgg tgccctcgac cgcctcctgg atctccccgc cgcagcctcc    300

tcagaagaca tcgagcggtc ctgagagcct cctgggcacg tttgtctgtg tgctgtaacc    360

tgaagtcaaa ccttaagata atggataatc ttcggccaat ttatgcggag tcagccattc    420

ctgttctctt tgccttgatg ttgtgttgtt atcatttaag attttttttt tttggtaatt    480

attttgagtg gcaaaataaa gaatagcaat ta                                  512
```

<210> SEQ ID NO 15
<211> LENGTH: 1637
<212> TYPE: DNA
<213> ORGANISM: Homo sapiens -continued

<400> SEQUENCE: 15
gaggcgaacc ggagcgcggg gccgcggtcg ccccgaccag agccgggaga ccgcagcacc 60
cgcagccgcc cgcgagcgcg ccgaagacag cgcgcaggcg agagcgcgcg ggcgggggcg 120
cgcaggccct gcccgcccct tccgtcccca ccccccctccg ccctttcctc tccccacctt 180
cctctcgcct cccgcgcccc cgcaccgggc gcccaccctg tcctcctcct gcgggagcgt 240
tgtccgtgtt ggcggccgca gcgggccggg ccggtccggc gggccggggg atggcgctgc 300
tggacctggc cttggaggga atggccgtct tcgggttcgt cctcttcttg gtgctgtggc 360
tgatgcattt catggctatc atctacaccc gattacacct caacaagaag gcaactgaca 420
aacagcctta tagcaagctc ccaggtgtct ctcttctgaa accactgaaa ggggtagatc 480
ctaacttaat caacaacctg gaaacattct ttgaattgga ttatcccaaa tatgaagtgc 540
tcctttgtgt acaagatcat gatgatccag ccattgatgt atgtaagaag cttcttggaa 600
aatatccaaa tgttgatgct agattgttta taggtggtaa aaaagttggc attaatccta 660
aaattaataa tttaatgcca ggatatgaag ttgcaaagta tgatcttata tggatttgtg 720
atagtggaat aagagtaatt ccagatacgc ttactgacat ggtgaatcaa atgacagaaa 780
aagtaggctt ggttcacggg ctgccttacg tagcagacag acagggcttt gctgccacct 840
tagagcaggt atattttgga acttcacatc caagatacta tatctctgcc aatgtaactg 900
gtttcaaatg tgtgacagga atgtcttgtt taatgagaaa agatgtgttg gatcaagcag 960
gaggacttat agcttttgct cagtacattg ccgaagatta ctttatggcc aaagcgatag 1020
ctgaccgagg ttggaggttt gcaatgtcca ctcaagttgc aatgcaaaac tctggctcat 1080
attcaatttc tcagtttcaa tccagaatga tcaggtggac caaactacga attaacatgc 1140
ttcctgctac aataatttgt gagccaattt cagaatgctt tgttgccagt ttaattattg 1200
gatgggcagc ccaccatgtg ttcagatggg atattatggt atttttcatg tgtcattgcc 1260
tggcatggtt tatatttgac tacattcaac tcaggggtgt ccagggtggc acactgtgtt 1320
tttcaaaact tgattatgca gtcgcctggt tcatccgcga atccatgaca atatacattt 1380
ttttgtctgc attatgggac ccaactataa gctggagaac tggtcgctac agattacgct 1440
gtgggggtac agcagaggaa atcctagatg tataactaca gctttgtgac tgtatataaa 1500
ggaaaaaaga gaagtattat aaattatgtt tatataaatg cttttaaaaa tctaccttct 1560
gtagttttat cacatgtatg ttttggtatc tgttctttaa tttatttttg catggcactt 1620
gcatctgtga aaaaaaa 1637

<210> SEQ ID NO 16
<211> LENGTH: 2172
<212> TYPE: DNA
<213> ORGANISM: Homo sapiens

<400> SEQUENCE: 16
agatcatcaa atcaaattcc acagggattg gtgaccaacc agaaggctca gacatctgat 60
tgctgacctg tccagacatc atctggtctc cctgaacctg aaatcacacc atggatgatt 120
ttgagcgtcg cagagaactt agaaggcaaa agagggagga gatgcgactc gaagcagaaa 180
gaatcgccta ccagaggaat gacgatgatg aagaggaggc agcccgggaa cgccgccgcc 240
gagcccgaca ggaacggctg cggcagaagc aggaggaaga atccttggga caggtgaccg 300
accaggtgga ggtgaatgcc cagaacagtg tgcctgacga ggaggccaag acaaccacca 360
caaacactca agtggaaggg gatgatgagg ccgcattcct ggagcgcctg gctcggcgtg 420

-continued aggaaagacg ccaaaaacgc cttcaggagg ctctggagcg gcagaaggag ttcgacccaa 480
caataacaga tgcaagtctg tcgctcccaa gcagaagaat gcaaaatgac acagcagaaa 540
atgaaactac cgagaaggaa gaaaaaagtg aaagtcgcca agaaagatac gagatagagg 600
aaacagaaac agtcaccaag tcctaccaga agaatgattg gagggatgct gaagaaaaca 660
agaaagaaga caaggaaaag gaggaggagg aagaggagaa gccaaagcga gggagcattg 720
gagaaaatca gatcaaagat gaaaagatta aaaaggacaa agaacccaaa gaagaagtta 780
agagcttcat ggatcgaaag aagggattta cagaagttaa gtcgcagaat ggagaattca 840
tgacccacaa acttaaacat actgagaata ctttcagccg ccctggaggg agggccagcg 900
tggacaccaa ggaggctgag ggcgcccccc aggtggaagc cggcaaaagg ctggaggagc 960
ttcgtcgtcg tcgcggggag accgagagcg aagagttcga gaagctcaaa cagaagcagc 1020
aggaggcggc tttggagctg gaggaactca agaaaaagag ggaggagaga aggaaggtcc 1080
tggaggagga agagcagagg aggaagcagg aggaagccga tcgaaaactc agagaggagg 1140
aagagaagag gaggctaaag gaagagattg aaaggcgaag agcagaagct gctgagaaac 1200
gccagaagat gccagaagat ggcttgtcag atgacaagaa accattcaag tgtttcactc 1260
ctaaaggttc atctctcaag atagaagagc gagcagaatt tttgaataag tctgtgcaga 1320
aaagcagtgg tgtcaaatcg acccatcaag cagcaatagt ctccaagatt gacagcagac 1380
tggagcagta taccagtgca attgagggaa caaaaagcgc aaaacctaca aagccggcag 1440
cctcggatct tcctgttcct gctgaaggtg tacgcaacat caagagtatg tgggagaaag 1500
ggaatgtgtt ttcatccccc actgcagcag gcacaccaaa taaggaaact gctggcttga 1560
aggtaggggt ttctagccgc atcaatgaat ggctaactaa aaccccagat ggaaacaagt 1620
cacctgctcc caaaccttct gacttgagac caggagacgt atccagcaag cggaacctct 1680
gggaaaagca atctgtggat aaggtcactt cccccactaa ggtttgagac agttccagaa 1740
agaacccaag ctcaagacgc aggacgagct cagttgtaga gggctaattc gctctgtttt 1800
gtatttatgt tgatttacta aattgggttc attatctttt atttttcaat atcccagtaa 1860
acccatgtat attatcacta tatttaataa tcacagtcta gagatgttca tggtaaaagt 1920
actgcctttg cacaggatcc tgtttctaaa gaaacccatg ctgtgaaata gagacttttc 1980
tactgatcat cataactctg tatctgagca gtgataccaa ccacatctga agtcaacaga 2040
agatccaagt ttaaaattgc tgcggaatgt gtgcagtatc tagaaaaatg aaccgtagtt 2100
tttgtttttt taaatacaga agtcatgttg tttctgcact ttataataaa gcatggaaga 2160
aattatctta gt 2172

<210> SEQ ID NO 17
<211> LENGTH: 5035
<212> TYPE: DNA
<213> ORGANISM: Homo sapiens

<400> SEQUENCE: 17
gcggcggcgg cggcggcggc ggcagcggcg gccaagcggc caggttggcg gccggggctc 60
cgggccgcgc gaggccacgg ccacgccgcg ccgctgcgca caaccaacga ggcagagcgc 120
cgcccggcgc gagactgcgg ccgaagcgtg gggcgcgcgt gcggaggacc aggcgcggcg 180
cggctgcggc tgagagtgga gcctttcagg ctggcatgga gagcttaagg ggcaactgaa 240
ggagacacac tggccaagcg cggagttctg cttacttcag tcctgctgag atactctctc 300

-continued

```
agtccgctcg caccgaagga agctgccttg ggatcagagc agacataaag ctagaaaaat    360
ttcaagacag aaacagtctc cgccagtcaa gaaaccctca aaagtatttt gccatggata    420
tagaagatga agaaaacatg agttccagca gcactgatgt gaaggaaaac cgcaatctgg    480
acaacgtgtc ccccaaggat ggcagcacac ctgggcctgg cgagggctct cagctctcca    540
atgggggtgg tggtggcccc ggcagaaagc ggcccctgga ggagggcagc aatggccact    600
ccaagtaccg cctgaagaaa aggaggaaaa caccagggcc cgtcctcccc aagaacgccc    660
tgatgcagct gaatgagatc aagcctggtt tgcagtacac actcctgtcc cagactgggc    720
ccgtgcacgc gcctttgttt gtcatgtctg tggaggtgaa tggccaggtt tttgagggct    780
ctggtcccac aaagaaaaag gcaaaactcc atgctgctga gaaggccttg aggtctttcg    840
ttcagtttcc taatgcctct gaggcccacc tggccatggg gaggaccctg tctgtcaaca    900
cggacttcac atctgaccag gccgacttcc ctgacacgct cttcaatggt tttgaaactc    960
ctgacaaggc ggagcctccc ttttacgtgg gctccaatgg ggatgactcc ttcagttcca   1020
gcggggacct cagcttgtct gcttccccgg tgcctgccag cctagcccag cctcctctcc   1080
ctgtcttacc accattccca cccccgagtg ggaagaatcc cgtgatgatc ttgaacgaac   1140
tgcgcccagg actcaagtat gacttcctct ccgagagcgg ggagagccat gccaagagct   1200
tcgtcatgtc tgtggtcgtg gatggtcagt tctttgaagg ctcggggaga aacaagaagc   1260
ttgccaaggc ccgggctgcg cagtctgccc tggccgccat tttaacttg cacttggatc    1320
agacgccatc tcgccagcct attcccagtg agggtcttca gctgcattta ccgcaggttt   1380
tagctgacgc tgtctcacgc ctggtcctgg gtaagtttgg tgacctgacc gacaacttct   1440
cctcccctca cgctcgcaga aaagtgctgg ctggagtcgt catgacaaca ggcacagatg   1500
ttaaagatgc caaggtgata agtgtttcta caggaacaaa atgtattaat ggtgaataca   1560
tgagtgatcg tggccttgca ttaaatgact gccatgcaga aataatatct cggagatcct   1620
tgctcagatt tctttataca caacttgagc tttacttaaa taacaaagat gatcaaaaaa   1680
gatccatctt tcagaaatca gagcgagggg ggtttaggct gaaggagaat gtccagtttc   1740
atctgtacat cagcacctct ccctgtggag atgccagaat cttctcacca catgagccaa   1800
tcctggaagg gtctcgctct tacacccagg ctggagtgca gtggtgcaat catggctcac   1860
tgcagcctcg acctcctggg ctcttaagcg atccttccac ctcaaccttc caaggagctg   1920
ggactacaga accagcagat agacacccaa atcgtaaagc aagaggacag ctacggacca   1980
aaatagagtc tggtgagggg acgattccag tgcgctccaa tgcgagcatc caaacgtggg   2040
acggggtgct gcaaggggag cggctgctca ccatgtcctg cagtgacaag attgcacgct   2100
ggaacgtggt gggcatccag ggatccctgc tcagcatttt cgtggagccc atttacttct   2160
cgagcatcat cctgggcagc ctttaccacg gggaccacct ttccagggcc atgtaccagc   2220
ggatctccaa catagaggac ctgccacctc tctacaccct caacaagcct ttgctcagtg   2280
gcatcagcaa tgcagaagca cggcagccag ggaaggcccc caacttcagt gtcaactgga   2340
cggtaggcga ctccgctatt gaggtcatca acgccacgac tgggaaggat gagctgggcc   2400
gcgcgtcccg cctgtgtaag cacgcgttgt actgtcgctg gatgcgtgtg cacggcaagg   2460
ttccctccca cttactacgc tccaagatta ccaagcccaa cgtgtaccat gagtccaagc   2520
tggcggcaaa ggagtaccag gccgccaagg cgcgtctgtt cacagccttc atcaaggcgg   2580
ggctgggggc ctgggtggag aagcccaccg agcaggacca gttctcactc acgccctgac   2640
ccgggcagac atgatggggg gtgcaggggg ctgtgggcat ccagcgtcat cctccagaac   2700
```

-continued

```
ctcacatctg aactgggggc aggtgcatac cttggggagg gagtaggggg acacggggga   2760
ccaccaggtg tccacggttg tccccagcat ctcacatcag acctggggca ggtgcgcagt   2820
gtggggaggg gatggggtgc gtcagggccc agcatcgccg cctggcatct ctctgccgca   2880
gcatttcccc ttctgaaccg tccagtgact gctttcaatc tcggtttacg tttagaaatt   2940
gagttctact gagtagggct tccttaagtt taggaaaata gaaattactt tgtgtgaaat   3000
tcttgaataa ataatttatt cagagctagg aatgtggttt ataaaatagg aagtaattgt   3060
gtcaggtcac ttttatgcca cattatttta attgcaaaaa agcatctata tatggaggag   3120
ggtgggaaaa tagaggtagg aaatagtagc ctaaaggaaa tcgccacacg tctgtctaaa   3180
cttaggtctc ttttctccgt aggtacctcc ctgggtagtt ccacacacta ggttgtaaca   3240
gtctctccct gaggagcaga ctcccagcat ggtgtagcgt ggccctgtca tgcacatggg   3300
gtcccgcagc agtgactgtg tgtcctgcag aggcgtgacc caggcccctg tagccctcag   3360
cctcctctag aagcttctgt actccttgta ggatcagatc atggaaaact tttctcagtt   3420
tacttctaag taatcacaga taatacatgg ccagtaatcc caggctggcc attcattcag   3480
gtttttttaaa ggatatttaa cttttatgga ctagaaggaa tcacgagggc tactgcacaa   3540
tacatggcct aagttccctc tgttccttcc tctgaatcga atggatgtgg gtgaccgccc   3600
gaaggccttc acaggatgga agtagaatga tttcagtaga tactcattct tggaaaatgc   3660
catagtttta aattattgtt tccagcttta tcaaagacat gtttgaaaaa taaaaagcat   3720
ccaagtgaga gctggtgaga ccacgtgctg ctggcgtagt gtaggccaga cattgacagt   3780
cctgacggga gctcagggct gcccagcgcc cagcgtgcac gggacggccc cacgacagag   3840
ggagtcagcc cgggaggtca ggagcgcggc gggcgagggc cctgtgtgga ccacctccac   3900
caagctcaga gatttgcaac caggtgcctt gttgcctccg ctcaggatga aagaggagct   3960
gagagaagtg ctctgcctgc cagtgcagtg cccagctcca aggctctaga gggtgttcag   4020
gtacactgag gaggggacgg ctccgtcttc acattgtgca cagatctgag gatgggatta   4080
gcgaagctgt ggagactgca catccggacc tgcccatgtc tcaaaacaaa cacatgtaca   4140
gtggctcttt ttccttctca aacactttac cccagaagca ggtggtctgc cccaggcata   4200
aagaaggaaa attggccatc tttcccacct ctaaattctg taaaattata gacttgctca   4260
aaagattcct ttttatcatc cccacgctgt gtaagtggaa agggcattgt gttccgtgtg   4320
tgtccagttt acagcgtctc tgccccctag cgtgttttgt gacaatctcc cctgggtgag   4380
gagtgggtgc acccagcccc gaggccagtg gttgctcggg gccttccgtg tgagttctag   4440
tgttcacttg atgccgggga atagaattag agaaaactct gacctgccgg gttccaggga   4500
ctggtggagg tggatggcag gtccgactcg accatgactt agttgtaagg gtgtgtcggc   4560
tttttcagtc tcatgtgaaa atcctcctgt ctctggcagc actgtctgca ctttcttgtt   4620
tactgtttga agggacgagt accaagccac aaggaacact tcttttggcc acagcataag   4680
ctgatggtat gtaaggaacc gatgggccat taaacatgaa ctgaacggtt aaaagcacag   4740
tctatggaac gctaatggag tcagccccta aagctgtttg ctttttcagg ctttggatta   4800
catgctttta atttgatttt agaatctgga cactttctat gaatgtaatt cggctgagaa   4860
acatgttgct gagatgcaat cctcagtgtt ctctgtatgt aaatctgtgt atacaccaca   4920
cgttacaact gcatgagctt cctctcgcac aagaccagct ggaactgagc atgagacgct   4980
gtcaaataca gacaaaggat ttgagatgtt ctcaataaaa agaaaatgtt tcact        5035
```

-continued

<210> SEQ ID NO 18
<211> LENGTH: 1700
<212> TYPE: DNA
<213> ORGANISM: Homo sapiens

<400> SEQUENCE: 18
gccgaggctg cctgactgga atgagggtag ctgcggcgac tgcggcggct ggagcggggc 60
cggccatggc ggtgtggacg cgggccacca aagcggggct ggtggagctg ctcctgaggg 120
agcgctgggt ccgagtggtg gccgagctga gcggggagag cctgagcctg acgggcgacg 180
ccgccgcggc cgagctggag cccgctctgg gacccgcggc cgccgccttc aacggcctcc 240
caaacggcgg cggcgcgggc gactcgctgc ccgggagccc aagccgcggc ctggggcccc 300
cgagcccgcc ggcgccgcct cggggccccg cgggtgaggc gggcgcgtcg ccgcccgtgc 360
gccgggtgcg ggtggtgaag caagaggcgg gcggcctggg catcagcatc aagggcggcc 420
gcgagaaccg gatgccgatc ctcatctcca agatcttccc cgggctggct gccgaccaga 480
gccgggcgct gcggctgggc gacgccatcc tgtcggtgaa cggcaccgac ctgcgccagg 540
ccacccacga ccaggccgtg caggcgctga agcgcgcggg caaggaggtg ctgctggagg 600
tcaagttcat ccgagaagta acaccatata tcaagaagcc atcattagta tcagatctgc 660
cgtgggaagg tgcagccccc cagtcaccaa gctttagtgg cagtgaggac tctggttcgc 720
caaaacacca gaacagcacc aaggacagga agatcatccc tctcaaaatg tgctttgctg 780
ctagaaacct aagcatgccg gatctggaaa acagattgat agagctacat tctcctgata 840
gcaggaacac gttgatccta cgctgcaaag atacagccac agcacactcc tggttcgtag 900
ctatccacac caacataatg gctctcctcc cacaggtgtt ggctgaactc aacgccatgc 960
ttggggcaac cagtacagca ggaggcagta aagaggtgaa gcatattgcc tggctggcag 1020
aacaggcaaa actagatggt ggaagacagc aatggagacc tgtcctcatg gctgtgactg 1080
agaaggattt gctgctctat gactgtatgc cgtggacaag agatgcctgg gcgtcaccat 1140
gccacagcta cccacttgtt gccaccaggt tggttcattc tggctccgga tgtcgatccc 1200
cctcccttgg atctgacctt acatttgcta ccaggacagg ctctcgacag ggcattgaga 1260
tgcatctctt cagggtggag acacatcggg atctgtcatc ctggaccagg atacttgttc 1320
agggttgcca tgctgctgct gagctgatca aggaagtctc tctaggctgc atgttaaatg 1380
gccaagaggt gaggcttact attcactatg aaaatgggtt caccatctca agggaaaatg 1440
gaggctccag cagcatattg taccgctacc cctttgaaag gctgaagatg tctgctgatg 1500
atggcatccg aaatctatac ttggattttg gtggtcccga gggagaactg accatggacc 1560
tgcactcttg tccgaagccg attgtatttg tgttgcacac gtttttatcg gccaaagtca 1620
ctcgtatggg actgcttgta tgagcaacaa aaaatcagaa aagagccttg actgtcacaa 1680
gaaatatttc cacctccaaa 1700

<210> SEQ ID NO 19
<211> LENGTH: 3086
<212> TYPE: DNA
<213> ORGANISM: Homo sapiens

<400> SEQUENCE: 19
actgccacct cggtcggtcg gtgcttactt cgctgccagc tggtctgtcg ccatgaaccc 60
ggacctgcgc agggagcggg attccgccag cttcaacccg gagctgctta cacacatcct 120
ggacggcagc cccgagaaaa cgcggcgccg ccgagagatc gagaacatga tcctgaacga 180

-continued

```
cccagacttc cagcatgagg acttgaactt cctaactcgc agccagcgtt atgaggtggc    240
tgtcaggaaa agtgccatca tggtgaagaa gatgagggag tttggcatcg ctgaccctga    300
tgaaattatg tggtttaaaa aactacattt ggtcaatttt gtggaacctg tgggcctcaa    360
ttactccatg tttattccta ccttgctgaa tcagggcacc actgctgaga aagagaaatg    420
gctgctttca tccaaaggac tccagataat tggcacctac gcccagacgg aaatgggcca    480
cggaactcac cttcgaggct tggaaaccac agccacgtat gaccctgaaa cccaggagtt    540
cattctcaac agtcctactg tgacctccat taaatggtgg cctggtgggc ttggaaaaac    600
ttcaaatcat gcaatagtcc ttgcccagct catcactaag gggaaatgct atggattaca    660
tgcctttatc gtacctatcc gtgaaatcgg gacccataag cctttgccag gaattaccgt    720
tggtgacatc gggcccaaat ttggttatga tgagatagac aatggctacc tcaaaatgga    780
caaccatcgt attcccagag aaaacatgct gatgaagtat gcccaggtga agcctgatgg    840
cacatacgtg aaaccgctga gtaacaagct gacttacggg accatggtgt ttgtcaggtc    900
cttccttgtg ggagaagctg ctcgggctct gtctaaggcg tgcaccattg ccatccgata    960
cagcgctgtg aggcaccagt ctgaaatgaa gccaggtgaa ccagaaccac agattttgga   1020
ttttcaaacc cagcagtata aactctttcc actcctggcc actgcctatg ccttccagtt   1080
tgtgggcgca tacatgaagg agacctatca ccggattaac gaaggcattg gtcaagggga   1140
cctgagtgaa ctgcctgagc ttcatgccct caccgctgga ctgaaggctt tcacctcctg   1200
gactgcaaac actggcattg aagcatgtcg gatggcttgt ggtgggcatg gctattctca   1260
ttgcagtggt cttccaaata tttatgtcaa tttcacccca agctgtacct ttgagggaga   1320
aaacactgtc atgatgctcc agacggctag gttcctgatg aaaagttatg atcaggtgca   1380
ctcaggaaag ttggtgtgtg gcatggtgtc ctatttgaac gacctgccca gtcagcgcat   1440
ccagccacag caggtagcag tctggccaac catggtggat atcaacagcc ccgaaagcct   1500
aaccgaagca tataaactcc gtgcagccag attagtagaa attgctgcaa aaaaccttca   1560
aaaagaagtg attcacagaa aaagcaagga ggtagcttgg aacctaactt ctgttgacct   1620
tgttcgagca agtgaggcac attgccacta tgtggtagtt aagctctttt cagaaaaact   1680
cctcaaaatt caagataaag ccattcaagc tgtcttaagg agtttatgtc tgctgtattc   1740
tctgtatgga atcagtcaga acgcgggga tttccttcag gggagcatca tgacagagcc   1800
tcagattaca caagtaaacc agcgtgtaaa ggagttactc actctgattc gctcagatgc   1860
tgttgctttg gttgatgcat ttgattttca ggatgtgaca cttggctctg tgcttggccg   1920
ctatgatggg aatgtgtatg aaaacttgtt tgagtgggct aagaactccc cactgaacaa   1980
agcagaggtc cacgaatctt accacaagca cctgaagtca ctgcagtcca agctctgaag   2040
tgtcacaagg acaagtttaa tctgcttcag aaagcgcctg tgtgcaactc aaattttgtg   2100
gaatcttttc gaattcaaat agctatagag caaatgataa attgacccct ttttataaat   2160
ggagggaaaa aatgaacaga tttcagagat taaatgaaaa aaagcagatg tgttttaagt   2220
gcaattaaca ctgaaagaga cctgttaaac cattcagaaa aagcttaaga aatgcgatat   2280
gacttccttt tgtaatgctg ctgatcccag tagactatga cttttgataa ttagcagaat   2340
ttaactactg agtagttgat tattttcaca ttttaattgc taatcactgg ctatataagt   2400
gtttttaagc aagggtattt ttgaagtggt gtagaaccct tccacgcttt cctgctcagt   2460
gttctaccag acaagaaaag ggacttgggg aaggaaactt attggaaact tgatgcgaat   2520
```

-continued

```
taggttcttc tttgcacaaa ctctgcctgc ttgctctccc ttgctgatgg gttgcaattc   2580

tcaaactatt catgctagca atttttccac ggggggggcct ttttcccacg ggggcctcta   2640

taggggccca tttctccggt aaataggaat ttccccttta aggggtgcca gtagtaggag   2700

tatagggaac ctctcagctg tggcactgtt gtagctttgg agtcagagtg tactctgggc   2760

aatcagattt ccacatattc tgcatcttgg ataagcatta aaagttggga tactaatttg   2820

gataaaaaaa tgcactaggc aaactccagc gagacagaaa gtatagggaa acctctcagc   2880

tgtggcactg ttgtagcttt ggagtgcaga gtgtaactct ggcgacaatc agatttcaca   2940

tattctgtca tcttggcata agccattaaa agcttggaga ttactgtatt tggcattaaa   3000

aaaaaatgtc acttaggtca gcactcccag acgtagcaca gaaaaaccct ttgacacaaa   3060

ccatgtgttc tgatttttgg ttcaga                                        3086
```

<210> SEQ ID NO 20
<211> LENGTH: 1302
<212> TYPE: DNA
<213> ORGANISM: Homo sapiens

<400> SEQUENCE: 20

```
gcttcgggtg ccatggggac tcctcccggc ctgcagaccg actgcgaggc gctgctcagc     60

cgcttccagg agacggacag tgtacgcttc gaggacttca cggagctctg gagaaacatg    120

aagttcggga ctatcttctg tggcagaatg agaaatttag aaaagaacat gtttacaaaa    180

gaagctttag ctttggcttg gcgatatttt ttacctccat acaccttcca gatcagagtt    240

ggtgctttgt atctgctata tggattatat aatacccaac tgtgtcaacc aaaacaaaag    300

atcagagttg ccctgaagga ttgggatgaa gttttaaaat ttcagcaaga tttagtaaat    360

gcacagcatt ttgatgcagc ttatattttt aggaagctac gactagacag agcatttcac    420

tttacagcaa tgcccaaatt gctgtcatat aggatgaaga aaaaaattca ccgagctgaa    480

gttacagaag aatttaagga cccaagtgat cgtgtgatga aacttatcac ttctgatgta    540

ttagaggaaa tgctgaatgt tcatgatcat tatcagaaca tgaaacatgt aatttcagtt    600

gataagtcca agccagataa agccctcagc ttgataaagg atgatttttt tgacaatatt    660

aagaacatag ttttggagca tcagcagtgg cacaaagaca gaaagaatcc atccttaaag    720

tcaaaaacta atgatggaga agaaaaaatg gaaggaaatt cacaagaaac ggagagatgt    780

gaaagggcag aatcattagc gaaaataaaa tcaaaggcct tttcagttgt catacaggca    840

tccaaatcaa gaaggcatcg tcaagtcaaa ctcgactctt ctgactctga ttctgcatct    900

ggtcaagggc aagtcaaagc aactaggaaa aaagagaaga aagaaagatt gaaaccagca    960

ggaaggaaga tgtctctcag aaacaaaggc aatgtgcaga atatacacaa ggaagataaa   1020

cctttaagtc tgagtatgcc tgtaattaca gaagaagaag agaatgaaag tttgagtgga   1080

acagagttca ctgcatccaa gaagaggaga aaacactgaa caaagagcct ggtgtagttt   1140

ttaattttga gttttctgac agaagaaaag attgatattt tgtgtattga acaggaagac   1200

tgccagtatt aaaaaaatcc ttctgggaat ctgtaggtta tttcttggaa attgcaatac   1260

gtagttctag aataaaagta caaaaaatta gaataagaat tc                      1302
```

<210> SEQ ID NO 21
<211> LENGTH: 2081
<212> TYPE: DNA
<213> ORGANISM: Homo sapiens

<400> SEQUENCE: 21

-continued

```
atggatggat ggcccgccaa gagaaggagc agtgcactgt ggtcagagat gctggacatc     60
accatgaagg agtctctcac caccagggag atcagacggc aggaggcaat atatgaaatg    120
tcccgaggtg aacaggattt aattgaggat ctcaaacttg caagaaaggc ctaccatgac    180
cccatgttaa agttgtccat catgtcagaa gaggaactca cacatatatt tggtgatctg    240
gactcttaca tacctctgca tgaagatttg ttgacaagaa taggagaagc aaccaagcct    300
gatggaacag tggagcagat tggtcacatt ctcgtgagct ggttaccgcg cttgaatgcc    360
tacagaggtt actgtagtaa ccagctggca gccaaagctc ttcttgatca aaagaaacag    420
gatccaagag tccaagactt cctccagcga tgtctcgagt ctcccttcag tcgaaaacta    480
gatctttgga gtttcctaga tatccctcga agtcgcctag tcaaataccc tttactgtta    540
aaagaaattc ttaaacacac tccaaaagag caccctgatg ttcagcttct ggaggatgct    600
atattgataa tacagggagt cctctctgat atcaacttga agaaaggtga atccgagtgc    660
cagtattaca tcgacaagct ggagtacctg gatgaaaagc agagggaccc cagaatcgaa    720
gcgagcaaag tgctgctgtg ccatggggag ctgcggagca agagtggaca taaactttac    780
attttcctgt ttcaagacat cttggttctg actcggcccg tcacacggaa cgaacggcac    840
tcttaccagg tttaccggca gccaatccca gtccaagagc tagtcctaga agacctgcag    900
gatggagatg tgagaatggg aggctccttt cgaggagctt tcagtaactc agagaaagct    960
aaaaatatct ttagaattcg cttccatgac ccctctccag cccagtctca cactctgcaa   1020
gccaatgacg tgttccacaa gcagcagtgg ttcaactgta ttcgagcggc cattgccccc   1080
ttccagtcgg caggcagtcc acctgagctg cagggcctgc cggagctgca cgaagagtgt   1140
gaggggaacc accccctctgc gaggaaactc acagcccaga ggagggcatc cacagtttcc   1200
agtgttactc aggtagaagt tgatgaaaac gcttacagat gtggctctgg catgcagatg   1260
gcagaggaca gcaagagctt aaagacacac cagacacagc ccggcatccg aagagcgagg   1320
gacaaagccc ttctggtggc aaacggaaag agactttggt gtagagaagg ctctgtgtgt   1380
taactgatgg gagagactgt ttgtttataa atgtgtacag ttttgttttc tcgtaagggg   1440
agcatcatag ggttacttta taccagttgt aacattttca ttgtttttgg ttgttctttt   1500
ttcttttttt aatggcagct aaagatatac agattactgt taaattgcag tccttttttt   1560
tttaaagata ttttcttgag ttatttagaa catggtaagc ctggtatttt ttaatcaaac   1620
aaaatattta tgaaatgggt tttctcttaa ttctggattc atcatggctt tctaatacca   1680
attgtaatat ttacaatatt caccaaaact tagaattttg caaatgcagg aattctgcca   1740
gtgtttcttt gctaagcctt gcatgcaaaa tttgaaattt taacattggc acccaaaacc   1800
tacatggaat gtatgtctgg agtatttcaa actttacatt gaaacataat ttccttggaa   1860
aacaaaccat aagcctgagg aggtttttat caactggaat gctttatatt agtttgtttt   1920
tcactgtaca ttcctcattt tacattcatt taacctgccg attatttaat ttttttattg   1980
taaagtagtt tttagcattt gcttttattt ttttactttg atgccttaac aaattggcac   2040
gtctttaaag tatttttctt cctgattaaa aatgtgtgtg t                       2081
```

<210> SEQ ID NO 22
<211> LENGTH: 968
<212> TYPE: DNA
<213> ORGANISM: Homo sapiens

<400> SEQUENCE: 22

-continued

```
gaattccgaa gccggcgacc ggtctgacgt cccgagcagg gcatggtcta gtggcccagt     60

caggacgcga aacactccct ggaggttctg acccactccc tctcagcctc cgcctggtct    120

ctggtgtagt cgccgccgcc agccgccatg ggcaaacaga acagcaagct gcggcccgag    180

gtgctgcagg acctgcggga gaagacggag ttcaccgacc acgagctgca ggagtggtac    240

aagggcttcc tcaaggactg ccccaccggc cacctgaccg tggacgagtt caagaagatc    300

tacgccaact tcttccccta cggcgacgct tccaagttcg ccgagcacgt cttccgcacc    360

ttcgacacca acggcgacgg caccatcgac ttccgggagt tcatcattgg cctgagcgtg    420

actcgcgggg gcaagctgga gcagaagctc aagtgggcct tcagcatgta cgacctggac    480

ggcaacggct acatcagccg cagcgagatg ctggagatcg tgcaggccat ctacaagatg    540

gtgtcgtctg tgatgaagat gccggaggat gagtccaccc cggagaagcg cacagacaag    600

atcttcaggc agatggacac caacaatgac ggcaaactgt ccttggaaga attcatcaga    660

ggtgccaaga gcgacccctc catcgtccgc ctgctgcagt gcgaccccag cagtgccagt    720

cagttctgag cgagcggccc ctggacagtt gcagagaaac acaggcttgt cgtgccgttt    780

aagctttgct tgcaagagtg gatgccccgc aatcgttcct gctctcccgg gcccccgctg    840

ggcatgtccg tttgcacctg cccgggcgcc ggtgcgcctc cctcctccac ctgaccaacg    900

cgacattcct cccctcacgc ctggcccggt cccttccagg aactccaggg atgtggtgac    960

atgcaggg                                                             968
```

<210> SEQ ID NO 23
<211> LENGTH: 1204
<212> TYPE: DNA
<213> ORGANISM: Homo sapiens

<400> SEQUENCE: 23

```
ctctgaggag aagcagcagc aaacatttgc tagtcagaca agtgacaggg aatggattcc     60

aaacagcagt gtgtaaagct aaatgatggc cacttcatgc ctgtattggg atttggcacc    120

tatgcacctc cagaggttcc gagaagtaaa gctttggagg tcacaaaatt agcaatagaa    180

gctgggttcc gccatataga ttctgctcat ttatacaata atgaggagca ggttggactg    240

gccatccgaa gcaagattgc agatggcagt gtgaagagag aagacatatt ctacacttca    300

aagctttggt ccacttttca tcgaccagag ttggtccgac cagccttgga aaactcactg    360

aaaaaagctc aattggacta tgttgacctc tatcttattc attctccaat gtctctaaag    420

ccaggtgagg aactttcacc aacagatgaa aatggaaaag taatatttga catagtggat    480

ctctgtacca cctgggaggc catggagaag tgtaaggatg caggattggc caagtccatt    540

ggggtgtcaa acttcaaccg caggcagctg gagatgatcc tcaacaagcc aggactcaag    600

tacaagcctg tctgcaacca ggtagaatgt catccgtatt tcaaccggag taaattgcta    660

gatttctgca agtcgaaaga tattgttctg gttgcctata gtgctctggg atctcaacga    720

gacaaacgat gggtggaccc gaactccccg gtgctcttgg aggacccagt cctttgtgcc    780

ttggcaaaaa agcacaagcg aaccccagcc ctgattgccc tgcgctacca gctgcagcgt    840

ggggttgtgg tcctggccaa gagctacaat gagcagcgca tcagacagaa cgtgcaggtt    900

tttgagttcc agttgactgc agaggacatg aaagccatag atggcctaga cagaaatctc    960

cactatttta acagtgatag ttttgctagc caccctaatt atccatattc agatgaatat   1020

taacatggag agctttgcct gatgtctacc agaagccctg tgtgtggatg gtgacgcaga   1080

ggacgtctct atgccggtga ctggacatat cacctctact taaatccgtc ctgtttagcg   1140
```

-continued acttcagtca actacagctg agtccatagg ccagaaagac aataaatttt tatcattttg 1200
aaat 1204

<210> SEQ ID NO 24
<211> LENGTH: 1698
<212> TYPE: DNA
<213> ORGANISM: Homo sapiens

<400> SEQUENCE: 24
tcggcacagg agcgaggaga cccgagagca gacgcgccct ggcgcccgcc ctgcgcagtc 60
accatggcga tgcatttcat cttctcagat acagcggtgc ttctgtttga tttctggagt 120
gtccacagtc ctgctggcat ggccctttcg gtgttggtgc tcctgcttct ggctgtactg 180
tatgaaggca tcaaggttgg caaagccaag ctgctcaacc aggtactggt gaacctgcca 240
acctccatca gccagcagac catcgcagag acagacgggg actctgcagg ctcagattca 300
ttccctgttg gcagaaccca ccacaggtgg tacttgtgtc actttggcca gtctctaatc 360
catgtcatcc aggtggtcat cggctacttc atcatgctgg ccgtaatgtc ctacaacacc 420
tggattttcc ttggtgtggt cttgggctct gctgtgggct actacctagc ttacccactt 480
ctcagcacag cttagatggt gaggaacgtg caggcactga ggctggaggg acatggagcc 540
ccctcttcca gacactatac ttccaactgc cctttcttct gatggctatt cctccacctt 600
attcccagcc cctggaaact ttgagctgaa gccagcactt gctccctgga gttcggaagc 660
cattgcagca accttccttc tcagccagcc tacgtagggc ccaggcatgg tcttgtgtct 720
taagacagct gctgtgacca aagggagaat ggagataaca ggggtggcag ggttactgag 780
cccatgacaa tgcttctctg tgactcaaac caggaatttc caaagatttc aagccaggga 840
gaagggttct tggtgatgca gggcatggaa cctggacacc ctcagctctc ctgctttgtg 900
ccttatctac aggagcatcg cccattggac ttcctgacct cttctgtctt tgagggacag 960
agaccaagct agatcctttt tctcaccttt ctgcctttgg aacacatgaa gatcatctcg 1020
tctatggatc atgttgacaa actaagtttt ttttattttt cccattgaac tcctagttgg 1080
caattttgca cattcataca aaaaaatttt taatgaaatg atttcattga ttcatgatgg 1140
atggcagaaa ctgctgagac ctatttccct ttcttgggga gagaataagt gacagctgat 1200
taaaggcaga gacacaggac tgctttcagg ctcctggttt attctctgat tgactgagct 1260
ccttccacca gaaggcactg cctgcaggaa gaagatgatc tgatggccgt gggtgtctgg 1320
gaagctcttc gtggcctcaa tgccctcctt tatcctcatc tttcttctat gcagaacaaa 1380
aagctgcatc taataatgtt caatacttaa tattctctat ttattactta ctgcttactc 1440
gtaatgatct agtggggaaa catgattcat tcacttaaaa tactgattaa gccatgggca 1500
ggtactgact gaagatgcaa tccaaccaaa gccattacat tttttgagtt agatgggact 1560
ctctggatag ttgaacctct tcactttata aaaaaggaaa gagagaaaat cactgctgta 1620
tactaaatac ctcacagatt agatgaaaag atggttgtaa gctttgggaa ttaaaaacaa 1680
atacatttta gtaaatat 1698

<210> SEQ ID NO 25
<211> LENGTH: 3213
<212> TYPE: DNA
<213> ORGANISM: Homo sapiens

<400> SEQUENCE: 25

-continued

```
aatcatcgct cgcagcggcg gcgcccgcag tggccgcagc agcgcgccgg gccctggccg     60
cgccccagcc gagcgcagcg cggagtcgcc ccgacctttc tctgcgcagt acggccgccg    120
ggaccgcagc atggcgggca tcgcggccaa gctggcgaag gaccgggagg cggccgaggg    180
gctgggctcc cacgagaggg ccatcaagta cctcaaccag gactacgagg cgctgcggaa    240
cgagtgcctg gaggccggga cgctcttcca ggacccgtcc ttcccggcca tcccctcggc    300
cctgggcttc aaggagttgg ggccctactc cagcaaaacc cggggcatga gatggaagcg    360
ccccacggag atctgcgctg acccccagtt tatcattgga ggagccaccc gcacagacat    420
ctgccaagga gccctaggtg actgctggct gctggcagcc attgcctccc tcaccttgaa    480
tgaagaaatc ctggctcgag tcgtccccct aaaccagagc ttccaggaaa actatgcagg    540
gatctttcac ttccagttct ggcaatacgg cgagtgggtg gaggtggtgg tggatgacag    600
gctgcccacc aaggacgggg agctgctctt tgtgcattca gccgaaggga gcgagttctg    660
gagcgccctg ctggagaagg catacgccaa gatcaacgga tgctatgaag ctctatcagg    720
gggtgccacc actgagggct tcgaagactt caccggaggc attgctgagt ggtatgagtt    780
gaagaagccc cctcccaacc tgttcaagat catccagaaa gctctgcaaa aaggctctct    840
ccttggctgc tccatcgaca tcaccagcgc cgcggactcg gaggccatca cgtttcagaa    900
gctggtgaag ggcacgcgt actcggtcac cggagccgag gaggttgaaa gtaacggaag    960
cctacagaaa ctgatccgca tccgaaatcc ctggggagaa gtggagtgga cagggcggtg   1020
gaatgacaac tgcccaagct ggaacactat agacccagag gagagggaaa ggctgaccag   1080
acggcatgaa gatggagaat tctggatgtc tttcagtgac ttcctgaggc actattcccg   1140
cctggagatc tgtaacctga ccccagacac tctcaccagc gatacctaca agaagtggaa   1200
actcaccaaa atggatggga actggaggcg gggctccacc gcgggaggtt gcaggaacta   1260
cccgaacaca ttctggatga accctcagta cctgatcaag ctggaggagg aggatgagga   1320
cgaggaggat ggggagagcg gctgcacctt cctggtgggg ctcattcaga agcaccgacg   1380
gcggcagagg aagatgggcg aggacatgca caccatcggc tttggcatct atgaggttcc   1440
agaggagtta agtgggcaga ccaacatcca cctcagcaaa aacttcttcc tgacgaatcg   1500
cgccagggag cgctcagaca ccttcatcaa cctccgggag gtgctcaacc gcttcaagct   1560
gccgccagga gagtacattc tcgtgccttc caccttcgaa cccaacaagg atggggattt   1620
ctgcatccgg gtcttttctg aaaagaaagc tgactaccaa gctgtcgatg atgaaatcga   1680
ggccaatctt gaagagttcg acatcagcga ggatgacatt gatgatggag tcaggagact   1740
gtttgcccag ttggcaggag aggatgcgga gatctctgcc tttgagctgc agaccatcct   1800
gagaagggtt ctagcaaagc gccaagatat caagtcagat ggcttcagca tcgagacatg   1860
caaaattatg gttgacatgc tagattcgga cgggagtggc aagctggggc tgaaggagtt   1920
ctacattctc tggacgaaga ttcaaaaata ccaaaaaatt taccgagaaa tcgacgttga   1980
caggtctggt accatgaatt cctatgaaat gcggaaggca ttagaagaag caggtttcaa   2040
gatgccctgt caactccacc aagtcatcgt tgctcggttt gcagatgacc agctcatcat   2100
cgattttgat aattttgttc ggtgtttggt tcggctggaa acgctattca agatatttaa   2160
gcagctggat cccgagaata ctggaacaat agagctcgac cttatctctt ggctctgttt   2220
ctcagtactt tgaagttata actaatctgc ctgaagactt ctcatgatgg aaaatcagcc   2280
aaggactaag cttccataga aatacacttt gtatctggac ctcaaaatta tgggaacatt   2340
tacttaaacg gatgatcata gctgaaaata atgatactgt caatttgaga tagcagaagt   2400
```

-continued ttcacacatc aaagtaaaag atttgcatat cattatacta aatgcaaatg agtcgcttaa 2460
cccttgacaa ggtcaaagaa agctttaaat ctgtaaatag tatacacttt ttacttttac 2520
acactttcct gttcatagca atattaaatc aggaaaaaaa aatgcaggga ggtatttaac 2580
agctgagcaa aaacattgag tcgctctcaa aggacacgag gcccttggca gggaatattt 2640
aaagcaactt caagtttaaa atgcagctgt tgattctacc aaacaacagt ccaagattac 2700
catttcccat gagccaactg ggaaacatgg tatatcatga agtaatcttg tcaaggcatc 2760
tggagagtcc aggagaggag actcacctct gtcgcttggg ttaaacaaga gacaggtttt 2820
gtagaatatt gattggtaat agtaaatcgt tctccttaca atcaagttct tgaccctatt 2880
cggccttata catctggtct tacaaagacc aaagggatcc tgcgcttgat caactgaacc 2940
agtatgccaa aaccaggcat ccaatttgta aaccaattat gataaaggac aaaataagct 3000
gtttgccacc tcaaaacttt atgaacttca ccaccactag tgtctgtcca tggagttaga 3060
ggggacatca cttagaagtt cttatagaaa ggacacaagt ttgtttcctg gctttacctt 3120
gggaaaatgc tagcaacatt atagaaattt tgccttgttg ccttatcttc ttccaaatgt 3180
actgttaaat aaaaataaag ggttacccca tcg 3213

<210> SEQ ID NO 26
<211> LENGTH: 5316
<212> TYPE: DNA
<213> ORGANISM: Homo sapiens

<400> SEQUENCE: 26
atcatggcgg atggccccag gtgtaagcgc agaaagcagg cgaacccgcg gcgcaataac 60
gttacaaatt ataatactgt ggtagaaaca aattcagatt cagatgatga agacaaactg 120
catattgtgg aagaagaaag tgttacagat gcagctgact gtgaaggtgt accagaggat 180
gacctgccaa cagaccagac agtgttacca gggaggagca gtgaaagaga agggaatgct 240
aagaactgct gggaggatga cagaaaggaa gggcaagaaa tcctggggcc tgaagctcag 300
gcagatgaag caggatgtac agtaaaagat gatgaatgcg agtcagatgc agaaaatgag 360
caaaaccatg atcctaatgt tgaagagttt ctacaacaac aagacactgc tgtcattttt 420
cctgaggcac ctgaagagga ccagaggcag ggcacaccag aagccagtgg tcatgatgaa 480
aatggaacac cagatgcatt ttcacaatta ctcacctgtc catattgtga tagaggctat 540
aaacgcttta cctctctgaa agaacacatt aaatatcgtc atgaaaagaa tgaagataac 600
tttagttgct ccctgtgcag ttacaccttt gcatacagaa cccaacttga acgtcacatg 660
acatcacata aatcaggaag agatcaaaga catgtgacgc agtctgggtg taatcgtaaa 720
ttcaaatgca ctgagtgtgg aaaagctttc aaatacaaac atcacctaaa agagcactta 780
agaattcaca gtggagagaa gccatatgaa tgcccaaact gcaagaaacg cttttcccat 840
tctggctcct atagctcaca cataagcagt aagaaatgta tcagcttgat acctgtgaat 900
gggcgaccaa gaacaggact caagacatct cagtgttctt caccgtctct ttcagcatca 960
ccaggcagtc ccacacgacc acagatacgg caaaagatag agaataaacc ccttcaagaa 1020
caactttctg ttaaccaaat taaaactgaa cctgtggatt atgaattcaa acccatagtg 1080
gttgcttcag gaatcaactg ttcaacccct ttacaaaatg gggttttcac tggtggtggc 1140
ccattacagg caaccagttc tcctcagggc atggtgcaag ctgttgttct gccaacagtt 1200
ggtttggtgt ctcccataag tatcaattta agtgatattc agaatgtact taaagtggcg 1260

-continued

```
gtagatggta atgtaataag gcaagtgttg gagaataatc aagccaatct tgcatccaaa   1320
gaacaagaaa caatcaatgc ttcacccata caacaaggtg gccattctgt tatttcagcc   1380
atcagtcttc ctttggttga tcaagatgga acaaccaaaa ttatcatcaa ctacagtctt   1440
gagcagccta gccaacttca agttgttcct caaaatttaa aaaaagaaaa tccagtcgct   1500
acaaacagtt gtaaaagtga aaagttacca gaagatctta ctgttaagtc tgagaaggac   1560
aaaagctttg aaggggggt gaatgatagc acttgtcttc tgtgtgatga ttgtccagga   1620
gatattaatg cacttccaga attaaagcac tatgacctaa agcagcctac tcagcctcct   1680
ccactccctg cagcagaagc tgagaagcct gagtcctctg tttcatcagc tactggagat   1740
ggcaatttgt ctcctagtca gccaccttta aagaacctct tgtctctcct aaaagcatat   1800
tatgctttga atgcacaacc aagtgcagaa gagctctcaa aaattgctga ttcagtaaac   1860
ctaccactgg atgtagtaaa aaagtggttt gaaaagatgc aagctggaca gatttcagtg   1920
cagtcttctg aaccatcttc tcctgaacca ggcaaagtaa atatccctgc caagaacaat   1980
gatcagcctc aatctgcaaa tgcaaatgaa ccccaggaca gcacagtaaa tctacaaagt   2040
cctttgaaga tgactaactc cccagtttta ccagtgggat caaccaccaa tggttccaga   2100
agtagtacac catccccatc acctctaaac ctttcctcat ccagaaatac acagggttac   2160
ttgtacacag ctgagggtgc acaagaagag ccacaagtag aacctcttga tctttcacta   2220
ccaaagcaac agggagaatt attagaaagg tcaactatca ctagtgttta ccagaacagt   2280
gtttattctg tccaggaaga acccttgaac ttgtcttgcg caaaaaagga gccacaaaag   2340
gacagttgtg ttacagactc agaaccagtt gtaaatgtaa tcccaccaag tgccaacccc   2400
ataaatatcg ctatacctac agtcactgcc cagttaccca caatcgtggc cattgctgac   2460
cagaacagtg ttccatgctt aagagcgcta gctgccaata agcaaacgat tctgattccc   2520
caggtggcat acacctactc aactacggtc agccctgcag tccaagaacc acccttgaaa   2580
gtgatccagc caaatggaaa tcaggatgaa agacaagata ctagctcaga aggagtatca   2640
aatgtagagg atcagaatga ctctgattct acaccgccca aaaagaaaat gcggaagaca   2700
gaaaatggaa tgtatgcttg tgatttgtgt gacaagatat tccaaaagag tagttcatta   2760
ttgagacata aatatgaaca cacaggtaaa agacctcatg agtgtggaat ctgtaaaaag   2820
gcatttaaac acaaacatca tttgattgaa cacatgcgat tacattctgg agaaaagccc   2880
tatcaatgtg acaaatgtgg aaagcgcttc tcacactctg ggtcttattc tcaacacatg   2940
aatcatcgct actcctactg taagagagaa gcggaagaac gtgacagcac agagcaggaa   3000
gaggcagggc ctgaaatcct ctcgaatgag cacgtgggtg ccagggcgtc tccctcacag   3060
ggcgactcgg acgagagaga gagtttgaca agggaagagg atgaagacag tgaaaaagag   3120
gaagaggagg aggataaaga gatggaagaa ttgcaggaag aaaaagaatg tgaaaaacca   3180
caaggggatg aggaagagga ggaggaggag gaagaagtgg aagaagaaga ggtagaagag   3240
gcagagaatg agggagaaga agcaaaaact gaaggtctga tgaaggatga cagggctgaa   3300
agtcaagcaa gcagcttagg acaaaaagta ggcgagagta gtgagcaagt gtctgaagaa   3360
aagacaaatg aagcctaatc gtttttctag aaggaaaata aattctaatt gataatgaat   3420
ttcgttcaat attatccttg cttttcatgg aaacacagta acctgtatgc tgtgattcct   3480
gttcactact gtgtgtgtgt gcgcgtgcat tgattactat ccatttcttt agtcaacgct   3540
ctccacttcc tgatttctgc tttaaggaaa actgtgaact ttctgcttca tgtatcagtt   3600
ttaaagcatc ccaggcaaag atcatctaca gattctagga attctctccc ctgaaatcaa   3660
```

-continued

```
aacctggaga cttttttttc ttattttagt tgagaagttc ataaactgct caaggattag   3720
ttttccagga ctctgcggag gaacggcagg aagaacctca gagagggcag aggtgacttc   3780
aaagtgctgg ggactccgtc ctgagggtca cttggccctg agcccctgcg tgcccttgcg   3840
gaagcccaga agcttcttcc tgctgcacct cccgtttccg ctgctgctga cgtttatgca   3900
tttcatgatg gggtccaaca agaacacctg acttgggtga agttgtgcaa tattggaggc   3960
tgactgtagg gctgggcagc tgggagacag gctcatggct catggctcat ggctcagggc   4020
ggtgcctgcc ctgggccggg acccccctcc ccacccccca cctaggcttt ttgggttttg   4080
ttcaaggaag gtaaagtgag aggtttaggt cagtgttttt aagtttttgt ttttttttta   4140
aagcaaatcc tgtatatgta tctacatggg agataggtag acactactta tttgttacat   4200
tttgtactat acgtttgtgt tccaggtttc agcttccctc gctcctgttg ttaagaagcg   4260
tccctgtcag cacaggtgtg cattgaggaa ggggccccag ggccttcgct ccctcagcac   4320
tggggtggag gcggcaggaa ggggcggccc ttacctggca ggtctgggcg cacctttagc   4380
aggtggactc cgtggggctc caccagccag aagcctctgg aaggcaacga aggcaatgct   4440
gctccctgag tccagtcccc gcccccaaac ccagcccagg tgccttcagc tacttcggct   4500
tcttaaaccc tgcagtgtta aacagaggca ttgagaaagg ggaaaggcgg gtatttttaa   4560
aagccaaaga ttgacccaag ttacttgagg gtagggaggc gggcccagtg caggaggctg   4620
catccctggc ctgctggtgc ccaccggggg ctgtgcctgt gccgggccgc aggaagctgg   4680
ctgcccccat tcctgctgct gctgctgctg ctgctctgtg gctgtttcaa agactgggcg   4740
aaaggctgtc cggagggcag accaggtgcc ttgccgcaga gaaaacacca aagtctcctg   4800
ttcgctcata aagaagtttt tgggatggga gagaatccag accatcttgg ggcagccagg   4860
cccttgcctt catttttaca gaggtagcac aactgattcc aacacaaaac cccttcccct   4920
ttttaaaatg atttctgttc taatgccata gatcaaaggc ctcagaaacc attgtgtgtt   4980
tcctctttga agcaatgaca agcactttac tttcacggtg gtttttgttt tttcttattg   5040
ctgtggaacc tcttttggag gacgttaaag gcgtgtttta cttgtttttt taagagtgtg   5100
tgatgtgtgt tttgtagatt tcttgacagt gctgtaatac agacggcaat gcaatagcct   5160
atttaaagaa ctacgtgatc tgattgagat gtacatagtt ttttttttta ccataactga   5220
attattttat ctcttatgtt atcatgagaa atgtatgcca aatgattagt tgatgtatgt   5280
tttttaattt aatatttaaa taaaatattt ggaagg                             5316
```

<210> SEQ ID NO 27
<211> LENGTH: 3045
<212> TYPE: DNA
<213> ORGANISM: Homo sapiens

<400> SEQUENCE: 27

```
aattcccttg aggtggtttc acatccacat ccagttgtcc ctaaaatgga gaaagaactg     60
gtgccagacc aggcagtaat atcagacagt actttctctc tggcaaacag tccaggcagt    120
gaatcagtaa ccaaggatga cgcactttct tttgtcccct cccagaaaga aaagggaaca    180
gcaactcctg aactacatac agctacagat tatagagatg gcccagatgg aaattcgaat    240
gagcctgata cgcggccact agaagacagg gcagtaggcc tgtccacatc ctccactgct    300
gcagagcttc agcacgggat ggggaatacc agtctcacag gacttggtgg agagcatgag    360
ggtcccgccc ctccagcaat cccagaagct ctgaatatca aggggaacac tgactcttcc    420
```

-continued

```
gtgcaaagtg tgggtaaggc cactttggct ttagattcag ttttgactga agaaggaaaa    480
gttctggtgg tttcagaaag ctctgcagct caggaacaag ataaggataa agcggtgacc    540
tgttcctcta ttaaggaaaa tgctctctct tcaggaactt tgcaggaaga gcagagaaca    600
ccacctcctg gacaagatac tcaacaattt catgaaaaat caatctcagc tgactgtgcc    660
aaggacaaag cacttcagct aagtaattca ccgggtgcat cctctgcctt tcttaaggca    720
gaaactgaac ataacaagga agtggcccca caagtctcac tgctgactca aggtggggct    780
gcccagagcc tggtgccacc aggagcaagt ctggccacag agtcaaggca ggaagccttg    840
ggggcagagc acaacagctc cgctctgttg ccatgtctgt tgccagatgg gtctgatggg    900
tccgatgctc ttaactgcag tcagccttct cctctggatg ttggagtgaa gaacactcaa    960
tcccagggaa aaactagtgc ctgtgaggtg agtggagatg tgacggtgga tgttacaggg   1020
gttaatgctc tacaaggtat ggctgagccc agaagagaga atatatcaca caacacccaa   1080
gacatcctga ttccaaacgt cttgttgagc caagagaaga atgccgttct aggtttgcca   1140
gtggctctac aggacaaagc tgtgactgac ccacagggag ttggaacccc agagatgata   1200
cctcttgatt gggagaaagg gaagctggag ggagcagacc acagctgtac catgggtgac   1260
gctgaggaag cccaaataga cgatgaagca catcctgtcc tactgcagcc tgttgccaag   1320
gagctcccca cagacatgga gctctcagcc catgatgatg gggccccagc tggtgtgagg   1380
gaagtcatgc gagccccgcc ttcaggcagg gaaaggagca ctccctctct accttgcatg   1440
gtctctgccc aggacgcacc tctgcctaag gggggcagact tgatagagga ggctgccagc  1500
cgtatagtgg atgctgtcat cgaacaagtc aaggccgctg gagcactgct tactgagggg   1560
gaggcctgtc acatgtcact gtccagccct gagttgggtc ctctcactaa aggactagag   1620
agtgctttta cagaaaaagt gagtactttc ccacctgggg agagcctacc aatgggcagt   1680
actcctgagg aagccacggg gagccttgca ggatgttttg ctggaaggga ggagccagag   1740
aagatcattt tacctgtcca ggggcctgag ccagcagcag aaatgccaga cgtgaaagct   1800
gaagatgaag tggattttag agcaagttca atttctgaag aagtggctgt agggagcata   1860
gctgctacac tgaagatgaa gcaaggccca atgacccagg cgataaaccg agaaaactgg   1920
tgtacaatag agccatgccc tgatgcagca tctcttctgg cttccaagca gagcccagaa   1980
tgtgagaact tcctggatgt tggactgggc agagagtgta cctcaaaaca aggtgtactt   2040
aaaagagaat ctgggagtga ttctgacctc tttcactcac ccagtgatga catggacagc   2100
atcatcttcc caaagccaga ggaagagcat ttggcctgtg atatcaccgg atccagttca   2160
tccaccgatg acacggcttc actggaccga cattcttctc atggcagtga tgtgtctctc   2220
tcccagattt taaagccaaa caggtcaaga gatcggcaaa gccttgatgg attctacagc   2280
catgggatgg gagctgaggg tcgagaaagt gagagtgagc ctgctgaccc aggcgacgtg   2340
gaggaggagg agatggacag tatcactgaa gtgcctgcaa actgctctgt cctaaggagc   2400
tccatgcgct ctctttctcc cttccggagg cacagctggg ggcctgggaa aaatgcagcc   2460
agcgatgcag aaatgaacca ccggagttca atgcgagttc ttggggatgt tgtcaggaga   2520
cctcccattc ataggagaag tttcagtcta gaaggcttga caggaggagc tggtgtcgga   2580
aacaagccat cctcatctct agaagtaagc tctgcaaatg ccgaagagct cagacaccca   2640
ttcagtggtg aggaacgggt tgactctttg gtgtcacttt cagaagagga tctggagtca   2700
gaccagagag aacataggat gtttgatcag cagatatgtc acagatctaa gcagcaggga   2760
tttaattact gtacatcagc catttcctct ccattgacaa aatccatctc attaatgaca   2820
```

-continued atcagccatc ctggattgga caattcacgg cccttccaca gtaccttcca caataccagt 2880
gctaatctga ctgagagtat aacagaagag aactataatt tcctgccaca tagcccctcc 2940
aagaaagatt ctgaatggaa gagtggaaca aaagtcagtc gtacattcag ctacatcaag 3000
aataaaatgt ctagcagcaa gaagagcaaa gaaaagaaaa aaaag 3045

<210> SEQ ID NO 28
<211> LENGTH: 3634
<212> TYPE: DNA
<213> ORGANISM: Homo sapiens

<400> SEQUENCE: 28
tcaacacagg acaatgcaag cccatgagct gttccggtat tttcgaatgc cagagctggt 60
tgacttccga cagtacgtgc gtactcttcc gaccaacacg cttatgggct tcggagcttt 120
tgcagcactc accaccttct ggtacgccac gagacccaaa cccctgaagc cgccatgcga 180
cctctccatg cagtcagtgg aagtggcggg tagtggtggt gcacgaagat ccgcactact 240
tgacagcgac gagcccttgg tgtatttcta tgatgatgtc acaacattat acgaaggttt 300 ccagaggggga atacaggtgt caaataatgg cccttgttta ggctctcgga aaccagacca 360
accctatgaa tggctttcat ataaacaggt tgcagaattg tcggagtgca taggctcagc 420
actgatccag aagggcttca agactgcccc agatcagttc attggcatct ttgctcaaaa 480
tagacctgag tgggtgatta ttgaacaagg atgctttgct tattcgatgg tgatcgttcc 540
actttatgat acccttggaa atgaagccat cacgtacata gtcaacaaag ctgaactctc 600
tctggttttt gttgacaagc cagagaaggc caaactctta ttagagggtg tagaaaataa 660
gttaatacca ggccttaaaa tcatagttgt catggatgcc tacggcagtg aactggtgga 720
acgaggccag aggtgtgggg tggaagtcac cagcatgaag gcgatggagg acctgggaag 780
agccaacaga cggaagccca agcctccagc acctgaagat cttgcagtaa tttgtttcac 840
aagtggaact acaggcaacc ccaaaggagc aatggtcact caccgaaaca tagtgagcga 900
ttgttcagct tttgtgaaag caacagagaa tacagtcaat ccttgcccag atgatacttt 960
gatatctttc ttgcctctcg cccatatgtt tgagagagtt gtagagtgtg taatgctgtg 1020
tcatggagct aaaatcggat ttttccaagg agatatcagg ctgctcatgg atgacctcaa 1080
ggtgcttcaa cccactgtct tccccgtggt tccaagactg ctgaaccgga tgtttgaccg 1140
aattttcgga caagcaaaca ccacgctgaa gcgatggctc ttggactttg cctccaagag 1200
gaaagaagca gagcttcgca gcggcatcat cagaaacaac agcctgtggg accggctgat 1260
cttccacaaa gtacagtcga gcctgggcgg aagagtccgg ctgatggtga caggagccgc 1320
cccggtgtct gccactgtgc tgacgttcct cagagcagcc ctgggctgtc agttttatga 1380
aggatacgga cagacagagt gcactgccgg gtgctgccta accatgcctg gagactggac 1440
cgcaggccat gttggggccc cgatgccgtg caatttgata aaacttgttg atgtggaaga 1500
aatgaattac atggctgccg agggcgaggg cgaggtgtgt gtgaaagggc caaatgtatt 1560
tcagggctac ttgaaggacc cagcgaaaac agcagaagct ttggacaaag acggctggtt 1620
acacacaggg gacattggaa aatggttacc aaatggcacc ttgaaaatta tcgaccggaa 1680
aaagcacata tttaagctgg cacaaggaga atacatagcc cctgaaaaga ttgaaaatat 1740
ctacatgcga agtgagcctg ttgctcaggt gtttgtccac ggagaaagcc tgcaggcatt 1800
tctcattgca attgtggtac cagatgttga gacattatgt tcctgggccc aaaagagagg 1860

-continued

```
atttgaaggg tcgtttgagg aactgtgcag aaataaggat gtcaaaaaag ctatcctcga   1920
agatatggtg agacttggga aggattctgg tctgaaacca tttgaacagg tcaaaggcat   1980
cacattgcac cctgaattat tttctatcga caatggcctt ctgactccaa caatgaaggc   2040
gaaaaggcca gagctgcgga actatttcag gtcgcagata gatgacctct attccactat   2100
caaggtttag tgtgaagaag aaagctcaga ggaaatggca cagttccaca atctcttctc   2160
ctgctgatgg ccttcatgtt gttaattttg aatacagcaa gtgtagggaa ggaagcgttc   2220
gtgtttgact tgtccattcg gggttcttct cataggaatg ctagaggaaa cagaacaccg   2280
ccttacagtc acctcatgtt gcagaccatg tttatggtaa tacacacttt ccaaaatgag   2340
ccttaaaaat tgtaaagggg atactataaa tgtgctaagt tatttgagac ttcctcagtt   2400
taaaaagtgg gttttaaatc ttctgtctcc ctgcttttct aatcaagggg ttaggacttt   2460
gctatctctg agatgtctgc tacttgctgc aaattctgca gctgtctgct gctctaaaga   2520
gtacagtgca ctagagggaa gtgttccctt taaaaataag aacaactgtc ctggctggag   2580
aatctcacaa gcggaccaga gatcttttta aatccctgct actgtccctt ctcacaggca   2640
ttcacagaac ccttctgatt cgtaagggtt acgaaactca tgttcttctc cagtcccctg   2700
tggtttctgt tggagcataa ggtttccagt aagcgggagg gcagatccaa ctcagaacca   2760
tgcagataag gagcctctgg caaatgggtg ctcatcagaa cgcgtggatt ctctttcatg   2820
gcagaatgct cttggactcg gttctccagg cctgattccc cgactccatc ctttttcagg   2880
ggttatttaa aaatctgcct tagattctat agtgaagaca agcatttcaa gaaagagtta   2940
cctggatcag ccatgctcag ctgtgacgcc tgaataactg tctactttat cttcactgaa   3000
ccactcactc tgtgtaaagg ccaacagatt tttaatgtgg ttttcatatc aaaagatcat   3060
gttgggatta acttgccttt ttccccaaaa aataaactct caggcaagca tttctttaaa   3120
gctattaagg gagtatatac ttgagtactt attgaaatgg acagtaataa gcaaatgttc   3180
ttataatgct acctgatttc tatgaaatgt gtttgacaag ccaaaattct aggatgtaga   3240
aatctggaaa gttcatttcc tgggattcac ttctccaggg attttttaaa gttaatttgg   3300
gaaattaaca gcagttcact ttattgtgag tctttgccac atttgactga attgagctgt   3360
catttgtaca tttaaagcag ctgttttggg gtctgtgaga gtacatgtat tatatacaag   3420
cacaacaggg cttgcactaa agaattgtca ttgtaataac actacttggt agcctaactt   3480
catatatgta ttcttaattg cacaaaaagt caataatttg tcaccttggg gttttgaatg   3540
tttgctttaa gtgttggcta tttctatgtt ttataaacca aaacaaaatt tccaaaaaca   3600
atgaaggaaa ccaaaataaa tatttctgca tttc                               3634
```

<210> SEQ ID NO 29
<211> LENGTH: 4573
<212> TYPE: DNA
<213> ORGANISM: Homo sapiens

<400> SEQUENCE: 29

```
cgcgtgtcta cgcggacgca ccggctaagc tgcttctgcc gccgccggcc gcctgggacc     60
ttgcggtgag gctgcgcggg gccgaggccg cctccgagcg ccaggtttat tcagtcacca    120
tgaagctgct gctgctgcac ccggccttcc agagctgcct cctgctgacc ctgcttggct    180
tatggagaac cacccctgag gctcacgctt catccctggg tgcaccagct atcagcgctg    240
cctccttcct gcaggatcta atacatcggt atggcgaggg tgacagcctc actctgcagc    300
agctgaaggc cctgctcaac cacctggatg tgggagtggg ccggggtaat gtcacccagc    360
```

-continued

```
acgtgcaagg acacaggaac ctctccacgt gctttagttc tggagacctc ttcactgccc    420
acaatttcag cgagcagtcg cggattggga gcagcgagct ccaggagttc tgccccacca    480
tcctccagca gctggattcc cgggcctgca cctcggagaa ccaggaaaac gaggagaatg    540
agcagacgga ggaggggcgg ccaagcgctg ttgaagtgtg gggatacggt ctcctctgtg    600
tgaccgtcat ctccctctgc tccctcctgg gggccagcgt ggtgcccttc atgaagaaga    660
ccttttacaa gaggctgctg ctctacttca tagctctggc gattggaacc ctctactcca    720
acgccctctt ccagctcatc ccggaggcat ttggtttcaa ccctctggaa gattattatg    780
tctccaagtc tgcagtggtg tttgggggct tttatctttt ctttttcaca gagaagatct    840
tgaagattct tcttaagcag aaaaatgagc atcatcatgg acacagccat tatgcctctg    900
agtcgcttcc ctccaagaag gaccaggagg aggggggtgat ggagaagctg cagaacgggg    960
acctggacca catgattcct cagcactgca gcagtgagct ggacggcaag gcgcccatgg   1020
tggacgagaa ggtcattgtg ggctcgctct ctgtgcagga cctgcaggct tcccagagtg   1080
cttgctactg gctgaaaggt gtccgctact ctgatatcgg cactctggcc tggatgatca   1140
ctctgagcga cggcctccac aatttcatcg atggcctggc catcggtgct tccttcactg   1200
tgtcagtttt ccaaggcatc agcacctcgg tggccatcct ctgtgaggag ttcccacatg   1260
agctaggaga ctttgtcatc ctgctcaacg ctgggatgag catccaacaa gctctcttct   1320
tcaacttcct ttctgcctgc tgctgctacc tgggtctggc ctttggcatc ctggccggca   1380
gccacttctc tgccaactgg atttttgcgc tagctggagg aatgttcttg tatatttctc   1440
tggctgatat gttccctgag atgaatgagg tctgtcaaga ggatgaaagg aagggcagca   1500
tcttgattcc atttatcatc cagaacctgg gcctcctgac tggattcacc atcatggtgg   1560
tcctcaccat gtattcagga cagatccaga ttgggtaggg ctctgccaag agcctgtggg   1620
actggaagtc gggccctggg ctgcccgatc gccagcccga ggacttacca tccacaatgc   1680
accacggaag aggccgttct atgaaaaact gacacagact gtattcctgc attcaaatgt   1740
cagccgtttg taaaatgctg tatcctagga ataagctgcc ctggtaacca gtctctagct   1800
agtgcctctt gccctctcct cacctccttt tctctcagtg actctggaac ctgaatgcag   1860
cttacaagac aagcctgact tttttctctg attaccttgg cctcctcttg gaaccagtgc   1920
tgaaaggttt tgaatccttt acccaacaat gcaaaaatag agccaatggt tataacttgg   1980
ctagaaatat caagagttga atccatagtg tggggcccat gactctagct gggcaccttg   2040
gacctccagc tggccaatag aagagacagg agacaggaag ccttcccatt ttttcaaagt   2100
ctgtttaatt gcctattact tctctcaaag agaacctgaa gtcagaacac atgagcaggg   2160
tgagaggtga ggcaaggttc atcctgaatg ggagaggaag tcgaaccact gctgtgtgtc   2220
ttgtcaggat gctcacttgt tcctactgag atgctggata ttgattttgt aacagcacct   2280
ggtgtttcac ggctgtccga gtgagctaac gtggcggtgt ggctgcctgg acctcctctt   2340
tcaggttaac gctgacagaa tggaggctca ggctgtctgc aagaaaacag ttggtttggc   2400
tgtgattttg acctcctctt ccccactgcc atcttctaag agactttgta gctgcctcct   2460
agaagcacat tctgagcaca tttgagacct ctgtgttaga ggggagactg cacaaactat   2520
cctcccccag gttgagacgt ctgcagagtg gcaagctgac ttgtagaaat ggggtgccat   2580
ttatgctcta cttagacaag ggtaatcaga aatggaatca gtgcaggcaa aatttaggat   2640
ttgccgcttc cataaatcaa agcatgacta atagggggtc tctgaaatgt aagggcacaa   2700
```

-continued

```
acttcactta gggcatcgca gatgtttgca gaatggttgg cctaatgatt atgctacaga   2760

tgggttttaa atgacccgtc taggttactg cttccttgca aaaaaagtcg aatcctgcat   2820

tgaattgaat atgaatttct ctaactctct ccagaaaatg gatggagata acttgtcttt   2880

aaaactgtag gccagcctta gccactgtgg agcccttgcc tccgagctct ggcttcaagg   2940

ggagctcttc tccaggttca ctaggtgaat tgatttatta ttatcatatt gataatgtga   3000

gattctttag ccactttggg gagcctgtct ctccagaagc ctttcttagt ggtgcccaca   3060

gttggagccc aggggccatg tttgcaaact gattcatgtg catggctgac aggagtactg   3120

gttcactacc aatgcctgag cttttctctt acatagaaaa actgtccact ctcagtaatc   3180

acaagcagca tccgttttgt tttctcttct tgggagacat ctgtcaaacc aggaatattc   3240

ttgaaaagaa cgtgagcagg aaaaactgct ggtgatactt tttttaagtt ttgtttttat   3300

cttgcctgtt ggcttcaata catttgagaa tacgctgaag agggaaaatt tcagtgatgg   3360

agattctaga ttaaatatca ggactgattt cctggtggga ttatggtcca gttttaccaa   3420

agaaccaatt ccttgaatgt tggaatctaa ctttttatat tgtcattatt attgttgttt   3480

ttaaacggtt ctttgtcttt tctgttttat ttttctcaag ctgctttcag gagctagcag   3540

aaaataactc aaagttgaag actctggaag attttgcttt aacctaactc gcattgatgt   3600

attaaattta taattttagc attcccaata gatcctatca ttccttaaac ataataccct   3660

ttgtcttgga gtagaatact aagttagagt tagtggattt ctagtttagg agaggagctc   3720

aaaactataa tctttaacaa attgaaaaat gaaataggggt gttttccctt tttgtgcaca   3780

cctatattac cttaagaaat ttccttccat agacagctgc ctcaaaggga aatcctcttt   3840

aaaccgtagt tggcgcagag gtcagtccta gtcggagctt aggaggggcg gagacgctca   3900

catcgtctga cttgagtcgc cactgattgt ggcaacagct ttgcctcatg agtcaaaaat   3960

tggcaatttc ttttgatttt tagttgttga atttgctgtt tcaagcattt gtacatatta   4020

gaagtctaag gagtagcaag tcagtgggag gactttttca cccctggcat tagcagcttc   4080

gacctcattt tccagatgca ccagctccta ttaataagtt agcaaggaaa gtgtatgtca   4140

cgtgcaggaa cagtgaggca gggacagggg ttctgctcct tctcacttca ccaccggcac   4200

acagcttgcc cctgtctttg cccccaaagg tattttgtgt ctagtgtcaa attggagcta   4260

ttcttcactg gtccttaacc ttgggtttta aaaagaaggc ttctctgttt gggtagcgta   4320

agagctgagt atagtaagtc ctcttccaaa gagatggcaa tatgctgggc atctacttta   4380

aaacaaagtt gtctgatttt tgcaagagag gttaggattt tattgttctt atttcccttt   4440

acagttctgc agttccatca cagtattttt ttaaataact caggtgtatg agcagaaatt   4500

agaaaagaaa attaacttat gtggactgta aatgttttat ttgtaagatt ctataaataa   4560

agctatattc tgt                                                       4573
```

<210> SEQ ID NO 30
<211> LENGTH: 1707
<212> TYPE: DNA
<213> ORGANISM: Homo sapiens

<400> SEQUENCE: 30

```
cggcgctggg ctgaggggag gggttgtctt aaaagtctct ccttccccct gtaggggcgg     60

ccggcgagtc ccagtgagag cggagggtgc cagaggtagg gggccgagaa acaaagttcc    120

cggggcttcc tccggggccg cggtcggggc tgcgcgtttg accgcccccc tcctcgcgaa    180

gcaatggctt ccaaactcct gcgcgcggtc atcctcgggc cgcccggctc gggcaagggc    240
```

-continued

```
accgtgtgcc agaggatcgc ccagaacttt ggtctccagc atctctccag cggccacttc    300

ttgcgggaga acatcaaggc cagcaccgaa gttggtgaga tggcaaagca gtatatagag    360

aaaagtcttt tggttccaga ccatgtgatc acacgcctaa tgatgtccga gttggagaac    420

aggcgtggac agcactggct ccttgatggt tttcctagga cattaggaca agccgaagcc    480

ctggacaaaa tctgtgaagt ggatctagtg atcagtttga atattccatt tgaaacactt    540

aaagatcgtc tcagccgccg ttggattcac cctcctagcg gaagggtata taacctggac    600

ttcaatccac ctcatgtaca tggtattgat gacgtcactg gtgaaccgtt agtccagcag    660

gaggatgata aacccgaagc agttgctgcc aggctaagac agtacaaaga cgtggcaaag    720

ccagtcattg aattatacaa gagccgagga gtgctccacc aattttccgg aacggagacg    780

aacaaaatct ggccctacgt ttacacactt ttctcaaaca agatcacacc tattcagtcc    840

aaagaagcat attgaccctg cccaatggaa gaaccaggaa gatgtggtca ttcattcaat    900

agtgtgtgta gtattggtgc tgtgtccaaa ttagaagcta gctgaggtag cttgcagcat    960

cttttctagt tgaaatggtg aactgatagg aaaacaaatg agtagaaaga gttcatgaag   1020

aggccctcct ctgcctttca aaaggctggt cacctacaca tgtttaaggt gtctctgcac   1080

atgtctcaag cccatcacaa gaaagcaagt acagtgtgga tttcaaatgg tgtgtaactt   1140

cagctccagc tggtttttga cagctgttgc tgtggtaata tttttgacat gtgatggtga   1200

tagtctctgg ttctccccat ccccacaaag gctgttgaac cacagcacca ggaagcctga   1260

gaatgaatcc tgagggctct agcccaggct ttgtcccagg ctttctggtg tgtgccctcc   1320

tggtaacagt gaaattgaag ctacttactc atagtggttg tttctctggt cttgagtgac   1380

tgtgtccaca gttcattttt ttccggtagg aataactcct tttctacatc cacgctccat   1440

agagtctctc cttttcagac atcctgggat gaaagaattt ggcttttttt tttctttttt   1500

ttttggacat ctgttttcac tcttaggctt ttaaacaata gttattgctt ttatccctct   1560

cagattctaa taactgagag cgatggggct atattgaatc tctgtatgca ctgagaactg   1620

agctatgaag agaatcttat taaactgctg gtctgacttt atggattgac actgttcctt   1680

tcttttattg tgaaaaaaaa aaaaaaa                                      1707
```

<210> SEQ ID NO 31
<211> LENGTH: 2916
<212> TYPE: DNA
<213> ORGANISM: Homo sapiens
<220> FEATURE:
<221> NAME/KEY: misc_feature
<222> LOCATION: (1)..(2916)
<223> OTHER INFORMATION: n = a, c, g or t

<400> SEQUENCE: 31

```
agcagagctt tcccnccatg nnagaagctt catgagtcac acattacatc tttgggttga     60

ttgaatgcca ctgaaacatt tctagtagcc tggagnagtt gacctacctg tggagatgcc    120

tgccattaaa tggcatcctg atggcttaat acacatcact cttctgtgna gggttttaat    180

tttcaacaca gcttactctg tagcatcatg tttacattgt atgtataaag attatacnaa    240

ggtgcaattg tgtatttctt ccttaaaatg tatcagtata ggatttagaa tctccatgtt    300

gaaactctaa atgcatagaa ataaaaataa taaaaaattt ttcattttgc cttttcagcc    360

tagtattaaa actgataaaa gcaaagccat gcacaaaact acctccctag agaaaggcta    420

gtccctttc ttccccattc atttcattat gaacatagta gaaaacagca tattcttatc      480
```

-continued

```
aaatttgatg aaaagcgcca acacgtttga actgaaatac gacttgtcat gtgaactgta    540
ccgaatgtct acgtattcca cttttcctgc tggggttcct gtctcagaaa ggagtcttgc    600
tcgtgctggt ttctattaca ctggtgtgaa tgacaaggtc aaatgcttct gttgtggcct    660
gatgctggat aactggaaaa gaggagacag tcctactgaa aagcataaaa agttgtatcc    720
tagctgcaga ttcgttcaga gtctaaattc cgttaacaac ttggaagcta cctctcagcc    780
tacttttcct tcttcagtaa cacattccac acactcatta cttccgggta cagaaaacag    840
tggatatttc cgtggctctt attcaaactc tccatcaaat cctgtaaact ccagagcaaa    900
tcaagaattt tctgccttga tgagaagttc ctacccctgt ccaatgaata acgaaaatgc    960
cagattactt actttcaga catggccatt gacttttctg tcgccaacag atctggcacg   1020
agcaggcttt tactacatag gacctggaga cagagtggct tgctttgcct gtggtggaaa   1080
attgagcaat tgggaaccga aggataatgc tatgtcagaa cacctgagac attttcccaa   1140
atgcccattt atagaaaatc agcttcaaga cacttcaaga tacacagttt ctaatctgag   1200
catgcagaca catgcagccc gctttaaaac attctttaac tggccctcta gtgttctagt   1260
taatcctgag cagcttgcaa gtgcgggttt ttattatgtg ggtaacagtg atgatgtcaa   1320
atgcttttgc tgtgatggtg gactcaggtg ttgggaatct ggagatgatc catgggttca   1380
acatgccaag tggtttccaa ggtgtgagta cttgataaga attaaaggac aggagttcat   1440
ccgtcaagtt caagccagtt accctcatct acttgaacag ctgctatcca catcagacag   1500
cccaggagat gaaaatgcag agtcatcaat tatccatttg gaacctggag aagaccattc   1560
agaagatgca atcatgatga atactcctgt gattaatgct gccgtggaaa tgggctttag   1620
tagaagcctg gtaaaacaga cagttcagag aaaaatccta gcaactggag agaattatag   1680
actagtcaat gatcttgtgt tagacttact caatgcagaa gatgaaataa gggaagagga   1740
gagagaaaga gcaactgagg aaaaagaatc aaatgattta ttattaatcc ggaagaatag   1800
aatggcactt tttcaacatt tgacttgtgt aattccaatc ctggatagtc tactaactgc   1860
cggaattatt aatgaacaag aacatgatgt tattaaacag aagacacaga cgtctttaca   1920
agcaagagaa ctgattgata cgattttagt aaaaggaaat attgcagcca ctgtattcag   1980
aaactctctg caagaagctg aagctgtgtt atatgagcat ttatttgtgc aacaggacat   2040
aaaatatatt cccacagaag atgtttcaga tctaccagtg gaagaacaat tgcggagact   2100
accagaagaa agaacatgta aagtgtgtat ggacaaagaa gtgtccatag tgtttattcc   2160
ttgtggtcat ctagtagtat gcaaagattg tgctccttct ttaagaaagt gtcctatttg   2220
taggagtaca atcaagggta cagttcgtac atttctttca tgaagaagaa ccaaaacatc   2280
gtctaaactt tagaattaat ttattaaatg tattataact ttaactttta tcctaatttg   2340
gtttccttaa aatttttatt tatttacaac tcaaaaaaca ttgttttgtg taacatattt   2400
atatatgtat ctaaaccata tgaacatata ttttttagaa actaagagaa tgataggctt   2460
ttgttcttat gaacgaaaaa gaggtagcac tacaaacaca atattcaatc caaatttcag   2520
cattattgaa attgtaagtg aagtaaaact taagatattt gagttaacct ttaagaattt   2580
taaatatttt ggcattgtac taataccggg aacatgaagc caggtgtggt ggtatgtacc   2640
tgtagtccca ggctgaggca agagaattac ttgagcccag gagtttgaat ccatcctggg   2700
cagcatactg agaccctgcc tttaaaaacn aacagnacca aanccaaaca ccagggacac   2760
atttctctgt cttttttgat cagtgtccta tacatcgaag gtgtgcatat atgttgaatc   2820
acattttagg gacatggtgt ttttataaag aattctgtga gnaaaaattt aataaagcaa   2880
```

-continued ccnaaattac tcttaaaaaa aaaaaaaaaa aaaaaa 2916

<210> SEQ ID NO 32
<211> LENGTH: 3188
<212> TYPE: DNA
<213> ORGANISM: Homo sapiens

<400> SEQUENCE: 32
cgggcagtga cagccggcgc ggatcgcgcg tccacggagg agaatcagct tagagaacta 60
tcaacacagg acaatgcaag cccatgagct gttccggtat tttcgaatgc cagagctggt 120
tgacttccga cagtgcgtga ctcttccgac caacacgctt atgggcttcg gagcttttc 180 cagacgactc accaccttct ggcggccacg ccacccaaaa cccctgaagc cgccatggca 240
cctctccatg cagtcagtgg aagtggcggg tagtggtggt gcacgaagat ccgcactact 300
tgacagcgac gagcccttgg tgtatttcta tgatgatgtt acaacattat acgaaggttt 360
ccagagaggg atacaggtgt caaataatgg cccttgttta ggctctcgga aaccagacca 420
accctatgaa tggctttcat ataaacaggt tgcagaattg tcggagtgca taggctcagc 480
actgatccag aagggcttca agactgcccc agatcagttc attggcatct ttgctcaaaa 540
tagacctgag tgggtgatta ttgaacaagg atgctttgct tattcgatgg tgatcgttcc 600
actttatgat acccttggaa atgaagccat cacgtacata gtcaacaaag ctgaactctc 660
tctggttttt gttgacaagc cagagaaggc caaactctta ttagagggtg tagaaaataa 720
gttaatacca ggccttaaaa tcatagttgt catggactcg tacggcagtg aactggtgga 780
acgaggccag aggtgtgggg tggaagtcac cagcatgaag gcgatggagg acctgggaag 840
agccaacaga cggaagccca agcctccagc acctgaagat cttgcagtaa tttgtttcac 900
aagtggaact acaggcaacc ccaaaggagc aatggtcact caccgaaaca tagtgagcga 960
ttgttcagct tttgtgaaag caacagagaa tacagtcaat ccttgcccag atgatacttt 1020
gatatctttc ttgcctctcg cccatatgtt tgagagagtt gtagagtgtg taatgctgtg 1080
tcatggagct aaaatcggat tttccaagg agatatcagg ctgctcatgg atgacctcaa 1140
ggtgcttcaa cccactgtct tccccgtggt tccaagactg ctgaaccgga tgtttgaccg 1200
aattttcgga caagcaaaca ccaccgtgaa gcgatggctc ttggactttg cctccaagag 1260
gaaagaagca gacgttcgca gcggcatcat cagaaacaac agcctgtggg accggctgat 1320
cttccacaaa gtacagtcga gcctgggcgg aagagtccgg ctgatggtga caggagccgc 1380
cccggtgtct gccactgtgc tgacgttcct cagagcagcc ctgggctgtc agttttatga 1440
aggatacgga cagacagagt gcactgccgg gtgctgccta accatgcctg gagactggac 1500
cacaggccat gttggggccc cgatgccgtg caatttgata aaacttggtt ggcagttgga 1560
agaaatgaat tacatggcgt ccgagggcga gggcgaggtg tgtgtgaaag ggccaaatgt 1620
atttcagggc tacttgaagg acccagcgaa aacagcagaa gctttggaca aagacggctg 1680
gttacacaca ggggacatcg gaaaatggtt accaaatggc accttgaaaa ttatcgaccg 1740
gaaaaagcac atatttaagc tggcacaagg agaatacata gcccctgaaa agattgaaaa 1800
tatctacatg cgaagtgagc ctgttgctca ggtgtttgtc cacggagaaa gcctgcaggc 1860
atttctcatt gcaattgtgg taccagatgt tgagacatta tgttcctggg cccaaaagag 1920
aggatttgaa gggtcgtttg aggaactgtg cagaaataag gatgtcaaaa aagctatcct 1980
cgaagatatg gtgagacttg ggaaggattc tggtctgaaa ccatttgaac aggtcaaagg 2040

-continued

```
catcacattg caccctgaat tattttctat cgacaatggc cttctgactc caacaatgaa   2100

ggcgaaaagg ccagagctgc ggaactattt caggtcgcag atagatgacc tctattccat   2160

catcaaggtt tagtgtgaag aagaaagctc agaggaaatg gcacagttcc acaatctctt   2220

ctcctgctga tggccttcat gttgttaatt ttgaatacag caagtgtagg gaaggaagcg   2280

ttctgtgttt gacttgtcca ttcggggttc ttctcatagg aatgctagag gaaacagaac   2340

actgccttac agtcacctca gtgttcagac catgtttatg gtaatacaca cttccaaaag   2400

tagccttaaa aattgtaaag ggatactata aatgtgctaa ttatttgaga cttcctcagt   2460

ttaaaaagtg ggttttaaat cttctgtctc cctgtttttc taatcaaggg gttaggactt   2520

tgctatctct gagatgtctg ctacttcgtc gaaattctgc agctgtctgc tgctctaaag   2580

agtacagtgc tctagaggga agtgttccct ttaaaaataa gaacaactgt cctggctgga   2640

gatctcacaa gcggaccaga gatcttttta aatccctgct actgtccctt ctcacaggca   2700

ttcacagaac ccttctgatt cgaagggtta cgaaactcat gttcttctcc agtcccctgt   2760

ggtttctgtt ggagcataag gtttccagta agcgggaggg cagatccaac tcagaaccat   2820

gcagataagg agcctctggc aaatgggtgc tgcatcagaa cgcgtggatt ctctttcatg   2880

gcagatgctc ttggactcgg ttctccaggc ctgattcccc gactccatcc tttttcaggg   2940

ttatttaaaa atctgcctta gattctatag tgaagacaag catttcaaga aagagttacc   3000

tggatcagcc atgctcagct gtgacgcctg ataactgtct actttatctt cactgaacca   3060

ctcactctgt gtaaaggcca acggattttt aatgtggttt tcatatcaaa agatcatgtt   3120

gggattaact tgcctttttc cccaaaaaat aaactctcag gcaaggcatt tcttttaaag   3180

ctattccg                                                            3188
```

<210> SEQ ID NO 33
<211> LENGTH: 1342
<212> TYPE: DNA
<213> ORGANISM: Homo sapiens

<400> SEQUENCE: 33

```
tcccccactc tcaaggatgc tgtgaggggt attcctccca tgtggtgart tgggaggwtt     60

tcctgaggtc cttttccatc ctgagacgct ggttttccat tttgtttctc acaggccagg    120

gctttgaccg acacttgttt gctctgcggc atctggcagc agccaaaggg atcatcttgc    180

ctgagctcta cctggaccct gcatacgggc agataaacca caatgtcctg tccacgagca    240

cactgagcag cccagcagtg aaccttgggg gctttgcccc tgtggtctct gatggctttg    300

gtgttgggta tgctgttcat gacaactgga taggctgcaa tgtctcttcc tacccaggcc    360

gcaatgcccg ggagtttctc caatgtgtgg agaaggcctt agaagacatg tttgatgcct    420

tagaaggcaa atccatcaaa agttaacttc tgggcagatg aaaagctacc atcacttcct    480

catcatgaaa actgggaggc cgggcatggt ggctcatgcc tgtaatccca gcattttgag    540

aggctgaggc gggtggatca cttgaggtca ggagtttgag accaacctgg ccaacatggt    600

gaaaccttgt ctctactaaa aatacaagaa ttagctgggt gtggtggcat gtgcctatat    660

cccagctact gggaggttga agcagaattg cttgaaccca ggaggtggag gttgcagtga    720

gctgagatca caccactgca ctccggcctg ggcgacagag cgagactgtc tcaaaaagac    780

aaaaaagaaa aaaaactggg gcctgtgtag ccagtgggtg ctattctgtg aaactaatca    840

taagctgcct aggcagccag ctacaggctt gagctttaaa ttcatggttt taaagctaaa    900

cgtaatttcc acttgggact agatcacaac tgaagrtaac aagagattta agttttaagg    960
```

-continued

```
gcatttaatc aggaggaaag gtttggaaaa ctaactcagg tgtatttatt gtttaagcag   1020
aaataaagtt taatttttgc ttgaagatgg ttcttaattt cttttaacct aattcctaat   1080
cctcacaaag atctttccaa cagcaagttc agtaagttca ggtaacagta cgtcaccatt   1140
ggcttctggc tcattgagtg atggtgggat cgcggtttca tctctgtaaa cttgcccttg   1200
actggggaga taccatctcc ttaaaaatac tcttcatttc tcctaaggag tgaactsctg   1260
ctgcacgaat tcttatttgt ggagggagta gcttgctccc ttactttcac cycccatgca   1320
accagtgcag ggtkaacagg gg                                            1342
```

<210> SEQ ID NO 34
<211> LENGTH: 4859
<212> TYPE: DNA
<213> ORGANISM: Homo sapiens

<400> SEQUENCE: 34

```
cacgttgggt gacataatgg ggttttttta attatagatt cacactgcat ttattcatca     60
cccctgtcct ctcatccata actcaaattt actaccagca acacaaaata caaagatgtg    120
tccagtttca ctacagctct tcgcgtttac aagtgtcgag cgcttgcttt cggaacgccc    180
ttgtgattgg ccgagccaat gccagtgaca tcaaccaact tacttttgat tggaaggctg    240
gttgctggga ctgtagcgtt tgcaggaagt cacttaactg tttgggagct ggaaaaccga    300
agctgaagtt ctcttttgcc ataggaacga gcgcaactga ctaggaaaga tgtgtcccaa    360
agctccgcaa gctggaacgt gagccaggag gcccggaccg gccacgggac cgcgaggcac    420
tccgaaagtg tgcggctgcc ccttccctgc ctcccagctg ttaccctttt aaatgtcagt    480
gttcgaggct gtaggggtag cacgaggcag cgaaacggaa cagtcggatt ggccgcacgc    540
ctcagttcta gacgcacctc tccaccgaag ccgttctgac tggcaggggg agaaagtaaa    600
cagagttgaa tcaccctccc cactggccaa ttggaggggg tttggtttgt gacgtgatgg    660
gattctgcga aattgttact gagcaagaga atgccggaac gtgcggaccg gccggagcag    720
gggttcagaa gccgtcagtg gactcgggaa aaagtgtctc ttagacctgg cgctcggcgg    780
ggccctcgcc acccgcgtcg gggtgatcgg gtgaatgtcc tggggctttg gctcgacggc    840
gaggcggccg agggcgtgca cctctcttgc agtttcctct cccagcgcct cgggggcgtt    900
ttcagtcgaa taaacttgcg accgccacgt gtggcatctt tccaagggag ccggctcaga    960
ggggccggcg cgcccgtcgg gggatcgcgg ccggcgcggg gcaggggcgg cggctagagg   1020
cggcggcgcg gcggagcccg gggccgtgga tgctgcgtgc ggaggcgctg ccggttacgt   1080
aaagatgagg ggctgaggtc gcctcggcgc tcctgcgagt cggaagcgcc ccgcgccccc   1140
gccccccttgg ccgccgcgcc gtgccgggcg ggcgggtcgt cgtccgaggc cagggagggc   1200
gagccgaacc tccgcagcca ccgccaagtt tgtccgcgcc gcctgggctg ccgtcgcccg   1260
caccatgtcc gcggccgcct acatggactt cgtggctgcc cagtgtctgg tttccatttc   1320
gaaccgcgct gcggtgccgg agcatggggt cgctccggac gccgagcggc tgcgactacc   1380
tgagcgcgag gtgaccaagg agcacggtga cccgggggac acctggaagg attactgcac   1440
actggtcacc atcgccaaga gcttgttgga cctgaacaag taccgaccca tccagacccc   1500
ctccgtgtgc agcgacagtc tggaaagtcc agatgaggat atgggatccg acagcgacgt   1560
gaccaccgaa tctgggtcga gtccttccca cagcccggag gagagacagg atcctggcag   1620
cgcgcccagc ccgctctccc tcctccatcc tggagtggct gcgaaggggga aacacgcctc   1680
```

-continued cgaaaagagg cacaagtgcc cctacagtgg ctgtgggaaa gtctatggaa aatcctccca 1740
tctcaaagcc cattacagag tgcatacagg tgaacggccc ttcccctgca cgtggccaga 1800
ctgccttaaa aagttctccc gctcagacga gctgacccgc cactaccgga cccacactgg 1860
ggaaaagcag ttccgctgtc cgctgtgtga gaagcgcttc atgaggagtg accacctcac 1920
aaagcacgcc cggcggcaca ccgagttcca ccccagcatg atcaagcgat cgaaaaaggc 1980
gctggccaac gctttgtgag gtgctgcccg tggaagccag ggagggatgg accccgaaag 2040
gacaaaagta ctcccaggaa acagacgcgt gaaaactgag ccccagaaga ggcacacttg 2100
acggcacagg aagtcactgc tctttggtca atattctgat tttcctctcc ctgcattgtt 2160
tttaaaaagc acattgtagc ctaagatcaa agtcaacaac actcggtccc cttgaagagg 2220
caactctctg aacccgtctc tgactgttgg agggaaggca aatgcttttg ggtttttttgg 2280
tttttgtttt tgtttttttt tctcctttta tttttttgcg ggggagggta gggagtgggt 2340
gggggggagg gggtaaggcc aagactgggt agattttaaa gattcaacac tggtgtacat 2400
atgtccgctg ggtgagttga cctgtggcct cgcacagtga ttctaggccc tttatgcttg 2460
ctgtctctca gaattgtttt cttacctttt aatgtaatga cgagtgtgct tcagtttgtt 2520
tagcaaaacc actctcttga atcacgttaa cttttgagat taaaaaaaaa aacgccatag 2580
cacagctgtc tttatgcaag caagagcaca tctactccag catgatctgt catctaaaga 2640
cttgaaaaca aaaaacagtt acttatagtc aatgggtaag cagagtctga atttatacta 2700
atcaagacaa acctttgaaa ggttacacta agtacagaac ttttaaacct tgctttgtat 2760
gagttgtact ttttgaacat aagctgcact tttattttct aatgcagagg atgaataagt 2820
taaatacatg ctttgaggat agaagcagat gttctgtttg gcaccacgtt ataatctgct 2880
tattttacaa tatacacgtt tccctaagaa atcatgcgca gagatgtgag ggcagaatat 2940
acacaacaga tgctgaagga gaaggagggt agtgttttgc aaaagaaaaa gaaaagaacc 3000
aacagaattt taactctatt aacttttcca aattttccta tgcttttagt taacatcatt 3060
attgtatcct aatgccacta ggggagagag cttttgactc tgttgggttt tatttgaatg 3120
tgtgcataac agtaatgaga tctggaaaca cctatttttt ggggaaaaag gtttgttggt 3180
ctccttcctg tgttcctaca aaactcccac tctcaggtgc aagagttatg tagaaggaaa 3240
gggagctgaa ataggaacag aaaaatcaac ccctataact agtgaacacc aagggaaaat 3300
accacaatga tttcagagga gactctgcaa aatcgtccct tgtggagaat gcaggcaaca 3360
tggaatacta cgaatgaaat cacatcactg tatcttttac atcaatagcc tcaccactaa 3420
tatatcttgt atctaggtgt ctataatggc tgaaaccact acatccatct atgccattta 3480
cctgaaaact taactgtggc ctttatgagg ccagaaaagt gaactgagtt ttgtagttaa 3540
gacctcaaat gaggggagtc agcagtgatc atgggggaaa tgtttacatt ttttttttct 3600
tcagaagtaa cgctttctga tgattttatc tgatatttaa aacagggagc tatggtgcac 3660
tctagtttat acttgcgctc tgaaatgtgt aaacataggg tgcctaccta tttcacctga 3720
cccatactcg tttctgattc agaatcagtg tgggctcctg cagtgggcgc gggtcacggc 3780
tgactccaac ttccaataca acagccatca ctagcacagt gtttttttgt ttaaccaacg 3840
tagtgttatt agtagttcta taaagagaac tgcttttaac attagggact gggagcagtc 3900
catgggataa aaaggaaagt gttttctcac gagaaaacat gtcaggaaaa ataaagaaca 3960
ctttctacct ctgtttcaga tttttgaaac acttatttta aaccaaattt taatttctgt 4020
gtccaaaata agttttaagg acatctgttc ttccatacga aataggttag gctgcctatt 4080

-continued tctcactgag ctcatggaat ggttctgctt atgatactct gcacgctgcc ttttagtgag 4140
tgaggagttt ggggttgcct agcacttgct aacttgtaaa aagtcatctt tccctcacag 4200
aaagaaacga aagaaagcaa agcaaagtca gtgaaagaca atctttatag tttcaggagt 4260
aaatctaaat gtggcttttg tcaagcactt agatggatat aaatgcagca acttgtttta 4320
aaaaaatgca catttacttc ccaaaaaagt tgttacttgc cttttcaagt gtgacaaact 4380
cacatttgat attctcttat atgttatagt aatgtaacgt ataaactcaa gcctttttat 4440
tctttgtgat taaatcctgt tttaaaatgt cacaaaacag gaaccagcat tctaattaga 4500
tttactatat caagatatgg ttcaaatagg actactagag ttcattgaac actaaaacta 4560
tgaaacaatt actttttata ttaaaaagac catggattta acttatgaaa atccaaatgc 4620
aggatagtaa tttttgttta cttttttaac caaactgaat ttttgaaaga ctattgcagg 4680
tgtttaaaaa gaaagaaaag ttgttttatc taatactgta agtagttgtc atattctgga 4740
aaatttaata gttttagagt taagatatct cctctctttg gttagggaag aagaaagccc 4800
ttcaccattg tggaatgatg ccctggcttt aaggtttagc tccacatcat gcttctctt 4859

<210> SEQ ID NO 35
<211> LENGTH: 1941
<212> TYPE: DNA
<213> ORGANISM: Homo sapiens

<400> SEQUENCE: 35
tctcttgatt cctagtctct cgatatggca cctccgtcag tctttgccga ggttccgcag 60
gcccagcctg tcctggtctt caagctcact gccgacttca gggaggatcc ggaccccccgc 120 aaggtcaacc tgggagtggg agcatatcgc acggatgact gccatccctg ggttttgcca 180
gtagtgaaga aagtggagca gaagattgct aatgacaata gcctaaatca cgagtatctg 240
ccaatcctgg gcctggctga gttccggagc tgtgcttctc gtcttgccct tggggatgac 300
agcccagcac tcaaggagaa gcgggtagga ggtgtgcaat ctttgggggg aacaggtgca 360
cttcgaattg gagctgattt cttagcgcgt tggtacaatg gaacaaacaa caagaacaca 420
cctgtctatg tgtcctcacc aacctgggag aatcacaatg ctgtgttttc cgctgctggt 480
tttaaagaca ttcggtccta tcgctactgg gatgcagaga agagaggatt ggacctccag 540
ggcttcctga atgatctgga gaatgctcct gagttctcca ttgttgtcct ccacgcctgt 600
gcacacaacc caactgggat tgacccaact ccggagcagt ggaagcagat tgcttctgtc 660
atgaagcacc ggtttctgtt ccccttcttt gactcagcct atcagggctt cgcatctgga 720
aacctggaga gagatgcctg ggccattcgc tattttgtgt ctgaaggctt cgagttcttc 780
tgtgcccagt ccttctccaa gaacttcggg ctctacaatg agagagtcgg gaatctgact 840
gtggttggaa aagaacctga gagcatcctg caagtccttt cccagatgga gaagatcgtg 900
cggattactt ggtccaatcc ccccgcccag ggagcacgaa ttgtggccag caccctctct 960
aaccctgagc tctttgagga atggacaggt aatgtgaaga caatggctga ccggattctg 1020
accatgagat ctgaactcag ggcacgacta gaagccctca aaacccctgg gacctggaac 1080
cacatcactg atcaaattgg catgttcagc ttcactgggt tgaaccccaa gcaggttgag 1140
tatctggtca atgaaaagca catctacctg ctgccaagtg gtcgaatcaa cgtgagtggc 1200
ttaaccacca aaaatctaga ttacgtggcc acctccatcc atgaagcagt caccaaaatc 1260
cagtgaagaa acaccacccg tccagtacca ccaaagtagt tctctgtcat gtgtgttccc 1320

-continued

```
tgcctgcaca aacctacatg tacataccat ggattagaga cacttgcagg actgaaagct   1380

gctctggtga ggcagcctct gtttaaaccg gccccacatg aagagaacat cccttgagac   1440

gaatttggag actgggatta gagcctttgg aggtcaaagc aaattaagat ttttatttaa   1500

gaataaaaga gtactttgat catgagacat aggtatcttg tccctctcac taaaaaggag   1560

tgttgtgtgt ggcggccacg tgcttctatg tggtgtttga ctctgtacaa attctagtcc   1620

caaagatcaa gttgtctgaa ggagccaaag tgtgaatgtg ggtgtcggct gcggcattaa   1680

attcatcatc tcaacccaga gtgtctggtc tccctgctct ttctgcatgg ttgtgtccct   1740

agtcctaagc tttggttctt tagggtgact gtggtaagaa ggatatttaa tcatgacatg   1800

cacggacacg tacatattta actgaaacaa gttttaccaa acagtattta ctcgtgatgt   1860

gcgtagtgca ttctgatatt tttgagccat tctattgtgt tctacttcac ctaaaaaaat   1920

aaaataaaaa tgttgatcaa g                                             1941
```

<210> SEQ ID NO 36
<211> LENGTH: 2727
<212> TYPE: DNA
<213> ORGANISM: Homo sapiens

<400> SEQUENCE: 36

```
agaagagcgg agctgtgagc agtactgcgg cctcctctcc tctcctaacc tcgctctcgc     60

ggcctagctt tacccgcccg cctgctcggc gaccagaaca ccttccacca tgaccacctc    120

agcaagttcc cacttaaata aaggcatcaa gcaggtgtac atgtccctgc ctcagggtga    180

gaaagtccag gccatgtata tctggatcga tggtactgga gaaggactgc gctgcaagac    240

ccggaccctg gacagtgagc ccaagtgtgt ggaagagttg cctgagtgga atttcgatgg    300

ctctagtact ttacagtctg agggttccaa cagtgacatg tatctcgtgc ctgctgccat    360

gtttcgggac cccttccgta aggaccctaa caagctggtg ttatgtgaag ttttcaagta    420

caatcgaagg cctgcagaga ccaatttgag gcacacctgt aaacggataa tggacatggt    480

gagcaaccag cacccctggt ttggcatgga gcaggagtat accctcatgg ggacagatgg    540

gcaccccttt ggttggcctt ccaacggctt cccagggccc cagggtccat attactgtgg    600

tgtgggagca gacagagcct atggcaggga catcgtggag gcccattacc gggcctgctt    660

gtatgctgga gtcaagattg cggggactaa tgccgaggtc atgcctgccc agtgggaatt    720

tcagattgga ccttgtgaag gaatcagcat gggagatcat ctctgggtgg cccgtttcat    780

cttgcatcgt gtgtgtgaag actttggagt gatagcaacc tttgatccta agcccattcc    840

tgggaactgg aatggtgcag gctgccatac caacttcagc accaaggcca tgcgggagga    900

gaatggtctg aagtacatcg aggaggccat tgagaaacta agcaagcggc accagtacca    960

catccgtgcc tatgatccca agggaggcct ggacaatgcc cgacgtctaa ctggattcca   1020

tgaaacctcc aacatcaacg acttttctgc tggtgtagcc aatcgtagcg ccagactacg   1080

cattccccgg actgttggcc aggagaagaa gggttacttt gaagatcgtc gcccctctgc   1140

caactgcgag ccccttttcgg tgacagaagc cctcatccgc acgtgtcttc tcaatgaaac   1200

cggcgatgag cccttccagt acaaaaatta agtggactag acctccagct gttgagcccc   1260

tcctagttct tcatccctga ctccaactct tccccctctc ccagttgtcc cgattgtaac   1320

tcaaagggtg gaatatcaag gtcgtttttt tcattccatg tgcccagtta atcttgcttt   1380

cttttgtttg gctgggatag aggggtcaag ttattaattt cttcacacct accctccttt   1440

ttttccctat cactgaagct ttttagtgca ttagtgggga ggagggtggg gagacataac   1500
```

-continued

```
cactgcttcc atttaatggg gtgcacctgt ccaataggcg tacgtatccg gacagagcac   1560
gtttgcagag ggtctctct ccaggtagct gaaagggaag acctgacgta ctctggttag   1620
gttaggactt gccctcgtgg tggaaacttt tcttaaaaag ttataaccaa cttttctatt   1680
aaaagtggga attaggagag aaggtagggg ttgggaatca gagagaatgg ctttggtctc   1740
ttgcttgtgg gactagcctg gcttgggact aaatgccctg ctctgaacac aagcttagta   1800
taaactgatg gatatcccta ccttgaaaga agaaaaggtt cttactgctt ggtccttgat   1860
ttatcacaca aagcagaata gtatttttat atttaaatgt aaagacaaaa aactatatgt   1920
atggttttgt ggattatgtg tgttttggct aaaggaaaaa accatccagg tcacggggca   1980
ccaaatttga gacaaatagt cggattagaa ataaagcatc tcattttgag tagagagcaa   2040
ggaagtggtt cttagatggt gatctgggat taggccctca agaccccttt tgggtttctg   2100
ccctgcccac cctctggaga aggtggcact gattagttaa cagaccaaca ccgttactag   2160
cagtcactga tctccgtggc tttggtttaa aagacacact tgtccacata ggtttagaga   2220
taagagttgg ctggtcaact tgagcatgtt actgacagag ggggtattgg ggttattttc   2280
tggtaggaat agcatgtcac taaagcaggc ctttgatatt aaattttta aaaagcaaaa   2340
ttatagaagt ttagatttta atcaaatttg tagggtttct aggtatttac agatgctgtt   2400
gctcaacgtc tcctacctct gctctgagag atgggacagg ctgagtcaaa cactgtaatt   2460
ttgtatcttg atgtctttgt taagactgct gaagaattat tttttctttt ataataagga   2520
ataaacccca cctttattcc ttcatttcat ctaccatttt ctggttcttg tgttggctgt   2580
ggcaggccag ctgtggtttt cttttgccat gacaacttct aattgccatg tacagtatgt   2640
tcaaagtcaa ataactcctc attgtaaaca aactgtgtaa ctgcccaaag cagcacttat   2700
aaatcagcct aacataaaaa aaaaaaa                                       2727
```

<210> SEQ ID NO 37
<211> LENGTH: 831
<212> TYPE: DNA
<213> ORGANISM: Homo sapiens

<400> SEQUENCE: 37

```
gttgacaaga gacattccag cccaccactt cccaagtaaa gaattaaaat gcagcatgat     60
ggctaaggca agggcctgca gaagaatgta aaggagggag gaagagcagg ggattcagag    120
caggaaggag gagacagtac tgtctatccc gcagacgtgg tgctctttga agggatcctg    180
gccttctact cccaggaaag gtacgagacc tgttccagat gaagcttttt gtggatacag    240
atgcggacac ccggctctca cgcagagtat taagggacat cagcgagaga ggcagggatc    300
ttgagcagat tttatctcag tacattacgt tcgtcaagcc tgcctttgag gaattctgct    360
tgccaacaaa gcagtatgct gatgtgatca tccctagagg tgcagataat ctggtggcca    420
tcaacctcat cgagcagcac atccaggaca tcctgaatgg agggccctcc aaacggcaga    480
ccaatggctg tctcaacggc tacacccctt cacgcaagag gcaggcatcg gagtccagca    540
gcaggccgca ttgacccgtc tccatcggac cccagcccct atctccaaga gacagaggag    600
gcgtcaggag gcactgctca tctgtacata ctgtttccta tgacattact gtatttaaga    660
aaacaccatg gagatgaaat gcctttgatt tttttttct ttttgtactt tggaacgaca    720
aaatgaaaca gaacttgacc ctgagcttaa ataacaaaac tgtgccaact actactggtg    780
atgcctaatt atgaatccaa cgtgtaacca gtaataaata catatatata t             831
```

-continued

<210> SEQ ID NO 38
<211> LENGTH: 3288
<212> TYPE: DNA
<213> ORGANISM: Homo sapiens

<400> SEQUENCE: 38
cttcctctcc acgcggttga gaagaccggt cggcctgggc aacctgcgct gaagatgccg 60
ggaaaactcc gtagtgacgc tggtttggaa tcagacaccg caatgaaaaa aggggagaca 120
ctgcgaaagc aaatcgagga gaaagagaaa aaagagaagc caaaatctga taagactgaa 180
gagatagcag aagaggaaga aactgttttc cccaaagcta aacaagttaa aaagaaagca 240
gagccttctg aagttgacat gaattctcct aaatccaaaa aggcaaaaaa gaaagaggag 300
ccatctcaaa atgacatttc tcctaaaacc aaaagtttga gaaagaaaaa ggagcccatt 360
gaaaagaaag tggtttcttc taaaaccaaa aaagtgacaa aaaatgagga gccttctgag 420
gaagaaatag atgctcctaa gcccaagaag atgaagaaag aaaaggaaat gaatggagaa 480
actagagaga aaagccccaa actgaagaat ggatttcctc atcctgaacc ggactgtaac 540
cccagtgaag ctgccagtga agaaagtaac agtgagatag agcaggaaat acctgtggaa 600
caaaaagaag gcgctttctc taattttccc atatctgaag aaactattaa acttctcaaa 660
ggccgaggag tgaccttcct atttcctata caagcaaaga cattccatca tgtttacagc 720
gggaaggact taattgcaca ggcacggaca ggaactggga agacattctc ctttgccatc 780
cctttgattg agaaacttca tggggaactg caagacagga agagaggccg tgcccctcag 840
gtactggttc ttgcacctac aagagagttg gcaaatcaag taagcaaaga cttcagtgac 900
atcacaaaaa agctgtcagt ggcttgtttt tatggtggaa ctccctatgg aggtcaattt 960
gaacgcatga ggaatgggat tgatatcctg gttggaacac caggtcgtat caaagaccac 1020
atacagaatg gcaaactaga tctcaccaaa cttaagcatg ttgtcctgga tgaagtggac 1080
cagatgttgg atatgggatt tgctgatcaa gtggaagaga ttttaagtgt ggcatacaag 1140
aaagattctg aagacaatcc ccaaacattg ctttttttctg caacttgccc tcattgggta 1200
tttaatgttg ccaagaaata catgaaatct acatatgaac aggtggacct gattggtaaa 1260
aagactcaga aaacggcaat aactgtggag catctggcta ttaagtgcca ctggactcag 1320
agggcagcag ttattgggga tgtcatccga gtatatagtg gtcatcaagg acgcactatc 1380
atcttttgtg aaaccaagaa agaagcccag gagctgtccc agaattcagc tataaagcag 1440
gatgctcagt ccttgcatgg agacattcca cagaagcaaa gggaaatcac cctgaaaggt 1500
tttagaaatg gtagttttgg agttttggtg gcaaccaatg ttgctgcacg tgggttagac 1560
atccctgagg ttgatttggt tatacaaagc tctccaccaa aggatgtaga gtcctacatt 1620
catcgatccg ggcggacagg cagagctgga aggacggggg tgtgcatctg cttttatcag 1680
cacaaggaag aatatcagtt agtacaagtg gagcaaaaag cgggaattaa gttcaaacga 1740
ataggtgttc cttctgcaac agaaataata aaagcttcca gcaaagatgc catcaggctt 1800
ttggattccg tgcctcccac tgccattagt cacttcaaac aatcagctga gaagctgata 1860
gaggagaagg gagctgtgga agctctggca gcagcactgg cccatatttc aggtgccacg 1920
tccgtagacc agcgctcctt gatcaactca aatgtgggtt ttgtgaccat gatcttgcag 1980
tgctcaattg aaatgccaaa tattagttat gcttggaaag aacttaaaga gcagctgggc 2040
gaggagattg attccaaagt gaagggaatg gtttttctca aaggaaagct gggtgtttgc 2100
tttgatgtac ctaccgcatc agtaacagaa atacaggaga aatggcatga ttcacgacgc 2160

-continued

```
tggcagctct ctgtggccac agagcaacca gaactggaag gaccacggga aggatatgga   2220

ggcttcaggg gacagcggga aggcagtcga ggcttcaggg gacagcggga cggaaacaga   2280

agattcagag gacagcggga aggcagtaga ggcccgagag gacagcgatc aggaggtggc   2340

aacaaaagta acagatccca aaacaaaggc cagaagcgga gtttcagtaa agcatttggt   2400

caataattag aaatagaaga tttatatagc aaaaagagaa tgatgtttgg caatatagaa   2460

ctgaacatta tttttcatgc aaagttaaaa gcacattgtg cctccttttg accacttgcc   2520

aagtccctgt ctctttcaga cacagacaag cttcatttaa attatttcat ctgatcatta   2580

tcatttataa ctttattgtt acttcttcat cagtttttcc ttttgaaagg tgtatgaatt   2640

cattacattt ttattctaat gtattatctg tagattagaa gataaaatca agcatgtatc   2700

tgcctatact ttgtgagttc acctgtcttt atactcaaaa gtgtccctta atagtgtcct   2760

tccctgaaat aaatacctaa gggagtgtaa cagtctctgg aggaccactt tgagcctttg   2820

gaagttaagg tttcctcagc cacctgccga acagtttctc atgtggtcct attatttgtc   2880

tactgagact taatactgag caatgttttg aaacaagatt tcaaactaat ctgggttgta   2940

atacagttta taccagtgta tgctctagac ttggaagatg tagtatgttt gatgtggatt   3000

acctatactt atgttcgttt tgatacattt ttagcttctc attataaggt gattcatgct   3060

ttagtgaatt cttatagatg atatataaaa gtacatttta atagaagcca gggtttaagg   3120

aatttcacat gtataaggtg gctccatagc tttatttgta agtaggctgg ataaatggtg   3180

cttaaatggt aatgtactcc acttcttccc attggaagat taacattatt taccaagaag   3240

gacttaaggg agtagggggc gcagattagc attgctcaag agtatgga               3288
```

<210> SEQ ID NO 39
<211> LENGTH: 3442
<212> TYPE: DNA
<213> ORGANISM: Homo sapiens

<400> SEQUENCE: 39

```
agccggtgcg ccgcagacta gggcgcctcg ggccagggag cgcggaggag ccatggccac     60

cgctaacggg gccgtggaaa acgggcagcc ggacgggaag ccgccggccc tgccgcgccc    120

catccgcaac ctggaggtca agttcaccaa gatatttatc aacaatgaat ggcacgaatc    180

caagagtggg aaaaagtttg ctacatgtaa cccttcaact cgggagcaaa tatgtgaagt    240

ggaagaagga gataagcccg acgtggacaa ggctgtggag gctgcacagg ttgccttcca    300

gaggggctcg ccatggcgcc ggctggatgc cctgagtcgt gggcggctgc tgcaccagct    360

ggctgacctg gtggagaggg accgcgccac cttggccgcc ctggagacga tggatacagg    420

gaagccattt cttcatgctt ttttcatcga cctggagggc tgtattagaa ccctcagata    480

ctttgcaggg tgggcagaca aaatccaggg caagaccatc cccacagatg acaacgtcgt    540

atgcttcacc aggcatgagc ccattggtgt ctgtggggcc atcactccat ggaacttccc    600

cctgctgatg ctggtgtgga agctggcacc cgccctctgc tgtgggaaca ccatggtcct    660

gaagcctgcg gagcagacac ctctcaccgc cctttatctc ggctctctga tcaaagaggc    720

cgggttccct ccaggagtgg tgaacattgt gccaggattc gggcccacag tgggagcagc    780

aatttcttct caccctcaga tcaacaagat cgccttcacc ggctccacag aggttggaaa    840

actggttaaa gaagctgcgt cccggagcaa tctgaagcgg gtgacgctgg agctgggggg    900

gaagaacccc tgcatcgtgt gtgcggacgc tgacttggac ttggcagtgg agtgtgccca    960
```

-continued

```
tcagggagtg ttcttcaacc aaggccagtg ttgcacggca gcctccaggg tgttcgtgga   1020
ggagcaggtc tactctgagt ttgtcaggcg gagcgtggag tatgccaaga aacggcccgt   1080
gggagacccc ttcgatgtca aaacagaaca ggggcctcag attgatcaaa agcagttcga   1140
caaaatctta gagctgatcg agagtgggaa gaaggaaggg gccaagctgg aatgcggggg   1200
ctcagccatg gaagacaagg ggctcttcat caaacccact gtcttctcag aagtcacaga   1260
caacatgcgg attgccaaag aggagatttt cgggccagtg caaccaatac tgaagttcaa   1320
aagtatcgaa gaagtgataa aaagagcgaa tagcaccgac tatggactca cagcagccgt   1380
gttcacaaaa aatctcgaca aagccctgaa gttggcttct gccttagagt ctggaacggt   1440
ctggatcaac tgctacaacg ccctctatgc acaggctcca tttggtggct ttaaaatgtc   1500
aggaaatggc agagaactag gtgaatacgc tttggccgaa tacacagaag tgaaaactgt   1560
caccatcaaa cttggcgaca agaacccctg aaggaaaggc ggggctcctt cctcaaacat   1620
cggacggcgg aatgtggcag atgaaatgtg ctggaggaaa aaaatgacat ttctgacctt   1680
cccgggacac attcttctgg aggctttaca tctactggag ttgaatgatt gctgttttcc   1740
tctcactctc ctgtttattc accagactgg ggatgcctat aggttgtctg tgaaatcgca   1800
gtcctgcctg gggagggagc tgttggccat ttctgtgttt ccctttaaac cagatcctgg   1860
agacagtgag atactcaggg cgttgttaac agggagtggt atttgaagtg tccagcagtt   1920
gcttgaaatg ctttgccgaa tctgactcca gtaagaatgt gggaaaaccc cctgtgtgtt   1980
ctgcaagcag ggctcttgca ccagcggtct cctcagggtg gacctgctta cagagcaagc   2040
cacgcctctt tccgaggtga aggtgggacc attccttggg aaaggattca cagtaaggtt   2100
ttttggtttt tgttttttgt tttcttgttt ttaaaaaaag gatttcacag tgagaaagtt   2160
ttggttagtg cataccgtgg aagggcgcca gggtctttgt ggattgcatg ttgacattga   2220
ccgtgagatt cggcttcaaa ccaatactgc ctttggaata tgacagaatc aatagcccag   2280
agagcttagt caaagacgat atcacggtct accttaacca aggcactttc ttaagcagaa   2340
aatattgttg aggttacctt tgctgctaaa gatccaatct tctaacgcca caacagcata   2400
gcaaatccta ggataattca cctcctcatt tgacaaatca gagctgtaat tcactttaac   2460
aaattacgca tttctatcac gttcactaac agcttatgat aagtctgtgt agtcttcctt   2520
ttctccagtt ctgttaccca atttagatta gtaaagcgta cacaactgga aagactgctg   2580
taataacaca gccttgttat ttttaagtcc tattttgata ttaatttctg attagttagt   2640
aaataacacc tggattctat ggaggacctc ggtcttcatc caagtggcct gagtatttca   2700
ctggcaggtt gtgaattttt cttttcctct ttgggaatcc aaatgatgat gtgcaatttc   2760
atgttttaac ttgggaaact gaaagtgttc ccatatagct tcaaaaacaa aaacaaatgt   2820
gttatccgac ggatactttt atggttacta actagtactt tcctaattgg gaaagtagtg   2880
cttaagtttg caaattaagt tggggagggc aataataaaa tgagggcccg taacagaacc   2940
agtgtgtgta taacgaaaac catgtataaa atgggcctat cacccttgtc agagatataa   3000
attaccacat ttggcttccc ttcatcagct aacacttatc acttatacta ccaataactt   3060
gttaaatcag gatttggctt catacactga attttcagta ttttatctca agtagatata   3120
gacactaacc ttgatagtga tacgttagag ggttcctatt cttccattgt acgataatgt   3180
ctttaatatg aaatgctaca ttatttataa ttggtagagt tattgtatct ttttatagtt   3240
gtaagtacac agaggtggta tatttaaact tctgtaatat actgtattta gaaatggaaa   3300
tatatatagt gttaggtttc acttctttta aggtttaccc ctgtggtgtg gtttaaaaat   3360
```

-continued ctataggcct gggaattccg atcctagctg cagatcgcat cccacaatgc gagaatgata 3420
aaataaaatt ggatatttga ga 3442

<210> SEQ ID NO 40
<211> LENGTH: 1540
<212> TYPE: DNA
<213> ORGANISM: Homo sapiens

<400> SEQUENCE: 40
gccctcggcc ccgggccggc ccgccccgcc tcggccgccg cctggcgagc cgccgggtcc 60
ccgctcggcc ggtggccgag gccggagggc cgcggcgggc ggcggccgag gcggctccgg 120
ccagggccgg gccgggggcc gggggcggc ggcgggcagg cggccgcgtc ggccggggcc 180
gggacgatga ctctggagtc catgatggcg tgttgcctga gcgatgaggt gaaggagtcc 240
aagcggatca acgccgagat cgagaagcag ctgcggcggg acaagcgcga cgcccggcgc 300
gagctcaagc tgctgctgct cggcacgggc gagagcggga agagcacgtt catcaagcag 360
atgcgcatca tccacggcgc cggctactcg gaggaggaca agcgcggctt caccaagctc 420
gtctaccaga acatcttcac cgccatgcag gccatgatcc gggccatgga gacgctcaag 480
atcctctaca agtacgagca gaacaaggcc aatgcgctcc tgatccggga ggtggacgtg 540
gagaaggtga ccaccttcga gcatcagtac gtcagtgcca tcaagaccct gtgggaggac 600
ccgggcatcc aggaatgcta cgaccgcagg cgcgagtacc agctctccga ctctgccaag 660
tactacctga ccgacgttga ccgcatcgcc accttgggct acctgcccac ccagcaggac 720
gtgctgcggg tccgcgtgcc caccaccggc atcatcgagt accctttcga cctggagaac 780
atcatcttcc ggatggtgga tgtgggggc cagcggtcgg agcggaggaa gtggatccac 840
tgctttgaga acgtgacatc catcatgttt ctcgtcgccc tcagcgaata cgaccaagtc 900
ctggtggagt cggacaacga gaaccggatg gaggagagca aagccctgtt ccggaccatc 960
atcacctacc cctggttcca gaactcctcc gtcatcctct tcctcaacaa gaaggacctg 1020
ctggaggaca agatcctgta ctcgcacctg gtggactact tccccgagtt cgatggtccc 1080
cagcgggagc cccaggcggc gcgggagttc atcctgaaga tgttcgtgga cctgaacccc 1140
gacagcgaca agatcatcta ctcacacttc acgtgtgcca ccgacacgga gaacatccgc 1200
ttcgtgttcg cggccgtgaa ggacaccatc ctgcagctca acctcaagga gtacaacctg 1260
gtctgagcgc cccaggccca gggagacggg atggagacac ggggcaggac cttccttcca 1320
cggagcctgc gctgccgggc gggtggcgct gccgagtccg ggccggggct ctgccgcggg 1380
aggagatttt tttttttca tatttttaac aaatggtttt tatttcacag ttatcagggg 1440
atgtacatct ctccctccgt acacttcgcg caccttctca ccttttgtca acggcaaagg 1500
cagccttttt ctggccttga cttatggctc gctttttct 1540

<210> SEQ ID NO 41
<211> LENGTH: 1517
<212> TYPE: DNA
<213> ORGANISM: Homo sapiens

<400> SEQUENCE: 41
attctttggg gaggcaacta ggatggtgtg gccgaccacg gatttgcatt gccgaggacg 60
ggaccccagg gcagcgaagc agaatggcca acatgcaggg actggtggaa agactggaac 120
gagctgtcag ccgcctggag tcgctgtctg cagagtccca caggccccct gggaactgcg 180

-continued

```
gggaagtcaa tggtgtcatt gcaggtgtgg caccctccgt ggaagccttt gacaagctga    240

tggacagtat ggtggccgag tttttaaaga acagtaggat ccttgctggg gacgtggaga    300

cccatgcaga aatggtgcac agtgctttcc aggcccagcg ggctttcctt ctgatggcct    360

ctcagtacca acaaccccac gagaatgacg tggccgcact tctgaaaccc atatcggaaa    420

agattcagga aatccaaact ttcagagaga gaaaccgggg gagtaacatg tttaatcatc    480

tttcggccgt cagcgaaagc atccctgccc ttggatggat agctgtgtct cccaaacctg    540

gtccttatgt caaggagatg aatgacgctg ccacctttta cactaacagg gtcttaaagg    600

actacaaaca cagtgatttg cgtcatgtgg attgggtgaa gtcatatttg aacatttgga    660

gtgaacttca agcatacatc aaggaacacc acaccacggg cctcacatgg agcaaaacag    720

gtcctgtagc atccacagta tcagcgtttt ctgtcctctc ctctgggcct ggccttcctc    780

cacccccctcc tcctctgcct cctccagggc cacctccact tttcgagaat gaaggcaaaa    840

aagaggaatc ttctccttca cgctcagctt tatttgccca acttaaccag ggagaagcaa    900

ttacaaaagg gctccgccat gtcacagatg accagaagac atacaaaaat cccagcctgc    960

gggctcaagg agggcaaact caatctccca ccaaaagtca cactccaagt cccacatctc   1020

ctaaatctta tccttctcaa aaacatgccc cagtgttgga gttggaagga aagaaatgga   1080

gagtggagta ccaagaggac aggaatgacc ttgtgatttc agagactgag ctgaaacaag   1140

tggcttacat tttcaaatgc gaaaaatcaa ctattcagat aaaagggaaa gtaaactcca   1200

ttataattga caactgtaag aaactcggcc tggtgtttga caatgtggtg ggcattgtgg   1260

aagtgatcaa ctcccaggac attcaaatcc aggtaatggg gagagtgcca acaatttcca   1320

ttaataagac agaaggttgc cacatatacc tcagtgaaga tgcattagac tgtgagatcg   1380

tgagcgccaa gtcatctgaa atgaacatac ttatccctca ggatggtgat tatagagaat   1440

ttcccattcc tgaacagttc aagacagcat gggatggatc caagttaatc actgaacctg   1500

cagaaattat ggcctaa                                                  1517
```

<210> SEQ ID NO 42
<211> LENGTH: 1616
<212> TYPE: DNA
<213> ORGANISM: Homo sapiens

<400> SEQUENCE: 42

```
tgctgaacca tttttcttag gatgcagccg tctcactccc ttgtcctgta aatcgtgtat     60

tcatgttgat gattcttgga gataggtttc actttttccc agctgcgtcc acaggaaagg    120

ggagtcggat gccagctgca ccccgcctgg ctcgcacagg ctaagaccac agacagagca    180

gggcttcccg gagccacaca ggccacgcac cccaggaacc cttgctgccg cgggccagga    240

acaggaatgt gttggtgcct gagacaccaa atggaagaag cacatcaaga ctgttctcct    300

gcggccaaca ctggcccgga agccgccctc catacaggcc ctcagggggc ctgccttctg    360

cgcctcagtc ccccgtgcat ccctgggcct gggtatcaca tgctctccag gaaagggacg    420

gaatcaatcg tgtgaccgat gggctcgcaa ggatgggtgc cgccgtggga gccctgcctc    480

tggtgctggc aagggattgg gtttgtgtgg gtgtctctag cctgcagagt gcagtgagtg    540

agagtccttg ggagcgcggc gctgcctgta gctgtgcctg gggatgcacg tggccacggg    600

atttcagtgg gacagcgctc ccacaggggc tgggggtggg ggtggggttt cttagttact    660

gttggaaagg gaaaaattca ccatatccaa ggggagagac gatgggctgg gtttgtttac    720

tccaacttcc cttctacacc cctcctgcag gacagtacga tttggggaga acccagctcc    780
```

-continued

```
ccactttatc tgcagactct gggacctgac aaaacagtca gagcctgagt gcactgcagc    840

ctgaactccc ttgagcagcg ctataaggga ctttgcactt taaaaagggg atgcctgtca    900

gtaaatcccc tgtgcattga ctagaactgg ggggctgcgc ccgctccctc cttaatccta    960

gatgatttgc tcatgaaata gaggtggggg acgaccgcat gcactctggg aggtgcagcc   1020

ctaaggggtg gactccagat ctccctgcaa gagacagctt ggcttggctt tggctgttgg   1080

ggaggagtcc ctgccatccc ggtgagcctg gggctgttgc ttagggtctt ctgggtggac   1140

acgtggagaa agagaaggca aacgttggaa cactaggaaa agctagaaat tcagacaaca   1200

cacatggatc cccttaaaac atgtaaatgt gtcagaacac ggttgacctg ccgccttctt   1260

gaacctggtg gcccccgttg gaactatcag tggcgtctcc catgcacacg ccctctgctt   1320

tctctttcct agactcgcgg tgctcacatc cagacattac cttgttggta gcccccaagt   1380

ggcgtgcagt gacaccagta tcttctctgt tgcatttttg caatcttgtg tcccgctcgg   1440

tgatgttcta caactctgtt ttaaggttga gaaagtttca agggtgaaga tctcaaaaca   1500

gtgctaaaat caaaggtgtt tgctgtgaag aaaaacatgt gtatatattg caccttgagt   1560

tgtcagaagg tagaaactga aataaactaa ctttaaaaaa aaaaaaaaaa aaaaaa       1616
```

<210> SEQ ID NO 43
<211> LENGTH: 2408
<212> TYPE: DNA
<213> ORGANISM: Homo sapiens

<400> SEQUENCE: 43

```
ccgcgcctcc tcggccgcct gtcgggcatg aaaaccaaat tctgcaccgg gggcgaggcg     60

gagccctcgc cgctcgggct gctgctgagc tgcggtagcg gcagcgcggc cccggcgccc    120

ggcgtggggc agcagcgcga cgccgccagc gacctcgagt ccaagcagct ggcgccaaca    180

gccgcgctcg cgctgccccc tccgccgccg ctgccgctgc cgctgccgct gccccagccc    240

ccgccgccgc agccgccccgc agacgagcag ccggagcccc gggcgcggcg cagggcctat    300

ctgtggtgca aggagttcct gcccggcgcc tggcggggcc tccgcgagga cgagttccac    360

atcagtgtca tcagaggcgg ccttagcaac atgctgttcc agtgctccct acctgacacc    420

acagccaccc ttggtgatga gcctcggaaa gtgctcctgc ggctgtatgg agcgattttg    480

cagatgaggt cctgtaataa agagggatcc gaacaagctc agaaagaaaa tgaatttcaa    540

ggggctgagg ccatggttct ggagagcgtt atgtttgcca ttctcgcaga gaggtcactt    600

gggccaaaac tctatggcat ctttccccaa ggccgactgg agcagttcat cccgagccgg    660

cgattagata ctgaagaatt aagtttgcca gatatttctg cagaaatcgc cgagaaaatg    720

gctacatttc atggtatgaa aatgccattc aataaggaac caaaatggct tttggcaca     780

atggaaaagt atctaaagga agtgctgaga attaaattta ctgaggaatc cagaattaaa    840

aagctccaca aattgctcag ttacaatctg cccttggaac tggaaaacct gagatcattg    900

cttgaatcta ctccatctcc agttgtattt tgtcataatg actgtcaaga aggtaatatc    960

ttgttgctgg aaggccgaga gaattctgaa aaacagaaac tgatgctcat tgatttcgaa   1020

tacagcagtt acaattacag ggattcgac attggaaatc acttctgtga gtggatgtat    1080

gattatagct atgaaaaata cccttttttc agagcaaaca tccggaagta tcccaccaag   1140

aaacaacagc tccattttat ttccagttac ttgcctgcat tccaaaatga ctttgaaaac   1200

ctcagtactg aagaaaaatc cattataaaa gaagaaatgt tgcttgaagt taataggttt   1260
```

-continued

```
gcccttgcat ctcatttcct ctggggactg tggtccattg tacaagccaa gatttcatct   1320

attgaatttg ggtacatgga ctacgcccaa gcaaggtttg atgcctattt ccaccagaag   1380

aggaagcttg ggtgtgactt gtggggagga ctccatccac ctcatcactg gactgcatgg   1440

ggaggcagca gagcgcggtc ccctctgtgc ttcgactact gctcctgtgg caggaggctt   1500

tgggtggctc actactgaac acatgtgtat gatactaaag acggtattaa aatggagcga   1560

cgtttatttc atctcttgtt tacgatttca ctaggactca gaaacgagat cgggaagacg   1620

aaatatagtg caatagtgca acatctctga atccttttaa tctagagaag gcatttcata   1680

tttgggggct aaggtttcca gtcagatgag gcaaacagca agagtaagca gtgttacttg   1740

caggtacttt ggttaatgtt gactttaaat tttcatgaat gtgctggtga acactgtgac   1800

caggcttttg tagatggcga ctgtgttata gacggtgctc actcccaagg gacagcaagt   1860

gagcagagat gtactgcaaa gtcgccagtc actgcgtgca aggtggcctc tgcctggggc   1920

cgtccagaag ctgctccttt accctcttgg tcccatggct gaagcggagc agctggattg   1980

ctctggagca gccaaggccg ccactgtgga gacagagctc tcccctcctg ctgggcgtgt   2040

gtgacactgt agagtttcac tgtactcgat gtgacttctc ccctgccctt cctcctgatg   2100

gagtgtgcag acagccatgc gtggccacgg gggcagtgtg aggacctccc tgtctcccgc   2160

tcccctccca gggagcagct gcttgaccta gctctttggg cctctcctgc cctctgctct   2220

gcctggagtg tcggatcctg tgagtaggct gggcctcccc tgggcagggt tctccaaggc   2280

cggtttcccg gcccttacca aacctgatgc ccctgacatc atcattcttg tgggagacag   2340

cagcctgtat gtggtgtggg gcgtggatcg agtgtagctg tgaaatccat atatatgaaa   2400

tgtccaat                                                            2408
```

```
<210> SEQ ID NO 44
<211> LENGTH: 1610
<212> TYPE: DNA
<213> ORGANISM: Homo sapiens
<220> FEATURE:
<221> NAME/KEY: misc_feature
<222> LOCATION: (1)..(1610)
<223> OTHER INFORMATION: n = a, c, g or t

<400> SEQUENCE: 44

cgtaacagga caaggagtcc tgctccggca cgtggccaca gaaaactact taggaagcct     60

gtggtgagaa caacaacagt gcctggagaa tcccacggct ctggggaagt gagccccgag    120

gatgaggctg ctcgcctggc tgattttcct ggctaactgg ggaggtgcca gggctgaacc    180

agggaagttc tggcacatcg ctgacctgca ccttgaccct gactacaagg tatccaaaga    240

ccccttccag gtgtgcccat cagctggatc ccagccagtg cccgacgcag gcccctgggg    300

tgactacctc tgtgattctc cctgggccct catcaactcc tccatctatg ccatgaagga    360

gattgagcca gagccagact tcattctctg gactggtgat gacacgcctc atgtgcccga    420

tgagaaactg ggagaggcag ctgtactgga aattgtggaa cgcctgacca agctcatcag    480

agaggtcttt ccagatacta aagtctatgc tgctttggga aatcatgatt ttcaccccaa    540

aaaccagttc ccagctggaa gtaacaacat ctacaatcag atagcagaac tatggaaacc    600

ctggcttagt aatgagtcca tcgctctctt caaaaaaggt gccttctact gtgagaagct    660

gccgggtccc agcggggctg ggcgaattgt ggtcctcaac accaatctgt actataccag    720

caatgcgctg acagcagaca tggcggaccc tggccagcag ttccagtggc tggaagatgt    780

gctgaccgat gcatccaaag ctggggacat ggtgtacatt gtcggccacg tgcccccggg    840
```

-continued

```
gttctttgag aagacgcaaa acaaggcatg gttccgggag ggcttcaatg aaaaatacct    900
gaaggtggtc cggaagcatc atcgcgtcat agcagggcag ttcttcgggc accaccacac    960
cgacagcttt cggatgctct atgatgatgc aggtgtcccc ataagcgcca tgttcatcac   1020
acctggagtc accccatgga aaaccacatt acctggagtg gtcaatgggg ccaacaatcc   1080
agccatccgg gtgttcgaat atgaccgagc cacactgagc ctnnaggaca tggtgaccta   1140
cttcatgaac ctgagccagg cgaatgctca ggggacgccg cgctgggagc tcgagtacca   1200
gctgaccgag gcctatgggg tgccggacgc cagcgcccac tccatcgaca cagtgctgga   1260
ccgcatcgct ggcgaccaga gcacactgca gcgctactac gtctataact cagtcagcta   1320
ctctgctggg gtctgcgacg aggcctgcag catgcagcac gtgtgtgcca tgcgccaggt   1380
ggacattgac gcttacacca cctgtctgta tgcctctggc accacgcccg tgccccagct   1440
nccgntgctg ctgatggccc tgctggggct gtgcacgact cgtgctgtga cctgccaggc   1500
tcaccattct tcctggtaac gggtaacggg ggcagcgccc aggatcaccc agagctgggc   1560
cttccaccat ttcctccgcg cctgaggagt gaactgaatg gacaccgatc              1610
```

<210> SEQ ID NO 45
<211> LENGTH: 1882
<212> TYPE: DNA
<213> ORGANISM: Homo sapiens

<400> SEQUENCE: 45

```
gggcaggaag acggcgctgc ccggaggagc ggggcgggcg ggcgcgcggg ggagcgggcg     60
gcgggcggga gccaggcccg ggcgggggcg ggggcggcgg ggccagaaga ggcggcgggc    120
cgcgctccgg ccggtctgcg gcgttggcct tggctttggc tttggcggcg gcggtggaga    180
agatgctgca gtccctggcc ggcagctcgt gcgtgcgcct ggtggagcgg caccgctcgg    240
cctggtgctt cggcttcctg gtgctgggct acttgctcta cctggtcttc ggcgcagtgg    300
tcttctcctc ggtggagctg ccctatgagg acctgctgcg ccaggagctg cgcaagctga    360
agcgacgctt cttggaggag cacgagtgcc tgtctgagca gcagctggag cagttcctgg    420
gccgggtgct ggaggccagc aactacggcg tgtcggtgct cagcaacgcc tcgggcaact    480
ggaactggga cttcacctcc gcgctcttct tcgccagcac cgtgctctcc accacaggtt    540
atggccacac cgtgcccttg tcagatggag gtaaggcctt ctgcatcatc tactccgtca    600
ttggcattcc cttcaccctc ctgttcctga cggctgtggt ccagcgcatc accgtgcacg    660
tcacccgcag gccggtcctc tacttccaca tccgctgggg cttctccaag caggtggtgg    720
ccatcgtcca tgccgtgctc cttgggtttg tcactgtgtc ctgcttcttc ttcatcccgg    780
ccgctgtctt ctcagtcctg gaggatgact ggaacttcct ggaatccttt tatttttgtt    840
ttatttccct gagcaccatt ggcctggggg attatgtgcc tggggaaggc tacaatcaaa    900
aattcagaga gctctataag attgggatca cgtgttacct gctacttggc cttattgcca    960
tgttggtagt tctggaaacc ttctgtgaac tccatgagct gaaaaaattc agaaaaatgt   1020
tctatgtgaa gaaggacaag gacgaggatc aggtgcacat catagagcat gaccaactgt   1080
ccttctcctc gatcacagac caggcagctg gcatgaaaga ggaccagaag caaaatgagc   1140
cttttgtggc cacccagtca tctgcctgcg tggatggccc tgcaaaccat tgagcgtagg   1200
atttgttgca ttatgctaga gcaccagggt cagggtgcaa ggaagaggct taagtatgtt   1260
catttttatc agaatgcaaa agcgaaaatt atgtcacttt aagaaatagc tactgtttgc   1320
```

-continued aatgtcttat taaaaaacaa caaaaaaaga cacatggaac aaagaagctg tgaccccagc 1380
aggatgtcta atatgtgagg aaatgagatg tccacctaaa attcatatgt gacaaaatta 1440
tctcgacctt acataggagg agaatacttg aagcagtatg ctgctgtggt tagaagcaga 1500
ttttatactt ttaactggaa actttggggt ttgcatttag atcatttagc tgatggctaa 1560
atagcaaaat ttatatttag aagcaaaaaa aaaaagcata gagatgtgtt ttataaatag 1620
gtttatgtgt actggtttgc atgtacccac ccaaaatgat tatttttgga gaatctaagt 1680
caaactcact atttataatg cataggtaac cattaactat gtacatataa agtataaata 1740
tgtttatatt ctgtacatat ggtttaggtc accagatcct agtgtagttc tgaaactaag 1800
actatagata ttttgtttct tttgatttct ctttatacta aagaatccag agttgctaca 1860
ataaaataag gggaataata aa 1882

<210> SEQ ID NO 46
<211> LENGTH: 1805
<212> TYPE: DNA
<213> ORGANISM: Homo sapiens

<400> SEQUENCE: 46
aagagactga actgtatctg cctctatttc caaaagactc acgttcaact ttcgctcaca 60
caaagccggg aaaattttat tagtcctttt tttaaaaaaa gttaatataa aattatagca 120
aaaaaaaaaa ggaacctgaa ctttagtaac acagctggaa caatcgcagc ggcggcggca 180
gcggcgggag aagaggttta atttagttga ttttctgtgg ttgttggttg ttcgctagtc 240
tcacggtgat ggaagctgca cattttttcg aagggaccga gaagctgctg gaggtttggt 300
tctcccggca gcagcccgac gcaaaccaag gatctgggga tcttcgcact atcccaagat 360
ctgagtggga catacttttg aaggatgtgc aatgttcaat cataagtgtg acaaaaactg 420
acaagcagga agcttatgta ctcagtgaga gtagcatgtt tgtctccaag agacgtttca 480
ttttgaagac atgtggtacc accctcttgc tgaaagcact ggttcccctg ttgaagcttg 540
ctagggatta cagtgggttt gactcaattc aaagcttctt ttattctcgt aagaatttca 600
tgaagccttc tcaccaaggg tacccacacc ggaatttcca ggaagaaata gagtttctta 660
atgcaatttt cccaaatgga gcaggatatt gtatgggacg tatgaattct gactgttggt 720
acttatatac tctggatttc ccagagagtc gggtaatcag tcagccagat caaaccttgg 780
aaattctgat gagtgagctt gacccagcag ttatggacca gttctacatg aaagatggtg 840
ttactgcaaa ggatgtcact cgtgagagtg gaattcgtga cctgatacca ggttctgtca 900
ttgatgccac aatgttcaat ccttgtgggt attcgatgaa tggaatgaaa tcggatggaa 960
cttattggac tattcacatc actccagaac cagaattttc ttatgttagc tttgaaacaa 1020
acttaagtca gacctcctat gatgacctga tcaggaaagt tgtagaagtc ttcaagccag 1080
gaaaatttgt gaccaccttg tttgttaatc agagttctaa atgtcgcaca gtgcttgctt 1140
cgccccagaa gattgaaggt tttaagcgtc ttgattgcca gagtgctatg ttcaatgatt 1200
acaattttgt ttttaccagt tttgctaaga agcagcaaca acagcagagt tgattaagaa 1260
aaatgaagaa aaaacgcaaa aagagaacac atgtagaagg tggtggatgc tttctagatg 1320
tcgatgctgg gggcagtgct ttccataacc accactgtgt agttgcagaa agccctagat 1380
gtaatgatag tgtaatcatt ttgaattgta tgcattatta tatcaaggag ttagatatct 1440
tgcatgaatg ctctcttctg tgtttaggta ttctctgcca ctcttgctgt gaaattgaag 1500
tggatgtaga aaaaaccttt tactatatga aactttacaa cacttgtgaa agcaactcaa 1560

-continued

```
tttggtttat gcacagtgta atatttctcc aagtatcatc caaaattccc cacagacaag   1620
gctttcgtcc tcattaggtg ttggcctcag cctaaccctc taggactgtt ctattaaatt   1680
gctgccagaa ttttacatcc agttacctcc actttctaga acatattctt tactaatgtt   1740
attgaaacca atttctactt catactgatg tttttggaaa cagcaattaa agtttttctt   1800
ccatg                                                               1805
```

<210> SEQ ID NO 47
<211> LENGTH: 2653
<212> TYPE: DNA
<213> ORGANISM: Homo sapiens

<400> SEQUENCE: 47

```
gagcgcggct ggagtttgct gctgccgctg tgcagtttgt tcaggggctt gtggcggtga     60
gtccgagagg ctgcgtgtga gagacgtgag aaggatcctg cactgaggag gtggaaagaa    120
gaggattgct cgaggaggcc tggggtctgt gagacagcgg agctgggtga aggctgcggg    180
ttccggcgag gcctgagctg tgctgtcgtc atgcctcaaa cccgatccca ggcacaggct    240
acaatcagtt ttccaaaaag gaagctgtct cgggcattga acaaagctaa aaactccagt    300
gatgccaaac tagaaccaac aaatgtccaa accgtaacct gttctcctcg tgtaaaagcc    360
ctgcctctca gccccaggaa acgtctgggc gatgacaacc tatgcaacac tccccattta    420
cctccttgtt ctccaccaaa gcaaggcaag aaagagaatg gtccccctca ctcacataca    480
cttaagggac gaagattggt atttgacaat cagctgacaa ttaagtctcc tagcaaaaga    540
gaactagcca aagttcacca aaacaaaata ctttcttcag ttagaaaaag tcaagagatc    600
acaacaaatt ctgagcagag atgtccactg aagaaagaat ctgcatgtgt gagactattc    660
aagcaagaag gcacttgcta ccagcaagca aagctggtcc tgaacacagc tgtcccagat    720
cggctgcctg ccagggaaag ggagatggat gtcatcagga atttcttgag ggaacacatc    780
tgtgggaaaa aagctggaag cctttacctt tctggtgctc ctggaactgg aaaaactgcc    840
tgcttaagcc ggattctgca agacctcaag aaggaactga aaggctttaa aactatcatg    900
ctgaattgca tgtccttgag gactgcccag gctgtattcc cagctattgc tcaggagatt    960
tgtcaggaag aggtatccag gccagctggg aaggacatga tgaggaaatt ggaaaaacat   1020
atgactgcag agaagggccc catgattgtg ttggtattgg acgagatgga tcaactggac   1080
agcaaaggcc aggatgtatt gtacacgcta tttgaatggc catggctaag caattctcac   1140
ttggtgctga ttggtattgc taataccctg gatctcacag atagaattct acctaggctt   1200
caagctagag aaaaatgtaa gccacagctg ttgaacttcc caccttatac cagaaatcag   1260
atagtcacta ttttgcaaga tcgacttaat caggtatcta gagatcaggt tctggacaat   1320
gctgcagttc aattctgtgc ccgcaaagtc tctgctgttt caggagatgt tcgcaaagca   1380
ctggatgttt gcaggagagc tattgaaatt gtagagtcag atgtcaaaag ccagactatt   1440
ctcaaaccac tgtctgaatg taaatcacct tctgagcctc tgattcccaa gagggttggt   1500
cttattcaca tatcccaagt catctcagaa gttgatggta acaggatgac cttgagccaa   1560
gagggagcac aagattcctt ccctcttcag cagaagatct tggtttgctc tttgatgctc   1620
ttgatcaggc agttgaaaat caaagaggtc actctgggga agttatatga agcctacagt   1680
aaagtctgtc gcaaacagca ggtggcggct gtggaccagt cagagtgttt gtcactttca   1740
gggctcttgg aagccagggg cattttagga ttaaagagaa acaaggaaac ccgtttgaca   1800
```

-continued

```
aaggtgtttt tcaagattga agagaaagaa atagaacatg ctctgaaaga taaagcttta   1860

attggaaata tcttagctac tggattgcct taaattcttc tcttacaccc cacccgaaag   1920

tattcagctg gcatttagag agctacagtc ttcattttag tgctttacac attcgggcct   1980

gaaaacaaat atgacctttt ttacttgaag ccaatgaatt ttaatctata gattctttaa   2040

tattagcaca gaataatatc tttgggtctt actattttta cccataaaag tgaccaggta   2100

gacccttttt aattacattc actacttcta ccacttgtgt atctctagcc aatgtgcttg   2160

caagtgtaca gatctgtgta gaggaatgtg tgtatattta cctcttcgtt tgctcaaaca   2220

tgagtgggta ttttttttgtt tgttttttttt gttgttgttg tttttgaggc gcgtctcacc   2280

ctgttgccca ggctggagtg caatggcgcg ttctctgctc actacagcac ccgcttccca   2340

ggttgaagtg attctcttgc ctcagcctcc cgagtagctg ggattacagg tgcccaccac   2400

cgcgcccagc taattttttta atttttagta gagacagggt tttaccatgt tggccaggct   2460

ggtcttgaac tcctgaccct caagtgatct gcccaccttg gcctccctaa gtgctgggat   2520

tataggcgtg agccaccatg ctcagccatt aaggtatttt gttaagaact ttaagtttag   2580

ggtaagaaga atgaaaatga tccagaaaaa tgcaagcaag tccacatgga gatttggagg   2640

acactggtta aag                                                        2653
```

<210> SEQ ID NO 48
<211> LENGTH: 1618
<212> TYPE: DNA
<213> ORGANISM: Homo sapiens

<400> SEQUENCE: 48

```
atgtcccggc cgcagcttcg acgctggcgc ctcgtctcta gcccgccgag cggcgtcccg     60

ggtctagcgc tgctggcgct gctggcgctg ctggcgctgc ggctcgcggc cgggaccgac    120

tgcccatgcc cggagcctga gctctgccgc ccgattcgcc accatccaga tttcgaggtc    180

tttgtgtttg atgttggaca gaaaacttgg aaatcttatg attggtcaca gattacaact    240

gtggcaacat ttggaaaata tgactcagaa cttatgtgct acgctcattc aaaaggagcc    300

agagtagtac ttaaaggaga tgtatcctta aaggatatca ttgatcctgc tttcagagca    360

tcctggatag ctcaaaaact taatttggcc aaaacacaat atatggatgg aattaatata    420

gatatagagc aagaagttaa ttgtttatca cctgaatatg atgcattaac tgctttagtc    480

aaagaaacta cagactcttt ccatcgtgaa attgagggat cacaggtaac ctttgatgta    540

gcttggtctc caaagaacat agacagaaga tgctataatt atactggaat cgcagatgct    600

tgtgacttcc tctttgtgat gtcttatgat gaacaaagtc agatctggtc agaatgtatt    660

gcagcagcca atgctcccta taatcagaca ttaactggat ataatgacta catcaagatg    720

agcattaatc ctaagaaact tgtaatgggt gttccttggt atggttatga ttatacctgc    780

ctgaatctgt ctgaggatca tgtttgtacc attgcaaaag tccctttccg gggggctcct    840

tgtagtgacg ctgcaggacg tcaggtgccc tacaaaacga tcatgaagca aataaatagt    900

tctatttctg gaaacctatg ggataaagat cagcgggctc cttattataa ctataaagat    960

cctgctggcc actttcatca agtatggtat gataaccctc agagtatttc tttaaaggca   1020

acatatatac aaaactatcg cttacggggc attggcatgt ggaatgcaaa ctgtcttgac   1080

tactctggag atgctgtagc caaacagcaa actgaagaaa tgtgggaagt cttaaagcca   1140

aagctgttac agagatgaac atctttgtc aaaccattaa gagttagaaa gatgatctgt    1200

atcaacagat ctagtttctt gcatttttat tatgttgcta tatacttttg ttatccgtat   1260
```

-continued

```
actaaaaaaa aagaataaat aaatgttttg attgtttgaa tttgaaaaat acacacgaat   1320
gtcctcagta tccaggaaca taaaggcaag aagcaagtca acttacctat taaatattcc   1380
tctattagat gtttcaacac tataatttaa ttgggaaaaa ttgctttcag aattttatta   1440
tgccatattt cccttcatta tagtaaaata tatgctcacg aatcaatgct gatttttaaa   1500
atatgtataa tctgaagtgg aaattgtttg cttagagttt ttaaaaacct agtctttgaa   1560
aagcagtttg tgctatactt ttcccccaac cctccaataa atcttaaatt taaaacct     1618
```

```
<210> SEQ ID NO 49
<211> LENGTH: 4814
<212> TYPE: DNA
<213> ORGANISM: Homo sapiens

<400> SEQUENCE: 49

ggcggcggga gccctggaac ggagcttcgt ggagctaagc ggagctgagc gcgaaaggcc     60
gaggcacttt cgggaattca cagtctgcag cattgggact gcaaatgccg tggctggcgc    120
cgtaaaatac agtgaaagcg cgggaggctt ttactacgtg gagagtggca agttgttctc    180
cgtaaccaga aacaggttca ttcattggaa gacctctgga gatacattgg agctgatgga    240
ggagtcactg gacataaatc tgttgaataa tgccattcgc ctaaaattcc aaaattgcag    300
tgttttacct ggaggggttt atgtctctga gactcagaat cgtgtgataa tcttgatgtt    360
aaccaatcaa acagtgcaca ggttactttt accacacccc tcccggatgt ataggagtga    420
gttggtagtt gacagtcaga tgcagtcaat attcactgac attggaaaag ttgatttcac    480
agatccttgc aactatcagt taattccagc agtacctgga atatctccta attccaccgc    540
ctctacagcc tggctcagca gtgatgggga ggccctgttt gccttaccat gtgcttctgg    600
gggaatcttt gttcttaagc tacctcctta tgacatacct ggtatggtgt cagtcgtgga    660
actgaaacag agttcagtaa tgcaacgatt gcttacaggc tggatgccaa cagctatcag    720
gggtgaccag tcgccttcag atcgtcccct cagtcttgct gttcattgtg tggagcatga    780
tgccttcatc tttgctttgt gtcaggatca taaactacga atgtggtctt acaaggagca    840
aatgtgccta atggtagctg acatgctgga gtatgtccct gtgaagaaag accttcggct    900
tactgctgga actggacaca aattacggct tgcttattcc cccaccatgg gactctacct    960
ggggatatac atgcatgcac caaaacgagg acagttctgc attttccagt tggtgagcac   1020
tgagagtaat cgctatagtc tcgatcatat ttcttcactg ttcacttctc aggagacact   1080
gattgacttt gccttaactt ccacggatat ctgggccctg tggcatgatg ctgagaacca   1140
aacagtagtg aaatacatca actttgaaca taatgttgca ggtcagtgga atccagtttt   1200
tatgcagcct ctgccagagg aagagattgt catcagagat gatcaagacc ccagagagat   1260
gtatctgcaa agtcttttta caccaggaca attcacaaat gaagctttat gtaaggcttt   1320
acagattttc tgccgaggaa ctgagaggaa tttggatctt tcctggagtg aactgaagaa   1380
agaagttact ttagctgttg aaaatgagct tcaaggaagt gtaacagagt atgaattctc   1440
ccaggaggag tttcgaaatt tacaacaaga attctggtgc aagttctatg cctgttgtct   1500
tcagtatcaa gaagccctct ctcaccctct tgccctacat ttgaatccac acacaaacat   1560
ggtgtgcctg ctgaaaaaag ggtacctgtc tttccttatt ccctcatcct tagtggatca   1620
tttgtatctc ctgccttatg agaacctttt gacagaagat gagacaacca tatctgatga   1680
tgtggatatc gctcgggatg tcatatgtct tataaaatgc ctccggctga ttgaagagtc   1740
```

-continued

```
agtaactgtg gatatgtcag ttataatgga aatgagttgt tataacctac agtctccgga   1800
aaaggctgca gagcagattc tggaagatat gatcactatt gatgtagaaa atgtgatgga   1860
ggatatttgt agtaaactgc aagagattag gaacccaatc catgcaattg gactacttat   1920
acgggaaatg gattatgaaa cagaagtgga aatggaaaag ggattcaatc cagctcagcc   1980
tttgaatatt cgaatgaatc ttacccagct ctatggtagt aacacagcag ggtatattgt   2040
gtgcagaggg gtgcataaaa tcgccagtac tcgtttcctg atctgcagag atcttttgat   2100
cttacagcag ctgttaatga ggcttggaga tgctgtgatt tggggaactg gtcagctctt   2160
tcaagctcag caagacctac tacatcgaac agctccccta ctcttatctt attacctcat   2220
taaatgggga agtgagtgct tggcaactga tgttccactt gacacactgg agtctaatct   2280
ccaacactta tcagtactgg aattaacaga ctctggtgct ttaatggcaa ataggtttgt   2340
atctagtcct cagactattg tggagttatt cttccaagaa gttgcaagaa aacacattat   2400
atctcacctc ttctctcagc caaaggcacc tctgagccaa actggattga attggcctga   2460
aatgattact gcaattacca gttatttatt gcagctttta tggcctagca atcctggttg   2520
tctctttcta gaatgtttga tgggaaattg ccaatatgta caattgcagg attatattca   2580
actgctacat ccctggtgtc aagtcaatgt tggttcctgt cgatttatgc tgggaaggtg   2640
ttacctagtt acaggagaag gacagaaggc tctggaatgt ttttgtcagg cagcatctga   2700
agtaggcaaa gaggaattct tggatcgctt gattcgctca gaggatgggg agatcgtgtc   2760
tacccccagg ctgcagtatt atgacaaggt tttacgacta ctagatgtca ttggtttgcc   2820
tgaactggtt attcagttgg ctacatcagc cataactgaa gcaagtgatg actggaaaag   2880
tcaggctact ctaaggacat gtattttcaa acatcatttg gatttgggtc acaatagcca   2940
agcatatgaa gccttaaccc aaattcctga ttccagcagg caattagatt gtttacggca   3000
gttggtggta gttctttgtg aacgctcaca gctacaggat cttgtagagt ttccctatgt   3060
gaatctgcat aatgaggttg tgggaataat tgagtcacgt gctagagctg tggaccttat   3120
gactcacaat tactatgaac ttctgtatgc ctttcacatc tatcgccaca attaccgcaa   3180
ggctggcaca gtgatgtttg agtatggaat gcggcttggc agagaagttc gaactctccg   3240
gggacttgag aaacaaggca actgttatct ggctgctctc aattgtttac gacttattcg   3300
tccagaatat gcgtggattg tgcagccagt gtctggtgca gtgtatgatc gccctggagc   3360
atcccctaag aggaatcatg atggagaatg cacagctgcc cccacaaatc gacaaattga   3420
aatcctggaa ctggaagatc tggagaaaga gtgttccttg gctcgcatcc gcctcacttt   3480
ggctcagcat gatccatcag cggttgcagt tgctggaagt tcatcagcag aggaaatggt   3540
cactctcttg gttcaggcgg gcctctttga cactgccata tcactctgtc agacttttaa   3600
gcttccctta acgccagtct ttgaagggct tgccttcaaa tgcatcaaat tgcaatttgg   3660
aggagaggca gcacaagcag aagcctgggc ctggctagca gccaatcagc tctcatctgt   3720
catcactact aaggagtcta gtgctacaga tgaagcatgg cgactattat ccacttacct   3780
ggagaggtac aaagtccaga ataacttgta tcaccactgt gtaatcaaca agctcttgtc   3840
tcatggagtg cctctgccta attggcttat aaacagtcac aacatcgcac tgtcccaaaa   3900
agttgataag gcaacacggg atttattata tcgtcggacc ttgtgatttg gattgtcacc   3960
tagcctttgt aaccgcttgg tgcctcttag gacttaagac taccctacag gaaccctgta   4020
ctcaaggccg atttttgtaa ctgtaaatga tgtgtacaac attcaagtct gcattctgca   4080
caagatagga gggcggaaga gtcagaggac cctgtgcttg ctggtggtgc taacacaatt   4140
```

-continued

```
tctggtgttc aaccttggtc tcaaatagct gcttttgtat atgattcacg agcttttta   4200

gagtttatat tttttaaac taccgaagac attcattatc tgcaaattaa gactcacctt   4260

cactttccaa aatagctgag ggttgttggc ttgttgtagc tgaccaccaa aagcagtcac   4320

tgcaaatctt ttaattcttc cctatcacct tttgtatttt aatgcaatta ttttggtcca   4380

gaactgacct gtattttctg tattgtacac aaaagctaat aattttgtgt actttttatt   4440

tattttggag gttttatatg atcttcaatt gagtattaaa taatttgcct agattaagcc   4500

taaaatgatg accagctaat taaagaagat attttgaatc tggttctgag ctaaagttga   4560

gtaaattctt agctaagaaa aaattggaaa tccatcatct atattagcaa cagattctca   4620

gagtaaattg ttaacttcta tgatttatga taatcaagct ggacttgatc atacaagtta   4680

gtctcataat gtattggacc aaaatgtaaa cttcattggt cagatttaga agcattcatg   4740

ctcacaagtt ttgggaaagt gaaaaataat aaaatcatct tggattttat tctgtatatt   4800

aaaatttatc tttt                                                    4814
```

```
<210> SEQ ID NO 50
<211> LENGTH: 6493
<212> TYPE: DNA
<213> ORGANISM: Homo sapiens
<220> FEATURE:
<221> NAME/KEY: misc_feature
<222> LOCATION: (1)..(6493)
<223> OTHER INFORMATION: n = a, c, g or t

<400> SEQUENCE: 50

gaattcaagt cttgttcctg cacattccac cctggagaaa tctggggcaa gtgactgttc     60

cccgggcctt agcttctcct gtcactggga catcacaaca gcacctacct tagggcaact    120

caggccaggg aagttggtgc tgcctcacct cccaatgtgc gtcctcctgg gcctggagcc    180

tcagggcctc tggaaggagg aagtgagcgc ctctgggcag gattcctggg aggcctggga    240

gagcaaggga agcgccaaga gctgagcaga gttctgggac tgatccatgg ccctttctct    300

ctcacctttc aggaggtggg ccccctccac ccccagcact tcccacctgg tcggtcccga    360

acggcccctc cccggaggag gtggagcagc agaaaaggtg gggctgggcc ctgggtgggg    420

aaccttagcc gctgccagag ttccatatgt tctggaaccc ttgactccta gagttcagaa    480

cccagccaac ttgcagtttt cagaatgttc aagaaacttc tgacactcag agttgcagaa    540

cctcctggtc cctgcagatt cctggaaatc agaatatggt ggttgaaaga atcttgtggc    600

tgggcgtggt ggctcacgcc tgtaatccca gcactctggg aggccgaggc gggcagatcg    660

cctgaggtca ggagtttgag accagcctgg ccaacatggc gaaatcccgt ctctactgaa    720

gataacaaaa attagccggt catggtggcg cccgtgcctg taatcccagc tcggcaggcc    780

gaggcaggag aatcgcttga acccgggagg cagaggttgc agtgagccaa gatcgagcca    840

ctgcactcca gcctgggtga cagagtctca aaaaaaaaaa aagaaaagaa agaatcttgg    900

gcattttgta attcggtgtt cctgacagtt tagtgactgg gatctcgcat cctgatctct    960

ccctgtcgct gccctgccct ccattccccc tactctcacc cagccccctt cttggttccc   1020

taggggagga aggcttgggt gagtattagg agccagccac cctggagacc tctgagagag   1080

aggacggagg tcgctggccc cttcgctggc catccttagg accctgattg acggcagctc   1140

tctcgcctcc ccccacaggc agcagcccgg cccgtcggag cacatagagc gccgggtctc   1200

caatgcaggt gatgctcaga tagcttcggg agttgggagg gggcctccct ggaggaagtg   1260
```

-continued

```
gccagccagc tggacagtga agaatgaggc ttctctctct cagctgcccc cttttctgtg   1320
tttgtttcag gaggcccacc tgctcccccc gctgggggtc cacccccacc accaggacct   1380
ccccctcctc caggtccccc cccacccccca ggtttgcccc cttcnggggt cccagctgca   1440
gcgcacggag cagggggagg accacccccct gcaccccctc tcccggcagc acagggccct   1500
ggtggtgggg gagctggggc cccaggcctg gccgcagcta ttgctggagc caaactcagg   1560
aaagtcagca aggtgagggg ccgggagagg tgggcagggg gcaacagggc ttttatgggg   1620
gatgaggcca gggctgccgg cggtgtcatt gggctggaag gccaaaaggc ctgcccctaa   1680
agctcctgcc ccttttaaat ttctccagca ggaggaggcc tcagggggggc ccacagcccc   1740
caaagctgag agtggtcgaa gcggaggtgg gggactcatg gaagagatga acgccatgct   1800
ggcccggagg tgagcctgag cctggacccc caagtcacct ggagttccag ttcagtaggg   1860
cccagtcaga ggagggctcc aattcctgtt tagtttgttt cttttggtga atgttccccc   1920
tttgataacc aggtttggga tataatggtg gggtttgtca tgaaatgcct gaggcttgca   1980
accacctagg tagcctgtag atgttctaaa acccagaatt ctagaaccgt aggagatctt   2040
tcctcagaat tctgggaact caggttcctg caatctcagt gttccaacac agcaccgctc   2100
caccctcgga atcttactgt tccctaatat aagaatcata gaacctcctc caccctgatt   2160
ctagaaccac aatctcttga attttttttt tttttttttt tttttttttg agatggagtc   2220
ttgctctgtc acccaggctg gagtgcagtg gtatgatctc ggtccactgc aacctccgcc   2280
tcctgggttc aggcagttct tctgcctcag cctcctaagt agccgggatt acaggcatga   2340
gtcaccacac ccggctaatt tttgtatttt tagtagacac aggatttcac catgttggcc   2400
aggctggtct tgaactcttg acctcaagag atccacctgc ttcagcctct caaagtgttg   2460
gcattacagg ccactgcgcc cagcacaatc tcttgaattt ctaaaactag agtttcctta   2520
ggttttcgga gttccagaat tctatgcgct aggatctaca tttctagaac tcccctcaga   2580
aggggatggg ttgggtgacg gaagcacgtg tttttgcttt tctctcctgc agaaggaaag   2640
ccacgcaagt tggggagaaa acccccaagg atgaatctgc caatgtaagt cagggactct   2700
tcttgcccta catctcttag gccgtaccat gagggtaggg atagtgggat gtgtggggtt   2760
tgaacctgaa agaggaaatg ggcagaggtg tggcaggggc tggctcatgg cagttttatt   2820
tcctaccagc aggaggagcc agaggccaga gtcccggccc agagtggtga gtagagtgcc   2880
cagtccagcc acaggaacta caaatcccag aatactctgt tctcacatgt taagcaccct   2940
tataggagag tcagggcgaa tggtgctggg gattgtagtc tcctgagatg gggctttgat   3000
caggggctga tgaggttggg ggagtaagat tgattggggg gcagtctttt gtccctgatc   3060
tttctgattt cttgcctatc cccagaatct gtgcggagac cctgggagaa gaacagcaca   3120
accttgccaa ggtaggccat cggtcctggg gcccttgggg aggtaaaggc gggcagatcg   3180
cttgagccca ggaggtcaag accagcctgg gcaacatggc gacaccccat ctctacaaaa   3240
attagccagg cgtggtagca cttacctgtg gtcccagcta ctcaggaggc tgaggtggga   3300
ggattacttg agcccaggaa gttgaggcct cagcgagcca tcatcatgcc tgcactccag   3360
cctgagaaat agaatgtgac tgtctcaaaa caaaacacaa caaaccaaaa ccaaaaaaaa   3420
aaaaaactgg ggccccaaaa atacttggac ttgcccaatt tataaggcag agctcaatgt   3480
gatccctgga ataggaggcg gggaagcagg tcctctctct aatctcattg ctgtcccaaa   3540
ccacaccaac tcccccagga tgaagtcgtc ttcttcggtg accacttccg agacccaacc   3600
ctgcacgccc agctccagtg attactcgga cctacagagg gtgaaacagg taacttgggg   3660
```

-continued gggaagttgg ggaccacagc aagagagatc taggtctggc ccctgccact ggcatgccgt 3720
atgatcctag ataacatctc agaaacctca ggtttccaat ctgacaaatg gagaaactgg 3780
attgggtcaa ggatgaccga gactccacac cccttttct ggcacctgtg acagacatta 3840
ttaatctatc accgcgctca ttccagatga gtgccttgaa ttctttccgc acattgaccc 3900
agctgtccat caccaattgg agttggcagg aggctggaat gcgcttgcca accttggtac 3960
tggatgttct ccagtacttt tccggctcca aggatccaga attctcccct agaatcctcc 4020
agtcactctg cgaccttgac agcgatgtca tggtgtcgat gtaggggtag gtctcaaacc 4080
tactccccct ggcttttcca tcaacaagaa agaggggact ctggcagggc acggtggctc 4140
atgtgtgtaa tttcagcaca ttgcgaggct gaggtgggag cattgcttga ggccaggagt 4200
ttgagaccag cctggggcaa catcgggaga cccccatctc taaaaataac ttttaaaagt 4260
tacctgagaa ggccaggtgc ggtggctcat gcctgtaatc ccagcacttt gggaggccga 4320
ggtgggtgga tcacctgagg tcaggggttc aagaccagcc tggccaacat ggtgaaaccc 4380
atcgctacta aaaatacaaa aattaggctg ggaatggtgg ctcacagcca taatcccagc 4440
agtttggaag gctgatgggg acggatcacg tgaagtcaaa agttcgagac cagcctggcc 4500
aacatggcga aaccctgtct ctactaaaaa tacaaaaatt agctgggcct tgtgggggc 4560
acctgtaatc cagttatttg ggcggctgag gcaggagaat cgcttgaacc cgggagccag 4620
agattgcagt cagccgagat tgggccactg cactgcagtc tgggtgacag ggagactctg 4680
tttcaaaaaa aaaaagaaaa agaaaaagtt acctgattgt ggcggcaggt gactgtggtc 4740
ccagctactt gggaggctaa ggcaggagga ttacctgagc ctgggaagtt gaggctgcaa 4800
tgagctgtga tcatgccatt gcaccctagc ctaggcaaca gagcaaggtt ccttctcaaa 4860
aaataaaaga aggggattc attcctgcaa gtcccggtac ccctcctgat tagttttacc 4920
ccattaattt taggagcttc tggaagaggt gaagaaggaa ttgcagaaag tgaaagagga 4980
aatcattgaa ggtgaggtgg tttgctttgg ttttgttctt aaacatttac ttattttgga 5040
ggcatcatgt ccctgggcaa gagccctgtt ttggaaggga ggaggcagag actctgcccc 5100
tgacctctgc tccttgtttc cttccagcct tcgtccagga gctgaggaag cggggttctc 5160
cctgaccaca gggacccaga agacccgctt ctcctttccg cacacccggc ctgtcaccct 5220
gctttccctg cctctacttg acttggaatt ggctgaagac tacacaggaa tgcatcgttc 5280
ccactcccca tcccacttgg aaaactccaa gggggtgtgg cttccctgct cacacccaca 5340
ctggctgctg attggctggg gaggccccg cccttttctc cctttggtcc ttcccctctg 5400
ccatcccctt ggggccggtc cctctgctgg ggatgcacca atgaacccca caggaagggg 5460
gaaggaagga gggaatttca cattcccttg ttctagattc actttaacgc ttaatgcctt 5520
caaagttttg gtttttttaa gaaaaaaaaa tatatatata tttgggtttt gggggaaaag 5580
ggaaattttt ttttctcttt ggttttgata aaatgggatg tgggagtttt taaatgctat 5640
agccctgggc ttgccccatt tggggcagct atttaagggg aggggatgtc tcaccgggct 5700
gggggtgaga catcccccca ccccagggac tccccttccc tctggctcct tccccttttc 5760
tatgaggaaa taagatgctg taactttttg gaacctcagt tttttgattt tttatttggg 5820
taggttttgg ggtccaggcc atttttttta ccccttggag gaaataagat gagggagaaa 5880
ggaaaagggg aggaaacttc tcccctccca ccttcacctt tagcttcttg aaaatgggcc 5940
cctgcagaat aaatctgcca gtttttataa atgctaagat ctctggagtg atttgaaggc 6000

-continued

```
ctgttctgat ggggatggag gtgtgctcgg cccccggtgc ccctccagga agatttggtc   6060
ctctgctgag aacccctgcc tcctcccagg aatccacctt cccttcatct tccttcccac   6120
cctgcatatt gcgcctgctc actcatcctc aggcccgcag ccaggatgat ctctgccccc   6180
tccagcctcc ctccccatgc cccttaggag gccacttcct ccccatccca ccctgccctt   6240
caccacccta ggggaggcca gaagcagcct cactttgtgt agccttgggc aagtccattt   6300
gcttacctca ggcctcagtt tctgatttgg gaaagggctc ataagatgat tctctgcccc   6360
cactctacca ctctcccagc ttctttcctc tttttttttt tttttttttt ttaatgagtt   6420
ggggtcttgc tctttcaccc agtctggagt gtagtggcag gatcacagct cactgcagcc   6480
ttgaactcct ggg                                                      6493
```

<210> SEQ ID NO 51
<211> LENGTH: 5629
<212> TYPE: DNA
<213> ORGANISM: Homo sapiens

<400> SEQUENCE: 51

```
gcgcgaccgt cccgggggtg gggccgggcg cagcggcgag aggaggcgaa ggtggctgcg     60
gtagcagcag cgcggcagcc tcggacccag cccggagcgc agggcggccg ctgcaggtcc    120
ccgctcccct ccccgtgcgt ccgcccatgg ccgccgccgg gcagctgtgc ttgctctacc    180
tgtcggcggg gctcctgtcc cggctcggcg cagccttcaa cttggacact cgggaggaca    240
acgtgatccg gaaatatgga gaccccggga gcctcttcgg cttctcgctg gccatgcact    300
ggcaactgca gcccgaggac aagcggctgt tgctcgtggg ggccccgcgc ggagaagcgc    360
ttccactgca gagagccaac agaacgggag ggctgtacag ctgcgacatc accgcccggg    420
ggccatgcac gcggatcgag tttgataacg atgctgaccc cacgtcagaa agcaaggaag    480
atcagtggat gggggtcacc gtccagagcc aaggtccagg gggcaaggtc gtgacatgtg    540
ctcaccgata tgaaaaaagg cagcatgtta atacgaagca ggaatcccga gacatctttg    600
ggcggtgtta tgtcctgagt cagaatctca ggattgaaga cgatatggat gggggagatt    660
ggagcttttg tgatgggcga ttgagaggcc atgagaaatt tggctcttgc cagcaaggtg    720
tagcagctac ttttactaaa gactttcatt acattgtatt tggagccccg ggtacttata    780
actggaaagg gattgttcgt gtagagcaaa agaataacac tttttttgac atgaacatct    840
ttgaagatgg gccttatgaa gttggtggag agactgagca tgatgaaagt ctcgttcctg    900
ttcctgctaa cagttactta ggtttttctt tggactcagg gaaaggtatt gtttctaaag    960
atgagatcac ttttgtatct ggtgctccca gagccaatca cagtggagcc gtggttttgc   1020
tgaagagaga catgaagtct gcacatctcc tccctgagca catattcgat ggagaaggtc   1080
tggcctcttc atttggctat gatgtggcgg tggtggacct caacaaggat gggtggcaag   1140
atatagttat tggagcccca cagtattttg atagagatgg agaagttgga ggtgcagtgt   1200
atgtctacat gaaccagcaa ggcagatgga ataatgtgaa gccaattcgt cttaatggaa   1260
ccaaagattc tatgtttggc attgcagtaa aaaatattgg agatattaat caagatggct   1320
acccagatat tgcagttgga gctccgtatg atgacttggg aaaggttttt atctatcatg   1380
gatctgcaaa tggaataaat accaaaccaa cacaggttct caagggtata tcaccttatt   1440
ttggatattc aattgctgga aacatggacc ttgatcgaaa ttcctaccct gatgttgctg   1500
ttggttccct ctcagattca gtaactattt tcagatcccg gcctgtgatt aatattcaga   1560
aaaccatcac agtaactcct aacagaattg acctccgcca gaaaacagcg tgtggggcgc   1620
```

-continued

```
ctagtgggat atgcctccag gttaaatcct gttttgaata tactgctaac cccgctggtt   1680
ataatccttc aatatcaatt gtgggcacac ttgaagctga aaaagaaaga agaaaatctg   1740
ggctatcctc aagagttcag tttcgaaacc aaggttctga gcccaaatat actcaagaac   1800
taactctgaa gaggcagaaa cagaaagtgt gcatggagga aaccctgtgg ctacaggata   1860
atatcagaga taaactgcgt cccattccca taactgcctc agtggagatc caagagccaa   1920
gctctcgtag gcgagtgaat tcacttccag aagttcttcc aattctgaat tcagatgaac   1980
ccaagacagc tcatattgat gttcacttct taaaagaggg atgtggagac gacaatgtat   2040
gtaacagcaa ccttaaacta gaatataaat tttgcacccg agaaggaaat caagacaaat   2100
tttcttattt accaattcaa aaaggtgtac cagaactagt tctaaaagat cagaaggata   2160
ttgctttaga aataacagtg acaaacagcc cttccaaccc aaggaatccc acaaaagatg   2220
gcgatgacgc ccatgaggct aaactgattg caacgtttcc agacacttta acctattctg   2280
catatagaga actgagggct ttccctgaga aacagttgag ttgtgttgcc aaccagaatg   2340
gctcgcaagc tgactgtgag ctcggaaatc cttttaaaag aaattcaaat gtcacttttt   2400
atttggtttt aagtacaact gaagtcacct ttgacacccc atatctggat attaatctga   2460
agttagaaac aacaagcaat caagataatt tggctccaat tacagctaaa gcaaaagtgg   2520
ttattgaact gcttttatcg gtctcgggag ttgctaaacc ttcccaggtg tattttggag   2580
gtacagttgt tggcgagcaa gctatgaaat ctgaagatga agtgggaagt ttaatagagt   2640
atgaattcag ggtaataaac ttaggtaaac ctcttacaaa cctcggcaca gcaaccttga   2700
acattcagtg gccaaaagaa attagcaatg ggaaatggtt gctttatttg gtgaaagtag   2760
aatccaaagg attggaaaag gtaacttgtg agccacaaaa ggagataaac tccctgaacc   2820
taacggagtc tcacaactca agaaagaaac gggaaattac tgaaaaacag atagatgata   2880
acagaaaatt ttctttattt gctgaaagaa aataccagac tcttaactgt agcgtgaacg   2940
tgaactgtgt gaacatcaga tgcccgctgc gggggctgga cagcaaggcg tctcttattt   3000
tgcgctcgag gttatggaac agcacatttc tagaggaata ttccaaactg aactacttgg   3060
acattctcat gcgagccttc attgatgtga ctgctgctgc cgaaaatatc aggctgccaa   3120
atgcaggcac tcaggttcga gtgactgtgt ttccctcaaa gactgtagct cagtattcgg   3180
gagtaccttg gtggatcatc ctagtggcta ttctcgctgg gatcttgatg cttgctttat   3240
tagtgtttat actatggaag tgtggtttct tcaagagaaa taagaaagat cattatgatg   3300
ccacatatca caaggctgag atccatgctc agccatctga taaagagagg cttacttctg   3360
atgcatagta ttgatctact tctgtaattg tgtggattct ttaaacgctc taggtacgat   3420
gacagtgttc cccgatacca tgctgtaagg atccggaaag aagagcgaga gatcaaagat   3480
gaaaagtata ttgataacct tgaaaaaaaa cagtggatca caaagtggaa cagaaatgaa   3540
agctactcat agcgggggcc taaaaaaaaa aaagcttcac agtacccaaa ctgctttttc   3600
caactcagaa attcaatttg gatttaaaag cctgctcaat ccctgaggac tgatttcaga   3660
gtgactacac acagtacgaa cctacagttt taactgtgga tattgttacg tagcctaagg   3720
ctcctgtttt gcacagccaa atttaaaact gttggaatgg atttttcttt aactgccgta   3780
atttaacttt ctgggttgcc tttgtttttg gcgtggctga cttacatcat gtgttgggga   3840
agggcctgcc cagttgcact caggtgacat cctccagata gtgtagctga ggaggcacct   3900
acactcacct gcactaacag agtggccgtc ctaacctcgg gcctgctgcg cagacgtcca   3960
```

-continued

```
tcacgttagc tgtcccacat cacaagacta tgccattggg gtagttgtgt ttcaacggaa   4020

agtgctgtct taaactaaat gtgcaataga aggtgatgtt gccatcctac cgtcttttcc   4080

tgtttcctag ctgtgtgaat acctgctcac gtcaaatgca tacaagtttc attctccctt   4140

tcactaaaaa cacacaggtg caacagactt gaatgctagt tatacttatt tgtatatggt   4200

atttattttt tcttttcttt acaaaccatt ttgttattga ctaacaggcc aaagagtctc   4260

cagtttaccc ttcaggttgg tttaatcaat cagaattaga attagagcat gggagggtca   4320

tcactatgac ctaaattatt tactgcaaaa agaaaatctt tataaatgta ccagagagag   4380

ttgttttaat aacttatcta taaactataa cctctccttc atgacagcct ccacccccaca   4440

acccaaaagg tttaagaaat agaattataa ctgtaaagat gtttatttca ggcattggat   4500

atttttttact ttagaagcct gcataatgtt tctggattta catactgtaa cattcaggaa   4560

ttcttggaga agatgggttt attcactgaa ctctagtgcg gtttactcac tgctgcaaat   4620

actgtatatt caggacttga aagaaatggt gaatgcctat ggaactagtg gatccaaact   4680

gatccagtat aagactactg aatctgctac caaaacagtt aatcagtgag tcgagtgttc   4740

tattttttgt tttgtttcct cccctatctg tattcccaaa aattactttg gggctaattt   4800

aacaagaact ttaaattgtg ttttaattgt aaaaatggca gggggtggaa ttattactct   4860

atacattcaa cagagactga atagatatga aagctgattt tttttaatta ccatgcttca   4920

caatgttaag ttatatgggg agcaacagca aacaggtgct aatttgtttt ggatatagta   4980

taagcagtgt ctgtgttttg aaagaataga acacagtttg tagtgccact gttgttttgg   5040

ggggggcttt ttttcttttt ccggaaaatc cttaaacctt aagatactaa ggacgttgtt   5100

ttggttgtac ttggaattct tagtcacaaa atatattttg tttacaaaaa tttctgtaaa   5160

acaggttata acagtgttta aagtctcagt ttcttgcttg gggaacttgt gtccctaatg   5220

tgttagattg ctagattgct aaggagctga tacttgacag ttttttagac ctgtgttact   5280

aaaaaaaaga tgaatgtcgg aaaagggtgt tgggagggtg gtcaacaaag aaacaaagat   5340

gttatggtgt ttagacttat ggttgttaaa aatgtcatct caagtcaagt cactggtctg   5400

tttgcatttg atacattttt gtactaacta gcattgtaaa attatttcat gattagaaat   5460

tacctgtgga tatttgtata aaagtgtgaa ataaattttt tataaaagtg ttcattgttt   5520

cgtaacacag cattgtatat gtgaagcaaa ctctaaaatt ataaatgaca acctgaatta   5580

tctatttcat caaaaaaaaa aaaaaaaaaa actttatggg cacaactgg              5629
```

<210> SEQ ID NO 52
<211> LENGTH: 4994
<212> TYPE: DNA
<213> ORGANISM: Homo sapiens

<400> SEQUENCE: 52

```
ccgcagcgct cggctggctg cagcggcacc gcgggttgcg cggccgggga tgctccagcg     60

ggcgcgatgg cccccgccat gcagccggcc gagatccaat ttgcccagcg gctggcgtcc    120

agcgagaagg gcatccggga ccgagcggtg aagaagctgc gccagtacat cagcgtgaag    180

acgcagaggg agacaggagg tttcagtcag gaagaacttc tacaggaaga gctcgccaac    240

accattgcac agctagtcca tgctgttaac aactcagcgg ctcaacacct gttcattcag    300

accttttggc aaaccatgaa tcgagaatgg aaaggaatag acaggctacg cctggacaaa    360

tactatatgc tgattcgtct ggtcctgagg cagtcctttg aagtcttgaa gcgaaatggc    420

tgggaagaaa gccgaatcaa ggttttcttg gatgtcctga tgaaggaggt cctgtgtcct    480
```

-continued

```
gagagtcagt ctcctaatgg agtgagattc cacttcattg atatttacct ggatgaactc    540
tccaaagtcg gggggaagga gcttttagca gatcagaatc tcaagtttat cgatccattc    600
tgcaaaattg ctgcaaagac gaaggaccac accctggtac agaccatagc tcggggtgtc    660
ttcgaagcta tcgtagatca gtctcctttt gtgcctgaag agacgatgga ggaacagaag    720
acaaaagtgg gtgatggtga cctctctgct gaggagatac ctgaaaatga ggtatccttg    780
agaagagctg tcagtaaaaa gaagacagca ctgggcaaaa accattccag aaaagatgga    840
ctcagtgatg aaagaggaag agatgactgt ggaacctttg aggacacagg gccccttctc    900
cagtttgact ataaggctgt tgctgatcga ctcctggaaa tgaccagcag gaagaacacg    960
ccccacttca acaggaagcg cctctccaaa ctcatcaaga aattccaaga cctttctgaa   1020
ggaagcagta tatctcaact cagttttgcg gaggacattt ctgctgatga agatgaccaa   1080
atcctcagtc aaggaaagca taagaagaaa ggaaataaac ttttagagaa aactaacttg   1140
gaaaaggaga aaggaagcag agtcttttgt gtagaggaag aggacagtga aagcagtctt   1200
caaaagagaa gaaggaagaa gaagaagaag caccacctgc agcctgaaaa tccaggccca   1260
gggggtgcag ccccgtccct ggaacagaac cggggcaggg agcccgaggc ctctgggccg   1320
aaagccctga aggcacgtgt ggccgagcca ggtgcagagg ccacgtccag cactggggag   1380
gagagtggct ccgagcatcc tccagccgtc cccatgcaca ataaaaggaa acggccacgg   1440
aagaagagcc cgagggccca cagggaaatg ttggaatcag cagtgttgcc cccagaggac   1500
atgtctcaga gtggcccgag tggcagtcat cctcagggac ctagagggtc cccgacaggt   1560
ggagcccaac tcctaaaaag gaagcggaaa cttggagttg tgcccgtcaa tggcagtggc   1620
ctgtccacgc cggcctggcc tccattgcag caggaaggcc ctcccacagg ccccgcagag   1680
ggggcgaaca gccacaccac gctgccccag cgcaggaggc tgcagaaaaa gaaggcaggg   1740
cccggcagcc tggagctctg tggcctgccc agccagaaaa cagcaagttt gaaaaagagg   1800
aagaaaatga gagtgatgtc aaacttggtg gagcacaacg gggtgctgga gtccgaagct   1860
gggcaacccc aggctctggg aagcagtggg acttgcagtt ccctgaagaa gcagaagctg   1920
agggcagaga gcgactttgt gaagtttgac acccccttct taccaaagcc cctgttcttc   1980
agaagagcca agagcagcac tgccacccac cctccaggcc ctgccgtcca gctaaacaag   2040
acaccatcca gctccaagaa agtcaccttt gggctgaaca gaaacatgac tgccgaattc   2100
aagaagacag acaagagtat cttggtcagt cccacgggcc cttctcgagt ggccttcgac   2160
cctgaacaga agcccctcca cggggtgctg aagaccccca ccagctcacc tgccagctca   2220
cccctggtgg ccaagaagcc cctgaccacc acaccaagga gaaggcccag ggctatggat   2280
ttcttctgag gagcagcaga gtcccttgta aaagactgct tttgtacaga atgcgctata   2340
aattatacct ttaagaatgt ggggcctttt ttatgatttt gtaagttccc ataagttgtg   2400
tgcacgaggt tctgagagtg cccgcaggct gctgcgtcct ggcccctctg tagtggctgc   2460
gggcgtcttg gttgaatctt ttgctacaaa ccatgtttgc gtttgagctc tccaggattt   2520
tacatttttg ggtaacctca gtgattccca ttggtgtagg aaatgagacc ctctctgaag   2580
ctgaggagag cacgttgatc tgaactttaa atcaatcagt gctgctggca caatgaaagg   2640
tggaactgca cttgtgttga gctctcagtt ctgcggaatt tggtactcat taccgtattc   2700
gccgtactaa gttggtttct gttagtctta acagtctgtt ttcttttaaa agcatgtagg   2760
gcttcattgc catgttctgt gggtgtttgg caggttaccg atggggaaga ttcttgtcac   2820
```

-continued

```
agaatcagca ataccatagt ttttctacat gtgctcagct gggggtgtgg acaggtaggg   2880

gtggggaaag aagaggctct gcgttctggg ggctttttct tctcctcccc ctacccggtt   2940

tccctccctg ttttcctacc tctacggcaa gcccaaagtg tcttcccggg agcccagcgc   3000

agcccccggc tcttacccag gaccccgccc cgtgctgagc cttctgctga ggtccttgcg   3060

tggagcacac tcattcctcc aagcccttgc gctcccgttt ctctctctct ccgtccacgt   3120

tccagccgag tcactgcctg cctgaccggc tccatggcag ctccccatct tccctagagg   3180

ctgcctgcgc atctggagcc tgcgctccgg ctcagcgacc tttcctctca aatgcggaag   3240

cgtgcactta cagttcagac cgttctcctg taagttcatt acaaacacgg gcggaaggca   3300

ctcaggcttt cgttggagaa acagaaataa ggccttcttt tgagcagcga ttgctggatc   3360

attgatctgt ttgaggaagt gtctgacctg ggcctgagag ctggagaagg tgcagattca   3420

aagtgagcgg ctcctgagga gagccgccaa ggctgctcgc cttctccgtg gcttccgcag   3480

ctaccgtctg cacggtgaga gggcacgggc acacggttcg ggctggcgtg cagctctccc   3540

agccagccac gctctgctca ggcctggaag tgaaagccgc ctccttcccg ttatgccccc   3600

catacaggag cctcggtttt tcagcaaaac gcggccagtc cccttctcca ctgctgcctc   3660

ccagcagagg gccccaggat ctccaaggtc ccagctatgg ctttggacaa cgtggcttcg   3720

gcccctgggg ttgcagagct tgcattgggt ttacctcggt ctcattcatt catggagcca   3780

agggtggggt ttcacctgcg aacatcagac tgacttgctg gcgtcaagag cagttgactc   3840

actgatgaag gccctggtga ggagaaagca ctctgttctt cgcctactct gtaatcgttt   3900

tgtcataatg agccatgaaa aaagtaatga acttgtgctg ttaatcgtca ctgtaatgag   3960

aagtcttacg tacaacatag ctgtggtggc tgcgtggttt aatggctgca ttagatagga   4020

tcctcacatc ccattcagaa ccaaaactga tacagtgaaa caattaaggt gagcaaatag   4080

ttttaacttt tctttttttt ttaagtttca ttcttcctag aatatttttc taacaatttt   4140

tatttcagct ttaaagatgg gtcatatagc caaacgggcc atataatcca acattgttga   4200

gatgtcttag gacatctaag gcaaaactgg cacatttgtt ctgcagacta ttgcaggaat   4260

gtttttttcct agcatttcta tattatctgt ccattctgag gaaccagtga atgtcctata   4320

aatgcacctc ctgtcaaaac catgcctgag aggtcccggc tgggagtgac agggtgcttc   4380

ttagattcta ttggtccttc tctcattctc cgaacttact ccttttttatg ggtaagtcaa   4440

ctaggtttac agtcccttat ttttaatgcc taagttttga cagcaggaag aaaacaattt   4500

tttaaaaatt ctcattacat agacgcacaa gaatatgtca cataaagaaa atgtgtttag   4560

aatactggtt ttctatttac gcatgatatt ttcctaagta aaattgccaa gtggacttgg   4620

aagtccagaa aggaaaataa tttaaattaa tgctggtgat cttaacaata ttttgtaaaa   4680

tgatgcttcc cccttctcca tggtctagtc aattttgtac aattaggtat ctgactttac   4740

aagtttgtta tcctttctaa tttttactga actgaaagca caaagaagac tacacagaaa   4800

atctggaaac agttgcaggt gttgggagga agatgaaatc gagctgtctt ttaacttttg   4860

tatgtgtttt atcagaattt gctggactat gctggcaagg actttgttta cgatcaaatt   4920

gtactagtgt ctgcagggtt tgtcagtact cgtcaaagcc aagtccaatt aaaaaaaaaa   4980

agtctttgcc ctcc                                                     4994
```

<210> SEQ ID NO 53
<211> LENGTH: 1202
<212> TYPE: DNA
<213> ORGANISM: Homo sapiens -continued

<400> SEQUENCE: 53

```
ggcacgaggc gccatttgct gccgccgagc gtggacgcag gcggatctct gaagagctgg     60
gtcgccagcc tctcccgcgc acgttgcctg gcctccagca cctacttggt cccgcgcgct    120
ccctcgtgtc gcccctcgga gcagcagccg ccgcggtcgc cgctacccgg aaagaagtca    180
gagacgccgc gagtcgccgc caccgccatg cccaagaata aaggtaaagg aggtaaaaac    240
agacgcaggg gtaagaatga gaatgaatct gaaaaaagag aactggtatt caaagaggat    300
gggcaggagt atgctcaggt aatcaaaatg ttgggaaatg gacggctaga agcaatgtgt    360
ttcgatggtg taaagaggtt atgtcacatc agaggaaaat tgagaaaaaa ggtttggata    420
aatacctcgg acattatttt ggttggtctc cgagactacc aggataacaa agctgatgta    480
attttaaaat acaatgcaga cgaagctaga agtctgaagg catacggcga gcttccagag    540
catgctaaaa tcaatgaaac tgatacattt ggtcctggag atgatgatga aattcagttt    600
gatgacattg gagatgatga tgaagatatt gatgacatct aaattgaact caacatttta    660
cattccatct tttctgaaga ttgtcctaca atttggattt tgatcatgac aaagaagatt    720
aaaatttcat tagcatgaat gcaatttgtt aaagcagact gatttgtttc taagatattt    780
ttggtttttt taaaactgat aataatgctg aattatctta agtgagatgt taagcccact    840
ttgttctttt aatgtaatgg agcttatggg tagaagacca tgtctactaa ttacaaaaaa    900
aaaaaaaaac catgattgct gcttttccta ccacttccag taagaaaatg ggtgttttga    960
agaaatcatt tgccttgtct cacggaatct gattaagccc tggcctcttg atgtatagag   1020
tcatggatat tccagttacc tagatattcc cttgagattt tgatacaatt tgagggaggc   1080
agaagtctgc agttgaagaa aaaaaataag tctgtttgtc atatttaagt agcctgtgcg   1140
tatttttata ctgattttga tatcatgttc ttttcatagt cgtattttgc caccgtaaac   1200
at                                                                  1202
```

<210> SEQ ID NO 54
<211> LENGTH: 1745
<212> TYPE: DNA
<213> ORGANISM: Homo sapiens

<400> SEQUENCE: 54

```
ctgctcgaga aggagctgga gcagagccag aaggaggcct cagaccttct ggagcagaac     60
cggctcctgc aggaccagct gagggtggcc ctgggccggg agcagagcgc ccgtgagggc    120
tacgtgctgc aggccacgtg cgagcgaggg tttgcagcaa tggaagaaac gcaccagaag    180
attgaagatc tccagaggca gcaccagcgg gagctagaga aacttcgaga agagaaagac    240
cgcctcctag ccgaggagac agcggccacc atctcagcca tcgaagccat gaagaacgcc    300
caccgggagg aaatggagcg ggagctggag aagagccagc ggtcccagat cagcagcgtc    360
aactcggatg ttgaggccct gcggcgccag tacctggagg agctgcagtc ggtgcagcgg    420
gaactggagg tcctctcgga gcagtactcg cagaagtgcc tggagaatgc ccatctggcc    480
caggcgctgg aggccgagcg gcaggccctg cggcagtgcc agcgtgagaa ccaggagctc    540
aatgcccaca accaggagct gaacaaccgc ctggctgcag agatcacacg gttgcggacg    600
ctgctgactg gggacggcgg tggggaggcc actgggtcac cccttgcaca gggcaaggat    660
gcctatgaac tagaggtctt attgcgggta aaggaatcgg aaatacagta cctgaaacag    720
gagattagct ccctcaagga tgagctgcag acggcactgc gggacaagaa gtacgcaagt    780
```

-continued

```
gacaagtaca aagacatcta cacagagctc agcatcgcga aggctaaggc tgactgtgac    840

atcagcaggt tgaaggagca gctcaaggct gcaacggaag cactggggga gaagtcccct    900

gacagtgcca cggtgtccgg atatgatata atgaaatcta aaagcaaccc tgacttcttg    960

aagaaagaca gatcctgtgt cacccggcaa ctcagaaaca tcaggtccaa gagtctgaag   1020

gaaggcctga cggtgcaaga acggttgaag ctctttgaat ccagggactt gaagaaagac   1080

taggtgtgtc ccatccaagt tgagcacgcg ccttccccag cttgcagcag cacaccccaa   1140

gcgctgcttt tcacctgtac ctttgtttta ttattattat tattattgct gttgttgtca   1200

tcgttaactg tgggcatgga atgcgtgagg ctggcttctg ggttgtccac accactctct   1260

gctgtgttga cttcctgttg tcttcaacaa agctttttc cgtggtattc taaaattagg   1320

ccagcagtgg gggctgggag ggcatctgtg ttagtccttt cctggctgtg acccgccaca   1380

ctcactgtca gtattaaggc ccagcagcct gttgataagc taccctgtct caccatgtgc   1440

tggtgtggaa acggggccca gccagcacgc ctcaaggtag atggaatccc cactggtcag   1500

agaaaaagct atgcggacac tccagcttgg cctgggtcac agcactgact cctcacccgc   1560

tagtctggct gttaagagga gaaagtgcac tgccttccag cccaggagga ggacagcatt   1620

ttgtatttgt tccactgatg cagcttagac ccacacccct gagagtcgtg gcaaaccttt   1680

cacaacctgg aaaatgttga aagcaaccat tcctattttt gtttgttttt tattaaatct   1740

tgcac                                                               1745
```

<210> SEQ ID NO 55
<211> LENGTH: 976
<212> TYPE: DNA
<213> ORGANISM: Homo sapiens

<400> SEQUENCE: 55

```
cccggaacct ggcgcaactc ctagagcggt ccttggggag acgcgggtcc cagtcctgcg     60

gctcctactg gggagtgcgc tggtcggaag attgctggac tcgctgaaga gagactacgc    120

aggaaagccc cagccaccca tcaaatcaga gagaaggaat ccaccttctt acgctatggc    180

aggtaagaaa gtactcattg tctatgcaca ccaggaaccc aagtctttca acggatcctt    240

gaagaatgtg gctgtagatg aactgagcag gcagggctgc accgtcacag tgtctgattt    300

gtatgccatg aactttgagc cgagggccac agacaaagat atcactggta ctctttctaa    360

tcctgaggtt ttcaattatg gagtggaaac ccacgaagcc tacaagcaaa ggtctctggc    420

tagcgacatc actgatgagc agaaaaaggt tcgggaggct gacctagtga tatttcagtt    480

cccgctgtac tggttcagcg tgccggccat cctgaagggc tggatggata gggtgctgtg    540

ccagggcttt gcctttgaca tcccaggatt ctacgattcc ggtttgctcc agggtaaact    600

agcgctcctt tccgtaacca cgggaggcac ggccgagatg tacacgaaga caggagtcaa    660

tggagattct cgatacttcc tgtggccact ccagcatggc acattacact tctgtggatt    720

taaagtcctt gcccctcaga tcagctttgc tcctgaaatt gcatccgaag aagaaagaaa    780

ggggatggtg gctgcgtggt cccagaggct gcagaccatc tggaaggaag agcccatccc    840

ctgcacagcc cactggcact tcgggcaata actctgtggc acgtgggcat cacgtaagca    900

gcacactagg aggcccaggc gcaggcaaag agaagatggt gctgtcatga aataaaatta    960

caacatagct acctgg                                                    976
```

<210> SEQ ID NO 56
<211> LENGTH: 3394

-continued

<212> TYPE: DNA
<213> ORGANISM: Homo sapiens

<400> SEQUENCE: 56
gtcccgagcg ccggcctgcg gagcgtagca gcccgggcca gacgccggag gagggcgcgc 60
aggccttggc cgagttcgcg gcgctgcacg gcccggcgct gcgcgcttcg ggggtccccg 120
aacgttactg gggccgcctc ctgcacaagc tggagcacga ggttttcgac gctggggaag 180
tgtttgggat catgcaagtg gaggaggtag aagaggagga ggacgaggca gcccgggagg 240
tgcggaagca gcagcccaac ccggggaacg agctgtgcta caaggtcatc gtgaccaggg 300
agagcgggct ccaggcagcc caccccaaca gcatcttcct catcgaccac gcctggacgt 360
gccgtgtgga gcacgcgcgc cagcagctgc agcaggtgcc cgggctgctg caccgcatgg 420
ccaacctgat gggcattgag ttccacggtg agctgcccag tacagaggct gtggccctgg 480
tgctggagga gatgtggaag ttcaaccaga cctaccagct ggcccatggg acagctgagg 540
agaagatgcc ggtgtggtat atcatggacg agttcggttc gcggatccag cacgcggacg 600
tgcccagctt cgccacggca cccttcttct acatgccgca gcaggtggcc tacacgctgc 660
tgtggcccct gagggacctg gacactggcg aggaggtgac ccgagacttt gcctacggag 720
agacggaccc cctgatccgg aagtgcatgc tgctgccctg ggcccccacc gacatgctgg 780
acctcagctc ttgcacaccc gagccgcccg ccgagcacta ccaggccatt ctggaggaaa 840
acaaggagaa gctgccactt gacatcaacc ccgtggtgca cccccacggc cacatcttca 900
aggtctacac ggacgtgcag caggtggcca gcagcctcac ccacccgcgc ttcaccctca 960
cccagagtga ggcggacgcc gacatcctct tcaacttctc acacttcaag gactacagga 1020
aactcagcca ggagaggcca ggcgtgctgc tgaaccagtt cccctgcgag aacctgctga 1080
ctgtcaagga ctgcctggcc tccatcgcgc gccgggcagg tggccccgag ggcccaccct 1140
ggctgccccg aaccttcaac ctgcgcactg agctgcccca gtttgtcagc tacttccagc 1200
agcgggaaag gtggggcgag gacaaccact ggatctgcaa gccctggaac ctggcgcgca 1260
gcctggacac ccacgtcacc aagagcctgc acagcatcat ccggcaccga gagagcaccc 1320
ccaaggttgt gtccaagtac atcgaaagtc ccgtgttgtt ccttcgagaa gacgtgggaa 1380
aggtcaagtt cgacatccgc tacatcgtgc tgctgcggtc agtgaggccc ctacggttgt 1440
tcgtgtatga tgtgttctgg ctgcggttct ccaaccgggc ctttgcactc aacgacctgg 1500
atgactacga gaagcacttc acggtcatga actatgaccc ggatgtggtg ctgaagcagg 1560
tgcactgtga agagttcatc cccgagtttg agaagcaata cccagaattt ccctggacgg 1620
acgtccaggc tgagatcttc cgggccttca cggagctgtt ccaggtggcc tgtgccaagc 1680
caccacccct gggcctctgc gactacccct catcccgggc catgtatgcc gtcgacctca 1740
tgctgaagtg ggacaacggc ccagatggaa ggcgggtgat gcagccgcag atcctggagg 1800
tgaacttcaa ccccgactgt gagcgagcct gcaggtacca ccccaccttc ttcaacgacg 1860
tcttcagcac cttgtttctg gaccagcccg gtggctgcca cgttacctgc cttgtctagg 1920
cactcgctgt ccccaaaacc tgtgcttggg gcaggattcc aacctcagtt ctctgagctg 1980
cttctgcaaa ggcccccatg tccctcccca caccggccct gggcatagcc tcagccccag 2040
gcctctgtcc tgccgagcca tcctcccggc gccacactcc gggagcacag catcctcctc 2100
tcacctgtgg gtcagagcag gacagtgatg gtgtccccag ggctgagcac caccccacgc 2160
cctgccctca cccctcacca ccatctgtgc actgatgagt ctccagttta gccaagggct 2220

-continued

```
tcgttcctgg catggagaat ttgttcctgg ctgctgtgtt tccagggggt gctgggggaa   2280
gggttccgtg gagcgagaca aggtgtcctc gggagcaggg ttccaccggg aagcgtttgg   2340
gagccctgta tcacacgggg caggcgggtt tctcttccgg ggtctctgct cttatgcatc   2400
aggacgaccc cgggacggct gtggggcccc acactgcacc cacagggctc tatgcgacag   2460
gggcccagga acagcctgag gccaccaccc agcaagcccg ccttatcacc cattccagct   2520
cacccagaac cttcaccagc aaacctcctg ctgaggtcct ggcaggaggc caccgtcttg   2580
ttaccgtttc cttttcgttt gctgagggtc acagacccca acagggaaat cagtatctgt   2640
cttcccagtg gttgccctgc tcgccgggca ctccacgggg tcccgccctt gtgtgagatg   2700
ggccaggatc cttcggcaag gggcgcctgg ggctggggct gattgtgggc ggtggagcgc   2760
cagacagaaa aggattccaa tgagccccag ccccaggcgc cccttgccga aggatcctgg   2820
ggctggggct gattgtgggc ggtggagcgc cagacagaaa aggattccaa tgagaacttc   2880
aggttaaagt cagatgccac ctaccagggt ctacagtcaa aatgttggct ttttcttatt   2940
ttttaatgta tgggagaaaa atgtaaaatt ccagttcttt tctaattgtg tttctgaaat   3000
taggagtcag ctgccagcgt ttttgtgtgg ctgcagtgtg cctgggccca gctcacgggc   3060
agtgggtgga cctaactgcc caggcaggcg agagctactt ccagagcctt ccagtgcatg   3120
ggagggcagg gctaggtgta gcggtgtctc ctctttgaaa ttaagaacta tctttcttgt   3180
agcaaagctg cacctgatga tgctgcctct cctctctgtg ttgtctgggc ccttgtttac   3240
aagcacgcgt tacccttcct gaggggagcc atgctctagc ccctggaggg cctgttgcag   3300
gggcagggcg ggcccgtcgc ctttggcagc tcctggagag ctgtggacat gcagtccccc   3360
tcagttcgtg ctgcaataaa ggccatcttc tctt                               3394
```

<210> SEQ ID NO 57
<211> LENGTH: 1526
<212> TYPE: DNA
<213> ORGANISM: Homo sapiens

<400> SEQUENCE: 57

```
gttttttttt tttttttaa ttgcaagcat atttctttta atgactccag taaaattaag     60
catcaagtaa acaagtggaa agtgacctac acttttaact tgtctcacta gtgcctaaat    120
gtagtaaagg ctgcttaagt tttgtatgta gttggatttt ttggagtccg aaggtatcca    180
tctgcagaaa ttgaggccca aattgaattt ggattcaagt ggattctaaa tactttgctt    240
atcttgaaga gagaagcttc ataaggaata aacaagttga atagagaaaa cactgattga    300
taataggcat tttagtggtc tttttaatgt tttctgctgt gaaacatttc aagatttatt    360
gatttttttt tttcactttc cccatcacac tcacacgcac gctcacactt tttatttgcc    420
ataatgaacc gtccagcccc tgtggagatc tcctatgaga acatgcgttt tctgataact    480
cacaacccta ccaatgctac tctcaacaag ttcacagagg aacttaagaa gtatggagtg    540
acgactttgg ttcgagtttg tgatgctaca tatgataaag ctccagttga aaaagaagga    600
atccacgttc tagattggcc atttgatgat ggagctccac cccctaatca gatagtagat    660
gattggttaa acctgttaaa aaccaaattt cgtgaagagc caggttgctg tgttgcagtg    720
cattgtgttg caggattggg aagggcacct gtgctggttg cacttgcttt gattgaatgt    780
ggaatgaagt acgaagatgc agttcagttt ataagacaaa aaagaagggg agcgttcaat    840
tccaaacagc tgctttattt ggagaaatac cgacctaaga tgcgattacg cttcagagat    900
accaatgggc attgctgtgt tcagtagaag gaaatgtaaa cgaaggctga cttgattgtg    960
```

-continued ccatttagag ggaactcttg gtacctggaa atgtgaatct ggaatattac ctgtgtcatc 1020
aaagtagtga tggattcagt actcctcaac cactctccta atgattggaa caaaagcaaa 1080
caaaaaagaa atctctctat aaaatgaata aaatgtttaa gaaaagagaa agagaaaagg 1140
aattaattca gtgaaggatg attttgctcc tagttttgga gtttgaattt ctgccaggat 1200
tgaattattt tgaaatctcc tgtcttttta aactttttca aaataggtct ctaaggaaaa 1260
ccagcagaac attagcctgt gcaaaaccat ctgtttgggg agcacactct tccattatgc 1320
ttggcacata gatctccctg tggtgggatt ttttttttcc cttttttttgt gggggagggt 1380
tggtggtata tttttcccct cttttttcct tcctctccta catctccctt ttcccccgat 1440
ccaagttgta gatggaatag aagcccttgt tgctgtagat gtgcgtgcag tctggcagcc 1500
ttaagcccac ctgggcactt ttagat 1526

<210> SEQ ID NO 58
<211> LENGTH: 8213
<212> TYPE: DNA
<213> ORGANISM: Homo sapiens

<400> SEQUENCE: 58
cccccagcag aagggcgcga cggctgcaac atcagcggtt aaattgtaca gcctttcata 60
ggccggttca atgcatccgt actaagattg ttaaggctga gggtccctag cctggggaaa 120
aacgaaagga ggcagagggt agggagacgg gaaggaagac aaggagggtg tagaaaacgg 180
ggagaggagg gggcgggaca gcatggggaa ggcctcaggt ttactggaga gatcgtggcg 240
ttcccataga aacgtatccc tccgcccatg acccgcgtgt tagtctcttc agttccttcc 300
gcgtcgtttc ttggctgttt ccgcccagct cctttgtgcc gcgcagaaca acgagatgac 360
gcatgcgcaa agcgcagcgg ccgcatatat aaacgcgaac ccgggctctt cctcgtagtg 420
ccgccgggac tcttggcggg tgaaggtgtg tgtcagcttt tgcgtcactc gagccctggg 480
cgctgcttgc taaagagccg agcacgcggg tctgtcatca tgtcgcgtta cgggcggtac 540
ggaggaggta agaagctgga gtccggtgag ggacgttggt gtgggtgtag tgagcactgc 600
gaggccgtag ggttgtcgcg gaggttggga gacggttatt ccgcgtgcgt aatggcggct 660
taggagcacg ccagacgaag ccggaggcag cggaggcggg gtgctgaagg gagacgggat 720
ggcgggtgta catctctgcc gagttccgta ctcttgggca tttttgtggc ccaatccagc 780
ctaaagcagg gttgagatga cggttttcgc gttgcctttc tcggagctgc ccgccggccc 840
ccctcccccc ccgccctcgg ccggcggctg ccattttgcg cacattgagg accgtggtgg 900
cgcatttcct cagcgctttc ccgccacttc agcggacaga tctggccgca gctgtaagat 960
cgtggttgtg tttgagatag aacgaaattg gcagctgtga gctgcatgtt ctcgtcaaac 1020
aatcggttaa attgcggaat gggaatgggg acgtaatctg cgactggcgg ctgggttttt 1080
ttttagttat ttccagcgcg gtttatggct ctggggcggg gagctggagt cttgggcgag 1140
cctgtgcctg ggacgtttgc cgcggaggac gagagccggc gcagccctgc tctcctggcc 1200
cggcccctac cgaggccctc ccgccgccga cgcgctgccg ctgcgggccc gcgcgctccc 1260
ggtgcgcccg gggctgccgg gactcatggg tggggccggg ccaggtcccg ccccacgcct 1320
cggtgtatcc taccacgcgt ttctgcttgt gttcgggagg gtcaccccgc attatttaga 1380
acgttaagaa ttttgtcaaa agtctagttt ctcggggatt tgcggacttc accagtttta 1440
cgactaagtt ttgtcttgga tagagggcat taaatgtgct ttacccaatc ttgaggatgg 1500

-continued

```
cccgttttaa ggcaagtaag taattgaaac ttgggccaga ttttgcataa cgtgcattct   1560
tctatttgcg tttttaaaca gaaaccaagg tgtatgttgg taacctggga actggcgctg   1620
gcaaaggaga gttagaaagg gctttcagtt attatggtcc tttaagaact gtatggattg   1680
cgagaaatcc tccaggattt gcctttgtgg aattcgaaga tcctagagat gcagaagatg   1740
cagtacgagg actggatgga aagtaagtaa gatgttatga atcttctgtt cattaaaata   1800
tactgtggct agataatgaa cttagtgcta aatttggatt ctgaagtctg gaagagacct   1860
taaatagctg gtcatagtgt taaatgctaa aggcacacga aggttaaaga agatagcgga   1920
gatggagtta gggcttggta aagaccgcca aagtttgttg ggggggaagg agtggttgga   1980
aagagtgagt ggttggaaag agttcttttt aaatctataa gtcctgaata tatttttaac   2040
tttagaattt tgttaatttg cttttattag ggtgatttgt ggctcccgag tgagggttga   2100
actatcgaca ggcatgcctc ggagatcacg ttttgataga ccacctgccc gacgtccctt   2160
tgatccaaat gatagatgct atgagtgtgg cgaaaaggga cattatgctt atgattgtca   2220
tcgttacagc cggcgaagaa gaagcaggta tttattttaa taaaggaatg gttggtattc   2280
tagttaatca agtaattctt ttattagcaa ggcagaaact agtgtttttc tataaacttg   2340
aatgttaatt gtacaggtgt attttacaat ttgtgtttaa ttaaaaaaat gttactatat   2400
taataatcaa cctggtcaaa acctttcagg tttcttcgtt tgagtcagtc gccttgattc   2460
agaatgtcac gagccttatg atatcatgct gaggcgcctt gcaaatccga caattaagat   2520
cctcctagac cttgaggtga tcagcataag aggccagatc ccctcgagtc atctacacct   2580
agcttcacct tattctttaa agggcagaaa atttgagacg gtgatcgccg taacagtaaa   2640
tttggcttac aattggggcc cccctccggt ttagaaagag gaacaccaga ttgaccacat   2700
tcccaactag aaaaatcttc ttgcgtcaat caagcctcac ctggctcatt tggctgtcag   2760
tttgatcgtc gttagattga agaaaacatc tagatgcagc gatcggctat agatacttct   2820
agatcgtcta gatctactag accatgggcc aaagagggtc gacctgcaaa cttgcaaggt   2880
ttatgttaaa tacacattac agtgttttat attatgtaat gctaagttgt aattcagctt   2940
ttaacaaatc ttttttttagg tagtaaaaaa aaaaatactc aacaactaat aggcccagag   3000
tttatttcca aatgagacac taaatttaaa tagttttgag atttgatttc agcagaggca   3060
cacaaactct taaaaacgag ttattgtctg acattttgtt ttttctctaa cttgaaaaat   3120
aggtcacggt ctagatcaca ttctcgatcc agaggaaggc gatactctcg ctcacgcagc   3180
aggagcaggg gacgaaggtg agatcttgtt taactgaagt ctttctgtat tattattaaa   3240
ttcactggta gtccaacaca gaaaaagctc attatttttt ttggagacag ggtcttgctc   3300
tgtcacccgg gctggagtac aggggcataa ccacgactca ctgctgcctt gatgatctct   3360
tgggtttaag cagttctcct acctcagcct cccgagtagc tgggactgta ggcactgcca   3420
ccatacccag ctaattttta tttttgtaga aatggtcttg cactgtttcc caggctggtc   3480
tcaagctcct gggctcaaac gatcctcccg cagtgctggg attatgggca tgagccactg   3540
caccgttccc cagttgaagt cttaacaggc caaaaaaaaa aaaaactgtg gagatggact   3600
taaagttctt tattttaggt caaggtcagc atctcctcga cgatcaagat ctatctctct   3660
tcgtagatca agatcagctt cactcagaag atctaggtct ggttctataa aaggatcgag   3720
gtatttccag tatgtaacac tttttttcct tacttgtgtt tggattgttc acatcttatc   3780
agtagagtgt cttaaggaca taattcaaat ggattgcttc agggaatatt tgagatgtaa   3840
aagtttggaa tttatgtgta acttgtaaca taaatattac cctagtttca cagatgaaga   3900
```

-continued

```
aaagggctac tagagatttt aaggcttgtt aggccgtgtg gtagacaagg gtcccaagca   3960
atacagctct actcaacact ctgggtaggc atgttgctat aaacttttct ggcttcagat   4020
tggatgatac tagctctgaa agatggtaat tgattttccc gacaaaaagg cctattagca   4080
ccaggaaaag agatcagaag caagtagaaa catttctcat tttggaatg atggggttga    4140
tttgagacac tggaaagttg actagggcag tagtgtgtac acagaaatga atgtggattt   4200
ttttttaga ccgtttcaga cctgaaaaaa ctaaagaacc agagctttac tatttgtaga    4260
aggccttaaa aggagataga atggaaaaaa ttgtaaaata agtattgcaa catgtaatta   4320
acaatattgt tatctgtacc aacgataaaa ccgtggtacg gaatgctact gggagttaaa   4380
ttgctgttta atagcacaaa acctttaaat gcaggaattc tgaatcttgt ggtctatttg   4440
agaaagctat gaaccatctc tttagataaa tttaaaagat agatatgtca gtctgatttg   4500
gtttgtctga cagattgatg gctctcaaac ataacttgat ccgggaagaa gcctgacaaa   4560
tggggggcgg ctttcttttc gtctggcctt atcacctgaa ttagtctcag ttcaggggtc   4620
tggttatttt catcctgcct tagcctcctg agtagctggg actgccattg tgtaccacag   4680
tgcccagctg agggatctgt gccttaagtg aggttagttt tgcttccttc ataccagtct   4740
catcaaatga aaaccatgta tttcccttgg atattacaca gtgtttgaga atgttatacc   4800
tgtacagaaa ctaaccaatt gagtgataga aacaagtaat tgaaatgggg gttccttatg   4860
tctggtaaca ctttgtttga cagtgtgtta gacagaataa ggcaagtgtt gcatcttgtt   4920
tagttttagc ttctttatgc ctgaccaacc taatacagtg ttgagtagtt aaggaaattc   4980
ctttggactg attgatataa ttgtgttttt tcactttttt tattaagatc cccgtcgagg   5040
tcaagatcaa gatccaggtc tatttcacga ccaagaagca ggtagggtaa aaatttgatt   5100
atccttttct agttatatgg caccaatatc caaagagttc aaagtgtttt taattgttga   5160
aattttaagt gttaactcta aacttaggtt ttagtgggaa cacagtacct tatttgtgta   5220
tgtcctattt attactggct gactttccct gaacaaggga atgtaaaact atagtgagaa   5280
agaagcttat gacttggggg attatattaa agaggccctt gttagaactg ataggtgcat   5340
ggagaagcat cctgaaatcg atgtgcttaa agcagaatgt aaaagattaa tcatgatgta   5400
gtaattgagt catttttga aaaacagttg ttgaaagatt ggcttttgtt agcaacaact    5460
ggtaggatgt ttttcagttt aagtgcagtc tgacatttta agcttaggac atttgggggt   5520
tttacggtat tggtgactac aagaaaggga ttggttagta ctctttcttt aatagaattt   5580
ctcatgtttt gacagccgat caaagtccag atctccatct ccaaaaagaa ggtaagctaa   5640
atgttttgtt gccaaatctt gcctgtcaag tgtggcctct gcagaatttg tttgcttact   5700
gctttgcagt ctttgagctc tttggagaat tggtgctata tagattaaaa tactatgcta   5760
agtttctgaa atactttttt tttttgattc agtaacatta gtttatactt ttgctggaaa   5820
tacttagtca taaaatgtta gggtgattat taagatgtga ttggtcctgt gagtacttgg   5880
tagaaatttt ggtaagatag atgccttttc cccacatgta caatagatac aaagtgtgga   5940
gaaaagtctt ggaaatagtt acctgcctag tgcttcttta tgaccagaaa acttcaaata   6000
gttgtcatat ttatctagtg cttcttaatg accagaagac ttcaaatagt tgtcatattt   6060
aactgcaggt tgaccttgca attttgacaa ggaggatagc ctaatttttt ttttttttctg  6120
ggatggagtt ttcgctctgt ccccaggctt ggagtgcagt ggctcaatct tggctcactg   6180
cagcctccga ttcccgggtt caagcaatta tcctgtctca gcctcttgag cagttgggat   6240
```

-continued tacaggcacc caccgccaag cctggctaat tttttgtatt tctagtagag acggagtttc 6300
accatgttgg cgaggttggt cttaaactcc tgatcttagg tgatcacctg cctcggcctc 6360
tcccaaagtg ctggggttac aggcgtgagc caccgtgcct ggccagggta gcctaatctt 6420
aagccaggga caaaagatga atatatgtaa gtttcatgtc atttttaggt ctttgctata 6480
ggaaattagt accttaggcc acctttgaag ttattgaaag ttagtacatg tacatgagag 6540
tttcaattga cactaattgg atccaaacct aatgtttttc tttttagtcg ttccccatca 6600
ggaagtcctc gcagaagtgc aagtcctgaa agaatggact gaagctctca agttcaccct 6660
ttagggaaaa gttattttgt ttacattatt ataagggatt tgtgatgtct gtaaagtgta 6720
acctaggaaa gataattcaa ccatctaatc aaaatggatc tggattacta tgtaaattca 6780
cagcagtaag gataatataa attttgttga atgtatgaac atcatatggt ctgaaaatgt 6840
gggtttttat ttggcacatt taaataacat gtttctaact agatttttga tttgtgttca 6900
atattaacac ttcttaattt gatatatttg agagtcagac attataattg ttaatcctta 6960
ttcatacata cctacattca gaattgaaag gtgttggtta agtcttgaac atcactattc 7020
tatgcataaa acttggccag gatcttaagg gactttgaaa attccatctt acccttgtag 7080
ctctgggtaa gatgacctga gtcccttatg atacagcctg aatgcatcat gacagatcct 7140
tagttagcta atccgtttga agttggtgtt agtaggtatt gtatgatcag tggtgaagca 7200
agtaggacca ctgatgtgtc taaatgagca tgacaggaac taaacgaaac tgattaaatg 7260
tatgagaaat agaaactgat ttctggatga tctttatact aattgcagct ttcaggctac 7320
taggtggcat agtgttaatt aggactcccc aagatatggg gagttctact ctcaatggtc 7380
ttgtttcttt gctttctaca ttagttaacc agttttatac caaaaaatgc atgtttgagg 7440
aattgtctga aattgggaca aaacaccttc atgtaaacca gctttgcaaa attttccagc 7500
ccagatactc ttcatctatt caaatggatt gtcttattct gagcaaagac ctgttgttaa 7560
tcttcaagct aggttttgca gttcccaacc acaacattct tctattttgc caggctggtg 7620
caaagtaatt aaagatgtca atcagaaatg tcaatgagac taaagtggtt ttgtaaatct 7680
cagctatatt tagcaacact ccatgtagct aatatttttt ggtagcatct ggtagacctt 7740
agaatgttac atagccagta ggttctttat tcaaatttta agtatcttaa gaatagtagg 7800
gcagtaacag ttacttttga gagttttctg gtcaagcttt taccaggcat tctctagcct 7860
tggtacaaaa aaaaaaaaaa cctgctggtt gcgcagatac ctaggcttgt ccattttatg 7920
catttcagca aagtcattgg agactattgc aacttgggaa tactggtctg catcaagttt 7980
aattcggtag tttgaccgct agtatgttgg aagttatttg gattgttttt ggaattttga 8040
ctggctgaat tatggttggt ataaagttat gtgtataact ggcaggctta tttatctgtt 8100
gcacttggtt agctttaatt gttctgtatt atttaaagat aagtttactc aacaataaat 8160
ctgcagagat tgaacaaata atcctgatac ttaatttttg gaagtgggag ctc 8213

<210> SEQ ID NO 59
<211> LENGTH: 2042
<212> TYPE: DNA
<213> ORGANISM: Homo sapiens

<400> SEQUENCE: 59
gcgcctgtca gggaagcggc gcgcgcgcgc gggcggcggg cgggctgggg atccgccgcg 60
cagtgccagc gccagcgcca gacccgcgcc ccgcgctctc cggcccgtcg cctgccttgg 120
gactcgcgag cccgcactcc cgccctgcct gttcgctgcc cgagtatgga gctgctgtgt 180

-continued

```
tgcgaaggca cccggcacgc gccccgggcc gggccggacc cgcggctgct gggggaccag    240
cgtgtcctgc agagcctgct ccgcctggag gagcgctacg taccccgcgc ctcctacttc    300
cagtgcgtgc agcgggagat caagccgcac atgcggaaga tgctggctta ctggatgctg    360
gaggtatgtg aggagcagcg ctgtgaggag gaagtcttcc ccctggccat gaactacctg    420
gatcgctacc tgtcttgcgt ccccacccga aaggcgcagt tgcagctcct gggtgcggtc    480
tgcatgctgc tggcctccaa gctgcgcgag accacgcccc tgaccatcga aaaactgtgc    540
atctacaccg accacgctgt ctctccccgc cagttgcggg actgggaggt gctggtccta    600
gggaagctca agtgggacct ggctgctgtg attgcacatg atttcctggc cttcattctg    660
caccggctct ctctgccccg tgaccgacag gccttggtca aaaagcatgc ccagaccttt    720
ttggccctct gtgctacaga ttataccttt gccatgtacc cgccatccat gatcgccacg    780
ggcagcattg gggctgcagt gcaaggcctg ggtgcctgct ccatgtccgg ggatgagctc    840
acagagctgc tggcagggat cactggcact gaagtggact gcctgcgggc ctgtcaggag    900
cagatcgaag ctgcactcag ggagagcctc agggaagcct ctcagaccag ctccagccca    960
gcgcccaaag ccccccgggg ctccagcagc caagggccca gccagaccag cactcctaca   1020
gatgtcacag ccatacacct gtagccctgg agaggccctc tggagtggcc actaagcaga   1080
ggaggggccg ctgccaccca cctccctgcc tccaggaacc acaccacatc taagcctgaa   1140
ggggcgtctg ttccccttc acaaagccca agggatctgg tcctacccat ccccgcagtg   1200
tgcactaagg ggcccggcca gccatgtctg catttcggtg gctagtcaag ctcctcctcc   1260
ctgcatctga ccagcagcgc ctttcccaac tctagctggg ggtgggccag gctgatggga   1320
cagaattgga tacatacacc agcattcctt ttgaacgccc cccccccacc cctgggggct   1380
ctcatgtttt caactgccaa aatgctctag tgccttctaa aggtgttgtc ccttctaggg   1440
ttattgcatt tggattgggg tccctctaaa atttaatgca tgatagacac atatgagggg   1500
gaatagtcta gatggctcct ctcagtactt tggaggcccc tatgtagtcc gtgctgacag   1560
ctgctcctag agggaggggc ctaggcctca gccagagaag ctataaattc ctctttgctt   1620
tgctttctgc tcagcttctc ctgtgtgatt gacagctttg ctgctgaagg ctcattttaa   1680
tttattaatt gctttgagca caactttaag aggacataat gggggcctgg ccatccacaa   1740
gtggtggtaa ccctggtggt tgctgttttc ctcccttctg ctactggcaa aaggatcttt   1800
gtggccaagg agctgctata gcctggggtg gggtcatgcc ctcctctccc attgtccctc   1860
tgccccatcc tccagcaggg aaaatgcagc agggatgccc tggaggtggc tgagcccctg   1920
tctagagagg gaggcaagcc ctgttgacac aggtctttcc taaggctgca aggtttaggc   1980
tggtggccca ggaccatcat cctactgtaa taaagatgat tgtgaaataa aactggcttt   2040
gg                                                                  2042
```

<210> SEQ ID NO 60
<211> LENGTH: 1783
<212> TYPE: DNA
<213> ORGANISM: Homo sapiens

<400> SEQUENCE: 60

```
cctctcggag ctggaaatgc agctattgag atcttcgaat gctgcggagc tggaggcgga     60
ggcagctggg gaggtccgag cgatgtgacc aggccgccat cgctcgtctc ttcctctctc    120
ctgccgcctc ctgtgtcgaa aataactttt ttagtctaaa gaaagaaaga caaaagtagt    180
```

-continued

```
cgtccgcccc tcacgccctc tcttcctctc agccttccgc ccggtgagga agcccggggt    240

ggctgctccg ccgtcggggc cgcgccgccg agccccagcg ccccgggccg cccccgcacg    300

ccgcccccat gcatcccttc tacacccggg ccgccaccat gataggcgag atcgccgccg    360

ccgtgtcctt catctccaag tttctccgca ccaaggggct gacgagcgag cgacagctgc    420

agaccttcag ccagagcctg caggagctgc tggcagaaca ttataaacat cactggttcc    480

cagaaaagcc atgcaaggga tcgggttacc gttgtattcg catcaaccat aaaatggatc    540

ctctgattgg acaggcagca cagcggattg gactgagcag tcaggagctg ttcaggcttc    600

tcccaagtga actcacactc tgggttgacc cctatgaagt gtcctacaga attggagagg    660

atggctccat ctgtgtgctg tatgaagcct caccagcagg aggtagcact caaaacagca    720

ccaacgtgca aatggtagac agccgaatca gctgtaagga ggaacttctc ttgggcagaa    780

cgagcccttc caaaaactac aatatgatga ctgtatcagg ttaagatata gtctgtggat    840

ggatcatctg atgatgatcc ataaatttga tttttgcttt gggtgggctc ctcttgggga    900

tggattatgg aatttaaacc atgtcacagc tgtgaagatc tggcacaaga tagaatggta    960

aaaaaaaaaa aaaattttaa gtgacagtgc catagtttgg acagtacctt tcaatgatta   1020

attttaatag cctgtgagtc caagtaaatg atcactttat ttgctaggga gggaagtcct   1080

agggtggttt cagtttctcc cagacatacc taaattttta catcaatcct tttaaagaaa   1140

atctgtattt caaagaatct ttctctgcag taaatctcgc aggggaattt gcactattac   1200

acttgaaagt tgttattgtt aaccttttcg gcagctttta ataggaaagt taaacgtttt   1260

aaacatggta gtactggaaa ttttacaaga cttttaccta gcacttaaat atgtataaat   1320

gtacataaag acaaactagt aagcatgacc tggggaaatg gtcagacctt gtattgtgtt   1380

tttggccttg aaagtagcaa gtgaccagaa tctgccatgg caacaggctt taaaaaagac   1440

ccttaaaaag acactgtctc aactgtggtg ttagcaccag ccagctctct gtacatttgc   1500

tagcttgtag ttttctaaga ctgagtaaac ttcttatttt tagaaagtgg aggtctggtt   1560

tgtaactttc cttgtactta attgggtaaa agtcttttcc acaaaccacc atctattttg   1620

tgaactttgt tagtcatctt ttatttggta aattatgaac tggtgtaaat ttgtacagtt   1680

catgtatatt gattgtggca aagttgtaca gatttctata ttttggatga gaaatttttc   1740

ttctctctat aataaatcgt ttcttatctt ggcattttta acc                     1783
```

<210> SEQ ID NO 61
<211> LENGTH: 1433
<212> TYPE: DNA
<213> ORGANISM: Homo sapiens

<400> SEQUENCE: 61

```
ttggacagcc cgggcaacct cgacaccctg caggcgaaaa agaacttctc cgtcagtcac     60

ctgctagacc tggaggaagc cggggacatg gtggcggcac aggcggatga gaacgtgggc    120

gaggctggcc ggagcctgct ggagtcgccg ggactcacca gcggcagcga caccccgcag    180

caggacaatg accagctgaa ctcagaagaa aaaaagaaga gaaagcagcg aaggaatagg    240

acaaccttca atagcagcca gctgcaggct ttggagcgtg tctttgagcg gacacactat    300

cctgatgctt ttgtgcgaga agaccttgcc cgccgggtga acctcaccga ggcgagagtg    360

caggtgtggt ttcagaaccg aagagccaag ttccgcagga atgagagagc catgctagcc    420

aataaaaacg cttccctcct caaatcctac tcaggagacg tgactgctgt ggagcagccc    480

atcgtacctc gtcctgctcc gagacccacc gattatctct cctgggggac agcgtctccg    540
```

-continued tacagatcct cgtccctccc aagatgttgt ttacacgagg ggcttcataa cggattctaa 600
cggaagacac tgaaaagcgc catggctact tattctgcca catgtgccaa caatagccct 660
gcacagggca tcaacatggc caacagcatt gccaacctga gactgaaggc caaggaatat 720
agtttacaga ggaaccaggt gccaacagtc aactgaggaa aaaaaataat taaacaggcc 780
taagaagaaa tcaaaaacca taagacacct atcctgctct gttatttctt catctgctgg 840
ggggaaaaag taaattacaa acaaacaaac aaagcagaac taaaatattg ggaccatggc 900
agagaaaagc aggagaggag caaaatgaaa attagttaac aaatgttcct cctcctctgg 960
gataccacca ccacttgttt ctgtgtgtgt ttattttgtt tttctttcat tcatgctttg 1020
cttaatgtac tccaggcttc ttcagctagg ttcagcccac ccacccccat gcttgtaatc 1080
ccagtgcttt gggaggccaa ggcaggtgga tcacctgagg tcaggagttc gagactagcc 1140
tgttccactg acatttctta gacattcagc aaaacccccca ccttaacctc ttttctttct 1200
tgagggttgg tcctgtcccc acctccaccc tcccaccccc tggaagagga agggcccggg 1260
catcagtggc tagtccaaat aaaatatggg cttggggatg gaatgggtgg tggtaagttc 1320
acagagtgta gttagatccc aactcccatg acctctggct tcagtggtgg gtggggcagg 1380
gcagatgaaa gggcttcagt gggaacctct gagagcattt tcctgttccc aat 1433

<210> SEQ ID NO 62
<211> LENGTH: 643
<212> TYPE: DNA
<213> ORGANISM: Homo sapiens

<400> SEQUENCE: 62
ggtagcgacg gtagctctag ccgggcctga gctgtgctag cacctccccc aggagaccgt 60
tgcagtcggc cagccccctt ctccacggta accatgtgcg accgaaaggc cgtgatcaaa 120
aatgcggaca tgtcggaaga gatgcaacag gactcggtgg agtgcgctac tcaggcgctg 180
gagaaataca acatagagaa ggacattgcg gctcatatca agaaggaatt tgacaagaag 240
tacaatccca cctggcattg catcgtgggg aggaacttcg gtagttatgt gacacatgaa 300
accaaacact tcatctactt ctacctgggc caagtggcca ttcttctgtt caaatctggt 360
taaaagcatg gactgtgcca cacacccagt gatccatcca gaaacaagga ctgcagccta 420
aattccaaat accagagact gaaattttca gccttgctaa gggaacatct cgatgtttga 480
acctttgttg tgttttgtac agggcattct ctgtactagt ttgtcgtggt tataaaacaa 540
ttagcagaat agcctacatt tgtatttatt ttctattcca tacttctgcc cacgttgttt 600
tctctcaaaa tccattcctt taaaaaataa atctgatgca ccg 643

<210> SEQ ID NO 63
<211> LENGTH: 4792
<212> TYPE: DNA
<213> ORGANISM: Homo sapiens

<400> SEQUENCE: 63
ctcaaatatg tggatgacat acagaaggga aataccatca aaagactgaa catccagaag 60
aggcggaagc cgtccgtgcc atgcccagaa cccaggacca catctggtca gcaaggtata 120
tggacttcca ctgaatccct ctcatcctcc aacagtgatg acaacaagca gtgccccaac 180
ttcctcatag ccagaagtca agttacatca actccaatct caaagccacc tccccctctg 240
gagacctcac tccctttttct taccatccca gaaaatcgac agctgccacc tccctcacca 300

-continued

```
caactcccaa agcataacct tcatgtcacc aagacactga tggagacccg gagaagactg    360
gaacaggaga gagccaccat gcagatgaca ccgggtgagt tcagaaggcc caggctggcc    420
agttttggag gcatgggcac cacaagctcc ctcccttctt ttgtgggttc tggaaaccac    480
aatcctgcca agcaccagct tcagaatgga taccaaggta atggggatta tggtagctat    540
gccccagctg ctcccaccac ttcctccatg gggagctcca tccgccacag ccccctgagc    600
tcagggatct ccaccccagt gaccaacgtg agccccatgc acctgcagca catccgcgag    660
cagatggcca ttgctctgaa acgcctgaag gagctggagg agcaggtgcg aaccatccct    720
gtgctccagg taaagatctc tgtcttgcaa gaagagaaaa ggcagttggt ctcacagctg    780
aaaaaccaaa gggctgcatc ccagatcaat gtctgtggtg tgaggaagcg gtcctatagt    840
gcggggaacg cctcccagct ggaacagctc tcccgggccc gaagaagtgg cggggaatta    900
tacattgact atgaggagga agaaatggag accgtagaac agagcacgca gaggataaag    960
gagttccggc aacttacagc agacatgcaa gccctggagc agaagatcca ggacagcagc   1020
tgtgaggcct cctcagagct cagggagaat ggagagtgcc ggtctgtggc tgtgggtgcc   1080
gaggagaaca tgaacgacat cgtcgtgtac cacagaggct ccaggtcctg taaggatgca   1140
gctgtaggga cacttgttga gatgagaaat tgtggggtca gcgtgacaga ggccatgctt   1200
ggagtgatga ctgaagctga caaagaaatt gagctccaac agcagaccat agaagccttg   1260
aaggaaaaga tctatcgcct agaagtacag cttagagaaa ccacccatga ccgggagatg   1320
actaaactga aacaagagct gcaggctgct ggatcgagga aaaaggttga caaagccacg   1380
atggcccagc cgcttgtttt cagtaaggtg gtggaggcag tggtgcagac cagagaccaa   1440
atggtcggca gtcacatgga cctggtggac acgtgtgttg ggacctccgt ggaaacaaac   1500
agtgtaggca tctcctgcca gcctgaatgt aagaataaag tcgtagggcc tgagctgcct   1560
atgaattggt ggattgttaa ggagagggtg gaaatgcatg accgatgtgc tgggaggtct   1620
gtggaaatgt gtgacaagag tgtgagtgtg gaagtcagcg tctgcgaaac aggcagcaac   1680
acagaggagt ctgtgaacga cctcacactc ctcaagacaa acttgaatct caaagaagtg   1740
cggtctatcg gttgtggaga ttgttctgtt gacgtgaccg tctgctctcc aaaggagtgc   1800
gcctcccggg gcgtgaacac tgaggctgtt agccaggtgg aagctgccgt catggcagtg   1860
cctcgtactg cagaccagga cactagcaca gatttggaac aggtgcacca gttcaccaac   1920
accgagacgg ccaccctcat agagtcctgc accaacactt gtctaagcac tttggacaag   1980
cagaccagca cccagactgt ggagacgcgg acagtagctg taggagaagg ccgtgtcaag   2040
gacatcaact cctccaccaa gacgcggtcc attggtgttg gaacgttgct ttctggccat   2100
tctgggtttg acaggccatc agctgtgaag accaaagagt caggtgtggg gcagataaat   2160
attaacgaca actatctggt tggtctcaaa atgaggacta tagcttgtgg gccaccacag   2220
ttgactgtgg ggctgacagc cagcagaagg agcgtggggg ttggggatga ccctgtaggg   2280
gaatctctgg agaaccccca gcctcaagct ccacttggaa tgatgactgg cctggatcac   2340
tacattgagc gtatccagaa gctgctggca gaacagcaga cactgctggc tgagaactac   2400
agtgaactgg cagaagcttt cggggaacct cactcacaga tgggctccct caactctcag   2460
ctcatcagca ccctgtcgtc tatcaactct gtcatgaaat ctgcaagcac tgaagagctg   2520
aggaaccctg acttccagaa aaccagtctg ggtaaaatca caggcaatta tttgggatat   2580
acctgtaagt gtgggggcct tcagtcagga agtcccttaa gctcccagac atcccagcct   2640
gagcaagaag tggggacctc agaaggaaag ccaatcagca gcctggatgc cttccccact   2700
```

-continued

```
caggaaggta cgctgtctcc agtgaacctg acagacgacc agatcgccgc tggcctctat   2760

gcatgtacaa acaatgaaag tacactgaag tccatcatga agaagaaaga tggtaacaaa   2820

gattcaaatg gcgcaaaaaa gaatcttcag tttgttggca ttaatggagg gtatgaaaca   2880

acttcaagtg atgattccag ctcagatgaa agctcttctt ccgagtcaga tgacgagtgt   2940

gatgtcattg agtatcctct tgaagaagag gaggaggagg aggatgaaga cactcgggga   3000

atggcagaag ggcaccatgc agttaatatt gaaggtttga agtctgccag ggtggaagat   3060

gaaatgcagg ttcaagaatg tgaacctgag aaggtggaaa tcagagagag gtatgaatta   3120

agtgaaaaga tgttgtctgc atgcaactta ctgaaaaata ctataaatga ccccaaagct   3180

ttgaccagca aagatatgag gttctgtctg aacaccctcc agcacgagtg gttccgcgtg   3240

tccagtcaga agtcagccat tccagccatg gtgggggact acatagctgc ttttgaggcc   3300

atttccccag atgtcctccg ctatgtcatc aacttggcag acggcaacgg caacacagcc   3360

ctccattaca gcgtgtccca ctccaacttc gagattgtga agctgctgtt agatgccgat   3420

gtgtgtaatg tggatcacca gaacaaggca ggctacaccc ccatcatgtt ggcggccctc   3480

gccgctgtgg aagcagagaa ggacatgcgg attgtggaag aactctttgg ctgtggggat   3540

gtgaatgcca aagctagtca ggcgggacag acggccctca tgctggcggt cagtcacgga   3600

cggatagaca tggtgaaggg ccttctggcc tgtggggctg atgtcaacat ccaggatgac   3660

gagggctcca cggccctcat gtgtgccagc gagcacgggc acgtggagat tgtcaagctg   3720

ctgctggccc agcccggctg caacggtcac ctagaggaca acgatggcag cactgcgctc   3780

tcaatcgccc tggaagcagg acacaaggac atcgctgttc ttctgtatgc ccatgtcaac   3840

tttgcaaaag cccagtctcc gggcacccct aggcttggaa ggaagacgtc tcctggcccc   3900

acccaccgag gttcatttga ttgattgtat gcaaatagcc ctttatttac atgccactat   3960

taagctgcta attgttcctg ttggggtgac agatactgaa tgtatacgta ttgtgcctga   4020

gctcaccagc aaacagaagc atcaagccca ggggtaaagg ctgaagcttt cacagtgcag   4080

agactgctag cctgggcaca cgcacctcct ttctggccgt cttctgtgta gggcacactt   4140

taacccagtc tctgttgctg ttgagtctct gctccgtttt gtacagtcac agggaattct   4200

gatctgaagg ggcaccttct gttcactccc acaaagtggt gtctggttct cactgagacg   4260

ttttaagatt tttccacaaa tatttatatg tactaaatgt ggaaccatta gaaagttctt   4320

ccaaaatctc attccagcat agttttggat ttttcttttg tcttatttta aaataaggaa   4380

gtcgagatga ctttgatcat tggtaacttg ggcctgggcc agacaaagta taaaacttac   4440

aaaagaatat tctcatttgg tcttaactag gtagatgtaa tatatgactt tttataaaaa   4500

gggtatctat atgaacttga cacagtattt tcagcttttg tattccatac taaagccatg   4560

aagaactaca cgtaacatca tcatttgtat taattgcaca actccaatgc taaaggttgg   4620

attgtgttag aggaatcggc tctgtatttg cctctagaga aacacagtgt tctctttgta   4680

tttatggatt ccttttttacc gtgtcacatt tactttggtc ctctatgtat ttaaatgttt   4740

gaagtgcctt agactcttgc catattttca aaataaaatt ccattaagct ct           4792
```

<210> SEQ ID NO 64
<211> LENGTH: 2199
<212> TYPE: DNA
<213> ORGANISM: Homo sapiens

<400> SEQUENCE: 64

-continued

```
gtcgccgctg ccgggttgcc agcggagtcg cgcgtcggga gctacgtagg gcagagaagt      60
catggcttct ccgtccaaag gcaatgactt gttttcgccc gacgaggagg gcccagcagt     120
ggtggccgga ccaggcccgg ggcctggggg cgccgagggg gccgcggagg agcgccgcgt     180
caaggtctcc agcctgccct tcagcgtgga ggcgctcatg tccgacaaga agccgcccaa     240
ggaggcgtcc ccgctgccgg ccgaaagcgc ctcggccggg gccaccctgc ggccactgct     300
gctgtcgggg cacggcgctc gggaagcgca cagccccggg ccgctggtga agcccttcga     360
gaccgcctcg gtcaagtcgg aaaattcaga agatggagcg gcgtggatgc aggaacccgg     420
ccgatattcg ccgccgccaa gacatacgag ccctaccacc tgcaccctga ggaaacacaa     480
gaccaatcgg aagccgcgca cgccctttac cacatcccag ctcctcgccc tggagcgcaa     540
gttccgtcag aaacagtacc tctccattgc agagcgtgca gagttctcca gctctctgaa     600
cctcacagag acccaggtca aaatctggtt ccagaaccga agggccaagg cgaaaagact     660
gcaggaggca gaactggaaa agctgaaaat ggctgcaaaa cctatgctgc cctccagctt     720
cagtctccct ttccccatca gctcgcccct gcaggcagcg tccatatatg gagcatccta     780
cccgttccat agacctgtgc ttcccatccc gcctgtggga ctctatgcca cgccagtggg     840
atatggcatg taccacctgt cctaaggaag accagatcaa tagactccat gatggatgct     900
tgtttcaaag ggtttcctct ccctctccac gaaggcagta ccagccagta ctcctgctct     960
gctaaccctg cgtgcaccac cctaagcggc taggctgaca gggccacacg acatagctga    1020
aatttcgttc tgtaggcgga ggcaccaagc cctgttttct tggtgtaatc ttccagatgc    1080
ccccttttcc tttcacaaag attggctctg atggttttta tgtataaata tatatatata    1140
ataaaatata atacattttt atacagcaga cgtaaaaatt caaattattt taaaaggcaa    1200
aatttatata catatgtgct ttttttgtat atctcacctt cccaaaagac actgtgtaag    1260
tccatttgtt gtattttctt aaagagggag acaaattatt tgcaaaatgt gctaaagtca    1320
atgattttta cgggattatt gacttctgct tatggaaaac aaagaaacag acacagtgca    1380
cacagaaaat attagatatg gagagattat tcaaagtgaa ggggacacat catatttctg    1440
cattttactt gcattaaaag aaacctcttt atatactaca gttgttccta tttttccccc    1500
gccccccacc gccccaccac acacatattt ttaaagtttt tcctttttta agaatatttt    1560
tgtaagacca atacctggga tgagaagaat cctgagactg cctggaggtg aggtagaaaa    1620
ttagaaatac ttcctaattc ttctcaaggc tgttggtaac tttatttcag ataattggag    1680
agtaaaatgt taaaacctgt tgagaggaat tgatggtttc tgagaaatac taggtacatt    1740
catcctcaca gattgcaaag gtgatttggg tgggggttta gtaattttct gcttaaaaaa    1800
tgagtatctt gtaaccatta cctatatgct aaatattctt gaacaattag tagatccaga    1860
aagaaaaaaa aaatatgctt tctctgtgtg tgtacctgtt gtatgtccta aacttattag    1920
aaaattttat atactttttt acatgttggg gggcagaagg taaagccatg ttttgacttg    1980
gtgaaaatgg ggttgtcaaa cagcccatta agctccctgg tatttcacct tcctgtccat    2040
ctctcccctc cctccggtat acctttatcc ctttgaaagg gtgcttgtac aatttgatat    2100
attttattga agagttatct cttattctga attaaattaa gcatttgttt tattgcagta    2160
aagtttgtcc aaactcacaa ttaaaaaaaa aaaaaaaaa                           2199
```

<210> SEQ ID NO 65
<211> LENGTH: 1496
<212> TYPE: DNA
<213> ORGANISM: Homo sapiens -continued

<400> SEQUENCE: 65

```
tcactaaagg gaacaaaagc tggagctcca ccgcggtggc ggcccctcag aactagtgga     60
tcccccgggc tgcaaggaat tcggcacgag cgcgcgtcct gcccgtctgt ccccgcgggg    120
gtcgcccgcc acagcccgcg gaatgaccac ccagcagata gacctccagg gcccggggcc    180
gtggggcttc cgcctcgtgg ggcgaaagga cttcgagcag cctctcgcca tttcccgggt    240
cactcctgga agcaaggcgg ctctagctaa tttatgtatt ggagatgtaa tcacagccat    300
tgatggggaa aatactagca atatgacaca cttggaagct cagaacagaa tcaaaggctg    360
cacagacaac ttgactctca ctgtagccag atctgaacat aaagtctggt ctcctctggt    420
gacggaggaa gggaagcgtc atccatacaa gatgaattta gcctctgaac cccaggaggt    480
cctgcacata ggaagcgccc acaaccgaag tgccatgccc tttaccgcct cgcctgcctc    540
cagcactact gccagggtca tcacaaacca gtacaacaac ccagctggcc tctactcttc    600
tgaaaatatc tccaacttca acaatgccct ggagtcaaag actgctgcca gcggggtgga    660
ggcgaacagc agacccttag accatgctca gcctccaagc agccttgtca tcgacaaaga    720
atctgaagtt tacaagatgc ttcaggagaa acaggagttg aatgagcccc cgaaacagtc    780
cacgtctttc ttggttttgc aggaaatcct ggagtctgaa gaaaaagggg atcccaacaa    840
gccctcagga ttcagaagtg ttaaagctcc tgtcactaaa gtggctgcgt cgattggaaa    900
tgctcagaag ttgcctatgt gtgacaaatg tggcactggg attgttggtg tgtttgtgaa    960
gctgcgggac cgtcaccgcc accctgagtg ttatgtgtgc actgactgtg gcaccaacct   1020
gaaacagaag ggccatttct ttgtggagga tcaaatctac tgtgagaagc atgcccggga   1080
gcgagtcaca ccacctgagg gttatgaagt ggtcactgtg ttccccaagt gagccagcag   1140
atctgaccac tgttctccag caggcctctg ctgcagcttt tctctcagtg ttctggccct   1200
ctcctctctt gaaagttctc tgcttacttt ggttttccct ctgcttgtaa aacattgagg   1260
cccctccctg ccttggttaa ttgactcaca ccagctgtgg gatgcccgct tttacaatta   1320
aaggaaaact gttgtgttca gtgtcacctt gtcagcaaca ctgtgtccct tcgcccgccg   1380
ttcttctctg ctgcatttgg acatcagcca aatttgaacc caatcaaata taacgtgtct   1440
gacactgatt ttgtttttac tcaataaatg tatagactac aaaaaaaaaa aaaaaa       1496
```

<210> SEQ ID NO 66
<211> LENGTH: 5421
<212> TYPE: DNA
<213> ORGANISM: Homo sapiens

<400> SEQUENCE: 66

```
ccgggatccg gttttttttg tttttaaaag tgtaatttcc tttttatttg catctgttta     60
tgactgaaaa aaatgactag ttattatgaa gacactactg ttgaagatgg atattttaac    120
atggagtttc aacaaaatta cttcttgaga cagagctgat gtgtttttta aataacgtga    180
ttttaagcat atatttgaac aaaactaaaa catttagtat tatgaatatg aaaaaagatc    240
agtaaatcaa tgtactcttc taggctgaat taaggtagac tatttaaggt ttcaaaaaag    300
tttggctggg gcagaataag ttttacaaaa cccatgccat ccaaaattaa gatgacatgt    360
agcagcaaga agtattccaa tgtctcataa ccagttctcg caagcaatgt gtattcctta    420
ctttaaggaa gtgtcaaaca aatagaaaaa tctggaagaa tttactaagt gtaataaatt    480
agaggtaaat cgtaataaaa gaatttatgt ctcacaaaaa tattcacaag tgggagtttt    540
```

-continued

```
cttttaccaa cttctcagag tccttctagc cccctcttca cttctgaaag atgggattta    600
ccaaaatctg gtttacattt aacttttcag ggacacatga cctgaaaaga aagatgtcag    660
ataatactga cattgcctca tgcactttct ttgtatcagt ccttcttctg taagtaatca    720
gaattgggtc caaatggcat agaatcaaac attatgtatc atgccaaata ccacttcctg    780
cccaacaaaa tttcatcttt ctccagtaat gaagaggtgg acattcttgt tggactgtag    840
catctgtgcc gcccgctcca caccaaccac ggcagctaac ctctgggcat catatttgga    900
gtagagaaca gtgcaggtcc acgtggcctc ttctcctctg ttggtggctc tcagcatatt    960
acagatttca ctgtaaaagt gtggatatgt cggcagttca tagaaaatca ggttcctgat   1020
gccttttatt gctgtagttt atttccaccc ccttccctcc tgttttctct ctctccttct   1080
ctctctctct ctctctctct tttttttccg ccctagctgg ggctgtgttg gaggagagga   1140
agaaagagag acagaggatt gcattcatcc gttacgttct tgaaatttcc taatagcaag   1200
accagcgaag cggttgcacc cttttcaatc ttgcaaagga aaaaaacaaa acaaaacaaa   1260
aaaaacccaa gtccccttcc cggcagtttt tgccttaaag ctgccctctt gaaattaatt   1320
ttttcccagg agagagatgt cttatcaggg gaagaaaaat attccacgca tcacgagcga   1380
tcgtcttctg atcaaaggag gtaaaattgt taatgatgac cagtcgttct atgcagacat   1440
atacatggaa gatgggttga tcaagcaaat aggagaaaat ctgattgtgc caggaggagt   1500
gaagaccatc gaggcccact cccggatggt gatccccgga ggaattgacg tccacactcg   1560
tttccagatg cctgatcagg gaatgacgtc tgctgatgat ttcttccaag gaaccaaggc   1620
ggccctggct gggggaacca ctatgatcat tgaccacgtt gttcctgagc ctgggacaag   1680
cctgctcgct gcctttgacc agtggaggga atgggccgac agcaagtcct gctgtgacta   1740
ctctctgcat gtggacatca gcgagtggca taagggcatc caggaggaga tggaagcgct   1800
tgtgaaggat cacggggtaa attccttcct cgtgtacatg gctttcaaag atcgcttcca   1860
gctaacggat tgccagattt atgaagtact gagtgtgatc cgggatattg gcgccatagc   1920
ccaagtccac gcagaaaatg gcgacatcat tgcagaggag cagcagagga tcctggatct   1980
gggcatcacg ggccccgagg gacatgtgct gagccgacct gaggaggtcg aggccgaagc   2040
cgtgaatcgt gccatcacca tcgccaacca gaccaactgc ccgctgtata tcaccaaggt   2100
gatgagcaaa agctctgctg aggtcatcgc ccaggcacgg aagaagggaa ctgtggtgta   2160
tggcgagccc atcactgcca gcttgggaac ggacggctcc cattactgga gcaagaactg   2220
ggccaaggct gctgcctttg tcacctcccc acccttgagc cctgatccaa ccactccaga   2280
ctttctcaac tccttgctgt cctgtggaga cctccaggtc acgggcagtg cccattgcac   2340
gtttaacact gcccagaagg ctgtaggaaa ggacaacttc accctgattc cggagggcac   2400
caatggcact gaggagcgga tgtccgtcat ctgggacaag gctgtggtca ctgggaagat   2460
ggatgagaac cagtttgtgg ctgtgaccag caccaatgca gccaaagtct tcaaccttta   2520
cccccggaaa ggccgcattg ctgtgggatc cgatgccgac ctggtcatct gggaccccga   2580
cagcgttaaa accatctctg ccaagacaca caacagctct ctcgagtaca acatctttga   2640
aggcatggag tgccgcggct ccccactggt ggtcatcagc caggggaaga ttgtcctgga   2700
ggacggcacc ctgcatgtca ccgaaggctc tggacgctac attccccgga agcccttccc   2760
tgattttgtt tacaagcgta tcaaggcaag gagcaggctg gctgagctga gaggggttcc   2820
tcgtggcctg tatgacggac ctgtgtgtga agtgtctgtg acgcccaaga cagtcactcc   2880
agcctcctcg gccaagacgt ctcctgccaa gcagcaggcc ccacctgtcc ggaacctgca   2940
```

-continued

```
ccagtctgga ttcagtttgt ctggtgctca gattgatgac aacattcccc gccgcaccac   3000
ccagcgtatc gtggcgcccc ccggtggccg tgccaacatc accagcctgg gctagagctc   3060
ctgggctgtg cgtccactgg ggactgggga tgggacacct gaggacattc tgagacttct   3120
ttcttccttc cttttttttt tttgtttttt tttttaagag cctgtgatag ttactgtgga   3180
gcagccagtt catggggtcc cccttgggcc cacaccccgt ctctcaccaa gagttactga   3240
ttttgctcat ccacttccct acacatctat gggtatcaca cccaagacta cccaccaagc   3300
tcatacaggg aaccacaccc aacacttaga catgcgaaca agcagccccc agcgagggtc   3360
tccttcgcct tcaacctcct agtgtctgtt agcattcctt ttcatggggg gagggaagat   3420
aaagtgaatt gcccagagct gcctttttct tttcttttta aaaattttaa gaagttttcc   3480
ttgtggggct ggggaggggc cggggtcagg gagagtcttt tttttttttt ttttaaatac   3540
taaattggaa catttaattc catattaata caaggggttt gaactggaca tcctaatgat   3600
gcaattacgt catcacccag ctgattccgg gtggttggca aactcatcgt gtctgtcctg   3660
agaggctcca caatgcccac ccgcatcgcc attctgtagt cttcagggtc agctgttgat   3720
aaaggggcag gcttgcgtta ttggcctaga ttttgctgca gattaaatcc tttgaggatt   3780
ctcttctctt ttaccatttt tctgcgtgct ctcactctct ctttctctct ctagcttttt   3840
aattcatgaa tattttcgtg tctgtctctc tctctctctg tgtttcctcc agcccttgtc   3900
tcggagacgg tgttttcctc ccttgcccca ttatcttttc acctcccagg tctacatttc   3960
atggtggtcg ttgggtccgc ctaaaggatt tgagcgtttg ccattgcaag catagtgctg   4020
tgtcatcctg gtccatgtag gactggtgct aaccacctgc catcatgagg atgtgtgcta   4080
gagtgtggga ccctggccaa gtgcaggaat gggccatgcc gtctcaccca cagtatcaca   4140
cgtggaaccg cagacagggc ccagaagctt tagaggtatg aggctgcaga accggagaga   4200
ttttcctctg tgcagtgctc tctggctaaa gtcacggtca aacctaaaca ccgagcctca   4260
ttaacccaag tgaaccaacc aaagtcacca gttcagaagt gctaagctaa taggagtctg   4320
acccgagggc ctgctgcttc ctggttaagt atcttttgag attctagaac acatgggagc   4380
tttttatttt cggggaaaaa ccgtattttt ttcttgtcca attatttcta aagacacact   4440
acatagaaag aggccctata aactcaaaaa gtcattggga aacttaaagt ctattctact   4500
ttgccaagag gagaaatgtg ttttatgaac gatagatcac atcagaactc ctgtggggag   4560
gaaaccttat aaattaaaca catggccccc ttagagacca caggcgatgt ctgtctccat   4620
ccttccctct ccttttctgt cacctttccc cctagctggc tcctttggac ctacccctgt   4680
ccttgctgac ttgtgttgca ttgtattcca aacgtgttta caggttctct taagcaatgt   4740
tgtatttgca ggcttttctg aataccaaat ctgctttttg taaagcgtaa aaacatcaca   4800
aagtaggtca ttccatcacc acccttgtct ctctacacat tttgcctttg gggatctggt   4860
tggggttttg ggtttttttgt tgttgttgtt tatttgttat tttaaaggta aattgcactt   4920
ttaaaaaaat aattggttga cttaatatat ttgctttttt tctcacctgc acttagagga   4980
aatttgaaca agttggaaaa aaacaatttt tgtttcaatt ctaagaaaca cttgcagctc   5040
tagtattcac ttgagtcttc ctgtttttcc tgtaccgggt catggtaatt tttggttgtt   5100
ttggttgttt tcttaaaaaa caagttaaaa cctgacgatt tctgcagtga cttgatgctc   5160
taaaacagtg taggatttaa gaatagatgg tttttaatcc tggaaattgt gattgtgacc   5220
catgagtgga ggaactttca gttctaaagc tgataaagtg tgtagccaga agagtacttt   5280
```

-continued

```
tttttgtaa ccactgtctt gatggcaaaa taattatggt aaaaaacaag tctcgtgttt   5340

attattcctt aagaactctg tgttatatta ccatggaacg cctaataaag caaaatgtgg   5400

ttgtttcaaa aaaaaaaaaa a                                            5421
```

<210> SEQ ID NO 67
<211> LENGTH: 620
<212> TYPE: DNA
<213> ORGANISM: Homo sapiens

<400> SEQUENCE: 67

```
aaacatccta tcatctgtag gctcattcat ttctctaaca gcagcagcaa cagcgcatca     60

caggacacca aggagagctc tgaagagcct ccctcagaag agagccagga cacccccatt    120

tacacggagt ttgatgagga tttcgaggag gaacccacat cccccatagg tcactgtgtg    180

gccatctacc actttgaagg gtccagcgag ggcactatct ctatggccga gggtgaagac    240

ctcagtctta tggaagaaga caaaggggac ggctggaccc gggtcaggcg gaaagaggga    300

ggcgagggct acgtgcccac ctcctacctc cgagtcacgc tcaattgaac cctgccagag    360

acgggaagag gggggctgtc ggctgctgct tctgggccac ggggagcccc aggacctatg    420

cactttattt ctgaccccgt ggcttcggct gagacctgtg taacctgctg ccccctccac    480

ccccaaccca gtcctacctg tcacaccgga cggacccgct gtgccttcta ccatcgttcc    540

accattgatg tacatactca tgttttacat cttttctttc tgcgctcggc tccggccatt    600

ttgttttata caaaaatggg                                                620
```

<210> SEQ ID NO 68
<211> LENGTH: 1266
<212> TYPE: DNA
<213> ORGANISM: Homo sapiens

<400> SEQUENCE: 68

```
ctcggaagcc cgtcaccatg tcgtgcgagt cgtctatggt tctcgggtac tgggatattc     60

gtgggctggc gcacgccatc cgcctgctcc tggagttcac ggatacctct tatgaggaga    120

aacggtacac gtgcggggaa gctcctgact atgatcgaag ccaatggctg gatgtgaaat    180

tcaagctaga cctggacttt cctaatctgc cctacctcct ggatgggaag aacaagatca    240

cccagagcaa tgccatcttg cgctacatcg ctcgcaagca caacatgtgt ggtgagactg    300

aagaagaaaa gattcgagtg gacatcatag agaaccaagt aatggatttc cgcacacaac    360

tgataaggct ctgttacagc tctgaccacg aaaaactgaa gcctcagtac ttggaagagc    420

tacctggaca actgaaacaa ttctccatgt ttctgtggaa attctcatgg tttgccgggg    480

aaaagctcac ctttgtggat tttctcacct atgatatctt ggatcagaac cgtatatttg    540

accccaagtg cctggatgag ttcccaaacc tgaaggcttt catgtgccgt tttgaggctt    600

tggagaaaat cgctgcctac ttacagtctg atcagttctg caagatgccc atcaacaaca    660

agatggccca gtggggcaac aagcctgtat gctgagcagg aggcagactt gcagagcttg    720

ttttgtttca tcctgtccgt aaggggtcag cgctcttgct ttgctctttt caatgaatag    780

cacttatgtt actggtgtcc agctgagttt ctcttgggta taaaggctaa aagggaaaaa    840

ggatatgtgg agaatcatca agatatgaat tgaatcgctg cgatactgtg gcatttccct    900

actccccaac tgagttcaag ggctgtaggt tcatgcccaa gccctgagag tgggtactag    960

aaaaaacgag attgcacagt tggagagagc aggtgtgtta aatggactgg agtccctgtg   1020

aagactgggt gaggataaca caagtaaaac tgtggtactg atggacttaa ccggagttcg   1080
```

-continued

```
gaaaccgtcc tgtgtacaca tgggagttta gtgtgataaa ggcagtattt cagactggtg   1140

ggctagccaa tagagttggc aattgcttat tgaaactcat taaaaataat agagccccac   1200

ttgacactat tcactaaaat taatctggaa tttaaggccc aacattaaac acaaagctgt   1260

attgat                                                              1266
```

<210> SEQ ID NO 69
<211> LENGTH: 3858
<212> TYPE: DNA
<213> ORGANISM: Homo sapiens

<400> SEQUENCE: 69

```
agtctggttt aactggttgg aacgactaaa gcacgctggc gcaaggaaag ctctcaactt     60

cgggagctga ggcgcaggct ggccagagcg tggagaggaa agccctttcc atcctcaagg    120

ccgttgcagg agatgcccgc gagccacctt cgccagcacc acaccggggt gtaatggata    180

ggtaacagag aagacctcgt cccttcctag tcagggcatc agcatgactg agtgcttcct    240

gccccccacc agcagcccca gtgaacaccg cagggtggag catggcagcg ggcttacccg    300

gacccccagc tctgaagaga tcagccctac taagtttcct ggattgtacc gcactggcga    360

gccctcacct ccccatgaca tcctccatga gcctcctgat gtagtgtctg atgatgagaa    420

agatcatggg aagaaaaaag ggaaatttaa gaaaaaggaa aagaggactg aaggctatgc    480

agcctttcag gaagatagct ctggagatga ggcagaaagt ccttctaaaa tgaagaggtc    540

caagggaatc catgttttca agaagcccag cttttctaaa aagaaggaaa aggattttaa    600

aataaaagag aaacccaaag aagaaaagca taaagaagaa aagcacaaag aagaaaaaca    660

taaagagaag aagtcaaaag acttgacagc agctgatgtt gttaaacagt ggaaggaaaa    720

gaagaaaaag aaaaagccaa ttcaggagcc agaggtgcct cagattgatg ttccaaatct    780

caaacccatt tttggaattc ctttggctga tgcagtagag aggaccatga tgtatgatgg    840

cattcggctg ccagccgttt tccgtgaatg tatagattac gtagagaagt atggcatgaa    900

gtgtgaaggc atctacagag tatcaggaat taaatcaaag gtggatgagc taaaagcagc    960

ctatgaccgg gaggagtcta caaacttgga agactatgag cctaacactg tagccagttt   1020

gctgaagcag tatttgcgag accttccaga gaatttgctt accaaagagc ttatgcccag   1080

atttgaagag gcttgtggga ggaccacgga gactgagaaa gtgcaggaat tccagcgttt   1140

actcaaagaa ctgccagaat gtaactatct tctgatttct tggctcattg tgcacatgga   1200

ccatgtcatt gcaaaggaac tggaaacaaa aatgaatata cagaacattt ctatagtgct   1260

cagcccaact gtgcagatca gcaatcgagt cctgtatgtg tttttcacac atgtgcaaga   1320

actctttgga aatgtggtac taaagcaagt gatgaaacct ctgcgatggt ctaacatggc   1380

cacgatgccc acgctgccag agacccaggc gggcatcaag gaggagatca ggagacagga   1440

gtttcttttg aattgtttac atcgagatct gcagggtggg ataaaggatt tgtctaaaga   1500

agaaagatta tgggaagtac aaagaatttt gacagccctc aaaagaaaac tgagagaagc   1560

taaaagacag gagtgtgaaa ccaagattgc acaagagata gccagtcttt caaaagagga   1620

tgtttccaaa gaagagatga atgaaaatga agaagttata aatattctcc ttgctcagga   1680

gaatgagatc ctgactgaac aggaggagct cctggccatg gagcagtttc tgcgccggca   1740

gattgcctca gaaaaagaag agattgaacg cctcagagct gagattgctg aaattcagag   1800

tcgccagcag cacggccgaa gtgagactga ggagtactcc tccgagagcg agagcgagag   1860
```

-continued tgaggatgag gaggagctgc agatcattct ggaagactta cagagacaga acgaagagct 1920
ggaaataaag aacaatcatt tgaatcaagc aattcatgag gagcgcgagg ccatcatcga 1980
gctgcgcgtg cagctgcggc tgctccagat gcagcgagcc aaggccgagc agcaggcgca 2040
ggaggacgag gagcctgagt ggcgcggggg tgccgtccag ccgcccagag acggcgtcct 2100
tgagccaaaa gcagctaaag agcagccaaa ggcaggcaag gagccggcaa agccatcgcc 2160
cagcagggat aggaaggaga cgtccatctg agcagcctgc gtggccgtct ggagtccgtg 2220
agactgaaag gacccgtgca tcttactgta acccgggggc caggccggct ctctcgctgt 2280
acattctgta aaggtgtctt ctcttctcag actcttcctc tgtcacacgt ctgactcctt 2340
cacgtcaggc tcaggttcca tgggaggacg aagcagtgga cgcattgtgg gctttaggga 2400
cagatgagtt ttccagatag tgtcagctta tttgaagatt aattttcttt gttaacttaa 2460
aataactatt ttaacccttg agtggcttct ttttaaacca aaaaccgtct ttctttgctt 2520
ttttatcaca gcagaatcag gatctctttc tcattcaagg ggggaaccac accaggtcag 2580
cgctgcgcct gctgtggccg ccgcgagcca cgccctctgg gatctctggt accgtcactc 2640
ttgcttgtgc cttccacacc ttctcggtgc agatccctat gggggagctg cctcacgttc 2700
tctgactggt cagagcagcg cctggtgggt gttccctggc ccactctcct ctctccttct 2760
gcagttctaa accacagtct ataagcccga gtcaccagga cggcctgtct ggccacagac 2820
aggggctgcc tgtggagcct gcccaccggc ccccggcagt gcagtccagc ggggaggagg 2880
ctgcccgttc ctgccagttc ctcactgcgg ggaccagcaa aggccttctc actgggttgg 2940
tcaaaggtag tcaccttggc ctggtgcatc cacagaggat gttgttcaaa ccagaaatct 3000
tttaaacgac tgaccttcct taaaaacaga atgactccga ttgcttgctt gggctagaat 3060
gtacacgtct ccttgcctga ataagccata tatatgctct taaacaaaag tttgaaatta 3120
tccatatcat ctcagtgaac ctactggtgg actcccaatt gacaagattg agcaatagaa 3180
aaaaattcct ttcctttgaa tgatagctgt gattcacccc accccatttt cttgtttctg 3240
gtccatccga tgagacggat gctctgatgc tctgaggctt ctgggaggct gggccctgga 3300
ggcaacgtgc tgcaggcgca ctctgtcaga gtgaacagca ccgcgagaca ggccaggctc 3360
gtggctcgga agacaaaccc cacacacact caaggggtcg aaaacaaacc ccacacgagg 3420
gctctcacct ccttctccta ggtagtattt attttcagca cctgtttgat gcagttttta 3480
atcctctacc tattgcactg ttgtgactcg ttggccatta tttgattttg gtacgaaaaa 3540
aagctttgtt atagaaatca gcatactatt tttttaaatc tggagagaag atattctggt 3600
gactgaaagt atggtcgggt gtcagatata aatgtgcaaa tgccttcttg ctgtcctgtc 3660
ggtctcagta cgttcacttt atagctgctg gcaatatcga aggttccttt tttgtttgtg 3720
taaactctaa tttctatcaa ggtgtcatgg atttttaaaa ttagtatttc attacaaatg 3780
tctcagcatt ggttaactaa ttttgggcag gaccattatt gatcaagcaa ataaattcaa 3840
cagccatttg ggaaaaag 3858

<210> SEQ ID NO 70
<211> LENGTH: 4043
<212> TYPE: DNA
<213> ORGANISM: Homo sapiens

<400> SEQUENCE: 70
cgaagcgggt cctgccccgc tgtcagctgc ggcccccggc gccgggcggg ggtggccgcg 60
accattggcg gagaggcgaa aggggcgggg ccgccgccag ccgctgcggg caaggctgaa 120

-continued

```
caggcggagg tgggcagccg gccagggaag cacggtccag gcggctacat tcggcccggc    180
catggcagcg gcgcccctga aagtgtgcat cgtgggctcg ggaactgggg gttcagctgt    240
tgcaaaaata attggtaata acgtcaagaa acttcagaaa tttgcctcca cagtcaagat    300
gtgggtcttt gaagaaacag tgaatggcag aaaactgaca gacatcataa ataatgacca    360
tgaaaatgta aaatatcttc ctggacacaa gctgccagaa aatgtggttg ccatgtcaaa    420
tcttagcgag gctgtgcagg atgcagacct gctggtgttt gtcattcccc accagttcat    480
tcacagaatc tgtgatgaga tcactgggag agtgcccaag aaagcgctgg gaatcaccct    540
catcaagggc atagacgagg gccccgaggg gctgaaactc atttctgaca tcatccgtga    600
gaagatgggt attgacatca gtgtgctgat gggagccaac attgccaatg aggtggctgc    660
agagaagttc tgtgagacca ccatcggcag caaagtaatg gagaacggcc ttctcttcaa    720
agaacttctg cagactccaa attttcgaat tacggtggtt gatgatgcag acactgttga    780
actctgtggt gcgcttaaga acatcgtagc tgtgggagct gggttctgcg acggcctccg    840
ctgtggagac aacaccaaag cggccgtcat ccgcctggga ctcatggaaa tgattgcttt    900
tgccaggatc ttctgcaaag gccaagtgtc tacagccacc ttcctagaga gctgcggggt    960
ggccgacctg atcaccacct gttacggagg gcggaaccgc agggtggccg aggccttcgc   1020
cagaactggg aagaccattg aagagttgga gaaggagatg ctgaatgggc aaaagctcca   1080
aggaccgcag acttctgctg aagtgtaccg catcctcaaa cagaagggac tactggacaa   1140
gtttccattg tttactgcag tgtatcagat ctgctacgaa agcagaccag ttcaagagat   1200
gttgtcttgt cttcagagcc atccagagca tacataaagt gaatcatgca acgtgttggg   1260
ggaagttctg cctttctgat caatcttttg ggttcacgtg gaaaccagga cttggcaaca   1320
tgatgtttga ctgtaatctc atcacggata tgtatgaatt tttacaggtt cgtttttgaa   1380
ttgtgagagg cagttcatta gcaaagatgt actgggcagt aactaaacac acatgcaaac   1440
atgtgaatgg tggtttattc ctcattctgt ggatgtttct atgagccaaa atttgatgtc   1500
tttttttcaa aattgcttat gaaatttcca cacaatcgta gcttataaga ttggaacgat   1560
ctcagccaaa tattttaggt gtaattcata tgtatttgag tggaggattt tttttctcat   1620
ttttctagtg ttaaatttta accagcatta acatggtaga gtggaggagt gagtgtgttc   1680
aaagatcaac atatttaact tttaaacact atctcaaagc cagcataatt aactactttg   1740
attgtgggct gacctttgtt tttttaacaa tcaggcattt ttaattagat aatccactca   1800
tgtatttccc cctcactgca gttgtctgca tttttagcct cttttctctt cgttagttgt   1860
cagaatatgc ctttgtcaag gctcagaggt aacaagacag aaaattcatc tgggattttc   1920
ctgctgtggc tggcacattc ttctgattaa cagacacttg tatgatgctt taggctagtt   1980
agtgcatttt ttagcaaaca tttatcttaa acatcacaga tccactgggg ggtgcaaggg   2040
gctactgtta gtcctcttgt tagatgcagt cactcctcct ggtcacctag tgagcaggga   2100
cagagccagg agtcaagtgc agtgccaagg tgcatgaccc tctgagaagt cactgggctg   2160
atttgacctc cgactcattg gttgtgtaaa tgccatgtgc agcctttcct gaggccatag   2220
gagggcttcc tgcagctgag atctatgcag gccatcctct caacaggtgc cactccaagg   2280
gcggtcctcg gtgcagcagc atcagcttca cttgtggggg ggtgggggaa ggggcggtct   2340
cagaaatgca ggttcccagg tcccaccctg gacttctgaa ggggtgtggc atctgtgttt   2400
ctgatgctta ctacaatatg tgaaccacta ctttagaaaa tctgctttaa cttggtattc   2460
```

-continued

```
ctctaattgt gttccctagg aaatgactgt cccaagagcc agtgattatt ccaggtgttc   2520

cctggaaagg tcaagtgagt ctgggaaaca ctatgtctgt acacctcttg aaggtgtcga   2580

atgtatgttt atacatcagt ggaacccatt tttctagcct agcaagtccc aaacacatta   2640

cactgaagag attttggtga ggaaacttgc tggagttttc agggaacact gttctaggct   2700

taggtgacct taggatcact caagtagacc cttcactccc tgcgagaaat taggatgaat   2760

aactacctgt ggcattgttg gttctgaact tttacagttc aggcctgctg tgaatctttg   2820

atgaagcttt aaggtgacac tgttgtacaa gatgtcagct ttgctgaaac gcacattacc   2880

tggaataagt gctttaattg tagaattaga atgggattta ctgtactgtt ttaaatgaga   2940

ttggcttcag aatccattac agttacctta catagcactt gatacgtgtt aaatgaacat   3000

atgaatgtaa tttatatatt cctagaattt aagttacttt gtgagatttg ggcctgtccc   3060

tcaatgccag tttaggattt cttttttttct ataccttgaa atgattataa aatagatttt   3120

catgggaatt ttaaaaactc tatccaaaac atttttggag cattttaaag ccccatacac   3180

agaagtatac gaaagcacac aaaacactcc aagtttcagc agttttagcg ccaccattaa   3240

cccactttgc ttgtctcatg aaaaatcttt gttaaagttt gtacacaggt aacaaaaagt   3300

tactttaaaa gatatataaa gggctgtaag ctaattgtgg tgtctagtaa gtagcataat   3360

gagatgtgag gagttggaac tttgcgtgtt ttgcgtattt tcatctgcat tcagcttctt   3420

actctgggtt tgtactcgag tgttatttct ttacaaatgc ccttgtaatt accactctga   3480

agtctgctga ctgtgtctct tgaacatact taggatattc tgcacattat ggaaaaaggt   3540

aaattttaga agtttctgct ctactaactg tagatattta tgactctgcg agttatctat   3600

ttttataacc acctgtggtc cattgttcat tttaattcac atttcttatg aagtatggta   3660

acagggaggg agacacctag attagcagct caatttgtac tacttcagcc aatctgtgaa   3720

tgtaaaaact acactgttgc cttgctagga tccaccctcc tataatatgg aacaaatatc   3780

tgaatgaaat ccaccctagg agacggagtc aaactaaact tgtggttttt catttaactt   3840

ttgactacag catggcccca tggcatccac accaagaggg tgttgtgatg aggtgccggt   3900

gtgcaaaggg aactttagtt tttccactgg ttcttatctg ctagcctttt acatacatgt   3960

gtactatatt tgtttataga ctgtaggtgg atatataatt taaaagcttg atttaataaa   4020

catttaaccc cctaaacttg ggg                                           4043
```

<210> SEQ ID NO 71
<211> LENGTH: 2108
<212> TYPE: DNA
<213> ORGANISM: Homo sapiens

<400> SEQUENCE: 71

```
tgttcctcct ccgtcccacc cccataacta tactggctct gatgagacct tggttttctg     60

taaaagctct atttagaggt gtatcattat ttacttaatt gttctccttt acaacccacc    120

tgggatgagc atcttgccta gaagtctcta cttgcacagg atacatacga aatagattga    180

ggattcaaag cagatacaga actcttccca cttactttct taccctgtgt gtctccccac    240

agggttacaa gtgtataaca agtgttggaa gtttgagcat tgcaatttca acgacgtcac    300

aacccgcttg agggaaaatg agctaacgta ctactgctgc aagaaggacc tgtgtaactt    360

taacgaacag cttgaaaatg gtgggacatc cttatcagag aaaacagttc ttctgctggt    420

gactccattt ctggcagcag cctggagcct tcatccctaa gtcaacacca ggagagcttc    480

tcccaaactc cccgttcctg cgtagtccgc tttctcttgc tgccacattc taaaggcttg    540
```

-continued atattttcca aatggatcct gttgggaaag aataaaatta gcttgagcaa cctggctaag 600
atagaggggc tctgggagac tttgaagacc agtcctgttt gcagggaagc cccacttgaa 660
ggaagaagtc taagagtgaa gtaggtgtga cttgaactag attgcatgct tcctcctttg 720
ctcttgggaa gaccagcttt gcagtgacag cttgagtggg ttctctgcag ccctcagatt 780
atttttcctc tggctccttg gatgtagtca gttagcatca ttagtacatc tttggagggt 840
ggggcaggag tatatgagca tcctctctca catggaacgc tttcataaac ttcagggatc 900
ccgtgttgcc atggaggcat gccaaatgtt ccatatgtgg gtgtcagtca gggacaacaa 960
gatccttaat gcagagctag aggacttctg gcagggaagt ggggaagtgt tccagatagc 1020
agggcatgaa aacttagaga ggtacaagtg gctgaaaatc gagtttttcc tctgtcttta 1080
aattttatat gggctttgtt atcttccact ggaaaagtgt aatagcatac atcaatggtg 1140
tgttaaagct atttccttgc ctttttttta ttggaatggt aggatatctt ggctttgcca 1200
cacacagtta cagagtgaac actctactac atgtgactgg cagtattaag tgtgcttatt 1260
ttaaatgtta ctggtagaaa ggcagttcag gtatgtgtgt atatagtatg aatgcagtgg 1320
ggacaccctt tgtggttaca gtttgagact tccaaaggtc atccttaata acaacagatc 1380
tgcaggggta tgttttacca tctgcatcca gcctcctgct aactcctagc tgactcagca 1440
tagattgtat aaaatacctt tgtaacggct cttagcacac tcacagatgt ttgaggcttt 1500
cagaagctct tctaaaaaat gatacacacc tttcacaagg gcaaactttt tccttttccc 1560
tgtgtattct agtgaatgaa tctcaagatt cagtagacct aatgacattt gtattttatg 1620
atcttggctg tatttaatgg cataggctga cttttgcaga tggaggaatt tcttgattaa 1680
tgttgaaaaa aaacccttga ttatactctg ttggacaaac cgagtgcaat gaatgatgct 1740
tttctgaaaa tgaaatataa caagtgggtg aatgtggtta tggccgaaaa ggatatgcag 1800
tatgcttaat ggtagcaact gaaagaagac atcctgagca gtgccagctt tcttctgttg 1860
atgccgttcc ctgaacatag gaaaatagaa acttgcttat caaaacttag cattaccttg 1920
gtgctctgtg ttctctgtta gctcagtgtc tttccttaca tcaataggtt tttttttttt 1980
tttttggcct gaggaagtac tgaccatgcc cacagccacc ggctgagcaa agaagctcat 2040
ttcatgtgag ttctaaggaa tgagaaacaa ttttgatgaa tttaagcaga aaatgaattt 2100
ctgggaac 2108

<210> SEQ ID NO 72
<211> LENGTH: 1938
<212> TYPE: DNA
<213> ORGANISM: Homo sapiens

<400> SEQUENCE: 72
attccggttg ttgcaccatg gcgtccatgg ggaccctcgc cttcgatgaa tatgggcgcc 60
ctttcctcat catcaaggat caggaccgca agtcccgtct tatgggactt gaggccctca 120
agtctcatat aatggcagca aaggctgtag caaatacaat gagaacatca cttggaccaa 180
atgggcttga taagatgatg gtggataagg atggagatgt gactgtaact aatgatgggg 240
ccaccatctt aagcatgatg gatgttgatc atcagattgc caagctgatg gtggaactgt 300
ccaagtctca ggatgatgaa attggagatg gaaccacagg agtggttgtc ctggctggtg 360
ccttgttaga agaagcggag caattgctag accgaggcat tcacccaatc agaatagccg 420
atggctatga gcaggctgct cgtgttgcta ttgaacacct ggacaagatc agcgatagcg 480

-continued tccttgttga cataaaggac accgaacccc tgattcagac agcaaaaacc acgctgggct 540
ccaaagtggt caacagttgt caccgacaga tggctgagat tgctgtgaat gccgtcctca 600
ctgtagcaga tatggagcgg agagacgttg actttgagct tatcaaagta gaaggcaaag 660
tgggcggcag gctggaggac actaaactga ttaagggcgt gattgtggac aaggatttca 720
gtcacccaca gatgccaaaa aaagtggaag atgcgaagat tgcaattctc acatgtccat 780
ttgaaccacc caaaccaaaa acaaagcata agctggatgt gacctctgtc gaagattata 840
aagcccttca gaaatacgaa aaggagaaat ttgaagagat gattcaacaa attaaagaga 900
ctggtgctaa cctagcaatt tgtcagtggg gctttgatga tgaagcaaat cacttacttc 960
ttcagaacaa cttgcctgcg gttcgctggg taggaggacc tgaaattgag ctgattgcca 1020
tcgcaacagg agggcggatc gtccccaggt tctcagagct cacagccgag aagctgggct 1080
ttgctggtct tgtacaggag atctcatttg ggacaactaa ggataaaatg ctggtcatcg 1140
agcagtgtaa gaactccaga gctgtaacca tttttattag aggaggaaat aagatgatca 1200
ttgaggaggc gaaacgatcc cttcacgatg ctttgtgtgt catccggaac ctcatccgcg 1260
ataatcgtgt ggtgtatgga ggagggctg ctgagatatc ctgtgccctg gcagttagcc 1320
aagaggcgga taagtgcccc accttagaac agtatgccat gagagcgttt gccgacgcac 1380
tggaggtcat ccccatggcc ctctctgaaa acagtggcat gaatcccatc cagactatga 1440
ccgaagtccg agccagacag gtgaaggaga tgaaccctgc tcttggcatc gactgtttgc 1500
acaaggggac aaatgatatg aagcaacagc atgtcataga aaccttgatt ggcaaaaagc 1560
aacagatatc tcttgcaaca caaatggtta gaatgatttt gaagattgat gacattcgta 1620
agcctggaga atctgaagaa tgaagacatt gagaaaacta tgtagcaaga tccacttctg 1680
tgattaagta aatggatgtc tcgtgatgca tctacagtta tttattgtta catccttttc 1740
cagacactgt agatgctata ataaaaatag ctgtttggta accatagttt cacttgttca 1800
aagctgtgta atcgtggggg taccatctca actgcttttg tattcattgt attaaaagaa 1860
tctgtttaaa caacctttat cttctcttcg ggtttaagaa acgtttattg taacagtaat 1920
taaatgctgc cttaattg 1938

<210> SEQ ID NO 73
<211> LENGTH: 1231
<212> TYPE: DNA
<213> ORGANISM: Homo sapiens

<400> SEQUENCE: 73
aggtctcagc cggtcgtcgc gacgttcgcc cgctcgctct gaggctcctg aagccgaaac 60
tagctagact ttcctccttc ccgcctgcct gtagcggcgt tgttgccact ccgccaccat 120
gttcgaggcg cgcctggtcc agggctccat cctcaagaag gtgttggagg cactcaagga 180
cctcatcaac gaggcctgct gggatattag ctccagcggt gtaaacctgc agagcatgga 240
ctcgtcccac gtctctttgg tgcagctcac cctgcggtct gagggcttcg acacctaccg 300
ctgcgaccgc aacctggcca tgggcgtgaa cctcaccagt atgtccaaaa tactaaaatg 360
cgccggcaat gaagatatca ttacactaag ggccgaagat aacgcggata ccttggcgct 420
agtatttgaa gcaccaaacc aggagaaagt ttcagactat gaaatgaagt tgatggattt 480
agatgttgaa caacttggaa ttccagaaca ggagtacagc tgtgtagtaa agatgccttc 540
tggtgaattt gcacgtatat gccgagatct cagccatatt ggagatgctg ttgtaatttc 600
ctgtgcaaaa gacggagtga aattttctgc aagtggagaa cttggaaatg gaaacattaa 660

-continued attgtcacag acaagtaatg tcgataaaga ggaggaagct gttaccatag agatgaatga 720
accagttcaa ctaacttttg cactgaggta cctgaacttc tttacaaaag ccactccact 780
ctcttcaacg gtgacactca gtatgtctgc agatgtaccc cttgttgtag agtataaaat 840
tgcggatatg ggacacttaa aatactactt ggctcccaag atcgaggatg aagaaggatc 900
ttaggcattc ttaaaattca agaaaataaa actaagctct ttgagaactg cttctaagat 960
gccagcatat actgaagtct tttctgtcac caaatttgta cctctaagta catatgtaga 1020
tattgttttc tgtaaataac ctattttttt tctctattct ctccaatttg tttaaagaat 1080
aaagtccaaa gtctgatctg gtctagttaa cctagaagta tttttgtctc ttagaaatac 1140
ttgtgatttt tataatacaa aagggtcttg actctaaatg cagttttaag aagtgttttt 1200
gaatttaaat aaagttactt gaatttcaaa c 1231

<210> SEQ ID NO 74
<211> LENGTH: 2025
<212> TYPE: DNA
<213> ORGANISM: Homo sapiens

<400> SEQUENCE: 74
cggcacgagg caccccgaga ggagaagcgc agcgcagtgg cgagaggagc cccttgtggc 60
agcagcacta cctgcccaga aaaatgctgg aggctgggcg tggccccagg cctggggacc 120
tgtttttcct gtttcccgca gagttccctg cagcccggtc caggtccagg cgtgtgcatt 180
catgagtgag gaacccgtgc aggcgctgag catcctgacc tggagagcag gggctggtca 240
gggcgatggc agcagacctg ggcccctgga atgacaccat caatggcacc tgggatgggg 300
atgagctggg ctacaggtgc cgcttcaacg aggacttcaa gtacgtgctg ctgcctgtgt 360
cctacggcgt ggtgtgcgtg cttgggctgt gtctgaacgc cgtggcgctc tacatcttct 420
tgtgccgcct caagacctgg aatgcgtcca ccacatatat gttccacctg gctgtgtctg 480
atgcactgta tgcggcctcc ctgccgctgc tggtctatta ctacgcccgc ggcgaccact 540
ggcccttcag cacggtgctc tgcaagctgg tgcgcttcct cttctacacc aacctttact 600
gcagcatcct cttcctcacc tgcatcagcg tgcaccggtg tctgggcgtc ttacgacctc 660
tgcgctccct gcgctggggc cgggcccgct acgctcgccg ggtggccggg gccgtgtggg 720
tgttggtgct ggcctgccag gcccccgtgc tctactttgt caccaccagc gcgcgcgggg 780
gccgcgtaac ctgccacgac acctcggcac ccgagctctt cagccgcttc gtggcctaca 840
gctcagtcat gctgggcctg ctcttcgcgg tgccctttgc cgtcatcctt gtctgttacg 900
tgctcatggc tcggcgactg ctaaagccag cctacgggac ctcgggcggc ctccctaggg 960
ccaagcgcaa gtccgtgcgc accatcgccg tggtgctggc tgtcttcgcc ctctgcttcc 1020
tgccattcca cgtcacccgc accctctact actccttccg ctcgctggac ctcagctgcc 1080
acaccctcaa cgccatcaac atggcctaca aggttacccg gccgctggcc agtgctaaca 1140
gttgccttga ccccgtgctc tacttcctgg ctgggcagag gctcgtacgc tttgcccgag 1200
atgccaagcc acccactggc cccagccctg ccaccccggc tcgccgcagg ctgggcctgc 1260
gcagatccga cagaactgac atgcagagga taggagatgt gttgggcagc agtgaggact 1320
tcaggcggac agagtccacg ccggctggta gcgagaacac taaggacatt cggctgtagg 1380
agcagaacac ttcagcctgt gcaggtttat attgggaagc tgtagaggac caggacttgt 1440
gcagacgcca cagtctcccc agatatggac catcagtgac tcatgctgga tgaccccatg 1500

-continued

```
ctccgtcatt tgacaggggc tcaggatatt cactctgtgg tccagagtca actgttccca   1560

taacccctag tcatcgtttg tgtgtataag ttgggggaat taagtttcaa gaaaggcaag   1620

agctcaaggt caatgacacc cctggcctga ctcccatgca agtagctggc tgtactgcca   1680

aggtacctag gttggagtcc agcctaatca agtcaaatgg agaaacaggc ccagagagga   1740

aggtggctta ccaagatcac ataccagagt ctggagctga gctacctggg gtgggggcca   1800

agtcacaggt tggccagaaa accctggtaa gtaatgaggg ctgagtttgc acagtggtct   1860

ggaatggact gggtgccacg gtggacttag ctctgaggag tacccccagc ccaagagatg   1920

aacatctggg gactaatatc atagacccat ctggaggctc ccatgggcta ggagcagtgt   1980

gaggctgtaa cttatactaa aggttgtgtt gcctgctaaa aaaaa                   2025


<210> SEQ ID NO 75
<211> LENGTH: 4910
<212> TYPE: DNA
<213> ORGANISM: Homo sapiens

<400> SEQUENCE: 75

tagacgcacc ctctgaagat ggtgactccc tcctgagaag ctggacccct tggtaaaaga     60

caaggccttc tccaagaaga atatgaaagt gttactcaga cttatttgtt tcatagctct    120

actgatttct tctctggagg ctgataaatg caaggaacgt gaagaaaaaa taattttagt    180

gtcatctgca aatgaaattg atgttcgtcc ctgtcctctt aaccccaaatg aacacaaagg    240

cactataact tggtataaag atgacagcaa gacacctgta tctacagaac aagcctccag    300

gattcatcaa cacaaagaga aactttggtt tgttcctgct aaggtggagg attcaggaca    360

ttactattgc gtggtaagaa attcatctta ctgcctcaga attaaaataa gtgcaaaatt    420

tgtggagaat gagcctaact tatgttataa tgcacaagcc atatttaagc agaaactacc    480

cgttgcagga gacggaggac ttgtgtgccc ttatatggag ttttttaaaa atgaaaataa    540

tgagttacct aaattacagt ggtataagga ttgcaaacct ctacttcttg acaatataca    600

ctttagtgga gtcaaagata ggctcatcgt gatgaatgtg gctgaaaagc atagagggaa    660

ctatacttgt catgcatcct acacatactt gggcaagcaa tatcctatta cccgggtaat    720

agaatttatt actctagagg aaaacaaacc cacaaggcct gtgattgtga gcccagctaa    780

tgagacaatg gaagtagact tgggatccca gatacaattg atctgtaatg tcaccggcca    840

gttgagtgac attgcttact ggaagtggaa tgggtcagta attgatgaag atgacccagt    900

gctaggggaa gactattaca gtgtggaaaa tcctgcaaac aaaagaagga gtaccctcat    960

cacagtgctt aatatatcgg aaattgaaag tagattttat aaacatccat ttacctgttt   1020

tgccaagaat acacatggta tagatgcagc atatatccag ttaatatatc cagtcactaa   1080

tttccagaag cacatgattg gtatatgtgt cacgttgaca gtcataattg tgtgttctgt   1140

tttcatctat aaaatcttca agattgacat tgtgctttgg tacagggatt cctgctatga   1200

ttttctccca ataaaagctt cagatggaaa gacctatgac gcatatatac tgtatccaaa   1260

gactgttggg gaagggtcta cctctgactg tgatattttt gtgtttaaag tcttgcctga   1320

ggtcttggaa aaacagtgtg gatataagct gttcatttat ggaagggatg actacgttgg   1380

ggaagacatt gttgaggtca ttaatgaaaa cgtaaagaaa agcagaagac tgattatcat   1440

tttagtcaga gaaacatcag gcttcagctg gctgggtggt tcatctgaag agcaaatagc   1500

catgtataat gctcttgttc aggatggaat taaagttgtc ctgcttgagc tggagaaaat   1560

ccaagactat gagaaaatgc cagaatcgat taaattcatt aagcagaaac atggggctat   1620
```

-continued

```
ccgctggtca ggggacttta cacagggacc acagtctgca aagacaaggt tctggaagaa   1680
tgtcaggtac cacatgccag tccagcgacg gtcaccttca tctaaacacc agttactgtc   1740
accagccact aaggagaaac tgcaaagaga ggctcacgtg cctctcgggt agcatggaga   1800
agttgccaag agttctttag gtgcctcctg tcttatggcg ttgcaggcca ggttatgcct   1860
catgctgact tgcagagttc atggaatgta actatatcat cctttatccc tgaggtcacc   1920
tggaatcaga ttattaaggg aataagccat gacgtcaata gcagcccagg gcacttcaga   1980
gtagagggct tgggaagatc ttttaaaaag gcagtaggcc cggtgtggtg gctcacgcct   2040
ataatcccag cactttggga ggctgaagtg ggtggatcac cagaggtcag gagttcgaga   2100
ccagcccagc caacatggca aaaccccatc tctactaaaa atacaaaaat gagctaggca   2160
tggtggcaca cgcctgtaat cccagctaca cctgaggctg aggcaggaga attgcttgaa   2220
ccggggagac ggaggttgca gtgagccgag tttgggccac tgcactctag cctggcaaca   2280
gagcaagact ccgtctcaaa aaaagggcaa taaatgccct ctctgaatgt ttgaactgcc   2340
aagaaaaggc atggagacag cgaactagaa gaaagggcaa gaaggaaata gccaccgtct   2400
acagatggct tagttaagtc atccacagcc caagggcggg gctatgcctt gtctggggac   2460
cctgtagagt cactgaccct ggagcggctc tcctgagagg tgctgcaggc aaagtgagac   2520
tgacacctca ctgaggaagg gagacatatt cttggagaac tttccatctg cttgtatttt   2580
ccatacacat ccccagccag aagttagtgt ccgaagaccg aattttattt tacagagctt   2640
gaaaactcac ttcaatgaac aaagggattc tccaggattc caaagttttg aagtcatctt   2700
agctttccac aggagggaga gaacttaaaa aagcaacagt agcagggaat tgatccactt   2760
cttaatgctt tcctccctgg catgaccatc ctgtcctttg ttattatcct gcattttacg   2820
tctttggagg aacagctccc tagtggcttc ctccgtctgc aatgtccctt gcacagccca   2880
cacatgaacc atccttccca tgatgccgct cttctgtcat cccgctcctg ctgaaacacc   2940
tcccaggggc tccacctgtt caggagctga agcccatgct ttcccaccag catgtcactc   3000
ccagaccacc tccctgccct gtcctccagc ttcccctcgc tgtcctgctg tgtgaattcc   3060
caggttggcc tggtggccat gtcgcctgcc cccagcactc ctctgtctct gctcttgcct   3120
cgacccttcc tcctcctttg cctaggaggc cttctcgcat ttctctagc tgatcagaat   3180
tttaccaaaa ttcagaacat cctccaattc cacagtctct gggagacttt ccctaagagg   3240
cgacttcctc tccagccttc tctctctggt caggcccact gcagagatgg tggtgagcac   3300
atctgggagg ctggtctccc tccagctgga attgctgctc tctgagggag aggctgtggt   3360
ggctgtctct gtccctcact gccttccagg agcaatttgc acatgtaaca tagatttatg   3420
taatgcttta tgtttaaaaa cattccccaa ttatcttatt taatttttgc aattattcta   3480
attttatata tagagaaagt gacctatttt ttaaaaaaat cacactctaa gttctattga   3540
acctaggact tgagcctcca tttctggctt ctagtctggt gttctgagta cttgatttca   3600
ggtcaataac ggtccccccct cactccacac tggcacgttt gtgagaagaa atgacatttt   3660
gctaggaagt gaccgagtct aggaatgctt ttattcaaga caccaaattc caaacttcta   3720
aatgttggaa ttttcaaaaa ttgtgtttag attttatgaa aaactcttct actttcatct   3780
attctttccc tagaggcaaa catttcttaa aatgtttcat tttcattaaa aatgaaagcc   3840
aaatttatat gccaccgatt gcaggacaca agcacagttt taagagttgt atgaacatgg   3900
agaggacttt tggtttttat atttctcgta tttaatatgg gtgaacacca acttttattt   3960
```

-continued

```
ggaataataa ttttcctcct aaacaaaaac acattgagtt taagtctctg actcttgcct   4020

ttccacctgc tttctcctgg gcccgctttg cctgcttgaa ggaacagtgc tgttctggag   4080

ctgctgttcc aacagacagg gcctagcttt catttgacac acagactaca gccagaagcc   4140

catggagcag ggatgtcacg tcttgaaaag cctattagat gttttacaaa tttaattttg   4200

cagattattt tagtctgtca tccagaaaat gtgtcagcat gcatagtgct aagaaagcaa   4260

gccaatttgg aaacttaggt tagtgacaaa attggccaga gagtgggggt gatgatgacc   4320

aagaattaca agtagaatgg cagctggaat ttaaggaggg acaagaatca atggataagc   4380

gtgggtggag gaagatccaa acagaaaagt gcaaagttat tccccatctt ccaagggttg   4440

aattctggag gaagaagaca cattcctagt tccccgtgaa cttcctttga cttattgtcc   4500

ccactaaaac aaaacaaaaa acttttaatg ccttccacat taattagatt ttcttgcagt   4560

tttttatgg catttttta aagatgccct aagtgttgaa gaagagtttg caaatgcaac   4620

aaaaatattt aattaccggt tgttaaaact ggtttagcac aatttatatt ttccctctct   4680

tgcctttctt atttgcaata aaaggtattg agccattttt taaatgacat ttttgataaa   4740

ttatgtttgt actagttgat gaaggagttt tttttaacct gtttatataa ttttgcagca   4800

gaagccaaat tttttgtata ttaaagcacc aaattcatgt acagcatgca tcacggatca   4860

atagactgta cttattttcc aataaaattt tcaaactttg tactgttaaa             4910
```

<210> SEQ ID NO 76
<211> LENGTH: 2592
<212> TYPE: DNA
<213> ORGANISM: Homo sapiens

<400> SEQUENCE: 76

```
gccccacgca cggacaggag tgaacccgag ctgtgccgac caaccccag gatggcggaa     60

gctcaccagg ccgtggcctt ccagttcacg gtgaccccag acggggtcga cttccggctc    120

agtcgggagg ccctgaaaca cgtctacctg tctgggatca actcctggaa gaaacgcctg    180

atccgcatca agaatggcat cctcaggggc gtgtaccctg gcagccccac cagctggctg    240

gtcgtcatca tggcaacagt gggttcctcc ttctgcaacg tggacatctc cttggggctg    300

gtcagttgca tccagagatg cctccctcag ggtgtggcc cctaccagac cccgcagacc     360

cgggcacttc tcagcatggc catcttctcc acgggcgtct gggtgacggg catcttcttc    420

ttccgccaaa ccctgaagct gcttctctgc taccatgggt ggatgtttga gatgcatggc    480

aagaccagca acttgaccag gatctgggct atgtgtatcc gccttctatc cagccggcac    540

cctatgctct acagcttcca gacatctctg cccaagcttc ctgtgcccag ggtgtcagcc    600

acaattcagc ggtacctaga gtctgtgcgc cccttgttgg atgatgagga atattaccgc    660

atggagttgc tggccaaaga attccaggac aagactgccc ccaggctgca gaaatacctg    720

gtgctcaagt catggtgggc aagtaactat gtgagtgact ggtgggaaga gtacatctac    780

cttcgaggca ggagccctct catggtgaac agcaactatt atgtcatgga ccttgtgctc    840

atcaagaata cagacgtgca ggcagcccgc ctgggaaaca tcatccacgc catgatcatg    900

tatcgccgta aactggaccg tgaagaaatc aagcctgtga tggcactggg catagtgcct    960

atgtgctcct accagatgga gaggatgttc aacaccactc ggatcccggg caaggacaca   1020

gatgtgctac agcacctctc agacagccgg cacgtggctg tctaccacaa gggacgcttc   1080

ttcaagctgt ggctctatga gggcgcccgt ctgctcaagc ctcaggatct ggagatgcag   1140

ttccagagga tcctggacga cccctcccca cctcagcctg ggaggagaa gctggcagcc    1200
```

-continued

```
ctcactgcag gaggaagggt ggagtgggcg caggcacgcc aggccttctt tagctctgga   1260
aagaataagg ctgccttgga ggccatcgag cgtgccgctt tcttcgtggc cctggatgag   1320
gaatcctact cctatgaccc cgaagatgag gccagcctca gcctctatgg caaggccctg   1380
ctacatggca actgctacaa caggtggttt gacaaatcct tcactctcat ttccttcaag   1440
aatggccagt tgggtctcaa tgcagagcat gcgtgggcag atgctcccat cattgggcac   1500
ctctgggagt ttgtcctggg cacagacagc ttccacctgg gctacacgga gaccgggcac   1560
tgcctgggca aaccgaaccc tgcgctcgca cctcctacac ggctgcagtg ggacattcca   1620
aaacagtgcc aggcggtcat cgagagttcc taccaggtgg ccaaggcgtt ggcagacgac   1680
gtggagttgt actgcttcca gttcctgccc tttggcaaag gcctcatcaa gaagtgccgg   1740
accagccctg atgcctttgt gcagatcgcg ctgcagctgg ctcacttccg ggacaggggt   1800
aagttctgcc tgacctatga ggcctcaatg accagaatgt tccgggaggg acggactgag   1860
actgtgcgtt cctgtaccag cgagtccaca gcctttgtgc aggccatgat ggaggggtcc   1920
cacacaaaag cagacctgcg agatctcttc cagaaggctg ctaagaagca ccagaatatg   1980
taccgcctgg ccatgaccgg ggcagggatc gacaggcacc tcttctgcct ttacttggtc   2040
tccaagtacc taggagtcag ctctcctttc cttgctgagg tgctctcgga accctggcgt   2100
ctctccacca gccagatccc ccaatcccag atccgcatgt tcgacccaga gcagcacccc   2160
aatcacctgg gcgctggagg tggctttggc cctgtagcag atgatggcta tggagtttcc   2220
tacatgattg caggcgagaa cacgatcttc ttccacatct ccagcaagtt ctcaagctca   2280
gagacgaacg cccagcgctt tggaaaccac atccgcaaag ccctgctgga cattgctgat   2340
cttttccaag ttcccaaggc ctacagctga agcccttagg tacctgtgtt ttgtttggga   2400
actcggaggc cctccccctc ccccagctca gaccacagag gtggcaagag aagggctgaa   2460
gctggaagac tgttcatgag ggacttgtgt gacctgcttt gaaatgtgtg actctgctga   2520
gtgacgtagg ctctgagata gctgtccacg cccacgtgtt tgcttggaat aaatacttgc   2580
ctcagaacct tc                                                       2592
```

<210> SEQ ID NO 77
<211> LENGTH: 1429
<212> TYPE: DNA
<213> ORGANISM: Homo sapiens

<400> SEQUENCE: 77

```
cagcatggct acgaaatgtg ggaattgtgg acccggctac tccacccctc tggaggccat     60
gaaaggaccc agggaagaga tcgtctacct gccctgcatt taccgaaaca caggcactga    120
ggccccagat tatctggcca ctgtggatgt tgaccccaag tctccccagt attgccaggt    180
catccaccgg ctgcccatgc ccaacctgaa ggacgagctg catcactcag gatggaacac    240
ctacagcagc tgcttcggtg atagcaccaa gtcgcgcaac aagctggtct tgcccagtct    300
catctcctct cgcatctatg tggtggacgt gggctctgag cccgggcccc aaaagctgca    360
caaggtcatt gagcccaagg acatccatgc caagtgcgaa ctggcctgtc tccacaccag    420
ccactgcctg gccagcgggg aagtgatgat cagctccctg ggggacgtca agggcaatgg    480
caaagggggt tttgtgctgc tggatgggga gacgttcgag gtgaagggga catgggagag    540
acctgggggt gctgcaccgt tgggctatga cttctggtac cagcctcgac acaatgtcat    600
gatcagcact gagtgggcag ctcccaatgt cttacgagat ggctttaacc ccgctgatgt    660
```

-continued

```
ggaggctgga ctgtacggga gccacttata tgtatgggac tggcagcgcc atgagattgt    720

gcagaccctg tctctaaaag atgggctgat acccttggag atccgcttcc tgcacaaccc    780

aagtgccacc cagggttttg taggctgtgc ctcagctcca aacatccagc gcttctacaa    840

aacgagggaa ggtacatggt cagtggagaa ggtgatccag gtgcccccca agaaagtgaa    900

gggctggctg ctgccagggg tgccaggcct gatcaccgac atcctgctct ccctggacga    960

ccgcttcctc tacttcagca actggctgca tggggacctg aggcagtatg acatctctga   1020

cccacagaga ccccgcctca caggacagct cttcctcgga ggcagcattg ttaagggagg   1080

ccctgtgcaa gtgctggagg acgaggaact aaagtcccag ccagagcccc tagtggtcaa   1140

gggaaaacgg gtggctggag gccctcagat gatccagctc agcctggatg gcaagcgcct   1200

ctacatcacc acgtcgctgt acagtgcctg ggaaaagcag ttttaccctg atctcatcag   1260

ggaaggctct gtaatgctgc aggttgatgt agacacagta aaaggagggc tgaagttgaa   1320

ccccaactgc ctggtggact tcgggaagga gccccttggc ccagccctgg ctcacgagct   1380

tcgctaccct gggggcgatt gtagctctga catctggatt tgaaggctc               1429
```

<210> SEQ ID NO 78
<211> LENGTH: 5683
<212> TYPE: DNA
<213> ORGANISM: Homo sapiens

<400> SEQUENCE: 78

```
ccgcccggtg ttgcgctcct tcccagaatc cgctccggcc tttccttcct gccgcgattc     60

ccaactttgc tcaaagtcgc cggactctaa gctgtcggag ggaccgctgg acagacctgg    120

gaactgacag agggcctgga gggaaatagg ccaaagaccc acaggatgga gctgacctca    180

accgaaagag ggaggggaca gcctctgccc tgggaacttc gactgcccct actgctaagc    240

gtgctggctg ccacactggc acaggcccct gccccggatg tccctggctg ttccagggga    300

agctgctacc ccgccacggc cgacctgctg gtgggccgag ctgacagact gactgcctca    360

tccacttgtg gcctgaatgg ccgccagccc tactgcatcg tcagtcacct gcaggacgaa    420

aagaagtgct tcctttgtga ctcccggcgc cccttctctg ctagagacaa cccacacacc    480

catcgcatcc agaatgtagt caccagcttt gcaccacagc ggcgggcagc ttggtggcag    540

tcacagaatg gtatccctgc ggtcaccatc cagctggacc tggaggctga gtttcatttc    600

acacacctca ttatgacctt caagacattt cgccctgctg ccatgctggt cgaacgctca    660

gcagactttg gccgcacctg gcatgtgtac cgatatttct cctatcactg tggggctgac    720

ttcccaggag tcccactagc acccccacgg cactgggatg atgtagtctg tgagtcccgc    780

tactcagaga ttgagccatc cactgaaggc gaggtcatct atcgtgtgct ggaccctgcc    840

atccctatcc cagaccccta cagctcacgg attcagaacc tgttgaagat caccaaccta    900

cgggtgaacc tgactcgtct acacacgttg ggagacaacc tactcgaccc acggagggag    960

atccgagaga agtactacta tgccctctat gagctggttg tacgtggcaa ctgcttctgc   1020

tacggacacg cctcagagtg tgcacccgcc ccaggggcac cagcccatgc tgagggcatg   1080

gtgcacggag cttgcatctg caaacacaac acacgtggcc tcaactgcga gcagtgtcag   1140

gatttctatc gtgacctgcc ctggcgtccg gctgaggacg gccatagtca tgcctgtagg   1200

aagtgtgatc ggcatgggca cacccacagc tgccacttcg acatggccgt atacctcgga   1260

tctggcaatg tgagtggagg tgtgtgtgat ggatgtcagc ataacacagc gtggcgccac   1320

tgtgagctct gtcggccctt cttctaccgt gacccaacca aggacctgcg ggatccggct   1380
```

-continued

```
gtgtgccgct cctgtgattg tgaccccatg ggttctcaag acggtggtcg ctgtgattcc   1440
catgatgacc ctgcactggg actggtctcc ggccagtgtc gctgcaaaga acacgtggtg   1500
ggcactcgct gccagcaatg ccgtgatggc ttctttgggc tcagcatcag tgacccgtct   1560
gggtgccggc gatgtcaatg taatgcacgg ggcacagtgc ctgggagcac tccttgtgac   1620
cccaacagtg gatcctgtta ctgcaaacgt ctagtgactg gacgtggatg tgaccgctgc   1680
ctgcctggcc actggggcct gagcctcgac ctgctcggct gccgcccctg tgactgcgac   1740
gtgggtggtg ctttggatcc ccagtgtgat gagggcacag gtcaatgcca ctgccgccag   1800
cacatggttg ggcgacgctg tgagcaggtg caacctggct acttccggcc cttcctggac   1860
cacctaattt gggaggctga gaacacccga gggcaggtgc tcgatgtggt ggagcgcctg   1920
gtgacccccg gggaaactcc atcctggact ggctcaggct tcgtgcgact acaggaaggt   1980
cagaccctgg agttcctggt ggcctctgtg ccgaacgcga tggactatga cctgctgctg   2040
cgcttagagc cccaggtccc tgagcaatgg gcagagttgg aactgattgt gcagcgtcca   2100
gggcctgtgc ctgcccacag cctgtgtggg catttggtgc ccagggatga tcgcatccaa   2160
gggactctgc aaccacatgc caggtacttg atatttccta atcctgtctg ccttgagcct   2220
ggtatctcct acaagctgca tctgaagctg gtacggacag gggaagtgc ccagcctgag   2280
actccctact ctggacctgg cctgctcatt gactcgctgg tgctgctgcc ccgtgtcctg   2340
gtgctagaga tgtttagtgg gggtgatgct gctgccctgg agcgccaggc cacctttgaa   2400
cgctaccaat gccatgagga gggtctggtg cccagcaaga cttctccctc tgaggcctgc   2460
gcacccctcc tcatcagcct gtccaccctc atctacaatg gtgccctgcc atgtcagtgc   2520
aaccctcaag gttcactgag ttctgagtgc aaccctcatg gtggtcagtg cctgtgcaag   2580
cctggagtgg ttgggcgccg ctgtgacacg tgtgcccctg gctactatgg ctttggcccc   2640
acaggctgtc aagcctgcca gtgcagccca cgaggggcac tcagcagtct ctgtgaaagg   2700
accagtgggc aatgtctctg tcgaactggt gcctttgggc ttcgctgtga cgcctgccag   2760
cgtggccagt ggggattccc tagctgccgg ccatgtgtct gcaatgggca tgcagatgag   2820
tgcaacaccc acacaggcgc ttgcctgggc tgccgtgatc tcacaggggg tgagcactgt   2880
gaaaggtgca ttgctggttt ccacggggac ccacggctgc catatggggc gcagtgccgg   2940
ccctgtccct gtcctgaagg ccctgggagc caacggcact ttgctacttc ttgccaccag   3000
gatgaatatt cccagcagat tgtgtgccac tgccgggcag gctatacggg gctgcgatgt   3060
gaagcttgtg cccctgggca gtttggggac ccatcaaggc caggtggccg gtgccaactg   3120
tgtgagtgca gtgggaacat tgacccaatg gatcctgatg cctgtgaccc acaccccggg   3180
caatgcctgc gctgtttaca ccacacagag ggtccacact gtgcccactc gaagcctggc   3240
ttccatggcc aggctgcccg gcagagctgt caccgctgca catgcaacct gctgggcaca   3300
aatccgcagc agtgcccatc tcctgaccag tgccactgtg atccaagcag tgggcagtgc   3360
ccatgcctcc ccaatgtcca ggccctagct gtagaccgct gtgcccccaa cttctggaac   3420
ctcaccagtg gccatggttg ccagccttgt gcctgcctcc caagcccgga agaaggcccc   3480
acctgcaacg agttcacagg gcagtgccac tgcctgtgcg gctttggagg gcggacttgt   3540
tctgagtgcc aagagctcca ctggggagac cctgggttgc agtgccatgc ctgtgattgt   3600
gactctcgtg gaatagatac acctcagtgt caccgcttca caggtcactg cacgtgccgc   3660
ccaggggtgt ctggtgtgcg ctgtgaccag tgtgcccgtg gcttctcagg aatctttcct   3720
```

-continued

```
gcctgccatc cctgccatgc atgcttcggg gattgggacc gagtggtgca ggacttggca   3780

gcccgtacac agcgcctaga gcagcgggcg caggagttgc aacagacggg tgtgctgggt   3840

gcctttgaga gcagcttctg gcacatgcag gagaagctgg gcattgtgca gggcatcgta   3900

ggtgcccgca acacctcagc cgcctccact gcacagcttg tggaggccac agaggagctg   3960

cggcgtgaaa ttggggaggc cactgagcac ctgactcagc tcgaggcaga cctgacagat   4020

gtgcaagatg agaacttcaa tgccaaccat gcactaagtg gtctggagcg agataggctt   4080

gcacttaatc tcacactgcg gcagctcgac cagcatcttg acttgctcaa acattcaaac   4140

ttcctgggtg cctatgacag catccggcat gcccatagcc agtctgcaga ggcagaacgt   4200

cgtgccaata cctcagccct ggcagtacct agccctgtga gcaactcggc aagtgctcgg   4260

catcggacag aggcactgat ggatgctcag aaggaggact tcaacagcaa acacatggcc   4320

aaccagcggg cacttggcaa gctctctgcc catacccaca ccctgagcct gacagacata   4380

aatgagctgg tgtgtggggc ccagggattg catcatgatc gtacaagccc ttgtgggggt   4440

gccggctgtc gagatgagga tgggcagccg cgctgtgggg gcctcagctg caatggggca   4500

gcggctacag cagacctagc actgggccgg gcccggcaca cacaggcaga gctgcagcgg   4560

gcactggcag aaggtggtag catcctcagc agagtggctg agactcgtcg gcaggcaagc   4620

gaggcacagc agcgggccca ggcagccctg gacaaggcta atgcttccag ggacaggtg    4680

gaacaggcca accaggaact tcaagaactt atccagagtg tgaaggactt cctcaaccag   4740

gagggggctg atcctgatag cattgaaatg gtggccacac gggtgctaga gctctccatc   4800

ccagcttcag ctgagcagat ccagcacctg gcgggcgcga ttgcagagcg agtccggagc   4860

ctggcagatg tggatgcgat cctggcacgt actgtaggag atgtgcgtcg tgccgagcag   4920

ctactgcagg atgcacggcg ggcaaggagc tgggctgagg atgagaaaca gaaggcagag   4980

acagtacagg cagcactgga ggaggcccag cgggcacagg gtattgccca gggtgccatc   5040

cgggggggcag tggctgacac acgggacaca gagcagaccc tgtaccaggt acaggagagg   5100

atggcaggtg cagagcgggc actgagctct gcaggtgaaa gggctcggca gttggatgct   5160

ctcctggagg ctctgaaatt gaaacgggca ggaaatagtc tggcagcctc tacagcagaa   5220

gaaacggcag gcagtgccca gggtcgtgcc caggaggctg agcagctgct acgcggtcct   5280

ctgggtgatc agtaccagac ggtgaaggcc ctagctgagc gcaaggccca aggtgtgctg   5340

gctgcacagg caagggcaga acaactgccg gatgaggctc gggacctgtt gcaagccgct   5400

caggacaagc tgcagcggct acaggaattg gaaggcacct atgaggaaaa tgagcgggca   5460

ctggagagta aggcagccca gttggacggg ttggaggcca ggatgcgcag cgtgcttcaa   5520

gccatcaact tgcaggtgca gatctacaac acctgccagt gacccctgcc caaggcctac   5580

cccagttcct agcactgccc cacatgcatg tctgcctatg cactgaagag ctcttggccc   5640

ggcagggccc ccaataaacc agtgtgaacc cccaaaaaaa aaa                     5683
```

<210> SEQ ID NO 79
<211> LENGTH: 5177
<212> TYPE: DNA
<213> ORGANISM: Homo sapiens

<400> SEQUENCE: 79

```
ggactgcgaa aggagcaggg ttgcggagct agggctccag cctgcggccg cgcattcttg     60

cgtctggcca gccgcgagct ctaagggtcg gccccgcccg gtccgccccc gcggctccct    120

gccaggctct cgcgggcgcg ctcggggtgg ggcctcgcgg ctggcggaga tgcggccggg    180
```

-continued

```
gctgcgcggt ggtgatgcga gcctgctggg cggcgcgccg gggcagccgg agccgcgcgc    240
cgcggcgctg taatcggaca ccaagagcgc tcgcccccgg cctccggcca ctttccattc    300
actccgaggt gcttgattga gcgacgcgga gaagagctcc gggtgccgcg gcactgcagc    360
gctgagattc ctttacaaag aaactcagag gaccgggaag aaagaatttc acctttgcga    420
cgtgctagaa aataaggtcg tctgggaaaa ggactggaga cacaagcgca tccaaccccg    480
gtagcaaact gatgactttt ccgtgctgat ttctttcaac ctcggtattt tcccttggat    540
attaacttgc atatctgaag aaatggcatt ccggacaatt tgcgtgttgg ttggagtatt    600
tatttgttct atctgtgtga aaggatcttc ccagccccaa gcaagagttt atttaacatt    660
tgatgaactt cgagaaacca agacctctga atacttcagc ctttcccacc atcctttaga    720
ctacaggatt ttattaatgg atgaagatca ggaccggata tatgtgggaa gcaaagatca    780
cattctttcc ctgaatatta acaatataag tcaagaagct ttgagtgttt tctggccagc    840
atctacaatc aaagttgaag aatgcaaaat ggctggcaaa gatcccacac acggctgtgg    900
gaactttgtc cgtgtaattc agactttcaa tcgcacacat ttgtatgtct gtgggagtgg    960
cgctttcagt cctgtctgta cttacttgaa cagagggagg agatcagagg accaagtttt   1020
catgattgac tccaagtgtg aatctggaaa aggacgctgc tctttcaacc ccaacgtgaa   1080
cacggtgtct gttatgatca atgaggagct tttctctgga atgtatatag atttcatggg   1140
gacagatgct gctatttttc gaagtttaac caagaggaat gcggtcagaa ctgatcaaca   1200
taattccaaa tggctaagtg aacctatgtt tgtagatgca catgtcatcc cagatggtac   1260
tgatccaaat gatgctaagg tgtacttctt cttcaaagaa aaactgactg acaataacag   1320
gagcacgaaa cagattcatt ccatgattgc tcgaatatgt cctaatgaca ctggtggact   1380
gcgtagcctt gtcaacaagt ggaccacttt cttaaaggcg aggctggtgt gctcggtaac   1440
agatgaagac ggcccagaaa cacactttga tgaattagag gatgtgtttc tgctggaaac   1500
tgataacccg aggacaacac tagtgtatgg catttttaca acatcaagct cagttttcaa   1560
aggatcagcc gtgtgtgtgt atcatttatc tgatatacag actgtgttta atgggccttt   1620
tgcccacaaa gaagggccca atcatcagct gatttcctat cagggcagaa ttccatatcc   1680
tcgccctgga acttgtccag gaggagcatt tacacccaat atgcgaacca ccaaggagtt   1740
cccagatgat gttgtcactt ttattcggaa ccatcctctc atgtacaatt ccatctaccc   1800
aatccacaaa aggcctttga ttgttcgtat tggcactgac tacaagtaca caaagatagc   1860
tgtggatcga gtgaacgctg ctgatgggag ataccatgtc ctgtttctcg gaacagatcg   1920
gggtactgtg caaaaagtgg ttgttcttcc tactaacaac tctgtcagtg gcgagctcat   1980
tctggaggag ctggaagtct ttaagaatca tgctcctata acaacaatga aaatttcatc   2040
taaaaagcaa cagttgtatg tgagttccaa tgaaggggtt tcccaagtat ctctgcaccg   2100
ctgccacatc tatggtacag cctgtgctga ctgctgcctg gcgcgggacc cttattgcgc   2160
ctgggatggc cattcctgtt ccagattcta cccaactggg aaacggagga gccgaagaca   2220
agatgtgaga catggaaacc cactgactca atgcagagga tttaatctaa aagcatacag   2280
aaatgcagct gaaattgtgc agtatggagt aaaaaataac accacttttc tggagtgtgc   2340
ccccaagtct ccgcaggcat ctatcaagtg gctgttacag aaagacaaag acaggaggaa   2400
agaggttaag ctgaatgaac gaataatagc cacttcacag ggactcctga tccgctctgt   2460
tcagggttct gaccaaggac tttatcactg cattgctaca gaaaatagtt tcaagcagac   2520
```

-continued

```
catagccaag atcaacttca aagttttaga ttcagaaatg gtggctgttg tgacggacaa   2580
atggtccccg tggacctggg ccagctctgt gagggcttta cccttccacc cgaaggacat   2640
catgggggca ttcagccact cagaaatgca gatgattaac caatactgca aagacactcg   2700
gcagcaacat cagcagggag atgaatcaca gaaaatgaga ggggactatg gcaagttaaa   2760
ggccctcatc aatagtcgga aaagtagaaa caggaggaat cagttgccag agtcataata   2820
ttttcttatg tgggtcttat gcttccatta acaaatgctc tgtcttcaat gatcaaattt   2880
tgagcaaaga aacttgtgct ttaccaaggg gaattactga aaaaggtgat tactcctgaa   2940
gtgagtttta cacgaactga aatgagcatg cattttcttg tatgatagtg actagcacta   3000
gacatgtcat ggtcctcatg gtgcatataa atatatttaa cttaacccag attttattta   3060
tatctttatt caccttttct tcaaaatcga tatggtggct gcaaaactag aattgttgca   3120
tccctcaatt gaatgagggc catatccctg tggtattcct ttcctgcttt ggggctttag   3180
aattctaatt gtcagtgatt ttgtatatga aaacaagttc caaatccaca gcttttacgt   3240
agtaaaagtc ataaatgcat atgacagaat ggctatcaaa agaaatagaa aaggaagacg   3300
gcatttaaag ttgtataaaa acacgagtta ttcataaaga gaaaatgatg agtttttatg   3360
gttccaatga aatatcttcc ccttttttta agattgtaaa aataatcagt tactggtatc   3420
tgtcactgac ctttgtttcc ttattcagga agataaaaat cagtaaccta ccccatgaag   3480
atatttggtg ggagttatat cagtgaagca gtttggttta tattcttatg ttatcacctt   3540
ccaaacaaaa gcacttactt tttttggaag ttatttaatt tattttagac tcaaagaata   3600
taatcttgca ctactcagtt attactgttt gttctcttat tccctagtct gtgtggcaaa   3660
ttaaacaata taagaaggaa aaatttgaag tattagactt ctaaataagg ggtgaaatca   3720
tcagaaagaa aaatcaaagt agaaactact aattttttaa gaggaattta taacaaatat   3780
ggctagtttt caacttcagt actcaaattc aatgattctt ccttttatta aaaccagtct   3840
cagatatcat actgattttt aagtcaacac tatatatttt atgatctttt cagtgtgatg   3900
gcaaggtgct tgttatgtct agaaagtaag aaaacaatat gaggagacat tctgtctttc   3960
aaaaggtaat ggtacatacg ttcactggtc tctaagtgta aaagtagtaa attttgtgat   4020
gaataaaata attatctcct aattgtatgt tagaataatt ttattagaat aatttcatac   4080
tgaaattatt ttctccaaat aaaaattaga tggaaaaatg tgaaaaaaat tattcatgct   4140
ctcatatata ttttaaaaac actacttttg ctttttttatt taccttttaa gacattttca   4200
tgcttccagg taaaaacaga tattgtacca tgtacctaat ccaaatatca tataaacatt   4260
ttatttatag ttaataatct atgatgaagg taattaaagt agattatggc ctttttaagt   4320
attgcagtct aaaacttcaa aaactaaaat cattgtcaaa attaatatga ttattaatca   4380
gaatatcaga tatgattcac tatttaaact atgataaatt atgataatat atgaggaggc   4440
ctcgctatag caaaaatagt taaaatgctg acataacacc aaacttcatt ttttaaaaaa   4500
tctgttgttc caaatgtgta taattttaaa gtaatttcta aagcagttta ttataatggt   4560
ttgcctgctt aaaaggtata attaaacttc ttttctcttc tacattgaca cacagaaatg   4620
tgtcaatgta aagccaaaac catcttctgt gtttatggcc aatctattct caaagttaaa   4680
agtaaaattg tttcagagtc acagttccct ttatttcaca taagcccaaa ctgatagaca   4740
gtaacggtgt ttagttttat actatatttg tgctatttaa ttctttctat tttcacaatt   4800
attaaattgt gtacactttc attactttta aaaatgtaga aattcttcat gaacataact   4860
ctgctgaatg taaaagaaaa ttttttttca aaaatgctgt taatgtatac tactggtggt   4920
```

-continued tgattggttt tattttatgt agcttgacaa ttcagtgact taatatctat tccatttgta 4980
ttgtacataa aattttctag aaatacactt ttttccaaag tgtaagtttg tgaatagatt 5040
ttagcatgat gaaactgtca taatggtgaa tgttcaatct gtgtaagaaa acaaactaaa 5100
tgtagttgtc acactaaaat ttaattggat attgatgaaa tcattggcct ggcaaaataa 5160
aacatgttga attcccc 5177

<210> SEQ ID NO 80
<211> LENGTH: 9164
<212> TYPE: DNA
<213> ORGANISM: Homo sapiens

<400> SEQUENCE: 80
ggctggaggg gcgctgggct cggacctgcc aaggccacgg gggagcaagg gacagaggcg 60
ggggtcctag ctgacggctt ttactgccta ggatgacgct gcggcttctg gtggccgcgc 120
tctgcgccgg gatcctggca gaggcgcccc gagtgcgagc ccagcacagg gagagagtga 180
cctgcacgcg cctttacgcc gctgacattg tgttcttact ggatggctcc tcatccattg 240
gccgcagcaa tttccgcgag gtccgcagct ttctcgaagg gctggtgctg cctttctctg 300
gagcagccag tgcacagggt gtgcgctttg ccacagtgca gtacagcgat gacccacgga 360
cagagttcgg cctggatgca cttggctctg gggtgatgt gatccgcgcc atccgtgagc 420
ttagctacaa ggggggcaac actcgcacag ggctgcaat tctccatgtg gctgaccatg 480
tcttcctgcc ccagctggcc cgacctggtg tccccaaggt ctgcatcctg atcacagacg 540
ggaagtccca ggacctggtg gacacagctg cccaaaggct gaaggggcag gggtcaagc 600 tatttgctgt ggggatcaag aatgctgacc ctgaggagct gaagcgagtt gcctcacagc 660
ccaccagtga cttcttcttc ttcgtcaatg acttcagcat cttgaggaca ctactgcccc 720
tcgtttcccg gagagtgtgc acgactgctg gtggcgtgcc tgtgacccga cctccggatg 780
actcgacctc tgctccacga gacctggtgc tgtctgagcc aagcagccaa tccttgagag 840
tacagtggac agcggccagt ggccctgtga ctggctacaa ggtccagtac actcctctga 900
cggggctggg acagccactg ccgagtgagc ggcaggaggt gaacgtccca gctggtgaga 960
ccagtgtgcg gctgcggggt ctccggccac tgaccgagta ccaagtgact gtgattgccc 1020
tctacgccaa cagcatcggg gaggctgtga gcgggacagc tcggaccact gccctagaag 1080
ggccggaact gaccatccag aataccacag cccacagcct cctggtggcc tggcggagtg 1140
tgccaggtgc cactggctac cgtgtgacat ggcgggtcct cagtggtggg cccacacagc 1200
agcaggagct gggccctggg cagggttcag tgttgctgcg tgacttggag cctggcacgg 1260
actatgaggt gaccgtgagc accctatttg gccgcagtgt ggggcccgcc acttccctga 1320
tggctcgcac tgacgcttct gttgagcaga ccctgcgccc ggtcatcctg ggccccacat 1380
ccatcctcct ttcctggaac ttggtgcctg aggcccgtgg ctaccggttg gaatggcggc 1440
gtgagactgg cttggagcca ccgcagaagg tggtactgcc ctctgatgtg acccgctacc 1500
agttggatgg gctgcagccg ggcactgagt accgcctcac actctacact ctgctggagg 1560
gccacgaggt ggccacccct gcaaccgtgg ttcccactgg accagagctg cctgtgagcc 1620
ctgtaacaga cctgcaagcc accgagctgc ccgggcagcg ggtgcgagtg tcctggagcc 1680
cagtccctgg tgccacccag taccgcatca ttgtgcgcag cacccagggg gtggagcgga 1740
ccctggtgct tcctgggagt cagacagcat tcgacttgga tgacgttcag gctgggctta 1800

-continued

```
gctacactgt gcgggtgtct gctcgagtgg gtccccgtga gggcagtgcc agtgtcctca   1860
ctgtccgccg ggagctggaa actccacttg ctgttccagg gctgcgggtt gtggtgtcag   1920
atgcaacgcg agtgagggtg gcctggggac ccgtccctgg agccagtgga tttcggatta   1980
gctggagcac aggcagtggt ccggagtcca gccagacact gcccccagac tctactgcca   2040
cagacatcac agggctgcag cctggaacca cctaccaggt ggctgtgtcg gtactgcgag   2100
gcagagagga gggccctgct gcagtcatcg tggctcgaac ggacccactg ggcccagtga   2160
ggacggtcca tgtgactcag gccagcagct catctgtcac cattacctgg accagggttc   2220
ctggcgccac aggatacagg gtttcctggc actcagccca cggcccagag aaatcccagt   2280
tggtttctgg ggaggccacg gtggctgagc tggatggact ggagccagat actgagtata   2340
cggtgcatgt gagggcccat gtggctggcg tggatgggcc ccctgcctct gtggttgtga   2400
ggactgcccc tgagcctgtg ggtcgtgtgt cgaggctgca gatcctcaat gcttccagcg   2460
acgttctacg gatcacctgg gtaggggtca ctggagccac agcttacaga ctggcctggg   2520
gccggagtga aggcggcccc atgaggcacc agatactccc aggaaacaca gactctgcag   2580
agatccgggg tctcgaaggt ggagtcagct actcagtgcg agtgactgca cttgtcgggg   2640
accgcgaggg cacacctgtc tccattgttg tcactacgcc gcctgaggct ccgccagccc   2700
tggggacgct tcacgtggtg cagcgcgggg agcactcgct gaggctgcgc tgggagccgg   2760
tgcccagaga gcagggcttc cttctgcact ggcaacctga gggtggccag gaacagtccc   2820
gggtcctggg gcccgagctc agcagctatc acctggacgg gctggagcca gcgacacagt   2880
accgcgtgag gctgagtgtc ctagggccag ctggagaagg gccctctgca gaggtgactg   2940
cgcgcactga gtcacctcgt gttccaagca ttgaactacg tgtggtggac acctcgatcg   3000
actcggtgac tttggcctgg actccagtgt ccagggcatc cagctacatc ctatcctggc   3060
ggccactcag aggccctggc caggaagtgc ctgggtcccc gcagacactt ccagggatct   3120
caagctccca gcgggtgaca gggctagagc ctggcgtctc ttacatcttc tccctgacgc   3180
ctgtcctgga tggtgtgcgg ggtcctgagg catctgtcac acagacgcca gtgtgccccc   3240
gtggcctggc ggatgtggtg ttcctaccac atgccactca agacaatgct caccgtgcgg   3300
aggctacgag gagggtcctg gagcgtctgg tgttggcact tgggcctctt gggccacagg   3360
cagttcaggt tggcctgctg tcttacagtc atcggccttc cccactgttc ccactgaatg   3420
gctcccatga ccttggcatt atcttgcaaa ggatccgtga catgccctac atggacccaa   3480
gtgggaacaa cctgggcaca gccgtggtca cagctcacag atacatgttg gcaccagatg   3540
ctcctgggcg ccgccagcac gtaccagggg tgatggttct gctagtggat gaacccttga   3600
gaggtgacat attcagcccc atccgtgagg cccaggcttc tgggcttaat gtggtgatgt   3660
tgggaatggc tggagcggac ccagagcagc tgcgtcgctt ggcgccgggt atggactctg   3720
tccagacctt cttcgccgtg gatgatgggc caagcctgga ccaggcagtc agtggtctgg   3780
ccacagccct gtgtcaggca tccttcacta ctcagccccg gccagagccc tgcccagtgt   3840
attgtccaaa gggccagaag ggggaacctg gagagatggg cctgagagga caagttgggc   3900
ctcctggcga ccctggcctc ccgggcagga ccggtgctcc cggcccccag gggcccccctg   3960
gaagtgccac tgccaagggc gagaggggct tccctggagc agatgggcgt ccaggcagcc   4020
ctggccgcgc cgggaatcct gggacccctg gagcccctgg cctaaagggc tctccagggt   4080
tgcctggccc tcgtggggac ccgggagagc gaggacctcg aggcccaaag gggggagccgg   4140
gggctcccgg acaagtcatc ggaggtgaag gacctgggct tcctgggcgg aaaggggacc   4200
```

-continued

```
ctggaccatc gggccccct ggacctcgtg gaccactggg ggacccagga ccccgtggcc   4260
ccccagggct tcctggaaca gccatgaagg gtgacaaagg cgatcgtggg gagcggggtc   4320
cccctggacc aggtgaaggt ggcattgctc ctggggagcc tgggctgccg ggtcttcccg   4380
gaagccctgg accccaaggc cccgttggcc cccctggaaa gaaaggagaa aaaggtgact   4440
ctgaggatgg agctccaggc ctcccaggac aacctgggtc tccgggtgag cagggcccac   4500
ggggacctcc tggagctatt ggccccaaag gtgaccgggg ctttccaggg cccctgggtg   4560
aggctggaga gaagggcgaa cgtggacccc caggcccagc gggatcccgg gggctgccag   4620
gggttgctgg acgtcctgga gccaagggtc ctgaagggcc accaggaccc actggccgcc   4680
aaggagagaa gggggagcct ggtcgccctg gggaccctgc agtggtggga cctgctgttg   4740
ctggacccaa aggagaaaag ggagatgtgg ggcccgctgg gcccagagga gctaccggag   4800
tccaagggga acggggccca cccggcttgg ttcttcctgg agaccctggc cccaagggag   4860
accctggaga ccggggtccc attggcctta ctggcagagc aggaccccca ggtgactcag   4920
ggcctcctgg agagaaggga gaccctgggc ggcctggccc cccaggacct gttggccccc   4980
gaggacgaga tggtgaagtt ggagagaaag gtgacgaggg tcctccgggt gacccgggtt   5040
tgcctggaaa agcaggcgag cgtggccttc ggggggcacc tggagttcgg gggcctgtgg   5100
gtgaaaaggg agaccaggga gatcctggag aggatggacg aaatggcagc cctggatcat   5160
ctggacccaa gggtgaccgt ggggagccgg gtcccccagg acccccggga cggctggtag   5220
acacaggacc tggagccaga gagaagggag agcctgggga ccgcggacaa gagggtcctc   5280
gagggcccaa gggtgatcct ggcctccctg gagcccctgg ggaaaggggc attgaagggt   5340
ttcggggacc cccaggccca caggggggacc caggtgtccg aggcccagca ggagaaaagg   5400
gtgaccgggg tcccccctggg ctggatggcc ggagcggact ggatgggaaa ccaggagccg   5460
ctgggccctc tgggccgaat ggtgctgcag gcaaagctgg ggacccaggg agagacgggc   5520
ttccaggcct ccgtggagaa caaggcctcc ctggcccctc tggtccccct ggattaccgg   5580
gaaagccagg cgaggatggg aaacctggcc tgaatggaaa aaacggagaa cctggggacc   5640
ctggagaaga cgggaggaag ggagagaaag gagattcagg cgcctctggg agagaaggtt   5700
ttcctggtgt cccaggaggc acgggcccca agggtgaccg tggggagact ggatccaaag   5760
gggagcaggg cctccctgga gagcgtggcc tgcgaggaga gcctggaagt gtgccgaatg   5820
tggatcggtt gctggaaact gctggcatca aggcatctgc cctgcgggag atcgtggaga   5880
cctgggatga gagctctggt agcttcctgc ctgtgcccga acggcgtcga ggccccaagg   5940
gggactcagg cgaacaggc ccccaggca aggagggccc catcggcttt cctggagaac   6000
gcgggctgaa gggcgaccgt ggagaccctg gccctcaggg gccacctggt ctggcccttg   6060
gggagagggg ccccccggg ccttccggcc ttgccgggga gcctggaaag cctggtattc   6120
ccgggctccc aggcagggct gggggtgtgg gagaggcagg aaggccagga gagaggggag   6180
aacggggaga gaaaggagaa cgtggagaac agggcagaga tggccctcct ggactccctg   6240
gaacccctgg gcccccgga cccccctggcc ccaaggtgtc tgtggatgag ccaggtcctg   6300
gactctctgg agaacaggga ccccctggac tcaagggtgc taagggggag ccgggcagca   6360
atggtgacca aggtcccaaa ggagacaggg gtgtgccagg catcaaagga gaccggggag   6420
agcctggacc gaggggtcag gacggcaacc cgggtctacc aggagagcgt ggtatggctg   6480
ggcctgaagg gaagccgggt ctgcagggtc caagaggccc ccctggccca gtgggtggtc   6540
```

-continued

```
atggagaccc tggaccacct ggtgccccgg gtcttgctgg ccctgcagga ccccaaggac   6600
cttctggcct gaagggggag cctggagaga caggacctcc aggacggggc ctgactggac   6660
ctactggagc tgtgggactt cctggacccc ccggcccttc aggccttgtg ggtccacagg   6720
ggtctccagg tttgcctgga caagtggggg agacagggaa gccgggagcc ccaggtcgag   6780
atggtgccag tggaaaagat ggagacagag ggagccctgg tgtgccaggg tcaccaggtc   6840
tgcctggccc tgtcggacct aaaggagaac ctggccccac gggggcccct ggacaggctg   6900
tggtcgggct ccctggagca aagggagaga agggagcccc tggaggcctt gctggagacc   6960
tggtgggtga gccgggagcc aaaggtgacc gaggactgcc agggccgcga ggcgagaagg   7020
gtgaagctgg ccgtgcaggg gagcccggag accctgggga agatggtcag aaaggggctc   7080
caggacccaa aggtttcaag ggtgacccag gagtcggggt cccgggctcc cctgggcctc   7140
ctggccctcc aggtgtgaag ggagatctgg gcctccctgg cctgcccggt gctcctggtg   7200
ttgttgggtt cccgggtcag acaggccctc gaggagagat gggtcagcca ggccctagtg   7260
gagagcgggg tctggcaggc cccccaggga gagaaggaat cccaggaccc ctggggccac   7320
ctggaccacc ggggtcagtg ggaccacctg ggcctctgg actcaaagga gacaagggag   7380
accctggagt agggctgcct gggccccgag gcgagcgtgg ggagccaggc atccggggtg   7440
aagatggccg ccccggccag gagggacccc gaggactcac ggggcccccct ggcagcaggg   7500
gagagcgtgg ggagaagggt gatgttggga gtgcaggact aaagggtgac aagggagact   7560
cagctgtgat cctggggcct ccaggcccac ggggtgccaa gggggacatg ggtgaacgag   7620
ggcctcgggg cttggatggt gacaaaggac ctcggggaga caatggggac cctggtgaca   7680
agggcagcaa gggagagcct ggtgacaagg gctcagccgg gttgccagga ctgcgtggac   7740
tcctgggacc ccagggtcaa cctggtgcag cagggatccc tggtgacccg ggatccccag   7800
gaaaggatgg agtgcctggt atccgaggag aaaaaggaga tgttggcttc atgggtcccc   7860
ggggcctcaa gggtgaacgg ggagtgaagg gagcctgtgg ccttgatgga gagaagggag   7920
acaagggaga agctggtccc ccaggccgcc ccgggctggc aggacacaaa ggagagatgg   7980
gggagcctgg tgtgccgggc cagtcggggg cccctggcaa ggagggcctg atcggtccca   8040
agggtgaccg aggctttgac gggcagccag gccccaaggg tgaccagggc gagaaagggg   8100
agcggggaac cccaggaatt gggggcttcc caggccccag tggaaatgat ggctctgctg   8160
gtcccccagg gccacctggc agtgttggtc ccagaggccc cgaaggactt cagggccaga   8220
agggtgagcg aggtcccccc ggagagagag tggtgggggc tcctggggtc cctggagctc   8280
ctggcgagag aggggagcag gggcggccag ggcctgccgg tcctcgaggc gagaagggag   8340
aagctgcact gacggaggat gacatccggg gctttgtgcg ccaagagatg agtcagcact   8400
gtgcctgcca gggccagttc atcgcatctg gatcacgacc cctccctagt tatgctgcag   8460
acactgccgg ctcccagctc catgctgtgc ctgtgctccg cgtctctcat gcagaggagg   8520
aagagcgggt accccctgag gatgatgagt actctgaata ctccgagtat tctgtggagg   8580
agtaccagga ccctgaagct ccttgggata gtgatgaccc ctgttccctg ccactggatg   8640
agggctcctg cactgcctac accctgcgct ggtaccatcg ggctgtgaca ggcagcacag   8700
aggcctgtca cccttttgtc tatggtggct gtggagggaa tgccaaccgt tttgggaccc   8760
gtgaggcctg cgagcgccgc tgcccacccc gggtggtcca gagccagggg acaggtactg   8820
cccaggactg aggcccagat aatgagctga gattcagcat cccctggagg agtcggggtc   8880
tcagcagaac cccactgtcc ctccccttgg tgctagaggc ttgtgtgcac gtgagcgtgc   8940
```

-continued gagtgcacgt ccgttatttc agtgacttgg tcccgtgggt ctagccttcc cccctgtgga 9000
caaaccccca ttgtggctcc tgccaccctg gcagatgact cactgtgggg gggtggctgt 9060
gggcagtgag cggatgtgac tggcgtctga cccgcccctt gacccaagcc tgtgatgaca 9120
tggtgctgat tctgggggc attaaagctg ctgttttaaa aggc 9164

<210> SEQ ID NO 81
<211> LENGTH: 2148
<212> TYPE: DNA
<213> ORGANISM: Homo sapiens

<400> SEQUENCE: 81
gcttcagggt acagctcccc cgcagccaga agccgggcct gcagcccctc agcaccgctc 60
cgggacaccc cacccgcttc ccaggcgtga cctgtcaaca gcaacttcgc ggtgtggtga 120
actctctgag gaaaaaccat tttgattatt actctcagac gtgcgtggca acaagtgact 180
gagacctaga aatccaagcg ttggaggtcc tgaggccagc ctaagtcgct tcaaaatgga 240
acgaaggcgt ttgtggggtt ccattcagag ccgatacatc agcatgagtg tgtggacaag 300
cccacggaga cttgtggagc tggcagggca gagcctgctg aaggatgagg ccctggccat 360
tgccgccctg gagttgctgc ccagggagct cttcccgcca ctcttcatgg cagcctttga 420
cgggagacac agccagaccc tgaaggcaat ggtgcaggcc tggcccttca cctgcctccc 480
tctgggagtg ctgatgaagg gacaacatct tcacctggag accttcaaag ctgtgcttga 540
tggacttgat gtgctccttg cccaggaggt tcgccccagg aggtggaaac ttcaagtgct 600
ggatttacgg aagaactctc atcaggactt ctggactgta tggtctggaa acagggccag 660
tctgtactca tttccagagc cagaagcagc tcagcccatg acaaagaagc gaaaagtaga 720
tggtttgagc acagaggcag agcagccctt cattccagta gaggtgctcg tagacctgtt 780
cctcaaggaa ggtgcctgtg atgaattgtt ctcctacctc attgagaaag tgaagcgaaa 840
gaaaaatgta ctacgcctgt gctgtaagaa gctgaagatt tttgcaatgc ccatgcagga 900
tatcaagatg atcctgaaaa tggtgcagct ggactctatt gaagatttgg aagtgacttg 960
tacctggaag ctacccacct tggcgaaatt ttctccttac ctgggccaga tgattaatct 1020
gcgtagactc ctcctctccc acatccatgc atcttcctac atttccccgg agaaggaaga 1080
gcagtatatc gcccagttca cctctcagtt cctcagtctg cagtgcctgc aggctctcta 1140
tgtggactct ttatttttcc ttagaggccg cctggatcag ttgctcaggc acgtgatgaa 1200
ccccttggaa accctctcaa taactaactg ccggctttcg gaaggggatg tgatgcatct 1260
gtcccagagt cccagcgtca gtcagctaag tgtcctgagt ctaagtgggg tcatgctgac 1320
cgatgtaagt cccgagcccc tccaagctct gctggagaga gcctctgcca ccctccagga 1380
cctggtcttt gatgagtgtg ggatcacgga tgatcagctc cttgccctcc tgccttccct 1440
gagccactgc tcccagctta caaccttaag cttctacggg aattccatct ccatatctgc 1500
cttgcagagt ctcctgcagc acctcatcgg gctgagcaat ctgacccacg tgctgtatcc 1560 tgtcccctg gagagttatg aggacatcca tggtaccctc cacctggaga ggcttgccta 1620
tctgcatgcc aggctcaggg agttgctgtg tgagttgggg cggcccagca tggtctggct 1680
tagtgccaac ccctgtcctc actgtgggga cagaaccttc tatgacccgg agcccatcct 1740
gtgcccctgt ttcatgccta actagctggg tgcacatatc aaatgcttca ttctgcatac 1800
ttggacacta aagccaggat gtgcatgcat cttgaagcaa caaagcagcc acagtttcag 1860

-continued

```
acaaatgttc agtgtgagtg aggaaaacat gttcagtgag gaaaaaacat tcagacaaat   1920

gttcagtgag gaaaaaaagg ggaagttggg gataggcaga tgttgacttg aggagttaat   1980

gtgatctttg gggagataca tcttatagag ttagaaatag aatctgaatt tctaaaggga   2040

gattctggct tgggaagtac atgtaggagt taatccctgt gtagactgtt gtaaagaaac   2100

tgttgaaaat aaagagaagc aatgtgaagc aaaaaaaaaa aaaaaaaa               2148


<210> SEQ ID NO 82
<211> LENGTH: 3370
<212> TYPE: DNA
<213> ORGANISM: Homo sapiens

<400> SEQUENCE: 82

gcccccgccc ggcccgcccc gctctcctag tcccttgcaa cctggcgctg catccgggcc     60

actgtcccag gtcccaggtc ccggcccgga gctatggagc ggcgctggcc cctggggcta    120

gggctggtgc tgctgctctg cgccccgctg cccccggggg cgcgcgccaa ggaagttact    180

ctgatggaca caagcaaggc acagggagag ctgggctggc tgctggatcc cccaaaagat    240

gggtggagtg aacagcaaca gatactgaat gggacacccc tctacatgta ccaggactgc    300

ccaatgcaag gacgcagaga cactgaccac tggcttcgct ccaattggat ctaccgcggg    360

gaggaggctt cccgcgtcca cgtggagctg cagttcaccg tgcgggactg caagagtttc    420

cctgggggag ccgggcctct gggctgcaag gagaccttca accttctgta catggagagt    480

gaccaggatg tgggcattca gctccgacgg cccttgttcc agaaggtaac cacggtggct    540

gcagaccaga gcttcaccat tcgagacctt gcgtctggct ccgtgaagct gaatgtggag    600

cgctgctctc tgggccgcct gacccgccgt ggcctctacc tcgctttcca caacccgggt    660

gcctgtgtgg ccctggtgtc tgtccgggtc ttctaccagc gctgtcctga gaccctgaat    720

ggcttggccc aattcccaga cactctgcct ggccccgctg ggttggtgga agtggcgggc    780

acctgcttgc ccccacgcgcg ggccagcccc aggccctcag gtgcaccccg catgcactgc   840

agccctgatg gcgagtggct ggtgcctgta ggacggtgcc actgtgagcc tggctatgag    900

gaaggtggca gtggcgaagc atgtgttgcc tgccctagcg gctcctaccg gatggacatg    960

gacacacccc attgtctcac gtgcccccag cagagcactg ctgagtctga gggggccacc   1020

atctgtacct gtgagagcgg ccattacaga gctcccgggg agggccccca ggtggcatgc   1080

acaggtcccc cctcggcccc ccgaaacctg agcttctctg cctcagggac tcagctctcc   1140

ctgcgttggg aacccccagc agatacgggg ggacgccagg atgtcagata cagtgtgagg   1200

tgttcccagt gtcagggcac agcacaggac gggggggccct gccagccctg tggggtgggc  1260

gtgcacttct cgccgggggc ccgggcgctc accacacctg cagtgcatgt caatggcctt   1320

gaaccttatg ccaactacac ctttaatgtg gaagcccaaa atggagtgtc agggctgggc   1380

agctctggcc atgccagcac ctcagtcagc atcagcatgg ggcatgcaga gtcactgtca   1440

ggcctgtctc tgagactggt gaagaaagaa ccgaggcaac tagagctgac ctgggcgggg   1500

tcccggcccc gaagccctgg ggcgaacctg acctatgagc tgcacgtgct gaaccaggat   1560

gaagaacggt accagatggt tctagaaccc agggtcttgc tgacagagct gcagcctgac   1620

accacataca tcgtcagagt ccgaatgctg accccactgg gtcctggccc tttctcccct   1680

gatcatgagt ttcggaccag cccaccagtg tccaggggcc tgactggagg agagattgta   1740

gccgtcatct ttgggctgct gcttggtgca gccttgctgc ttgggattct cgttttccgg   1800

tccaggagag cccagcggca gaggcagcag aggcacgtga ccgcgccacc gatgtggatc   1860
```

-continued

```
gagaggacaa gctgtgctga agccttatgt ggtacctcca ggcatacgag gaccctgcac   1920
agggagcctt ggactttacc cggaggctgg tctaattttc cttcccggga gcttgatcca   1980
gcgtggctga tggtggacac tgtcatagga gaaggagagt ttggggaagt gtatcgaggg   2040
accctcaggc tccccagcca ggactgcaag actgtggcca ttaagacctt aaaagacaca   2100
tccccaggtg gccagtggtg gaacttcctt cgagaggcaa ctatcatggg ccagtttagc   2160
cacccgcata ttctgcatct ggaaggcgtc gtcacaaagc gaaagccgat catgatcatc   2220
acagaattta tggagaatgc agccctggat gccttcctga gggagcggga ggaccagctg   2280
gtccctgggc agctagtggc catgctgcag ggcatagcat ctggcatgaa ctacctcagt   2340
aatcacaatt atgtccaccg ggacctggct gccagaaaca tcttggtgaa tcaaaacctg   2400
tgctgcaagg tgtctgactt tggcctgact cgcctcctgg atgactttga tggcacatac   2460
gaaacccagg gaggaaagat ccctatccgt tggacagccc ctgaagccat tgcccatcgg   2520
atcttcacca cagccagcga tgtgtggagc tttgggattg tgatgtggga ggtgctgagc   2580
tttggggaca agccttatgg ggagatgagc aatcaggagg ttatgaagag cattgaggat   2640
gggtaccggt tgccccctcc tgtggactgc cctgcccctc tgtatgagct catgaagaac   2700
tgctgggcat atgaccgtgc ccgccggcca cacttccaga agcttcaggc acatctggag   2760
caactgcttg ccaaccccca ctccctgcgg accattgcca actttgaccc cagggtgact   2820
cttcgcctgc ccagcctgag tggctcagat gggatcccgt atcgaaccgt ctctgagtgg   2880
ctcgagtcca tacgcatgaa acgctacatc ctgcacttcc actcggctgg gctggacacc   2940
atggagtgtg tgctggagct gaccgctgag gacctgacgc agatgggaat cacactgccc   3000
gggcaccaga agcgcattct ttgcagtatt cagggattca aggactgatc cctcctctca   3060
ccccatgccc aatcagggtg caaggagcaa ggacggggcc aaggtcgctc atggtcactc   3120
cctgcgcccc ttcccacaac ctgccagact aggctatcgg tgctgcttct gcccgcttta   3180
aggagaaccc tgctctgcac cccagaaaac ctctttgttt taaaagggag gtgggggtag   3240
aagtaaaagg atgatcatgg gagggagctc aggggttaat atatatacat acatacacat   3300
atatatattg ttgtaaataa acaggaaatg attttctgcc tccatcccac ccatcagggc   3360
tgcaggcact                                                          3370
```

<210> SEQ ID NO 83
<211> LENGTH: 13863
<212> TYPE: DNA
<213> ORGANISM: Homo sapiens
<220> FEATURE:
<221> NAME/KEY: misc_feature
<222> LOCATION: (1)..(13863)
<223> OTHER INFORMATION: n = a, c, g or t

<400> SEQUENCE: 83

```
aagcttagga agcacaagag gctgagcctt tcaggtcagc aaagacttcc cagaggaggc     60
agtgcctaca ctgaggtcag agtgacaaga agagtaatgg accactgtaa agacttgggt    120
tcggccgggc gcggtggctc acgcctgtaa tcccagcact ttgggaggcc gaggcgggtg    180
gatcatgagg tcaggagatc gagaccatcc tggctaacaa ggtgaaaccc cgtctctact    240
aaaaatacag aaaattagcc gggcgcggtg gcgggcgcct gtggtcccag ctactcggga    300
ggctgaggca ggagaatggc gtgaacccgg gaagcggagc ttgcagtgag ccgagattgc    360
gccactgcag tccgcagtcc ggcctgggcg acagagcgag actccgtctc aaaaaaaaaa    420
```

-continued

```
aaagacttgg gtttgacttg attgagccca ggagttcgag acaagcctgg gcaatatagt    480
gagacctcat ctctacaaaa attttaaaaa ttagcctggt gcggtggctc atgcctgtaa    540
tcccagcact ctgggaggcc gaggtgggcg gatcacttga ggtcagaagt ttgagaccac    600
cctgaccaac atggagaaac cccgtctcta ctaaaaatac aaaattagcc gggcatggtg    660
gcgcatgcct gtaatcccag ctactcggga ggctgaggca ggagaattgt ttgaacctgg    720
gaggtggacg ttgcggtgag ccaagatcac actattgcac tccagcctgg gcaacaagag    780
caaaactccg tctcaaaaaa aaaaatttat ttttaaatta gccaggtgta gccacagctg    840
tagtcaaatc tactaggcag gctgaggtgg gaggattgct tgaacctggg aggcagaggt    900
tgcagtgagc caagatggtg ccacggcatt ccagcctgag caacagcaag accctgtgtc    960
caaaaaaaaa aaaaaaaaaa accgtaaaat aggccaggca cagtggttca tggttataag   1020
cctagcactt tggaaggctg aggagggtgg atcgcctgag ctcaggagtt caagaccagc   1080
ctgggcaaca cggtgaaacc ccatctctac caaaaaaaaa aaaaaaaaaa attagccagg   1140
catggtggtg tgtgcctgtg gtcccagcta ctcaggaggc tgaggtggaa gagtgcttgt   1200
gcctgggagg cagaggttcc agtgaaccga gatcacacca ttgtactcca gcctgggcaa   1260
cagagtaaga ccccatctca aaaaaaaaaa aaaaaattaa gataaaccct ttggcagctg   1320
cgtgctgctc ttagcctcaa acccaagtct tttttttccc cctttgagac ggggtctatt   1380
gcccaggctg gagtgcaatg gtatgatcca tactcactgc agccccgaac tcctgggctt   1440
ccaaagtgct gggattacag gtgtgagcca ccaggcccag actgctgaag ggtttaaacc   1500
agagaaagaa tgtgaccaga tttccaattt agaaagaccc gctctctgca gggtaaggag   1560
agcctggggg tccgggggcg gggggcaaga attgcaaggt aaccagggag gccagtgcaa   1620
tgtccaggtg ggagaggatg ctagctgaga ctagaagtgc taggaaaagg atgtgtgcag   1680
acaagaggtc actggggagg tgaaataaca aggcttggcc atgagtggaa cccaacaccc   1740
atggtgccct cttgagagag ggaagatggc acctgagatg gaagatggaa agaccagggt   1800
ccctgtgact gaggactgag cctctgtttg aggtttttgc agaggagtaa aggcaacaaa   1860
agaggcaaga gttggaagaa aggtgacaag gaacaaaagt cagctatgcc tgatgctact   1920
gggtggccag caacaatgct gacttggcca aggctctgag agctttacta tgctgggact   1980
ggaggtcaga gttgaggcta gggtaagagc aaggggctca gagatggagg gggaggagga   2040
cctgaacaag tccagaaggg aagagatttg tccctctatc caacagagta cccagtgagc   2100
agcacagagg gcacagcaag ggacatcacc cggttcccca aatgctcaga gccacaagtg   2160
aagccaaaag tgaaagacaa gatgcagaaa accgccacgg gcctttgagg aagggtaaag   2220
gcgaaagcga aagcaggaag tacagacgtg aagcctagca gaggactttt tagctgctca   2280
ctggccccgc ttgtctggcc gactcatccg cccgcgaccc ctaatcccct ctgcctgccc   2340
caagatgctg aagccagccc tggagccccg agggggcttc tccttcgaga actgccaaag   2400
gtgaagcggg ggcgcggggg gcggtcactc ctgagccgcc tctgcttgct cgtggccttt   2460
tttcctggct gggggtgggg gagggtgtgt tggtcgactt gggttccagg cttaccccgg   2520
aagatgaggg agacggggac caggttaggg gaagcaacag gggtcttgaa agcagagccg   2580
aaacatgggc gccctcctcc gtttccagaa atgcatcatt ggaacgcgtc ctcccggggc   2640
tcaaggtccc tcacgcacgc aagaccggga ccaccatcgc gggcctggtg ttccaagtga   2700
gcagcgggga gggacgggga gctggagggg agccgagagt atcgagcagg cactgaagct   2760
gcggtccctc cctctcctca ggacggggtc attctgggcg ccgatacgcg agccactaac   2820
```

-continued

```
gattcggtcg tggcggacaa gagctgcgag aagatccact tcatcgcccc caaaatctag   2880
tgagactccc gagcccagtt cccgtacgca aaaaagaacg gccccctcgt tcccactccg   2940
gtccccgcac gtcccagccc tgcccacacc gatcctccct tttgcctcag ctgctgtggg   3000
gctggagtag ccgcggacgc cgagatgacc acacggatgg tggcgtccaa gatggagcta   3060
cacgcgttat ctacgggccg cgagccccgc gtggccacgg tcactcgcat cctgcgccag   3120
acgctcttca ggtgcggggg cagggctaac aggaccccgg caggtagttt acggggttgg   3180
ggccattgga aggcgggaca gaaagaaggg cgggaccgcg acgggccagg tgaccggaag   3240
aggccggccc aagagaacct gggctacagg aaaaggcgat gtcagtcatc gggcgccagc   3300
ccacaggaag gagcggggat agcacctagg agctgggcat agagaggtgg gcctaggccc   3360
cagcttgtgg ccgaccccgc ccatcctcga gcaggtacca gggccacgtg ggtgcatcgc   3420
tgatcgtggg cggcgtagac ctgactggac cgcagctcta cggtgtgcat ccccatggct   3480
cctacagccg tctgcccttc acagccctgg gtgagcgctt ctgtcccttc tcctcgaact   3540
ctgcccctgg tgaccttggc ctcactccaa acggcgtcgc agcggttgac ttcagatgct   3600
tctcctgcct tcaggctctg gtcaggacgc ggccctggcg gtgctagaag accggttcca   3660
gccgaacatg acggtgagcg gcctctgtcc ccgactttgt ggtcgctggt gggatgtgca   3720
cccgggagct gggggagcac aggaccctgg cccagtgcgg gtggctaagg cttgtcggag   3780
gaggtgacca ctgaagggtg agtggagtaa gggcagagaa gtgcggtccc gacataacac   3840
cgtccaatac caaagcctgc acggctggga gaagtcgaag ctcacagagg atctttagga   3900
gccgagggcg gagagaagga ccagtagggt cctacttata tcaacgtctg gagcctagat   3960
tttgtttggg gtgggatgga agcaggtgat gttgcctcag aggtggctaa ggctcagagg   4020
gagaaacaca gtgggggttt ggagggcaag accagattgg gtaagtggac aggcaagtcc   4080
ccaggctgta gcctaagtta acagcagaga gagcccgtta ggtctcacac acccatcacc   4140
gcagctggag gctgctcagg ggctgctggt ggaagccgtc accgccggga tcttgggtga   4200
cctgggctcc gggggcaatg tggacgcatg tgtgatcaca aagactggcg ccaagctgct   4260
gcggacactg agctcaccca cagagcccgt gaagaggtga gagctggaga tcggggacca   4320
cagggatgtg tggggctata gcaggggaga tagggggctg caaaaagggg atgggccaca   4380
tgacaggccc atgttcagag gctgtccctc ctccctccca ggtctggccg ctaccacttt   4440
gtgcctggaa ccacagctgt cctgacccag acagtgaagc cactaaccct ggagctagtg   4500
gaggaaactg tgcaggctat ggaggtggag taagctgagg cttagagctt ggaacaaggg   4560
ggaataaacc cagaaaatac agttaaacag atggctgtgt cattcttgag tggaatgggg   4620
tgggcaggca gccagcaggg ctctgtagct aaggcgtccc tgcaggggcc attacctacc   4680
atagctctag tgtctggcct aagagatgcc cttcacccat aacctcaggc acctacaact   4740
ccagaacccc agccctggcc agcattgcag gcttggtctc cacccaaacc ttccttctga   4800
ctccacactt gaaggctccc ccaccactcc actgtcttgc tcttgccctc tagtccactg   4860
ggagacttgt aaattatgaa ataccccatg tactaccccc tcctagagac tttccatggc   4920
tcctcagtgg cccaggacaa gctcatacct ttcaatcagg cccccacagg ccccactgag   4980
ggctaaagtg ctgacaagag gagccgctcc ctgactccaa ggcaagttct caccaagcac   5040
tcctcaacct cgcaacatct ttacctgtga caccccttag atgacgaggc atgcctgcac   5100
tgctcacgtg aagctcgtct tctgtctgca catgctgggc ttgtgactcc aagttttcca   5160
```

-continued

```
ggctaataag ggtcacagga ctcacatggg gagagatgac acgtttctcc aacaaacctt   5220
tgctgggccc ctgctgagtc tcaggcctgg ctgctgggtg ccagcaagag catcctgtcc   5280
tcagcgagaa cggctgaact ccgctggagc ttcagaaatg tcagggagag tctacccagg   5340
gcccagggag ggtctatgcc gggctgcaca tccccaggct gctgagtgtg ctccctgcac   5400
cccaacattc tattaatgaa catttgtaaa tgtaacagaa aagtagaaag agttgtatat   5460
tgaataccct tatactgtca ggtcaccaca gacctgacag tattttgtta tatttgtttt   5520
atcatctatt catccctcta tccattaatt catcgctcct tttttttttt tttttttttt   5580
tttgagacgg cgtctcgctc tgtcacccag gctctggagt gcaaatattt tgttatattt   5640
gttttatcat ctattcatcc ctctatccat taattcatcg ctcctttttt tttttttttt   5700
tttgagacgg agtctcgctc tgtcacccag gctctggagt gcagtggcgc aatctcagct   5760
cactggaagc tccgcctccc aggttcacgc cattctcctg cctcagcctc ccgagtagct   5820
gggactacag gtgcccgcca ccacgcgcgg ctaatttttt tttttttttg tatttttagt   5880
agagacgagg ttctactgaa cctgttagcc aggatggtct ttgatctcct gacctcatga   5940
tccgcccgcg tcggcctccc aaagtgctgg gattacaggc gtgagccacc gtgcccagcc   6000
aattcatctc attttttggc tgatgctgtt tctttgagat ggggtctagc tccatcgccc   6060
aggccggaat gcagtggtgc actcatggct cactgcagcc ttgaacttaa gggctcaagt   6120
gatccctcct gcctcagcct tctgagttgc tgggactaca ggtgtgtacc atcataccca   6180
gcacatttct taatttaaaa aaattttttt tgtagagaca gggtttcatg atgttgctca   6240
ggctggtctc gaactcctgg aatcaagcct cctacgtctg cctcccaaag ttttgggatt   6300
acaggtgtga gccaccacac ccagccctga tctgttcttg aatcagttaa agccctcaca   6360
ctcccagaag gccgccagcc aatgcacctg ttggaacttt gcacacaggg tgtcttctcc   6420
cttcaagctt ggtctgcagc tcagtaacaa atgggctaca gacaccaggg gcttgcccat   6480
gggagcccca aggcctaaag agggtggcag agatttgatg tctgtcactc tccacctgca   6540
gcctcagtcc acggtcggcc aggcaccaag agctcacact ttgccctcct aaatgccagg   6600
cccttcataa gtatcatctc attgttaaga gcggaggctt cagcgccaga caaatgcgag   6660
tttgcgtaca actcaaccac gtgctggtgg gagagtcacc atctctgagc agacctgtga   6720
ctcctgttcc aaatggacga ggaaccactg cgatgatgtg ttaggactcc cagcctgcca   6780
gaacctcaca gcccctggcc cttcacagca aagttgaccg cagtgagcat tccatccacc   6840
agtcagaaca ccctggacgc tgagcggacc ttctctgaaa gcctggtgcc tttgttagcc   6900
ctgggtgact cctgtgatcc cagccaccag gttgtcacta tagacctaat ttaaccatct   6960
gtcctcagta ccgagggctc aacatttgga atgggaggtg gttctgggag ccaattagag   7020
gccaggcttt gggaggtggc agaggtgagt ctcacacctt gggctctgtc tgataagtct   7080
aggtctcggt caggggacct tggcctaaag ggcctgtctt gcctggagcg tgggaggggg   7140
ctgagtctac acagctggcc tggcctcagg cctggagctt tagctcaagg acgagaagac   7200
ccataaagcc agacccagct cccaacctca catctgccac gatgttgctg ctcagcctga   7260
ccctaagcct ggttctcctc ggctcctcct ggggtgagtg ggccaggacc agccctgatt   7320
cagccctggg agcaactcag ctcccagcaa cagcccaggg aaggagctag gctggctgga   7380
agggacgaag gtggacagag tgggtaaaag aaacaggata tgccagggca gtggagcagg   7440
gaacagtcct gcagggctgg gagggggcaa gaggtggggt ggtctcacaa ataggaccag   7500
agattgagcc aggccctgga gcccgggagg gtttaggaag ctgagacagg aagacctgtc   7560
```

-continued

```
catgtctttt agaaagaacc ttctggctgc atgaagggta tgaactgttc aggtcgggag   7620
ggggcagaga gaccaggggt agagatgggg aacagcgggg actaggctgg agacagatgt   7680
aggagaacag cagggctggg ggactgggtg gatagggata accaagatag ctgtggggcc   7740
cgaaggtgct tgcatgtacc ctgttgggga aggggtagtg ctgtaccctc tcgacagacc   7800
tctctggggt gcacagcctg gggcacccaa aaggaggtgg ggaaagatgg gctgaggcat   7860
gggaagcagg tcctcattag cccaatggcc aggctgcggc attcctgcca tcaaaccggc   7920
actgagcttc agccagagga ttgtcaacgg ggagaatgca gtgttgggct cctggccctg   7980
gcaggtgtcc ctgcaggtac accaccagag gggtgggcag ggtcctgggt acgtcatgcc   8040
taggggcagc ctcagcagcc catcccact ctgacctctg agccctgacc acaggacagc   8100
agcggcttcc acttctgcgg tggttctctc atcagccagt cctgggtggt cactgctgcc   8160
cactgcaatg tcaggtgagt gcctgcattc cacctgcccc gcccctcgcc tcttcctgcc   8220
tcctcccctg gctgtccccc tctcgcgctg gcctccctgc agctgcctaa tcccaccccc   8280
ttgcagccct ggccgccatt ttgttgtcct gggcgagtat gaccgatcat caaacgcaga   8340
gcccttgcag gttctgtccg tctctcgggt gagtgcctgg gctgcagaca cggaggaaaa   8400
gtgggcagtg caggtgggtg ggtgctggga acgaggaatt caggacatgc cctggcctac   8460
cctgctcagc acccatcaga acatggactg tttctgaccc cacaggccat tacacaccct   8520
agctggaact ctaccaccat gaacaatgac gtgacgctgc tgaagctcgc ctcgccagcc   8580
cagtacacaa cacgcatctc gccagtttgc ctggcatcct caaacgaggc tctgactgaa   8640
ggcctcacgt gtgtcaccac cggctggggt cgcctcagtg gcgtgggtag ggactcaggc   8700
caaagctcag ggtgggagga ctggggtggg gacagtgttc tgggccccat gtgaccaccc   8760
ctcctggcca caggcaatgt gacaccagca catctgcagc aggtggcttt gcccctggtc   8820
actgtgaatc agtgccggca gtactggggc tcaagtatca ctgactccat gatctgtgca   8880
ggtggcgcag gtgcctcctc gtgccaggta agccccagca cccgctcctc tgcgctgtcc   8940
tagtggtata cctccccaac ccccctact caattctccc tccctcttcc ctctcagggt   9000
gactccggag gccctcttgt ctgccagaag ggaaacacat gggtgcttat tggtattgtc   9060
tcctggggca ccaaaaactg caatgtgcgc gcacctgctg tgtatactcg agttagcaag   9120
ttcagcacct ggatcaacca ggtcatagcc tacaactgag ctcaccacag gccctcccca   9180
gctcaaccca ttaaagaccc aggccctgtc ccatcatgca ttcatgtctg tcttcctggc   9240
tcaggagaaa gaagaggctg ttgagggtcc gactccctac ttggacttct ggcacagaag   9300
gggctgagtg actccttgag tagcagtggc tcttcctaga gtagccatgc cgaggccggg   9360
gcccccaccc ctcctccagg gcaacccctt ggtcctacag caagaagcca gaactgttgg   9420
aatgaatggc agccctccct ggagaggcag cctgtttact gaatacagag gatacgttta   9480
caaactgaat acgcataata aataactgca cattctccat ccacaggcca tggcatgaag   9540
gcccaagtgg gtctatcaaa ggcccacatc tccaaacccc tgtcctgccc tcaggaccag   9600
gcccaccctg ggcaagagag aacgtaagcc ccagggcttc aggtccccag agacacttgg   9660
ggaactgggg ggaaattctg aggccatggg gcttggttct ccactgcctc ctgcccaggg   9720
ggatttgggg acggtaggag gatgtgtcta aggcatagtc gacttggcac agagtggtct   9780
ctttagtttt gtttcccact ggaggtggca catgcaggaa aagggcctgg cccaggctgc   9840
cgaccggcag aagctgagtg ggaaccaaac cctcctgcaa ttggcagggc cctgccgtca   9900
```

-continued

```
agctaaggcc aaagctgggc cctgggccca ttctacccac tgaaggcagc tgtggaggaa   9960
ggggcttggg ttccagcctg gtttgtggta gggggagata ccacaaaaga aatggggatg  10020
gttctggctc aggcctctgg gaaagcagcc acccaacccc acccacctcc cgcaggggct  10080
ccttccagct tgaggctcag tgggacccag actggaaggt taatgctgtg aagggaagca  10140
gcacagggtg gacggggcaa ggccagctgt gagaaggcag tgcccctggc accctggttt  10200
cagaggcagg tcacacagta tggctaagtt ccagggaggg gtgcgcagaa gctcagcaga  10260
aggggagagg tgagcagccc gggaccctcc cccagggcgg caactcctac cttcccatgt  10320
cctcatggag gactacaggt gtgcaccatg ggtgggtgtg cacgatgggc aggtgtgcac  10380
gatgggcgtg cagtgatcac tcccaggctg ccaacaccca tgcagacacc agatggcgcc  10440
ttcgtgcagc tgcagaggag ggagcaacag agcctgaagg gaaaaggcaa tggggctgca  10500
ccaaaggata gaacccaggc tgacactcga ccctaatcgg gaggaccccc ttccctctgc  10560
cttggccccc aggtgcccca ttccccaggt agcagcagtg gggctccctt taaccacccc  10620
cagttgggaa ggaggcacct ggggaatgga atggacatca acggggagag ggaggtagcg  10680
gtgctctaca aagaaggcac caagggcggt gggctgagac cctcagaat cttggagagg  10740
ctggagcctg ggcaagccga tgaccagcat ggccacacag tccagaaggg tgaaggtcca  10800
cgccatggcc ctccaccaga ggtcctggga ccaggaaggc tccctggagg caccatgaag  10860
gaagacagat cttggctggg aggtggaggg ctgtttcgac ctagccaggg gctacgggtc  10920
cagtcaaggc acaagctttg tgcctaccag ggtctcccac tggagcataa tcttaaggat  10980
caggatgcat gggaatgtgt gaaaccaggg agaagggctc tgtggaggaa agggggtccc  11040
agaagtaact gtcccaaagg gtcctgaggc cacaggacac tccacccagc actgcagttc  11100
cctttgattg gggaaaagtc aaagggcaag ggagacagtg aaggccaggt cctatccctt  11160
cccaactcca ccagagcagc tgcccaccaa gaggggtatc agtgccagcc aggctcccag  11220
ttcaggggga gtcacagccc cctgtgctac ctctactctg tcacacctgg cccaggccat  11280
ggtgaggaca ggggctgctg aaggcacaga gaaagggctg gagccagaca ttcttcacct  11340
actgtgggcc acataggcct atctccagag agggcatcgg acccagatgg caccacagtg  11400
tgtggccagg ctgggtcgtg ctgcatgtgt gcacagccag gcggctcagc cattgtattg  11460
ctgctggtag cgcaggttga gctcccgcag ctcccgttcc cgcacacggc gtgacttatt  11520
ggagcgtgtg gagcggctgg aacgcgtgga ctgggcagat ttggtgctct ggcagcgcga  11580
ggaggcacgt ttaaggaggt tctgggatat ggagcggtgc aggttcttca tggatgaaga  11640
ggcagccatg ctcaccaccc acgggtgcct cagggcctgc agtgcagtca tacgggctcc  11700
agggtccact gtcagcaggc ggtcaatgaa gtccttggcc aggttggaca cactaggcca  11760
gggctagaga ccaaggacaa gcattagagt gagagcatct gacactgccc accccatctg  11820
gatgaggcca ctactcagca accctcccct ttccagagag aggtgctgcc cctcctctca  11880
tgtagcactt ggggcctccc cgcccaacgc tggctcaggc tgaacaaggg ctgctctcca  11940
ggtgatggag tctggcaagg aaggaaagga cctgtgcact ctcccaggga gcaaattcta  12000
tggtgcactg gacccgaagc ctggctccag ggagatggcc tctgccaaga ccccccggaa  12060
cgtgtcccag gagtatcata actcagggga ctgttagaga atgattcaaa ctttcccacc  12120
acatcctaag tcagattgaa gctccaatct ctggatgacc aggatcaggc tacttaaagg  12180
ggaacttcct agtccttaca gagaagatcc aacctctctc caactgccga agcagtggca  12240
gaagaccact gctccctgcc tctcctcccg gcatggggag gaaaggaaac aattcaaggc  12300
```

-continued

```
aactagattt cccagtcggc tgagggcagg cgatcccggg ccaggaagga accaggaccc  12360
ttctcagtgg caccctctgg cccgcattac ttctctaagc cacaaagggc tcctggcagt  12420
gctgtgcgcc agcctcattt tagtacattc tgtcccctgg gaggaactcc ataaagccca  12480
ctctgccaca tgcaccccgg gctgcctcat ctcagccccg aacccagcag ctgtctgtct  12540
cagggcctca ggttgtacgg ctgtcttcac ctgactggat cctcaggttc tcagggtaaa  12600
ggacacttgc tcagactccc tcttagcccc cagtgcttcc agcaattatt ccagctgtaa  12660
cgtgagactg caatttcatg ttcgtttagt attcccatga gatcatgctg agctggatga  12720
gcccggcctg gtgctgcgca tacaggaagc actcagtagg cacaggctca gacagtaaac  12780
aacccacggt gctgccggat gggtgccctt tcctggagct gcttccaggc cttggggctc  12840
agccaggtga gtccttgcgt ccctgcatct cctaggaaca cttctggcac gggctctgag  12900
gctcccccaa ggataggcag ctaggacctt tcctgagcct gctgcagatg actcaacagg  12960
gatgctaacg atcccctcat cttccttcct gccaggtgag gtctgcctgt tccacccatg  13020
gtacccttca ccttgaggaa cccctgaaca tgccctccag gggggttcagg aggatctgag  13080
agaccacctt cagggcaggt gcacagccat ctagcagaca cacacactca ctgactactg  13140
ctactcccag tctggctcgc ctgacctcca actctttccc tacccccttc cccactgcca  13200
cagagggatg aggcanngag aacacgcttc caccgtcctg aggaaggcnt ggggctacct  13260
gcagctgctg tcttcaccca ctctttggaa ggttattcca agttttactg agctgaagtg  13320
ggagcaacag gggaaccata ttcccaaaca cacctaacag ggtcatcctc atcagtgggc  13380
cagcagcaca cagtgactcc tggggagatg ctggccccag gaggaggaag tcagggtcca  13440
ggagcatgca gccaacgaag gcccatagat gccttactat ccaagggctg tgggtgggcg  13500
cagagagcaa cagccctccc cgacaggcag gtaagtctcc tgggggcttg tgtagttcaa  13560
gattcatatt gagggccagg cgtggtggct catgcctgta atcccagcac tttggggagg  13620
ctgaggcagg tggatcacaa ggtcatgaga tcaagaccat cctggccaac atggtgaaac  13680
cccgtctcta ctaaaaatac aaaaattagt cgggcgtggt ggcgtgcctg tagtccagct  13740
actcaggaag ctgaggcagg agaattgctt gaacctgaga ggcggaggtt gcagtgagcc  13800
aagatcgcac cactgcactc caggctggga aagagggggg ttccgtttcc aaaaaaaaaa  13860
aaa                                                               13863
```

```
<210> SEQ ID NO 84
<211> LENGTH: 3044
<212> TYPE: DNA
<213> ORGANISM: Homo sapiens
<220> FEATURE:
<221> NAME/KEY: misc_feature
<222> LOCATION: (1)..(3044)
<223> OTHER INFORMATION: n = a, c, g or t

<400> SEQUENCE: 84

aggcagggcg ggcgggcgct ctaagggttc tgctctgact ccaggttggg acagcgtctt     60
cgctgctgct ggatagtcgt gttttcgggg atcgaggata ctcaccagaa accgaaaatg    120
ccgaaaccaa tcaatgtccg agttaccacc atggatgcag agctggagtt tgcaatccag    180
ccaaatacaa ctggaaaaca gctttttgat caggtggtaa agactatcgg cctccgggaa    240
gtgtggtact ttggcctcca ctatgtggat aataaaggat ttcctacctg gctgaagctg    300
gataagaagg tgtctgccca ggaggtcagg aaggagaatc cctccagtt caagttccgg    360
```

-continued

```
gccaagttct accctgaaga tgtggctgag gagctcatcc aggacatcac ccagaaactt    420
ttcttcctcc aagtgaagga aggaatcctt agcgatgaga tctactgccc ccctgagact    480
gccgtgctct tggggtccta cgctgtgcag gccaagtttg gggactacaa caaagaagtg    540
cacaagtctg ggtacctcag ctctgagcgg ctgatccctc aaagagtgat ggaccagcac    600
aaacttacca gggaccagtg ggaggaccgg atccaggtgt ggcatgcgga acaccgtggg    660
atgctcaaag ataatgctat gttggaatac ctgaagattg ctcaggacct ggaaatgtat    720
ggaatcaact atttcgagat aaaaaacaag aaaggaacag acctttggct tggagttgat    780
gcccttggac tgaatattta tgagaaagat gataagttaa ccccaaagat tggctttcct    840
tggagtgaaa tcaggaacat ctctttcaat gacaaaaagt ttgtcattaa acccatcgac    900
aagaaggcac ctgactttgt gttttatgcc ccacgtctga gaatcaacaa gcggatcctg    960
cagctctgca tgggcaacca tgagttgtat atgcgccgca ggaagcctga caccatcgag   1020
gtgcagcaga tgaaggccca ggcccgggag gagaagcatc agaagcagct ggagcggcaa   1080
cagctggaaa cagagaagaa aaggagagaa accgtggaga gagagaaaga gcagatgatg   1140
cgcgagaagg aggagttgat gctgcggctg caggactatg aggagaagac aaagaaggca   1200
gagagagagc tctcggagca gattcagagg gccctgcagc tggaggagga gaggaagcgg   1260
gcacaggagg aggccgagcg cctagaggct gaccgtatgg ctgcactgcg ggctaaggag   1320
gagctggaga gacaggcggt ggatcagata aagagccagg agcagctggc tgcggagctt   1380
gcagaataca cagccaagat tgccctcctg gaagaggcgc ggaggcgcaa ggaggatgaa   1440
gttgaagagt ggcagcacag ggccaaagaa gcccaggatg acctggtgaa gaccaaggag   1500
gagctgcacc tggtgatgac agcacccccg cccccaccac cccccgtgta cgagccggtg   1560
agctaccatg tccaggagag cttgcaggat gagggcgcag agcccacggg ctacagcgcg   1620
gagctgtcta gtgagggcat ccgggatgac cgcaatgagg agaagcgcat cactgaggca   1680
gagaagaacg agcgtgtgca gcggcagctc gtgacgctga gcagcgagct gtcccaggcc   1740
cgagatgaga ataagaggac ccacaatgac atcatccaca acgagaacat gaggcaaggc   1800
cgggacaagt acaagacgct gcggcagatc cggcagggca acaccaagca gcgcatcgac   1860
gagttcgagg ccctgtaaca gccaggccag gaccaagggc agaggggtgc tcatagcggg   1920
cgctgccagc cccgccacgc ttgtctttag tgctccaagt ctaggaactc cctcagatcc   1980
cagttccttt agaaagcagt tacccaacag aaacattctg ggctgggaac cagggaggcg   2040
ccctggtttg ttttccccag ttgtaatagt gccaagcagg cctgattctc gcgattattc   2100
tcgaatcacc tcctgtgttg tgctgggagc aggactgatt gaattacgga aaatgcctgt   2160
aaagtctgag taagaaactt catgctggcc tgtgtgatac aagagtcagc atcattaaag   2220
gaaacgtggc aggacttcca tctgtgccat acttgttctg tattcgaaat gagctcaaat   2280
tgattttttt aatttctatg aaggatccat ctttgtatat ttacatgctt agaggggtga   2340
aaattatttt ggaaattgag tctgaagcac tctcgcacac acagtgattc cctcctcccg   2400
tcactccacg cagctggcag agagcacagt gatcaccagc gtgagtggtg gaggaggaca   2460
cttggatatt tttttagttc tttttttttt ggcttaacag ttttagaata cattgtactt   2520
atacacctta ttaatgatca gctatatact atttatatac aagtgataat acagatttgt   2580
aacattagtt ttaaaaaggg aaagttttgt tctgtatatt ttgttacctt ttacagaata   2640
aaagaattac atatgaaaaa ccctctaaac catggcactt gatgtgatgt ggcaggaggg   2700
nagtggtgga gctggacctg cctgctgcag ctgcagtcac gtgtaaacag gattattatt   2760
```

-continued agtgttttat gcatgtaatg gactatgcac acttttaatt ttgtcagatt cacacatgcc 2820
actatgagct ttcagactcc agctgtgaag agactctgtc tgcttgtgtt tgtttgcagt 2880
ctctctctgc catggccttg gcaggctgct ggaaggcagc ttgtggaggc cgttggttcc 2940
gcccactcat tccttctcgt gcactgcttt ctccttcaca gctaagatgc catgtgcagg 3000
tggattccat gccgcagaca tgaaataaaa gctttgcaaa ggca 3044

<210> SEQ ID NO 85
<211> LENGTH: 1953
<212> TYPE: DNA
<213> ORGANISM: Homo sapiens

<400> SEQUENCE: 85
cgctcccacc cgcccgtggc ccgcgcccat ggccgcgcgc gctccacaca actcaccgga 60
gtccgcgccc tgcgccgccg accagttcgc agctccgcgc cacggcagcc agtctcacct 120
ggcggcaccg cccgcccacc gccccggcca cagcccctgc gcccacggca gcaatcgagg 180
cgaccgcgac agtggtgggg gacgctgctg agtggaagag agcgcagccc ggccaccgga 240
cctacttact cgccttgctg attgtctatt tttgcgttta caacttttct aagaactttt 300
gtatacaaag gaacttttta aaaaagacgc ttccaagtta tatttaatcc aaagaagaag 360
gatctcggcc aatttggggt tttgggtttt ggcttcgttt tttctcttcg ttgactttgg 420
ggttcaggtg ccccagctgc ttcgggctgc cgaggacctt ctgggccccc acattaatga 480
ggcagccacc tggcgagtct gacatggctg tcagcgacgc gctgctccca tctttctcca 540
cgttcgcgtc tggcccggcg ggaagggaga agacactgcg tcaagcaggt gccccgaata 600
accgctggcg ggaggagctc tcccacatga agcgacttcc cccagtgctt cccggccgcc 660
cctatgacct ggcggcggcg accgtggcca cagacctgga gagcggcgga gccggtgcgg 720
cttgcggcgg tagcaacctg gcgcccctac ctcggagaga gaccgaggag ttcaacgatc 780
tcctggacct ggactttatt ctctccaatt cgctgaccca tcctccggag tcagtggccg 840
ccaccgtgtc ctcgtcagcg tcagcctcct cttcgtcgtc gccgtcgagc agcggccctg 900
ccagcgcgcc ctccacctgc agcttcacct atccgatccg ggccgggaac gacccgggcg 960
tggcgccggg cggcacgggc ggaggcctcc tctatggcag ggagtccgct ccccctccga 1020
cggctccctt caacctggcg gacatcaacg acgtgagccc ctcgggcggc ttcgtggccg 1080
agctcctgcg gccagaattg gacccggtgt acattccgcc gcagcagccg cagccgccag 1140
gtggcgggct gatgggcaag ttcgtgctga aggcgtcgct gagcgcccct ggcagcgagt 1200
acggcagccc gtcggtcatc agcgtcagca aaggcagccc tgacggcagc cacccggtgg 1260
tggtggcgcc ctacaacggc gggccgccgc gcacgtgccc caagatcaag caggaggcgg 1320
tctcttcgtg cacccacttg ggcgctggac cccctctcag caatggccac cggccggctg 1380
cacacaactt ccccctgggg cggcagctcc ccagcaggag taccccgacc ctgggttttg 1440
aggaagtgct gagcagcagg gaatgtcacc ctgccctgcc gcttcctccc ggcttccatc 1500
cccacccggg gcccaattac ccatccttcc tgcccgatca gatgcagccg caagtcccgc 1560
cgctccatta ccaagagctc atgccacccg gttcctgcat gccagaggag cccaagccaa 1620
agaggggaag acgatcgtgg ccccggaaaa ggaccgccac ccacacttgt gattacgcgg 1680
gctgcggcaa aacctacaca aagagttccc atctcaaggc acacctgcga acccacacag 1740
gtgagaaacc ttaccactgt gactgggacg gctgtggatg gaaattcgcc cgctcagatg 1800

-continued aactgaccag gcactaccgt aaacacacgg ggcaccgccc gttccagtgc caaaaatgcg 1860
accgagcatt ttccaggtcg gaccacctcg ccttacacat gaagaggcat ttttaaatcc 1920
cagacagtgg atatgaccca cactgccaga aga 1953

<210> SEQ ID NO 86
<211> LENGTH: 1476
<212> TYPE: DNA
<213> ORGANISM: Homo sapiens

<400> SEQUENCE: 86
gccacccacc ctccggaccg cggcagctgc tgacccgcca tcgccatggc ccgcgggaaa 60
gccaaggagg agggcagctg gaagaaattc atctggaact cagagaagaa ggagtttctg 120
ggcaggaccg gtggcagttg gtttaagatc cttctattct acgtaatatt ttatggctgc 180
ctggctggca tcttcatcgg aaccatccaa gtgatgctgc tcaccatcag tgaatttaag 240
cccacatatc aggaccgagt ggccccgcca ggattaacac agattcctca gatccagaag 300
actgaaattt cctttcgtcc taatgatccc aagagctatg aggcatatgt actgaacata 360
gttaggttcc tggaaaagta caaagattca gcccagaggg atgacatgat tttgaagat 420 tgtggcgatg tgcccagtga accgaaagaa cgaggagact ttaatcatga acgaggagag 480
cgaaaggtct gcagattcaa gcttgaatgg ctgggaaatt gctctggatt aaatgatgaa 540
acttatggct acaaagaggg caaaccgtgc attattataa agctcaaccg agttctaggc 600
ttcaaaccta agcctcccaa gaatgagtcc ttggagactt acccagtgat gaagtataac 660
ccaaatgtcc ttcccgttca gtgcactggc aagcgagatg aagataagga taaagttgga 720
aatgtggagt attttggact gggcaactcc cctggttttc ctctgcagta ttatccgtac 780
tatggcaaac tcctgcagcc caaatacctg cagcccctgc tggccgtaca gttcaccaat 840
cttaccatgg acactgaaat tcgcatagag tgtaaggcgt acggtgagaa cattgggtac 900
agtgagaaag accgttttca gggacgtttt gatgtaaaaa ttaaatttta agtgacacta 960
cagaaaaaca caaaaaggtg atgggttgtg ttatgcttgt attgaatgct gtcttgacat 1020
ctcttgcctt gtcctccggt atgttctaaa gctgtgtctg agatctggat ctgcccatca 1080
ctttggctag tgacagggct aattaatttg ctttatacat tttcttttac tttccttttt 1140
tcctttctgg aggcatcaca tgctggtgct gtgtctttat gaatgtttta accattttca 1200
tggtggaaga attttatatt tatgcagttg tacaatttta tttttttctg caagaaaaag 1260
tgtaatgtat gaaataaacc aaagtcactt gtttgaaaat aaatctttat tttgaacttt 1320
ataaaaagca atgcagtacc ccatagactg gtgttaaatg ttgtctacag tgcaaaatcc 1380
atgttctaac atatgtaata attgccagga gtacagtgct cttgttgatc ttgtattcag 1440
tcaggttaaa acaacggtca ataaaagaat gaacac 1476

<210> SEQ ID NO 87
<211> LENGTH: 439
<212> TYPE: DNA
<213> ORGANISM: Homo sapiens

<400> SEQUENCE: 87
ggtgggtctg aatctagcac catgacggaa ctagagacag ccatgggcat gatcatagac 60
gtcttttccc gatattcggg cagcgagggc agcacgcaga ccctgaccaa gggggagctc 120
aaggtgctga tggagaagga gctaccaggc ttcctgcaga gtggaaaaga caaggatgcc 180
gtggataaat tgctcaagga cctggacgcc aatggagatg cccaggtgga cttcagtgag 240

-continued

```
ttcatcgtgt tcgtggctgc aatcacgtct gcctgtcaca agtactttga gaaggcagga    300

ctcaaatgat gccctggaga tgtcacagat tcctgcagag ccatggtccc aggcttccca    360

aaagtgtttg ttggcaatta ttcccctagg ctgagcctgc tcatgtacct ctgattaata    420

aatgcttatg aaaaaaaaa                                                 439
```

```
<210> SEQ ID NO 88
<211> LENGTH: 5431
<212> TYPE: DNA
<213> ORGANISM: Homo sapiens

<400> SEQUENCE: 88

ggcagccggg cgccccgcgg ggctctccgc gctgcgttcc cgacccctgg ggggaggtgt     60

ggagtccaag cggtgcattc ttgaaccatc ttgtcagacg ccggcggctc gcgggctgtg    120

gcgggggctg cggtcaaggc cgcgctcctg gggccgccg cctgggaggg tgggcgccca    180

ggcgtccctg cagccccggg tgctccgact gcgcggcggg gccgcggcgc gcgcgcccgg    240

gcgtccgggc gtccgggaca gtggtgccag acactcccaa atcccgagcc ggcccagcct    300

cgtacggagg acctttttt tggttctgtt ggtgacccgt tagccgccgc tggggcctaa    360

caccaagttg agggctcgcg gattagccgc ccgccagccg tggaaatgtg ataagagcgg    420

taccgtttgc agaaggaaat ttctgatgca actcttcgcc tttgctgatt gcctctccaa    480

acgcctgcct gacgactgcc ttggagcatg tgcgttatgg aaattaggct ttggcgctga    540

ccacaatgct gagcaggaag cagcagctgc aggcccagtg actggtagct cagtgaccag    600

cagcccagtg accggcagcc aggtcctcac ctgggtcctc tcagtgaagc cagggtggcc    660

gccccagcag acagtgctac agagccaact cctgacaggt tctgaaaata ttgtgcacag    720

ggcaggctga ggacacagcc acgtgatacc cactgtagag agagggagag agagacctcc    780

tatgcaagct gccggccctc tgttccgtag taaggacaag gtggagcaga cacctcgcag    840

tcaacaagac ccggcaggac caggactccc cgcacagtct gaccgacttg cgaatcacca    900

ggaggatgat gtggacctgg aagccctggt gaacgatatg aatgcatccc tggagagcct    960

gtactcggcc tgcagcatgc agtcagacac ggtgcccctc ctgcagaatg gccagcatgc   1020

ccgcagccag cctcgggctt caggccctcc tcggtccatc cagccacagg tgtccccgag   1080

gcagagggtg cagcgctccc agcctgtgca catcctcgct gtcaggcgcc ttcaggagga   1140

agaccagcag tttagaacct catctctgcc ggccatcccc aatccttttc ctgaactctg   1200

tggccctggg agccccgctg tgctcacgcc gggttcttta cctccgagcc aggccgccgc   1260

aaagcaggat gttaaagtct ttagtgaaga tgggacaagc aaagtggtgg agattctagc   1320

agacatgaca gccagagacc tgtgccaatt gctggtttac aaaagtcact gtgtggatga   1380

caacagctgg acactagtgg agcaccaccc gcacctagga ttagagaggt gcttggaaga   1440

ccatgagctg gtggtccagg tggagagtac catggccagt gagagtaaat ttctattcag   1500

gaagaattac gcaaaatacg agttctttaa aaatcccatg aatttcttcc cagaacagat   1560

ggttacttgg tgccagcagt caaatggcag tcaaacccag cttttgcaga attttctgaa   1620

ctccagtagt tgtcctgaaa ttcaagggtt tttgcatgtg aaagagctgg gaaagaaatc   1680

atggaaaaag ctgtatgtgt gtttgcggag atctggcctt tattgctcca ccaagggaac   1740

ttcaaaggaa cccagacacc tgcagctgct ggccgacctg gaggacagca acatcttctc   1800

cctgatcgct ggcaggaagc agtacaacgc ccctacagac cacgggctct gcataaagcc   1860
```

-continued

```
aaacaaagtc aggaatgaaa ctaaagagct gaggttgctc tgtgcagagg acgagcaaac   1920
caggacgtgc tggatgacag cgttcagact cctcaagtat ggaatgctcc tttaccagaa   1980
ttaccgaatc cctcagcaga ggaaggcctt gctgtccccg ttctcgacgc cagtgcgcag   2040
tgtctccgag aactccctcg tggcaatgga tttttctggg caaacaggac gcgtgataga   2100
gaatccggcg gaggcccaga gcgcagccct ggaggagggc cacgcctgga ggaagcgaag   2160
cacacggatg aacatcctag gtagccaaag tcccctccac ccttctaccc taagtacagt   2220
gattcacagg acacagcact ggtttcacgg gaggatctcc agggaggaat cccacaggat   2280
cattaaacag caagggctcg tggatgggct ttttctcctc cgtgacagcc agagtaatcc   2340
aaaggcattt gtactcacac tgtgtcatca ccagaaaatt aaaaatttcc agatcttacc   2400
ttgcgaggac gacgggcaga cgttcttcag cctagatgac gggaacacca aattctctga   2460
cctgatccag ctggttgact tttaccagct gaacaaagga gtcctgcctt gcaaactcaa   2520
gcaccactgc atccgagtgg ccttatgacc gcagatgtcc tctcggctga agactggagg   2580
aagtgaacac tggagtgaag aagcggtctg tgcgttggtg aagaacacac atcgattctg   2640
cacctgggga cccagagcga gatgggtttg ttcggtgcca gccgaccaag attgactagt   2700
ttgttggact taaacgacga tttgctgctg tgaacccagc agggtcgcct ccctctgcgt   2760
cagccaaatt ggggagggca tggaagatcc agcggaaagt tgaaaataaa ctggaatgat   2820
catcttggct tgggccgctt aggaacaaga accggagaga agtgattgga aatgaactct   2880
tgccctggaa taatcttgac aattaaaact gatatgttta cttttttttgt attgatcact   2940
tttttgcact ccttctttgt tttcaatatt gtattcagcc tattgtagga gggggatgtg   3000
gcgtttcaac tcatataata cagaaagagt tttgaatggg cagatttcaa actgaatatg   3060
ggtccccaaa tgttcccaga gggtcctcca caccctctgc cgactaccac ggtgtggatt   3120
cagctcccaa atgacaaacc cagcccttcc cagtatactt gaaaagcttt cttgttaaaa   3180
taaaaggtgt cactgtggta ggcatttggc atattttgtg gactcagtca agcaaccaca   3240
gtctgttaat catttctcta tgctcagatg tcagatcctc ttgttattag tgtgtcttgt   3300
tctgcacagt gcaggagact ttattccttt ggaaaattca ctgttccaca aacagcaggc   3360
tgaatggcct cgcctctaga ttgacgtggg ccagcctcct tgagacacac ctggcacccg   3420
tcatcggcca gcggtggatg ctgcataatc cacctgggta cttcagcctt gcgtttccac   3480
agccttcagc ctgttctaga acgatcactg ccttacccct gctgctgcag tggtgtgagt   3540
cgtttcacgg ctgatgtccc tcggggggatt aaaggatcta aagagaaaat ggcacctggt   3600
tgtcttcgtg ctgtgtctca tgggtttcca tagtgataaa gacaaggaaa cgctgcaggg   3660
gccacaggca caggctgata tttaaagatc tttgcttgca gccctccgtc ctgctgaaaa   3720
cccccataag ccagtgaaca cagagcagct agaggctcct cctctgctgg cttagggtca   3780
gaagtacctc acagtggttg tggacatgga agagttttgt caacacaaca ctttgtcccc   3840
gctccgggag atgagtcaga tggtggcttg agttgtcact tggtcccctc cgcccctcgg   3900
gtggccccct ttgccacgtc cccttagctt agtgatcagg tgtgagagtg gccatttcct   3960
tacctttgat ccctgtaaag cagaaaggac tcctttgaca ggcgacaaac tactgtggtg   4020
agcagaatga tttccttttt caagacaaca cctgcctggc ttctattaat gtgtgctggc   4080
catgatattg ccccaaatcc gccccactga agtgttccct aaggaacagc atttctctgc   4140
tcctcagtca acccccgtag cctagagcag tgtcacaagc ttcagtaagg ccagtcagct   4200
ggaagtcagt ctaccgtata gtaacactgt atttcagtct acagaccaca ctctagttgt   4260
```

-continued tttccatgaa aggtatacaa atgaagaatt ttctagcaaa acatgttttt aaccatcagt 4320
gctcaattgc attttcttcc tttcgcagcc agtcagtctt tcaaactatt gacagtaaga 4380
taattctcac gttcacacct ggtggcaggc ttcactgtag ggacggacat tgcagttaca 4440
ccacgattcc ttcctcttca ctggctcgag gtaaaccctt ttcaaggaaa aacaactcta 4500
ggatttcttt tttctgtgta cgtagaccag tcccatcagt gtataatctc tctctcacac 4560
gcctctctcc aatagacagc ttgtatttgc agtatttcat atttataaat atgcgtttat 4620
ttaaaaggag aacaaaagct tgactctgat tcacagtttt gtatgtagct ggtttgacgt 4680
agtcttttgt attttccctg ccgaagtgaa ttgttggaga atgtaaaccg cctccacgtg 4740
gcggcagact tcctaaggcc ccagctcgct ggcctcgcgc tgggcggctg ggaattccac 4800
ctgagaacaa gtcccgcaaa ccggggacgg aaggacattt gacttttatt tttgtattta 4860
attgacatga atgtaaaggg gacagctcag ggttgttttg gagcctgttg actttgtatc 4920
tctgcctgtg attttctttt ctaaatgaaa ctccatgtag caaccaggac gaagttgaga 4980
aggaaaacgc caaatgcttt ggttattaga gtttaatagg taagctctgt tacactaggt 5040
gttagagttc cagaatgttc ttttgtttgc taaaccttga agaaacatgt gcctcagcct 5100
agatgttttg tcttctcttt tctgcactta atacctgaca gtatgaccga tctctgcgcc 5160
tttctggggg cgggcaagct ggcggtagat ttgtgatgtc acagtgcaaa ctgcagtgac 5220
tgtaaattgg cctggcgtgt ataaacgttt tcagggaatg cagaaggtat taatgaagag 5280
acaaaacctt tattccatgt gctttgcttc attctgtaca tagctctttg gctcgtgaac 5340
ctaattgtaa actttcaggt atttttgtac aaataaggga ctgatgttct gtttcttgta 5400
attagaaata aacattaata cagtgttctt c 5431

<210> SEQ ID NO 89
<211> LENGTH: 1223
<212> TYPE: DNA
<213> ORGANISM: Homo sapiens

<400> SEQUENCE: 89
acactcgctc ggctcaccat gtgtcactct cgcagctgcc acccgaccat gaccatcctg 60
caggccccga ccccggcccc ctccaccatc ccgggacccc ggcggggctc cggtcctgag 120
atcttcacct tcgaccctct cccggagccc gcagcggccc ctgccgggcg ccccagcggc 180
tctcgcgggc accgaaagcg cagccgcagg gttctctacc ctcgagtggt ccggcgccag 240
ctgccagtcg aggaaccgaa cccagccaaa aggcttctct ttctgctgct caccatcgtc 300
ttctgccaga tcctgatggc tgaagagggt gtgcgggcgc ccctgcctcc agaggacgcc 360
cctaacgccg catccctggc gcccacccct gtgtcccccg tcctcgagcc ctttaatctg 420
acttcggagc cctcggacta cgctctggac ctcagcactt tcctccagca acacccggcc 480
gccttctaac tgtgactccc cgcactcccc aaaaagaatc cgaaaaacca caaagaaaca 540
ccaggcgtac ctggtgcgcg agagcgtatc cccaactggg acttccgagg caacttgaac 600
tcagaacact acagcggaga cgccacccgg tgcttgaggc gggaccgagg cgcacagaga 660
ccgaggcgca tagagaccga gcacagccca gctgggctag gcccggtggg aaggagagcg 720
tcgttaattt atttcttatt gctcctaatt aatatttata tgtatttatg tacgtcctcc 780
taggtgatga gatgtgtacg taatatttat tttaacttat gcaagggtgt gagatgttcc 840
ccctgctgta aatgcaggtc tcttggtatt tattgagctt tgtgggactg gtggaagcag 900

-continued

```
gacacctgga actgcggcaa agtaggagaa gaaatgggga ggactcgggt gggggaggac     960

gtcccggctg ggatgaagtc tggtggtggg tcgtaagttt aggaggtgac tgcatcctcc    1020

agcattctca actccgtctg tctactgtgt gagacttcgg cggaccatta ggaatgagat    1080

ccgtgagatc cttccatctt cttgaagtcg cctttaggt ggctgcgagg tagagggttg     1140

ggggttggtg ggctgtcacg gagcgactgt cgagatcgcc tagtatgttc tgtgaacaca    1200

aataaaattg atttactgtc tgc                                            1223
```

```
<210> SEQ ID NO 90
<211> LENGTH: 3536
<212> TYPE: DNA
<213> ORGANISM: Homo sapiens

<400> SEQUENCE: 90

ggcccctcga gcctcgaacc ggaacctcca aatccgagac gctctgctta tgaggacctc      60

gaaatatgcc ggccagtgaa aaaatcttat ggctttgagg gcttttggtt ggccaggggc     120

agtaaaaatc tcggagagct gacaccaagt cctcccctgc cacgtagcag tggtaaagtc     180

cgaagctcaa attccgagaa ttgagctctg ttgattctta gaactggggt tcttagaagt     240

ggtgatgcaa gaagtttcta ggaaaggccg gacaccaggt tttgagcaaa attttggact     300

gtgaagcaag gcattggtga agacaaaatg gcctcgccgg ctgacagctg tatccagttc     360

acccgccatg ccagtgatgt tcttctcaac cttaatcgtc tccggagtcg agacatcttg     420

actgatgttg tcattgttgt gagccgtgag cagtttagag cccataaaac ggtcctcatg     480

gcctgcagtg gcctgttcta tagcatcttt acagaccagt tgaaatgcaa ccttagtgtg     540

atcaatctag atcctgagat caaccctgag ggattctgca tcctcctgga cttcatgtac     600

acatctcggc tcaatttgcg ggagggcaac atcatggctg tgatggccac ggctatgtac     660

ctgcagatgg agcatgttgt ggacacttgc cggaagttta ttaaggccag tgaagcagag     720

atggtttctg ccatcaagcc tcctcgtgaa gagttcctca acagccggat gctgatgccc     780

caagacatca tggcctatcg ggtcgtgag gtggtggaga acaacctgcc actgaggagc      840

gcccctgggt gtgagagcag agcctttgcc cccagcctgt acagtggcct gtccacaccg     900

ccagcctctt attccatgta cagccacctc cctgtcagca gcctcctctt ctccgatgag     960

gagtttcggg atgtccggat gcctgtggcc aacccccttcc ccaaggagcg ggcactccca   1020

tgtgatagtg ccaggccagt ccctggtgag tacagccggc cgactttgga ggtgtccccc    1080

aatgtgtgcc acagcaatat ctattcaccc aaggaaacaa tcccagaaga ggcacgaagt    1140

gatatgcact acagtgtggc tgagggcctc aaacctgctg ccccctcagc ccgaaatgcc    1200

ccctacttcc cttgtgacaa ggccagcaaa gaagaagaga gaccctcctc ggaagatgag    1260

attgccctgc atttcgagcc ccccaatgca cccctgaacc ggaagggtct ggttagtcca    1320

cagagccccc agaaatctga ctgccagccc aactcgccca cagaggcctg cagcagtaag    1380

aatgcctgca tcctccaggc ttctggctcc cctccagcca agagccccac tgaccccaaa    1440

gcctgcaact ggaagaaata caagttcatc gtgctcaaca gcctcaacca gaatgccaaa    1500

ccagggggc ctgagcaggc tgagctgggc cgcctttccc cacgagccta cacggcccca     1560

cctgcctgcc agccacccat ggagcctgag aaccttgacc tccagtcccc aaccaagctg    1620

agtgccagcg gggaggactc caccatccca caagccagcc ggctcaataa catcgttaac    1680

aggtccatga cgggctctcc ccgcagcagc agcgagagcc actcaccact ctacatgcac    1740

cccccgaagt gcacgtcctg cggctctcag tccccacagc atgcagagat gtgcctccac    1800
```

-continued

```
accgctggcc ccacgttcgc tgaggagatg ggagagaccc agtctgagta ctcagattct   1860

agctgtgaga acggggcctt cttctgcaat gagtgtgact gccgcttctc tgaggaggcc   1920

tcactcaaga ggcacacgct gcagacccac agtgacaaac cctacaagtg tgaccgctgc   1980

caggcctcct tccgctacaa gggcaacctc gccagccaca agaccgtcca taccggtgag   2040

aaaccctatc gttgcaacat ctgtggggcc cagttcaacc ggccagccaa cctgaaaacc   2100

cacactcgaa ttcactctgg agagaagccc tacaaatgcg aaacctgcgg agccagattt   2160

gtacaggtgg cccacctccg tgcccatgtg cttatccaca ctggtgagaa gccctatccc   2220

tgtgaaatct gtggcacccg tttccggcac cttcagactc tgaagagcca cctgcgaatc   2280

cacacaggag agaaacctta ccattgtgag aagtgtaacc tgcatttccg tcacaaaagc   2340

cagctgcgac ttcacttgcg ccagaagcat ggcgccatca ccaacaccaa ggtgcaatac   2400

cgcgtgtcag ccactgacct gcctccggag ctccccaaag cctgctgaag catggagtgt   2460

tgatgctttc gtctccagcc ccttctcaga atctacccaa aggatactgt aacactttac   2520

aatgttcatc ccatgatgta gtgcctcttt catccactag tgcaaatcat agctgggggt   2580

tgggggtggt gggggtcggg gcctggggga ctgggagccg cagcagctcc ccctccccca   2640

ctgccataaa acattaagaa aatcatattg cttcttctcc tatgtgtaag gtgaaccatg   2700

tcagcaaaaa gcaaaatcat tttatatgtc aaagcagggg agtatgcaaa agttctgact   2760

tgactttagt ctgcaaaatg aggaatgtat atgttttgtg ggaacagatg tttcttttgt   2820

atgtaaatgt gcattctttt aaaagacaag acttcagtat gttgtcaaag agagggcttt   2880

aatttttta accaaaggtg aaggaatata tggcagagtt gtaaatatat aaatatatat   2940

atatataaaa taaatatata taaacctaac aaagatatat taaaaatata aaactgcgtt   3000

aaaggctcga ttttgtatct gcaggcagac acggatctga gaatctttat tgagaaagag   3060

cacttaagag aatattttaa gtattgcatc tgtataagta agaaaatatt ttgtctaaaa   3120

tgcctcagtg tatttgtatt tttttgcaag tgaaggttta caatttacaa agtgtgtatt   3180

aaaaaaaacc caaagaaccc aaaaatctgc agaaggaaaa atgtgtaatt ttgttctagt   3240

tttcagtttg tatatacccg tacaacgtgt cctcacggtg ccttttttca cggaagtttt   3300

caatgatggg cgagcgtgca ccatcccttt ttgaagtgta ggcagacaca gggacttgaa   3360

gttgttacta actaaactct ctttgggaat gtttgtctca tcccattctg cgtcatgctt   3420

gtgtgataac tactccggag acagggtttg gctgtgtcta aactgcatta ccgcgttgta   3480

aaaaatagct gtaccaatat aagaataaaa tgttggaaag tcgcaaaaaa aaaaaa       3536
```

<210> SEQ ID NO 91
<211> LENGTH: 8930
<212> TYPE: DNA
<213> ORGANISM: Homo sapiens

<400> SEQUENCE: 91

```
gaattccgga aagaaagaac atcgtttcag gaataaaaat gcacagtagt agttatagtt     60

accgtagcag tgattctgtg tttagtaaca ctaccagcac tcgaaccagt cttgattcaa    120

atgaaaatct tctcttggtt cattgtggtc caacactgat caactcttgc attagcttcg    180

gcagtgaatc ctttgatgga cacaggttag aaatgttgca acagattgcc aacagagttc    240

agagggacag tgtcatctgt gaagacaaac tgattcttgc tggaaatgct cttcagtctg    300

attctaaaag attagaatca ggagtgcagt ttcagaatga agcagaaatt gctgggtata    360
```

-continued

```
tacttgaatg tgagaacctt ttacgccagc atgtaattga tgtacagatt cttattgatg    420
gaaaatacta ccaggcagat caattggtac agagggttgc aaaactgcgt gacgaaatta    480
tggccttaag gaacgaatgt tcttctgtgt acagcaaagg acgcatactg acaacagaac    540
agacaaagct catgatatca ggaatcactc aaagtttaaa ctcaggattt gcacagacct    600
tacaccctag tctgacctca gggctgaccc agagtttaac accttcccta acctcttcta    660
gtatgacttc tggcctgtca tcagggatga cttcccgcct gactccatct gtcactccag    720
cttatacacc tggtttccca tcaggattag ttccaaattt cagttcagga gtagagccaa    780
attcattgca aactttgaag ttgatgcaga tccgaaaacc ccttctaaag tcttctttgc    840
tggatcaaaa tttaacagaa gaagaaatca atatgaaatt tgttcaggat cttttgaatt    900
gggttgatga gatgcaggta caactggacc gcactgagtg gggctcagat ttgccaagtg    960
ttgaaagcca tttagaaaat cataaaaatg ttcatagagc tattgaagaa tttgaatcta   1020
gtctcaaaga agctaaaatc agtgagattc aaatgacagc acctcttaaa ctgacttatg   1080
cagaaaagtt gcacagatta gagagtcagt atgcaaaact cttgaataca tccaggaatc   1140
aagaacggca ccttgataca ctccataatt ttgtaagtcg tgcgactaat gaacttattt   1200
ggttgaatga aaaagaagag gaggaagttg cttatgactg gagtgagaga aacaccaaca   1260
tagctaggaa aaaagattat catgctgaat taatgagaga acttgatcaa aaggaagaaa   1320
atattaaatc agttcaggag atagcagagc agctacttct agaaaatcat ccagcccggt   1380
taactattga ggcctacaga gcggcaatgc agacgcagtg gagctggatc ttacagctct   1440
gccagtgtgt ggagcagcac ataaaggaga acacagcgta tttcgagttt ttcaatgatg   1500
ccaaagaagc tactgattac ttaaggaatc taaaagatgc cattcagcgg aagtacagct   1560
gtgatagatc aagcagcatt cacaagctag aagaccttgt tcaggaatca atggaagaga   1620
aagaagaact tctgcagtac aaaagcacta tagcaaacct aatgggaaaa gcaaaaacaa   1680
taattcaact gaagccaagg aattctgact gtccactcaa aacttctatt ccgatcaaag   1740
ctatctgtga ctacagacaa attgagataa ccatttacaa agacgatgaa tgtgttttgg   1800
caaataactc tcatcgtgct aaatggaagg tcattagtcc tactgggaat gaggctatgg   1860
tcccatctgt gtgcttcacc gttcctccac caaacaaaga agcggtggac cttgccaaca   1920
gaattgagca acagtatcag aatgtcctga ctctttggca tgagtctcac ataaacatga   1980
agagtgtagt atcctggcat tatctcatca atgaaattga tagaattcga gctagcaatg   2040
tggcttcaat aaagacaatg ctacctggtg aacatcagca agttctaagt aatctacaat   2100
ctcgttttga agattttctg gaagatagcc aggaatccca agtcttttca ggctcagata   2160
taacacaact ggaaaaggag gttaatgtat gtaagcagta ttatcaagaa cttcttaaat   2220
ctgcagaaag agaggagcaa gaggaatcag tttataatct ctacatctct gaagttcgaa   2280
acattagact tcggttagag aactgtgaag atcggctgat tagacagatt cgaactcccc   2340
tggaaagaga tgatttgcat gaaagtgtgt tcagaatcac agaacaggag aaactaaaga   2400
aagagctgga acgacttaaa gatgatttgg gaacaatcac aaataagtgt gaggagtttt   2460
tcagtcaagc agcagcctct tcatcagtcc ctaccctacg atcagagctt aatgtggtcc   2520
ttcagaacat gaaccaagtc tattctatgt cttccactta catagataag ttgaaaactg   2580
ttaacttggg gttaaaaaac actcaagctg cagaagccct cgtaaaactc tatgaaacta   2640
aactgtgtga agaagaagca gttatagctg acaagaataa tattgagaat ctaataagta   2700
ctttaaagca atggagatct gaagtagatg aaaagagaca ggtattccat gccttagagg   2760
```

-continued

```
atgagttgca gaaagctaaa gccatcagtg atgaaatgtt taaaacgtat aaagaacggg   2820
accttgattt tgactggcac aaagaaaaag cagatcaatt agttgaaagg tggcaaaatg   2880
ttcatgtgca gattgacaac aggttacggg acttagaggg cattggcaaa tcactgaagt   2940
actacagaga cacttaccat cctttagatg attggatcca gcaggttgaa actactcaga   3000
gaaagattca ggaaaatcag cctgaaaata gtaaaaccct agccacacag ttgaatcaac   3060
agaagatgct ggtgtccgaa atagaaatga aacagagcaa aatggacgag tgtcaaaaat   3120
atgcagaaca gtactcagct acagtgaagg actatgaatt acaaacaatg acctaccggg   3180
ccatggtaga ttcacaacaa aaatctccag tgaaacgccg aagaatgcag agttcagcag   3240
atctcattat tcaagagttc atggacctaa ggactcgata tactgccctg gtcactctca   3300
tgacacaata tattaaattt gctggtgatt cattgaagag gctggaagag gaggagatta   3360
aaaggtgtaa ggagacttct gaacatgggg catattcaga tctgcttcag cgtcagaagg   3420
caacagtgct tgagaatagc aaacttacag gaaagataag tgagttggaa agaatggtag   3480
ctgaactaaa gaaacaaaag tcccgagtag aggaagaact tccgaaggtc agggaggctg   3540
cagaaaatga attgagaaag cagcagagaa atgtagaaga tatctctctg cagaagataa   3600
gggctgaaag tgaagccaag cagtaccgca gggaacttga aaccattgtg agagagaagg   3660
aagccgctga aagagaactg gagcgggtga ggcagctcac catagaggcc gaggctaaaa   3720
gagctgccgt ggaagagaac ctcctgaatt ttcgcaatca gttggaggaa aacaccttta   3780
ccagacgaac actggaagat catcttaaaa gaaaagattt aagtctcaat gatttggagc   3840
aacaaaaaaa taaattaatg gaagaattaa gaagaaagag agacaatgag gaagaactct   3900
tgaagctgat aaagcagatg gaaaaagacc ttgcatttca gaaacaggta gcagagaaac   3960
agttgaaaga aaagcagaaa attgaattgg aagcaagaag aaaaataact gaaattcagt   4020
atacatgtag agaaaatgca ttgccagtgt gtccgatcac acaggctaca tcatgcaggg   4080
cagtaacggg tctccagcaa gaacatgaca agcagaaagc agaagaactc aaacagcagg   4140
tagatgaact aacagctgcc aatagaaagg ctgaacaaga catgagagag ctgacatatg   4200
aacttaatgc cctccagctt gaaaaaacgt catctgagga aaggctcgt ttgctaaaag   4260
ataaactaga tgaaacaaat aatacactca gatgccttaa gttggagctg gaaaggaagg   4320
atcaggcgga gaaagggtat tctcaacaac tcagagagct tggtaggcaa ttgaatcaaa   4380
ccacaggtaa agctgaagaa gccatgcaag aagctagtga tctcaagaaa ataaagcgca   4440
attatcagtt agaattagaa tctcttaatc atgaaaaagg gaaactacaa agagaagtag   4500
acagaatcac aagggcacat gctgtagctg agaagaatat tcagcattta aattcacaaa   4560
ttcattcttt tcgagatgag aaagaattag aaagactaca aatctgccag agaaaatcag   4620
atcatctaaa agaacaattt gagaaaagcc atgagcagtt gcttcaaaat atcaaagctg   4680
aaaaagaaaa taatgataaa atccaaaggc tcaatgaaga attggagaaa agtaatgagt   4740
gtgcagagat gctaaaacaa aaagtagagg agcttactag gcagaataat gaaaccaaat   4800
taatgatgca gagaattcag gcagaatcag agaatatagt tttagagaaa caaactatcc   4860
agcaaagatg tgaagcactg aaaattcagg cagatggttt taaagatcag ctacgcagca   4920
caaatgaaca cttgcataaa cagacaaaaa cagagcagga ttttcaaaca aaaattaaat   4980
gcctagaaga agacctggcg aaaagtcaaa atttggtaag tgaatttaag caaaagtgtg   5040
accaacagaa cattatcatc cagaatacca agaaagaagt tagaaatctg aatgcggaac   5100
```

-continued

```
tgaatgcttc caaagaagag aagcgacgcg gggagcagaa agttcagcta caacaagctc   5160
aggtgcaaga gttaaataac aggttgaaaa aagtacaaga cgaattacac ttaaagacca   5220
tagaggagca gatgacccac agaaagatgg ttctgtttca ggaagaatct ggtaaattca   5280
aacaatcagc agaggagttt cggaagaaga tggaaaaatt aatggagtcc aaagtcatca   5340
ctgaaaatga tatttcaggc attaggcttg actttgtgtc tcttcaacaa gaaaactcta   5400
gagcccaaga aaatgctaag ctttgtgaaa caaacattaa agaacttgaa agacagcttc   5460
aacagtatcg tgaacaaatg cagcaagggc agcacatgga agcaaatcat taccaaaaat   5520
gtcagaaact tgaggatgag ctgatagccc agaagcgtga ggttgaaaac ctgaagcaaa   5580
aaatggacca acagatcaaa gagcatgaac atcaattagt tttgctccag tgtgaaattc   5640
aaaaaaagag cacagccaaa gactgtacct tcaaaccaga ttttgagatg acagtgaagg   5700
agtgccagca ctctggagag ctgtcctcta gaaacactgg acaccttcac ccaacaccca   5760
gatcccctct gttgagatgg actcaagaac cacagccatt ggaagagaag tggcagcatc   5820
gggttgttga acagataccc aaagaagtcc aattccagcc accaggggct ccactcgaga   5880
aagagaaaag ccagcagtgt tactctgagt actttttctca gacaagcacc gagttacaga   5940
taacttttga tgagacaaac cccattacaa gactgtctga aattgagaag ataagagacc   6000
aagccctgaa caattctaga ccacctgtta ggtatcaaga taacgcatgt gaaatggaac   6060
tggtgaaggt tttgacaccc ttagagatag ctaagaacaa gcagtatgat atgcatacag   6120
aagtcacaac attaaaacaa gaaaagaacc cagttcccag tgctgaagaa tggatgcttg   6180
aagggtgcag agcatctggt ggactcaaga aaggggattt ccttaagaag ggcttagaac   6240
cagagacctt ccagaacttt gatggtgatc atgcatgttc agtcagggat gatgaattta   6300
aattccaagg gcttaggcac actgtgactg ccaggcagtt ggtggaagct aagcttctgg   6360
acatgagaac aattgagcag ctgcgactcg gtcttaagac tgttgaagaa gttcagaaaa   6420
ctcttaacaa gtttctgacg aaagccacct caattgcagg gctttaccta gaatctacaa   6480
aagaaaagat ttcatttgcc tcagcggccg agagaatcat aatagacaaa atggtggctt   6540
tggcattttt agaagctcag gctgcaacag gttttataat tgatcccatt tcaggtcaga   6600
catattctgt tgaagatgca gttcttaaag gagttgttga ccccgaattc agaattaggc   6660
ttcttgaggc agagaaggca gctgtgggat attcttattc ttctaagaca ttgtcagtgt   6720
ttcaagctat ggaaaataga atgcttgaca gacaaaaagg taaacatatc ttggaagccc   6780
agattgccag tgggggtgtc attgaccctg tgagaggcat tcgtgttcct ccagaaattg   6840
ctctgcagca ggggttgttg aataatgcca tcttacagtt tttacatgag ccatccagca   6900
acacaagagt tttccctaat cccaataaca agcaagctct gtattactca gaattactgc   6960
gaatgtgtgt atttgatgta gagtcccaat gctttctgtt tccatttggg gagaggaaca   7020
tttccaatct caatgtcaag aaaacacata gaatttctgt agtagatact aaaacaggat   7080
cagaattgac cgtgtatgag gctttccaga gaaacctgat tgagaaaact atatatcttg   7140
aactttcagg gcagcaatat cagtggaagg aagctatgtt ttttgaatcc tatgggcatt   7200
cttctcatat gctgactgat actaaaacag gattacactt caatattaat gaggctatag   7260
agcagggaac aattgacaaa gccttggtca aaaagtatca ggaaggcctc atcacactta   7320
cagaacttgc tgattctttg ctgagccggt tagtccccaa gaaagatttg cacagtcctg   7380
ttgcagggta ttggctgact gctagtgggg aaaggatctc tgtactaaaa gcctcccgta   7440
gaaatttggt tgatcggatt actgccctcc gatgccttga agcccaagtc agtacagggg   7500
```

-continued

```
gcataattga tcctcttact gtcaaaaagt accgggtggc cgaagctttg catagaggcc   7560
tggttgatga ggggtttgcc cagcagctgc gacagtgtga attagtaatc acagggattg   7620
gccatcccat cactaacaaa atgatgtcag tggtggaagc tgtgaaggca aatattataa   7680
ataaggaaat gggaatccga tgtttggaat ttcagtactt gacaggaggg ttgatagagc   7740
cacaggttca ctctcggtta tcaatagaag aggctctcca agtaggtatt atagatgtcc   7800
tcattgccac aaaactcaaa gatcaaaagt catatgtcag aaatataata tgccctcaga   7860
caaaaagaaa gttgacatat aaagaagcct tagaaaaacc tgattttgat ttccacacag   7920
gacttaaact gttagaagta tctgagcccc tgatgacagg aatttctagc ctctactatt   7980
cttcctaatg ggacatgttt aaataactgt gcaaggggtg atgcaggctg gttcatgcca   8040
ctttttcaga gtatgatgat atcggctaca tatgcagtct gtgaattatg taacatactc   8100
tatttcttga gggctgcaaa ttgctaagtg ctcaaaatag agtaagtttt aaattgaaaa   8160
ttacataaga tttaatgccc ttcaaatggt ttcatttagc cttgagaatg gtttttttgaa  8220
acttggccac actaaaatgt tttttttttt acgtagaatg tgggataaac ttgatgaact   8280
ccaagttcac agtgtcattt cttcagaact ccccttcatt gaatagtgat catttattaa   8340
atgataaatt gcactcgctg aaagagcacg tcatgaagca ccatggaatc aaagagaaag   8400
atataaattc gttcccacag ccttcaagct gcagtgtttt agattgcttc aaaaaatgaa   8460
aaagttttgc ctttttctgt atatagtgac cttctttgca tattaaaatg tttaccacaa   8520
tgtcccattt ctagttaagt cttcgcactt gaaagctaac attatgaata ttatgtgttg   8580
gaggaggga aggattttct tcattctgtg tattttcctt acatgtacag tagacgttct   8640
ctattctatc agccttctat ggtacctttt tgtcaggaca attaggattg taatgctaat   8700
gcaaaggcag caattcaaag atcttctagt gcctcatgaa taaagttgag atttaaaatt   8760
tgtaacattg atggaacagc tgggaggtta gaccaatcat taaggaatgt atgccatacc   8820
tttctttgct accataaaca ttttggaggt gcatctgcta tgtgacatgg taaatatggt   8880
taagtgaatg aataaaatgt tttagtaacc tgtgtcggat tccgcggaat             8930
```

```
<210> SEQ ID NO 92
<211> LENGTH: 1675
<212> TYPE: DNA
<213> ORGANISM: Homo sapiens

<400> SEQUENCE: 92

gtgagacaga gacaaatgaa ccccccctcta aagtcattta actaatagcc agcacatccc    60
ttccccaaac tgtcaattga aatcttaact gaaagtttta ctgaataata ccaagctaat   120
tgctgttggg cacacctgga tggctttgca cctggtgttg aacctgctga agcaggtgga   180
tgctcaagat tacgtgcaag gaatccctcc catctggtac taaaatttca gtgtgttctg   240
agtgtctttt aaaccaaaat ggaaatacag atacagggct gtagtattca gtaatgtgtc   300
tgctccttgt tgggcagaca ccagcggtgt gcagggagag accaagtacc atctttatct   360
acacttgggc tggcttgtgg agaagggctg cttttttttca gtcctacatt ccttcatttt  420
ttttttcatt cttgaattca ttgttttgtg ggatctaaga cccaggggtc atttgagagg   480
tttgacagta tcttttctga ccagttgcca catgacttgc ttgaccctga gcctgtggaa   540
atggcatagg gaccagtcta ctacccactg ggcctggtgt gtagaggggg agagggtagc   600
aaggtgcttc tctacgccca tgacttggga gcaggtcttg gcctccttca tgagagtcta   660
```

-continued

```
gtgccatgtc ctgtcccatg atctggaccc tgggactgtc ttggcatctt aactgcagtt    720

tcaatgaggc agagggcaaa gagagaccaa gatcagaggg gttcattata cccctggcta    780

gagaacccag ctactgacat gcaagcagct tggggctggc tggacacagg tactaggccc    840

attgtttcca ggtgaagctt tcatcacaga acagtgttgt ctccacctgg ccttagatgg    900

cacgccatga ttcgggcctg gatagactgc ctgcgtcctt accactgatc tggccaagaa    960

tgaggccctc ccaacacttt cactccctct ccaagccttg atgggacctc cacttattta   1020

ggcctcatgt gctttgaaga agctttgaga gccaatgtgt cttccacggg tctctttttt   1080

gctacaagta atcagcccca tgtgttctct taaactgaga attgcacctg ggcaattcct   1140

gttttctaag gtggtctctg ctgctattta acaacccaga gtaggcctct gtgaggcttc   1200

agtggcctca gaaaccagag ggtccagata gggggcctgc ttgggccctc tgctgccaac   1260

tgctcaaacc tgctttagct ccagccactt gtggcaaaca acctcgtttc cttacaaatt   1320

ccagcatgtg actttggtgc cgttacttgt gaaaaatcta ttctgttgtc tttgatgtgt   1380

ccaagaaaat tcgtgtagtt tacgtaaaaa tatctgactc acaagaaagc caactgtatg   1440

tcttgtgatg ggacagttca taatgtagtt gctagaccac tttacaaatt gttcttgtca   1500

ccagatgtgt tcagacattg ctgtgcaatt gttggggagg gtagggggaa aggcgagagg   1560

agatacttat tggtcttttt gtttaatacc ttccccaaga ggggacagtc tggccaactt   1620

gctccagtaa tgcaataaag acattgcaat aaagtaaaaa aaaaaaaaaa aaaaa        1675
```

<210> SEQ ID NO 93
<211> LENGTH: 4180
<212> TYPE: DNA
<213> ORGANISM: Homo sapiens

<400> SEQUENCE: 93

```
ccagggtgat gctgaagatg atgaccttct tccaaggcct ctagagccat cagcctgtgc     60

caggcaccct cgacttgcct agaggccccc aaaagttgca gtccacatca gaggcagagt    120

cagaggcctc catgtcggag gcctcctctg aggacctggt gccacccctg gaggctgggg    180

cagccccata tagggaggag gaagaggcgg cgaagaagaa gaaggagaag aagaagaagt    240

ccaaaggcct ggccaatgtg ttctgcgtct tcaccaaagg gaagaagaag aagggtcagc    300

ccagctcagc ggagcccgag gacgcagccg ggtccaggca ggggctggat ggcccgcccc    360

ccacagtgga ggagctgaag gcggcgctgg agcgcgggca gctggaggcg gcgcggccgc    420

tgctggcgct ggagcgggag ctggcggcgg cggcggcggc gggcggtgtg agcgaggagg    480

agctggtgcg gcgccagagc aaggtggagg cgctgtacga gctgctgcgc gaccaggtgc    540

tgggcgtgct gcggcggccg ctggaggcgc cgcccgagcg gctgcgccag gcgctggccg    600

tggtggcgga gcaggagcgc gaggaccgcc aggcggcggc ggcggggccg gggacctcgg    660

ggctggcggc cacgcgcccg cggcgctggc tgcagctgtg gcggcgcggc gtggcggagg    720

cggccgagga gcgcatgggc cagcggccgg ccgcgggcgc cgaggtcccc gagagcgtct    780

ttctgcactt gggccgcacc atgaaggagg acctggaggc cgtggtggag cggctgaagc    840

cgctgttccc cgccgagttc ggcgtcgtgg cggcctacgc cgagagctac caccagcact    900

tcgcggccca cctggccgcc gtggcgcagt tcgagctgtg cgagcgcgac acctacatgc    960

tgctgctctg ggtggagaac ctctacccca atgacatcat caacagcccc aagctggtgg   1020

gtgagctgca gggtatgggg ctcgggagcc tcctgccccc caggcagatc cgactgctgg   1080

aggccacatt cctgtccagt gaggcggcca atgtgaggga gttgatggac cgagctctgg   1140
```

-continued agctagaggc acggcgctgg gctgaggatg tgcctcccca gaggctggac ggccactgcc 1200
acagcgagct ggccatcgac atcatccaga tcacctccca ggcccaggcc aaggccgaga 1260
gcatcacgct ggacttgggc tcacagataa agcgggtgct gctggtggag ctgcctgcgt 1320
tcctgaggag ctaccagcgc gcctttaatg aatttctgga gagaggcaag cagctgacga 1380
attacagggc caatgttatt gccaacatca acaactgcct gtccttccgg atgtccatgg 1440
agcagaattg gcaggtaccc caggacaccc tgagcctcct gctgggcccc ctgggtgagc 1500
tcaagagcca cggctttgac accctgctcc agaacctgca tgaggacctg aagccactgt 1560
tcaagaggtt cacgcacacc cgctgggcgg cccctgtgga gaccctggaa aacatcatcg 1620
ccactgtaga cacgaggctg cctgagttct cagagctgca gggctgtttc cgggaggagc 1680
tcatggaggc cttgcacctg cacctggtga aggagtacat catccaactc agcaaggggc 1740
gcctggtcct caagacggcc gagcagcagc agcagctggc tgggtacatc ctggccaatg 1800
ctgacaccat ccagcacttc tgcacccagc acggctcccc ggcgacctgg ctgcagcctg 1860
ctctccctac gctggccgag atcattcgcc tgcaggaccc cagtgccatc aagattgagg 1920
tggccactta tgccacctgc taccctgact tcagcaaagg ccacctgagc gctatcctgg 1980
ccatcaaggg gaacctatcc aacagtgagg tcaagcgcat ccggagcatc ttggacgtca 2040
gcatgggggc gcaggagccc tcccggcccc tattttccct tataaaggtt ggttagcttt 2100
tcctgtggcc tgacctgcct gtgagtgccc agcaagcctt gggcacaccc cgctgggagc 2160
tgttaagagc agcgctggtt ctcggttcct cccgggtctc ctgtgctctg atgctacttc 2220
tgcctagccc tggcggaggt gcaggccctg tcagctggaa ctggacagac cttggtttgt 2280
ttacatgtcc gatgggggca ggagctccca tcctgggcag ccaaccaggc aacaccaagg 2340
actctttgta aacgatagct gatcgtgtgc acgcaaggaa agaaccagga gggagagtgc 2400
agccaggctc agggatcccc ggacacctct gtccagagcc cctccacagt cggcctcatg 2460
actgtcctcc tcgtgggtgg ggccgagggc cctcttcagc tctctggaga caggggccga 2520
gcctcaccca tctgccctct gcagcccagg gccgccgtga gcgggattca gcaatggtgg 2580
aatggaagac agaactggaa gagaaagaag gaaaagatga gctctcgtct ggcaggggct 2640
tttagggtcc tgtggcgagc tgtgagcacc gccagcgtta gacgtcacat ccaggtggcc 2700
ccacggcccc tacaggctgg ccctgcaatg gggccctgag ccctccctct tcatccccca 2760
aggcctcaac tagagggtgg tcccccgagg gcttggtgtc tactaccgaa gggcccaaga 2820
cctcctgggt cctctcaggc tcccccttcc ccaaggcagg gacaggccct gggggtgcca 2880
ccgtgggccc tgccacccag aagtctggct gaggtctggg caggggcagg gcaagcttga 2940
cctctcactg ttgacccttt ggcctctgta tttgtttcct attgccgtga caggtttcca 3000
caaacttcgt ggatcaaaac gaggtcttcc agttctgcgg gtcagaaggc tgacctgggg 3060
ctcaaatctg ggtgtcggca gtcctgcact ccttctggag gctctagggg agaattcatt 3120
tctggccttt tcatttttag aggctgaccg taattcttga cttcaggctc ctccatcttc 3180
agagccagct gtgggtagtt gaatcttttt cccgtcacct cattgaggcc tcccctctcc 3240
tgcctccctc caccactttt tttttttttt ttttgagaca gggtcttgct gtgttgccca 3300
ggctggagtg cagtggcctg gtcatggcat caaggctcac tgcagcctgg acctcctggt 3360
tcaagtgatc ctcttgtctc agtcccctga gacaatcccc cacgcccagc tacatatttt 3420
tgtggataca gggtctcatt ctgttgccta ggcttgtctg gaactcctgg gctcaaggga 3480

-continued

```
tcttgtagcc ttagcctcct aaagtgctgg gattataggc atgagtcact cgtacccggc   3540

ctgctctacc gcttttaagg acgcttatga tcacattgcg cctacccaga gaacccaggt   3600

cgtctttcta ttttcaggtc agctgattag ccaccttagt tccatctgca actttagttc   3660

ccactggctg tgtaacctaa catagtcaca ggctctgggg actgtcacgt ggacatcttt   3720

gggaggccgt tattctgccc accgcaccct ccgttcatcc cctgccctgc cgggcacctc   3780

gctctacccc aggaaaatgt gagctcgttt tcctgctcgg catgtgctcc ccctaaggct   3840

ctgctcctcc ctgggcctga aagttccttc tcagcctgag agggggccct tcgatctcag   3900

gcatgactca gcccggctga tgcctctgca gtgctgagtc aggatttggg gccggctctc   3960

ttgggtctgt cccctttcc caggtactgc cttacaaagc tgtggccagg aagtggccgg   4020

tataaaggat gcccaaggtc tttgtacgtg tgtaggagtt agcgtgtttg atattgttaa   4080

tataataata attattttt agagtactgc ttttgtatgt atgttgaaca ggatccaggt   4140

ttttatagct tgatataaaa cagaattcaa aagtgaaaaa                          4180
```

<210> SEQ ID NO 94
<211> LENGTH: 1897
<212> TYPE: DNA
<213> ORGANISM: Homo sapiens

<400> SEQUENCE: 94

```
gacgagagaa agcgagtgtc cctctcgcgc cccaggccgg tgtacccccg cactccgcgc     60

cccggcctag aagctctctc tccccgctcc ccggcccggc ccccgccccg ccccgcccca    120

gcccgctggc gccatggagc gctggccttg gccgtcgggc ggcgcctggc tgctcgtggc    180

tgcccgcgcg ctgctgcagc tgctgcgctc agacctgcgt ctgggccgcc cgctgctggc    240

ggcgctggcg ctgctggccg cgctcgactg gctgtgccag cgcctgctgc ccccgccggc    300

cgcactcgcc gtgctggccg ccgccggctg gatcgcgttg tcccgcctgg cgcgcccgca    360

gcgcctgccg gtggccactc gcgcggtgct catcaccggc tgtgactctg gttttggcaa    420

ggagacggcc aagaaactgg actccatggg cttcacggtg ctggccaccg tattggagtt    480

gaacagcccc ggtgccatcg agctgcgtac ctgctgctcc cctcgcctaa ggctgctgca    540

gatggacctg accaaaccag gagacattag ccgcgtgcta gagttcacca aggcccacac    600

caccagcacc ggcctgtggg gcctcgtcaa caacgcaggc cacaatgaag tagttgctga    660

tgcggagctg tctccagtgg ccactttccg tagctgcatg gaggtgaatt tctttggcgc    720

gctcgagctg accaagggcc tcctgcccct gctgcgcagc tcaaggggcc gcatcgtgac    780

tgtggggagc ccagcggggg acatgccata tccgtgcttg gggggcctatg gaacctccaa    840

agcggccgtg gcgctactca tggacacatt cagctgtgaa ctccttccct gggggtcaa    900

ggtcagcatc atccagcctg gctgcttcaa gacagagtca gtgagaaacg tgggtcagtg    960

ggaaaagcgc aagcaattgc tgctggccaa cctgcctcaa gagctgctgc aggcctacgg   1020

caaggactac atcgagcact tgcatgggca gttcctgcac tcgctacgcc tggccatgtc   1080

cgacctcacc ccagttgtag atgccatcac agatgcgctg ctggcagctc ggccccgccg   1140

ccgctattac cccggccagg gcctggggct catgtacttc atccactact acctgcctga   1200

aggcctgcgg cgccgcttcc tgcaggcctt cttcatcagt cactgtctgc ctcgagcact   1260

gcagcctggc cagcctggca ctaccccacc acaggacgca gcccaggacc caaacctgag   1320

ccccggccct tccccagcag tggctcggtg agccatgtgc acctatggcc cagccactgc   1380

agcacaggag gctccgtgag cccttggttc ctccccgaaa acccccagca ttacgatccc   1440
```

-continued

```
ccaagtgtcc tggaccctgg cctaaagaat cccaccccca cttcatgccc actgccgatg   1500

cccaatccag gcccggtgag gccaaggttt cccagtgagc ctctgcgcct ctccactgtt   1560

tcatgagccc aaacaccctc ctggcacaac gctctaccct gcagcttgga gaactccgct   1620

ggatggggag tctcatgcaa gacttcactg cagcctttca caggactctg cagatagtgc   1680

ctctgcaaac taaggagtga ctaggtgggt tggggacccc ctcaggattg tttctcggca   1740

ccagtgcctc agtgctgcaa ttgagggcta aatcccaagt gtctcttgac tggctcaaga   1800

attagggccc caactacaca cccccaagcc acagggaagc atgtactgta cttcccaatt   1860

gccacatttt aaataaagac aaatttttat ttcttct                            1897
```

```
<210> SEQ ID NO 95
<211> LENGTH: 2291
<212> TYPE: DNA
<213> ORGANISM: Homo sapiens

<400> SEQUENCE: 95
```

```
gaacaatgaa gaaagcccca cagccactgt tgctgagcag ggagaggata ttacctccaa     60

aaaagacagg ggagtattaa agattgtcaa aagagtgggg aatggtgagg aaacgccgat    120

gattggagac aaagtttatg tccattacaa aggaaaattg tcaaatggaa agaagtttga    180

ttccagtcat gatagaaatg aaccatttgt ctttagtctt ggcaaaggcc aagtcatcaa    240

ggcatgggac attggggtgg ctaccatgaa gaaaggagag atatgccatt tactgtgcaa    300

accagaatat gcatatggct cggctggcag tctccctaaa attccctcga atgcaactct    360

ctttttgag attgagctcc ttgatttcaa aggagaggat ttatttgaag atggaggcat     420

tatccggaga accaaacgga aaggagaggg atattcaaat ccaaacgaag gagcaacagt    480

agaaatccac ctggaaggcc gctgtggtgg aaggatgttt gactgcagag atgtggcatt    540

cactgtgggc gaaggagaag accacgacat tccaattgga attgacaaag ctctggagaa    600

aatgcagcgg gaagaacaat gtattttata tcttggacca agatatggtt ttggagaggc    660

agggaagcct aaatttggca ttgaacctaa tgctgagctt atatatgaag ttacacttaa    720

gagcttcgaa aaggccaaag aatcctggga gatggatacc aaagaaaaat tggagcaggc    780

tgccattgtc aaagagaagg gaaccgtata cttcaaggga ggcaaataca tgcaggcggt    840

gattcagtat gggaagatag tgtcctggtt agagatggaa tatggtttat cagaaaagga    900

atcgaaagct tctgaatcat ttctccttgc tgcctttctg aacctggcca tgtgctacct    960

gaagcttaga gaatacacca aagctgttga atgctgtgac aaggcccttg gactggacag   1020

tgccaatgag aaaggcttgt ataggagggg tgaagcccag ctgctcatga acgagtttga   1080

gtcagccaag ggtgactttg agaaagtgct ggaagtaaac ccccagaata aggctgcaag   1140

actgcagatc tccatgtgcc agaaaaaggc caaggagcac aacgagcggg accgcaggat   1200

atacgccaac atgttcaaga agtttgcaga gcaggatgcc aaggaagagg ccaataaagc   1260

aatgggcaag aagacttcag aaggggtcac taatgaaaaa ggaacagaca gtcaagcaat   1320

ggaagaagag aaacctgagg gccacgtatg acgccacgcc aaggagggaa gagtcccagt   1380

gaactcggcc cctcctcaat gggctttccc ccaactcagg acagaacagt gtttaatgta   1440

aagtttgtta tagtctatgt gattctggaa gcaaatggca aaaccagtag cttcccaaaa   1500

acagcccccc tgctgctgcc cggagggttc actgaggggt ggcacgggac cactccaggt   1560

ggaacaaaca gaaatgactg tggtgtggag ggagtgagcc agcagcttaa gtccagctca   1620
```

-continued

```
tttcagtttc tatcaacctt caagtatcca attcagggtc cctggagatc atcctaacaa   1680
tgtggggctg ttaggtttta cctttgaact ttcatagcac tgcagaaacc ttttaaaaaa   1740
aaatgcttca tgaatttctc ctttcctaca gttgggtagg gtaggggaag gaggataagc   1800
ttttgttttt taaatgactg aagtgctata aatgtagtct gttgcatttt taaccaacag   1860
aacccacagt agaggggtct catgtctccc cagttccaca gcagtgtcac agacgtgaaa   1920
gccagaacct cagaggccac ttgcttgctg acttagcctc ctcccaaagt ccccctcctc   1980
agccagcctc cttgtgagag tggctttcta ccacacacag cctgtccctg gggagtaat    2040
tctgtcattc ctaaaacacc cttcagcaat gataatgagc agatgagagt ttctggatta   2100
gcttttccta ttttcgatga agttctgaga tactgaaatg tgaaaagagc aatcagaatt   2160
gtgctttttc tcccctcctc tattcctttt agggaataat attcaataca cagtacttcc   2220
tcccagaaaa aaaaaaaaaa aaaaaaaaaa aaaaaaaaaa aaaaaaaaaa aaaaaaaaaa   2280
aaaaaaaaaa a                                                        2291
```

<210> SEQ ID NO 96
<211> LENGTH: 15571
<212> TYPE: DNA
<213> ORGANISM: Homo sapiens

<400> SEQUENCE: 96

```
aagcttcctc actccttggc acctggctcc gacatcacat tgacttttcc cttcctgctt     60
ctaccatcac atcaccttct tctgactcca atctcctgcc tctttcttgc aaggatcctt    120
gtgattgtaa ttaggaccca gctggataat ccatgacaat ctcttcaaga tccttaactt    180
aatcacatct gcaaagtccc ttttgtcata gaacgataac attcacaggt tctgggtatt    240
aggacacgga taacttcggg gttccattac tcacccataa ctggtatgca gtgctgattt    300
ccatcctgta ggtacggttt agggatctct aggtcaatga gataatggac tcttgctcat    360
gttacatggc ataatgggaa gaaagccaaa cctagaaaaa gagggactca ggttcccttg    420
ttagagcctc ttcttactaa ctgtgggatt aggggctgat tccctgacct gctgtgttct    480
gtcttctctc caattcaatg ggaatgaact gtgagggcac tgagcaaaaa ctaaggtctc    540
aatacctagt agtagtggga cttgcctctg gatacccagt agtgatcctg ccgcctgttt    600
ctggatatcc tacagtagca atcccacctg tttctggata tcctacagta gtgatcctgc    660
ctgtttctgg atatcctaca gtagcaatcc cgcctgtttc tggatatcct acagtagtga    720
tcctgcctgc ttctggatac ccagaagtga tcatgcctgg ttctagatac ccagtagtga    780
ttgtgtttcc tctagatacc cagtaggtat tgtgcttgct tctagagatg tagtagtagc    840
tggacttagc tctagatacc cagtgctcat ctctagactg ggctgagatc agtgtctccc    900
ttgaagggtt attgtaagga tgaaaaaaga taatgcgttt aaagcacttg gtgtagtagg    960
tggtcttttt aaaagtgtga ataaatacta gttcttatta tttctgtgga tatccaacag   1020
ccacataatt gggccccaaa gccatgaaga aggaagagga aatgtcttaa aggttgtcga   1080
tggacagtgt ttgctgaaca tcaaaatcac tttccaggta ttacctctga tttgctctac   1140
caactccaca ccccacctgc agccacataa ccttccatga tcacggccat gcacaacaca   1200
ccatgtcccc caggcaaggg gaccttagaa acataaccag gcttgagaca gcactctgca   1260
ccggtgtctt ggaaatgctc ttaagagtgt atggctgagt tagggaacca ggatttcaaa   1320
gtagaaaggg agaatctacc caagcccata gaaatcctga atccactcct ttctcagcaa   1380
caagcactgg cctgggagtc agccacttat gcaccaaccc cactctgccc ctaattaaat   1440
```

-continued

```
gcatgacttt gaaaattccc ctcattcttc tgagccccaa ttcagtgatt ggtgcaatca   1500
caggcttggc tacagtgacc cattcattgc aggcatggtg agactctcaa tccctctcat   1560
ttccactaga atctaactgt tgggatctat gacccagtca gcatagcagg cctgtgggga   1620
gctctcaggt tcaagcatat gcccccccta atctacaaga aattagctgc agaaaaccaa   1680
ggaatagaac ctggaaaaag agagggtttg ctagagctgt ccctttccct gtctctggaa   1740
tgccaacaat agggaggctc tttggtcttg tctctcagga gtgcccatgc cattccagga   1800
aaatgatggc ccagctggtg gtgtaaggct tggggggcag cgagtgggca tcgtggtgaa   1860
agcctcggga tcagggagct gcgtctgcag gcaggcctgc tggccggaaa cctgccagga   1920
aaggaagggg ctgtctcggg gcggggccag ggaggggtgg agacagggcc ggctgtggtc   1980
agtgacaaat gctggctgca atccagccag ccctctgccc tttctgagcc cgagggactg   2040
ccacctccac tgtgtgcaca ctcagctacg ggacacagta agtaccgatg ccgcaaaggg   2100
aggtccccag ggcttgaggg catgtgaggc gaggagagga tggactctag agttttgggg   2160
tttggggtct gcaaagctct gaaggagtct catctctgca gtttcaggta tccaaggcag   2220
cagaggtgag tgggtccccc gagctctgtg accttatgct ccacactaac tctggcagag   2280
cctccgtttc ctcataggta agatggaaat aattacaccc tctggatggt gtgactgaag   2340
attaaataca gcgggtgctc tcactcagca catctggcca tgtctgcaga cacatttggt   2400
tgccacaact ggaagggggg tgggggttag tgacatctag aggccagcga tgctgctgat   2460
gatcccacaa tgcccaggac aagatcacaa agcatcatcc tgttcaaaag gtcaacagga   2520
tcaaggttga gagaccctga aataaggcca tggggacaaa atgtcggctg gataggaggt   2580
gctcagtaag tggcagcttc tgttgttttc tgtgcctgga gtcttggggc tttagaaatc   2640
aggaacaatg atccaatatt atcggcttcc gtgagataag ggcatcttgc ctggaggctg   2700
ccacccaggc cggtcatggc agctgctcat gaaggacagt aacaatttgg cagtttgtta   2760
aatgaacaaa atgtagaaat aaagtaagca gaatttttag tttttctgaa ggtagggctt   2820
ttggccagat atgcagcaat aaaagagcaa actgcttcct tgggccagtg tccttgctca   2880
tagatcagga aaccgaagca tgaagaatac aggcggcaga tgcctgaagg taacggacgt   2940
gttcatggtg ctgacggtga tgataagtga cagatgtaga ctcatctcca aacttgtcag   3000
gttatagaca ttaaatatgt gcaactttat gaatagcagt catgtctcaa tcaagtggtt   3060
ttaataaaga aataatagga agccagagct gagagacagg gagggagttg ttcaaggtca   3120
cctggcaagt gagctccggg gcggggagag ctcagctctg ggtggccagc ctggcttttt   3180
ccactgctca gtgtccagct tgcagtctaa tgtctcgaat tacagagaag gagactggtc   3240
agttcattca ttcattcatt ctacaaaggt ttatggagca tctctcctga ctgcaagctc   3300
ttgaaggtga gagcagcaca aatgagggtc ccatggagag agaggccgga atgaaaaatg   3360
tcaatgacaa atgcatatat aaaggcacat gtgtaattga aagagctttg agagaaagag   3420
tcaagggact gttccagaga atagccatgg aaggggaaaa ggtccagtgt gataaggtat   3480
tgcaaagaag tgacatttaa gcaaaagcct gcagcctatg cagaagttgg cctcagtgag   3540
aaaggttggg ggagggttcc agtagagagg gaaggtatgc aaaggcccag agttaggaca   3600
gaacttgctg tgtttgagaa actgggaaaa gaagagtgag cctgggggta tcacgtgatc   3660
cagggcagag caggtccagg ccaggtgcag ccaggtcaca gcagccctag tgggttagag   3720
cacaaatcaa agtttagcat ttatctgaaa cacaggagtt ggccatgagt ttcttaggcg   3780
```

-continued

```
aggaagcgct gtgaccatat ttatgattga aggagattct tttatatgct gtatatagaa   3840
agcctttcag ggcaaagaaa ggaagctact ggggtagccc tgggggagat gaagggagct   3900
tccactgggg gcagtaagaa agccagggaa aggcggcagc tttaagacct gttttggaga   3960
tagaacggac aagctttgct gatgggctgg agtggaacag gaagtcaaga ttacttcttc   4020
tgggaagttc tgttcctggg tctttaggat ctagaggaag ctgtgacttt gtctctcatc   4080
tctgcctggg ctccaagcct cacatccctt tttgtaatta gaagatattg gacagaccgt   4140
cctcactaac acaattccca cagctgagtc cagggtagaa ctgggcagga cttcactgcc   4200
caacacggga aatatcagtc agcagatttg ggtttcgggg atggtggtgg gccagcggga   4260
agactgacca gggcctaccc atcacatccc caccacctcc cacctcaatt caccttggcc   4320
tgagatgaca ggtgaacatg actgatcctc tctcttccct ctgcagaaac actaaagcca   4380
gggaccagga gaggggcagc ccaaccaagc tttcaaagca ctcagtagag gctggtctgg   4440
gggatgggag gctcccaggg cttcacctgt ctctgtcaaa gccatgtatt tccaccagag   4500
gcccaagagt gcgatggcaa accctggatt tgaaactaag aaacgtaaaa caagcactga   4560
ggactccact gcctcttgag tgacctctct gaccctctgt ttcttctgca ctgttaggat   4620
aatgatacta actccatgtt gttgtagaga agtataaatg agctaataca ggtgaaccgc   4680
ctggggatac caggaggtga ggtcgaggag gaacgaggta tcactcctca gagccactca   4740
gagagaggct gtgcacgagt cagaggaacc tggattttaa ttccggttcc atcactcagt   4800
agctgaaaca agctattcca cttcacttag cctcagtcta ttcaatctgt aaaatagagt   4860
gagtttactt ttggaaaact ctgtaaaata gagagcttac ttttggtgaa ggttaaacat   4920
agtaatattt atggagtgtc tagtatgtct ttaataatta gtggttttac tgaaaagtag   4980
agagagttgg cccagaggga gcaagatttc tgggtctcaa acatgtagcc caggagagcc   5040
taagtgaacc tggggccctc tccaaacaga tcctggggga gactcagtgc acacccggag   5100
aagcagctcc tccccatcgg atctctagtg cttggcaggg ggcggggtct tgagggggtg   5160
tccacaacac atggcagact gcagatgaag aaactgaggc ccagaggggg tgaggcttgc   5220
ccagggtgac ctagtagctg aatagatggg agaatggagc cagggcctca ctgagactct   5280
ctggtcagct gcccctgggc tgtatccaat aaggaaactc ccctgcttct gaagctgttc   5340
tcgaaattat cagctcagtg tgaccctgtg gggggttgag ccacattgtt tctttagaag   5400
catctccata catggctggt tccaaccctt ggcaggaggg accatattgt gctgtaaaat   5460
agactcattt agagaagccg gagattaaag cacccaccta tgtccttcaa agctctccag   5520
gcaagtgcca tggtgggaac aggtagggag tgtcagtggg gggaagccca gactctgctc   5580
actcattatc tgcagattag ggctattgtt ggtggctact aagtcaggga tttcaaaatc   5640
aggaagatgc agccaggaaa agaggaggca ggactctgca gaggaggcag gactctgcag   5700
agtcagagtg ataaccgagt ctgagtccaa gctttgccag tgttagcaag cgactccatc   5760
tctctgaacc tcggattacc catctgtaaa atagagctag cagcaagatg taccttttg    5820
ggtggtgcag ggctgaagga gttggcacag tgcctgaaag agggtgcggg caatgcgccc   5880
aactgctgtg gctgctgggt ttggtgccag gttcgattct gcaggcagaa acttctacat   5940
gaggctcctt ctcggaagga gctcaggaca caatttggag gctgggctgg caagggtgac   6000
ctgctggagc tattcaactt cacttaaaga caggcctgca gtccaagcct gcccaattcc   6060
tgagaccatt ctctctccac tgctgagccc cacggccact ctgcaaggga tttcccaccc   6120
acctgtttgg ggccctttgg agtttggttt taattgggtc acgggatgct gtgacaggct   6180
```

-continued

```
gcccctgcct ggtggggatc tggggtcact gatgacattg tgcccatgga gagagcccag   6240
cagaaaggga ttccctccaa ggcgacacac agggcaaagc tcacatcaga agccaggcag   6300
gccctctgca cctggtaatt agccggcccg ggtgctgtca ggctcacacg tgtgtgtgtg   6360
tgtgtgtgtg tgtgtgtgtg tgtgtgtgtg taaagcatgt accctatggt acagttgaga   6420
atatggaggc ctcagatggg gcttttgcag aaactgccat gcctactgct cacacttcca   6480
tagcacgtgc ccccaagcac cccatggtgt aggtgctgtt attatcacta tcttacagtt   6540
atggagcagt ggctcaaggt gtaactgatt tgcccaaaat cacactacaa ggacacagca   6600
gggctgagat ttgaacccag gcagtggctt cagagcctga gctgtttcct actgcagagg   6660
gaggaggcaa gacttctacc cgtagccaga tggggaggca tgggcacagg aacggctctt   6720
gggtgaagtg gagggaggaa gaggaggact gaaggcgaag gccacgtcag gagtgatggg   6780
ataccccaca aaggcctccc tgagaagcgc tagagacaaa gatgagtgcc tcctcatctg   6840
gaagatgaaa agatgtcttt gcctgcatgg gctgccgtca caaagtccca ggggctaggg   6900
ggcttcaaca acagaaattt ctttctttac aactctggaa gctggaagtc tgagattaag   6960
gcaccagcag gatttgttcc ttccaaggcc cctctccttg gctcacaggt ggctgccttc   7020
tccctgtctt cacctggtct tccctctgtg catgtctcta tcctgatctc ctctttttaa   7080
tttttgtgta aggacgtagt catattgggt tggggcccac tctagtgacc tcattctaac   7140
tcagtcccct ctttaaaagc cctatctcca gatatagtca cattctgggg tattgaaggt   7200
aaggacttca gtatatgcat tttgggggca caattcagcc agaacaggag gacggtgggg   7260
atgtccacat gaagaggttc aggcagaatt cctttaggag gggaagatgt ctctctgtgg   7320
gacaagggtg gcatggagca gcccctgggg gaaggagaag gggacagttt gcatactggt   7380
attctgccta ccccagggtg gacactcact cagcgtttgc tgaatgaaca gggcaaggcc   7440
agcagtgctg atggtcccag gcatgtagct ggtctgagtt catagaagga ccacagcgcc   7500
ctgccatgtg ccaaaccagg acaccagagt gaaggccaga agctcacatg gaagcagctt   7560
agttccctgg taacctcgag atgctgatga gacagagcag agcagaggga accctctccc   7620
tccatatccc atcctccaaa atgtgtccct tgatgtggat gggtagacag gattcctgcc   7680
ctggcagcca gacccctgcc ttgggtctgc acctcctctc cctccttcct ctccccgtca   7740
tccctaaatc ttgtcctcga gccactgcca ccctgtgtaa accctcatgt ccagtcttgg   7800
gggtgccatc ccttctcttt aaagctgaat ggaccaaaca tacccattga gtgttgggtg   7860
gggacatctc tggaaagtca gcacctggac cagctccacc cctctctgag gacaccttct   7920
ttccctttca gaacaaagaa cagccaccat gcagctcttc ctcctcttgt gcctggtgct   7980
tctcagccct caggggggcct cccttcaccg ccaccacccc cgggagatga agaagagagt   8040
cgaggacctc catgtaggtg ccacggtggc ccccagcagc agaagggact ttacctttga   8100
cctctacagg gccttggctt ccgctgcccc cagccagaac atcttcttct cccctgtgag   8160
catctccatg agcctggcca tgctctccct gggggctggg tccagcacaa agatgcagat   8220
cctggagggc ctgggcctca acctccagaa aagctcagag aaggagctgc acagaggctt   8280
tcagcagctc cttcaggaac tcaaccagcc cagagatggc ttccagctga gcctcggcaa   8340
tgccctttttc accgacctgg tggtagacct gcaggacacc ttcgtaagtg ccatgaagac   8400
gctgtacctg gcagacactt tccccaccaa ctttagggac tctgcagggg ccatgaagca   8460
gatcaatgat tatgtggcaa agcaaacgaa gggcaagatt gtggacttgc ttaagaacct   8520
```

-continued

```
cgatagcaat gcggtcgtga tcatggtgaa ttacatcttc tttaaaggta aggcccttgg   8580
gcccaaacct gcactttctt tggcttttct gctgctttta tctaaagaat acccaattcc   8640
ctcacataca taaaagacgg ggagtacgtt aagttctttt gggtgcctgt tgagaaaaat   8700
taagtaaaca agcagccaga gaaggtaaga tgaatgcctt cttgctgtgg atgggattag   8760
tgaggctgag atgctgtttc ctccacggag gaagagctgg ttgctgtctt cgggcccctg   8820
gggacatctg aagccccagc tttctacagg ctctgaagta tgaacccatt gtggccacca   8880
tggcaaagac accaacacct tagccactca gggcaggaca cagaccccag aagggcttaa   8940
agggcatttc ccagtccccc gtatccctca gatcttggcc cctctgccct catagaggcc   9000
aagactccct cagacaaatg cttgttcctc tgaaatgcct cctcctgact cctcagcaag   9060
agctgacctc tgcttatctc cccgacactc cttgtaagca ttcctgctcg cctctgcagc   9120
tcctgccagt tgctgaccct ggggaaagca agagtggata gagaggagaa gagaggagag   9180
gagagggtgg gaagggttgc gaaggaaggt aaattgttaa cacctcccct tcctatggtc   9240
acagatcatg agtatctttg gccatttggg tggctataac aaaataccat aaactgggtg   9300
gcttagcaac aacaaacata tatttctcat agttctggag gctgagaagt ccaggatcaa   9360
ggcactggca gatgcagtgc ccattccttg gttcatagag agtgccttct tagtatatcc   9420
ttgctggaag gaggaaggca gctctctgtg gtctcttttg taaggacacc gatcctgttc   9480
atgacagctc cacccccatg acctaatcaa ctcccaaagg ccccctgtcc taataccacc   9540
accttggggg ttaggtttca acatatgaac aatgtgggga cacaaacatt gagaccacag   9600
cagtgagtgt cgaacttgga ctctgagatt tcctatcccc tggtgcaggg cagtccccat   9660
tacaccagat tgctgagggc agctgggaaa taagctaagg acggtattga ctggggtctt   9720
ccttcgataa cgattaagaa gttggaaaca ggccaggcat ggtggctcac gcctataatc   9780
ccaacatttt aggaggccga gatgggcaga tcacctgagg tcaggagttc gagatcagcc   9840
tggccaacat agtgaaaccc cgtctctact aaaaaataca gaaattagcc aggcatggtg   9900
gtgggcgcct gtaattccag ctacttggga ggctgaggca ggagaatcac ttgaacctgg   9960
gaggtggggg ctgtagtgag ccaaaattgc gccactgcac tccagcatgg gtcacagagc  10020
gagactccat ctcaaaaaga agaaaaaaag aaaaaaaaga aaaaaagaaa taaaataaaa  10080
taaaaagaag ttggaaacaa tcacttgtag cgttttgttc agaagttccc ataggaaggt  10140
cagagaaggg tcattgaaga cttcccaatg ggaaaaacca ttcatttcca ggatccatac  10200
taacttcttt ctaaaattta aatcaaaata ttggaatgaa agtgcaaaca gagaagttca  10260
cccagatatc aggtagcatt cacagccagc cacatttttc accctcttca cttggagatt  10320
tggtcttgag taaaacgtta gagaatcaga gaacatcagg gatccagggc ctctgaagat  10380
gtgaaaacca acctccttgt tttgcaaatg tggaaggaaa agtcccacga aaagtccaag  10440
aatgtgccca atgttataaa gagacttgcc ttcatattca agaggttcaa cagtcactgc  10500
tctggggctg ccataaagat ggtctccgct ggctatcttt actgtcttca ctccttttat  10560
ttgcagctga gaatttctaa ttctgacaca aaattctttt tcatttttcc cttttttcat  10620
ctttagctaa gtgggagaca agcttcaacc acaaaggcac ccaagagcaa gacttctacg  10680
tgacctcgga gactgtggtg cgggtaccca tgatgagccg cgaggatcag tatcactacc  10740
tcctggaccg gaacctctcc tgcagggtgg tgggggtccc ctaccaaggc aatgccacgg  10800
ctttgttcat tctccccagt gagggaaaga tgcagcaggt ggagaatgga ctgagtgaga  10860
aaacgctgag gaagtggctt aagatgttca aaaagaggta ctttcagact accccagggc  10920
```

-continued

```
cagcctaaac ccacacagcc ccagggagac acacacgccc taccagggcc acacagcact  10980
ggtgggaagg actcacccag ccaaggagct gcctccaggc ccagaggcat cctgtgacat  11040
ccaagtcctg gggcctagc ccagttggag ggacaagagc tggaaactgg gttccttagg  11100
gtggtgccag agtgggcaga gacctctggg cagcccacgt ccaagtccag agcaagggga  11160
ggctcatcct agaaaagagg ccagaggagc cataaccacc attgttcctt gggttaagga  11220
gtccttttt aaaaccatca aaactaagaa tccagtgcat tatgaatcca aggggtgagg  11280
ctcagtgtgc caatgcccca gaacagtcta agaaagctcc ttttcccttt ccaggcagct  11340
cgagctttac cttcccaaat tctccattga gggctcctat cagctggaga aagtcctccc  11400
cagtctgggg atcagtaacg tcttcacctc ccatgctgat ctgtccggca tcagcaacca  11460
ctcaaatatc caggtgtctg aggtgggttc agaagctcct atgcatctgc ttcccaagat  11520
ctattctgtt ctattctttc tattctactc taccccattt cattccattc cattccactc  11580
aactccactc cactccactc cactccagtt cactctattc aattccactc cactccagtt  11640
cactctattc aattccactc cactccactc cagttcactc tattcagttc cactccactc  11700
cactccactc cactccagtt cactctattc cattccactc cattccactc ctccactcct  11760
ctcatccact ccactctact cctccactcc acatctccac tccactcctc cactccactc  11820
ctccactcca ctcatccact ccactcctcc actccactcc tccactccac tcctccactc  11880
cactccactc atccactcca ctcttccatt ccactccatt ccactcctcc actccactct  11940
tccactccac tccattccac tcctccactc cactccactc tattctattc tattccattc  12000
cattctactc tattctattc cattccattg cagtcaactc cactccactc tctactattc  12060
tattccactc ctctcccctc cactccattc cattgcagtc cactccactg cactccactc  12120
ctttattctg ttctgttcta ttctattcta ttctattcta ttctctccct ctccctctct  12180
tttcccacaa gtagtgaaag tttcactttg tgtcttatcc ttcatgtaat gggaagccat  12240
atccaccact gttccttgag ttaaggagtc ctgttttaaa caatcaaaac taagaaggca  12300
cttcctagct atgtgatctc caaaaaatac ttgactctct gagcttcctt tctctcttct  12360
ataaaattga agaattacac cttgctcaaa gatgccatga gaattcaatg acagacacat  12420
gcgaagtcac cccccagcac agtgcctggg gcagagtagc tgctccattg ttccatttcc  12480
tacttgctcc atggctcagt tgaacagata cttagaggtt gatgcccata ggcagaagct  12540
ttgccatttg ctatgatgac ttcacctgcc cctggtggcc tggtgatgcc tggtgtctcc  12600
cctgcagatg gtgcacaaag ctgtggtgga ggtggacgag tcgggaacca gagcagcggc  12660
agccacgggg acaatcttca ctttcaggtc ggcccgcctg aactctcaga ggctagtgtt  12720
caacaggccc tttctgatgt tcattgtgga taacaacatc ctcttccttg gcaaagtgaa  12780
ccgcccctga ggtggggctt ctcctgaaat ctacaggcct cagggtggga gatgaagggg  12840
gctatgctat ggcccatctg tatgctggta gctagtgatt tacacaggtt tagttgacta  12900
atgaggcatt acaaataata ttactctatg atgattgctt ccacccacac gactgcaaca  12960
tacaggtgcc ttggggaaat gtggagaaca ttcaatcttg ccgtcactat tcatcaatga  13020
agattagcac tgagatccag agaggctgga tgacttgctc aagttcacca gcatggtagt  13080
ggcaaagaga ggtccagagt cctggccctt gatgcccagc tcagtgccac aaagctcagt  13140
aggagggatg ttccagtgga tgagggccac caggaagcac aggtccaagg ctggtcccac  13200
acttatcagc agcaacaact gtcagttcat cctgcatggg aaaaatgttg gaatgggagt  13260
```

-continued

```
ctgaaatggg gctactgttt cagtcctaac gtgctgtgtg acattgggac aacactttcc  13320
ctctctggac ctcagtttcc ctctgtatac aaggatcaga ttcttgctgt gacccaagaa  13380
ctcctgaaat catatagaaa ggctggggtg ggccctgtca ttcgtggttg atttcaatac  13440
actcaagtgc cattcatcct ttaagaaaaa catctggata tcaaggtgga aatggcccat  13500
ttaatgattg attatatcat tttgtggata tagttataat ctgatgggcc tggctgggag  13560
tggaagaagg gaagcctttt gcaaatagta gagtgtcagt tgcaggtgcc aatgactaac  13620
tttttgaatt ctatgttggc attaacaata aagcattttg caaacactgg ttataactgt  13680
ctttatggag gcagctctgg gaatggtgac attgatagct taccatgctc caggccgggt  13740
gcctggccct tcacctggat ggtcgcattt gcccctcata agactcccat gaagaaaggc  13800
accactatta tcccatctgt tattcacaga tgggaaaggc aaggcttgaa gtggttaggt  13860
ggcttaccca gtcacatatc ttctaagtgg tgcagccaga atttggcggg gggagtgcga  13920
ccaagaaccc tacactcagt cctgtgctct gtgctgtgga ggagagatga ccaggagcag  13980
aaacttcatt caggggcatc tcaggcacca gctcccccat gagccagcta agttccctcc  14040
ctcccttcac caagcaccat gtgtttcctc atgtgccaaa tgaagaggat tagatactca  14100
agaatggaat gagtgggtga gtgagtcctt cgctgcaccc aagtctgatt ttctgtgcgc  14160
ctgctcaccc caccctgcat gttctaagca tgcttccata aggctgtgcc ccaccctctg  14220
attctagagt ctggactgta tcagaggtga gtgcctacta gaggtaacaa ggtcaggacc  14280
ccaaaccttg tccatccccc aaagtactga gcccccacca tgcaccagcc catgccagat  14340
gctttgcact tgtgatatca cccatccctt gacaacccag caagttctat tattgttccc  14400
attttacagg caataacata agtgctttcc cagggtccca cgctggtgac agtgagggcc  14460
cagggtctga gagcccagat cgcacatgtg cgggctggtg gcaggggaga tggcagcaac  14520
cagactcaga catttctctg cagttgtgct gtgggctcag ggtggctctt tacgaagggg  14580
ccccttcgtg gggtcatgca ctcctgtgtg ctttcccttg catcatgcct tgcctgtctt  14640
ggcaaatatt tctctggagt ttacccagcc agtccaaggt cacagggaag ccctgtctgt  14700
gtctcacaca gaaggtcaac gtccagcact gtccaaactt tactcagcaa acagtcacaa  14760
agcagctcct gtgtgggggt cggggtggct cactgtggtc tctgctgcat gtcacacatt  14820
gaagcactgt gctggggtca tcgcaggctg tttaactcaa ttgtcacatg agcctgggtg  14880
cacaaaatgg tagagcagct cagagagaga tggacagaca gcatgaacct ctgaggagtc  14940
aggttttctt ggatgaaggg acactaagat ggctttggag cgtgagaagg acctcaccta  15000
gcaaatgtgg gaaaggagtg agacctccag gcagagggac tggctggaga cgagcgtgat  15060
gtggtgagcc atggagtgta tgggtcccca cagaacttca gtctgggcct gcacagggca  15120
tgtggaggag acaaggagga gggaggtcgg tgccggcggt tcagtgacag agatcctaaa  15180
tgggaggcca gtgttttgtc tgatctcttt catcccaatt tcagggtagt ttggtcatcc  15240
acgccacatt ccaagtgtcc cctgggccct ttctctccct cacccccctg tctgcacatg  15300
agtagatgcc tccacgcagc cctcccagga cgctcacctc tatccacaga tgcttctcca  15360
aaacccacca ggccctccca tggaacgagc tcacctacag ggtaaaatca ggtcacggtc  15420
acatataggc ctgactactc ccctcaggac cctcattcac agccactgta ttaatttgct  15480
ggggctgcca aaacaaagtg tcctcatctg ggaggctgca gtagatttgc tgaaattgat  15540
ttgctagcgt tgctgaaatt gattcaagct t                                 15571
```

-continued

<210> SEQ ID NO 97
<211> LENGTH: 4279
<212> TYPE: DNA
<213> ORGANISM: Homo sapiens

<400> SEQUENCE: 97

```
cagacaggat attcactgct gtggcaaggc ctgtagagag tttcgaagtt aggaggactc     60
aagacggtcc ctccctggac ttttctgaag gggctcaaaa gatgacacgc gccagagctg    120
gaaggcgtcg ccaattggtc caacttttcc ctcctccctt tttgcggatg agaaaaactg    180
aggcccaggt ttgggatttc cagagcccgg gatttcccgg caacgccgac aaccacattc    240
ccccggctat tctgacccgc cccggttccg ggacgctccc tgggagccgc cgccgagggc    300
ctgctgggac tcccggggac cccgccgtcg gggcagcccc cacgcccggc gccgcccgcc    360
ggaacggcgc cgctgttgcg cacttgcagg ggagccggcg actgagggcg aggcagggag    420
ggagcaagcg gggctgggag ggctgctggc gcgggctcgc cggctgtgta tggtctatcg    480
caggcagctg acctttgagg aggaaatcgc tgctctccgc tccttcctgt agtaacagcc    540
gccgctgccg ccgccgccag gaacccggcc gggagcgaga gccgcggggc gcagagccgg    600
cccggctgcc ggacggtgcg gccccaccag gtgaacggcc atggcgggct ggatccaggc    660
ccagcagctg cagggagacg cgctgcgcca gatgcaggtg ctgtacggcc agcacttccc    720
catcgaggtc cggcactact tggcccagtg gattgagagc cagccatggg atgccattga    780
cttggacaat ccccaggaca gagcccaagc cacccagctc ctggagggcc tggtgcagga    840
gctgcagaag aaggcggagc accaggtggg ggaagatggg tttttactga agatcaagct    900
gaggcactac gccacgcagc tccagaaaac atatgaccgc tgccccctgg agctggtccg    960
ctgcatccgg cacattctgt acaatgaaca gaggctggtc cgagaagcca acaattgcag   1020
ctctccggct gggatcctgg ttgacgccat gtcccagaag caccttcaga tcaaccagac   1080
atttgaggag ctgcgactgg tcacgcagga cacagagaat gagctgaaga aactgcagca   1140
gactcaggag tacttcatca tccagtacca ggagagcctg aggatccaag ctcagtttgc   1200
ccagctggcc cagctgagcc cccaggagcg tctgagccgg gagacggccc tccagcagaa   1260
gcaggtgtct ctggaggcct ggttgcagcg tgaggcacag acactgcagc agtaccgcgt   1320
ggagctggcc gagaagcacc agaagaccct gcagctgctg cggaagcagc agaccatcat   1380
cctggatgac gagctgatcc agtggaagcg gcggcagcag ctggccggga acggcgggcc   1440
ccccgagggc agcctggacg tgctacagtc ctggtgtgag aagttggccg agatcatctg   1500
gcagaaccgg cagcagatcc gcagggctga gcacctctgc cagcagctgc ccatccccgg   1560
cccagtggag gagatgctgg ccgaggtcaa cgccaccatc acggacatta tctcagccct   1620
ggtgaccagc acattcatca ttgagaagca gcctcctcag gtcctgaaga cccagaccaa   1680
gtttgcagcc accgtacgcc tgctggtggg cgggaagctg aacgtgcaca tgaatccccc   1740
ccaggtgaag gccaccatca tcagtgagca gcaggccaag tctctgctta aaaatgagaa   1800
cacccgcaac gagtgcagtg gtgagatcct gaacaactgc tgcgtgatgg agtaccacca   1860
agccacgggc accctcagtg cccacttcag gaacatgtca ctgaagagga tcaagcgtgc   1920
tgaccggcgg ggtgcagagt ccgtgacaga ggagaagttc acagtcctgt ttgagtctca   1980
gttcagtgtt ggcagcaatg agcttgtgtt ccaggtgaag actctgtccc tacctgtggt   2040
tgtcatcgtc cacggcagcc aggaccacaa tgccacggct actgtgctgt gggacaatgc   2100
ctttgctgag ccgggcaggg tgccatttgc cgtgcctgac aaagtgctgt ggccgcagct   2160
```

-continued

```
gtgtgaggcg ctcaacatga aattcaaggc cgaagtgcag agcaaccggg gcctgaccaa   2220
ggagaacctc gtgttcctgg cgcagaaact gttcaacaac agcagcagcc acctggagga   2280
ctacagtggc ctgtccgtgt cctggtccca gttcaacagg gagaacttgc cgggctggaa   2340
ctacaccttc tggcagtggt ttgacggggt gatggaggtg ttgaagaagc accacaagcc   2400
ccactggaat gatggggcca tcctaggttt tgtgaataag caacaggccc acgacctgct   2460
catcaacaag cccgacggga ccttcttgtt gcgctttagt gactcagaaa tcgggggcat   2520
caccatcgcc tggaagtttg attccccgga acgcaacctg tggaacctga aaccattcac   2580
cacgcgggat ttctccatca ggtccctggc tgaccggctg gggacctga gctatctcat   2640
ctatgtgttt cctgaccgcc ccaaggatga ggtcttctcc aagtactaca ctcctgtgct   2700
ggctaaagct gttgatggat atgtgaaacc acagatcaag caagtggtcc ctgagtttgt   2760
gaatgcatct gcagatgctg ggggcagcag cgccacgtac atggaccagg cccccctcccc   2820
agctgtgtgc cccaggctc cctataacat gtacccacag aaccctgacc atgtactcga   2880
tcaggatgga gaattcgacc tggatgagac catggatgtg gccaggcacg tggaggaact   2940
cttacgccga ccaatggaca gtcttgactc ccgcctctcg ccccctgccg gtcttttcac   3000
ctctgccaga ggctccctct catgaatgtt tgaatcccac gcttctcttt ggaaacaata   3060
tgcaatgtga agcggtcgtg ttgtgagttt agtaaggctg tgtacactga cacctttgca   3120
ggcatgcatg tgcttgtgtg tgtgtgtgtg tgtccttgcg catgagctac gcctgcctcc   3180
cctgtgccag tcctgggatg tggctgcagc agcggtggcc ggcctctttt cagatcatgg   3240
catccaagag tgcgccgagt ctgtctctgt catggtagag accgagcctc tgtcactgca   3300
ggcactcaat gcagccagac ctattcctcc tgtgcccctc atctgctcag cagctatttg   3360
aatgagatga ttcagaaggg gaggggagac aggtaacgtc tgtaagctga agtttcactc   3420
cggagtgaga agctttgccc tcctaagaga gagagacaga gagacagaga gagagaaaga   3480
gagagtgtgt gggtctatgt aaatgcatct gtcctcatgt gttgatgtaa ccgattcatc   3540
tctcagaagg gaggctgggg ttcattttcg agtagtattt tatactttag tgaacgtgga   3600
ctccagactc tctgtgaacc ctatgagagc gcgtctgggc ccggccatgt ccttagcaca   3660
ggggggccgc cggtttgagt gagggtttct gagctgctct gaattagtcc ttgcttggct   3720
gcttggcctt gggttcattc aagctcacga tgctgttccc acgtttcccg ggatatatat   3780
tctctcccct ccgttgggcc ccagccttct ttgcttgcct ctctgtttgt aaccttgtcg   3840
acaaagaggt agaaaagatt gggtctagga tatggtgggt ggacaggggc cccgggactt   3900
ggagggttgg tcctcttgcc tcctggaaaa aacaaaaaca aaaaactgca gtgaaagaca   3960
agctgcaaat cagccatgtg ctgcgtgcct gtggaatctg gagtgagggg taaaagctga   4020
tctggtttga ctccgctgga ggtggggcct ggagcaggcc ttgcgctgtt gcgtaactgg   4080
ctgtgttctg gtgaggcctt gctcccaacc ccacacgctc ctccctctga ggcgtgagga   4140
ctcgcagtca ggggcagctg accatggaag attgagagcc caaggtttaa acttcttctc   4200
tgaagggagg tggggatgag aagaggggtt tttttgtact ttgtacaaag accacacatt   4260
tgtgtaaaca gtgttttgg                                                4279
```

<210> SEQ ID NO 98
<211> LENGTH: 3799
<212> TYPE: DNA
<213> ORGANISM: Homo sapiens

<400> SEQUENCE: 98

-continued

```
ctggcactgg gtggtaacca gcaagccagc tggcatccgc atccagggtt tgtttcaatg     60
atgtctcgtg gagaatatgg aggggctggt gccaggactg tccttggctt tgcctcgggg    120
tgtgaacggg gtcagtgacc tctaaaacta acctgcctct cagttctgaa tccagacaga    180
atcaatcctc agctgtgtct cgctccacac cccctgccct ggaagccagg gaaggttgga    240
ggtgctaggg ggtcaggctc ccctctgtga cccctgcagc tgttgtggtg actcatgtcc    300
caacctagct gcctctccca aggagacttt cccctgggac aagggggagg gaatggcatg    360
gaggaggccc acatcaagcg gggccaggaa cccacggtgg caggagctgg gctggtgacc    420
tacccagggc agaagggccc gggactcatc cagaggggaa ggaaggggtc ttcaggaaga    480
ccacggagat gccacaggca gaattggctt cccatctggg agataggtgg ggagaccctg    540
gcattttgac agccagaacc tggggtgctg agcagaatct tcatgcctgg cctggccgcc    600
ttcggaggga agctggaggg ttgggtgcga gaggagtggg gtcagagccc ctacatccgc    660
aggaccccaa atcggctggg ccccaaggcc cggactgcgc tccccggtgg ccccggcggc    720
cctccgcgaa tgcgtcctgc ccctcccctg cccaagccct ctgccctcac ccgggtccgg    780
cgccgccccc gaagtggcgg gaacaacccg aacccgaacc ttctgtcctc gggagccccc    840
agataagcgg ctgggaaccc gcggggcccg caggggaggc ccggctgttc cgcccgctaa    900
gtgcattagc acagctcacc tcccctatcg cgcctgccat cggacgggca gtgccgcgcc    960
ctgctctggg gcccccggag cgaccacagc ggaggccgga acggactgtc ctttctgggg   1020
cggggtgggg agggggtgtc gctggagggc ccggtggcat agcaacggac gagagaggcc   1080
tggaggaggg gcggggaggg ggagttgtgt ggcagttcta agggaagggt gggtgctggg   1140
acgggtgtcc gggagggagg ggagcctggc ggggtctggg gcctcgtcgc ggagggcgct   1200
gcgaggggga aactggggaa agggcctaat tccccagtct ccacctcgaa tcaggaaaga   1260
gaaggggcgg gctgctgggc aaaagaggtg aatggctgcg gggggctgga gaagagagat   1320
gggaggggcc ggccggcggg ggtgaggggg tctaaagatt gtgggggtga ggaactgagg   1380
gtgggggcg cccagaggcg ggactcgggg cggggcaggc gaggcggagg gcgagggctg   1440
cgggagcaag tacggagccg ggggtgtggg ggacgattgc cgctgcagcc gccgccccac   1500
tcacctccgg tgtgtctgca gcccggacac taagggagat ggatgaatgg gtggggagga   1560
tgcggcgcac atggccccgg gcggctcggc ggtcagctgc cgccccccaca gcggaccggt   1620
cggggcgggg gtcgggcggt agaaaaaagg gccgcgaggc gagcggggca ctgggcggac   1680
cgcggcggca gcatgagcgg cgcagaccgt agccccaatg cgggcgcagc ccctgactcg   1740
gccccgggcc aggcggcggt ggcttcggcc taccagcgct tcgagccgcg cgcctacctc   1800
cgcaacaact acgcgccccc tcgcggggac ctgtgcaacc cgaacggcgt cgggccgtgg   1860
aagctgcgct gcttggcgca gaccttcgcc accggtgagc gggggaaact gaggcacgag   1920
ggacaagagg tcgtcgggga gtgaaagcag gcgcagggaa ataaaaagaa ggaaagggag   1980
acagaccagg cgcctaacag atggggacca agaaacaaga gatagctgag aggtgcaaac   2040
agaagagaaa aaggagcaac atcccttagg agaggggcag aggagagaga ggtggagaga   2100
gggggcggag agtgctcaga attgagagct aaggtggggg atgcaggaca gactgaggtg   2160
gagatgcata ggaggaaatg gaggcagatg tgggacaggg gtgagaaact ccaggatttc   2220
ctcgctgagc ctggctggta ggtatagttg ttttctttct ttttctttat tttattttca   2280
tttatttact tatttttatt ttttatttgt tttgagacgg agtttcgctc ttgttgccca   2340
```

-continued

```
ggctggagta caatggcgcc atctcggctc actgcaacct ccgcctcccc gggttcaagc   2400

gattctcttg cctcagcttc cctagtagct gggattacag gcatgcgccc ccatgcctgg   2460

ctaatttatt tgtattttta gtagagacgg gacttctcca tgttggtcag gctggtctcg   2520

aactcccaac cttaggatcc acccaccccg gcctcccaaa gtgctgggat tacaggtgtg   2580

agccactgcg cccggccagt aggtatagtc ttctagatgt gaaacctgag tctcagagcg   2640

gtgaagttcc cttccgaagg gcagcccatg ttggagctgg gttcagtcta actctggggc   2700

caatgctttt tccagatgga gacacatttg cagaggagaa ggaagaacta gagagaggca   2760

gggagatgca ggggagggaa gggtaaggag gcaggggctg cctgggctgg ctggcaccag   2820

gaccctcttc ctctgccctg cccaggtgaa gtgtccggac gcaccctcat cgacattggt   2880

tcaggcccca ccgtgtacca gctgctcagt gcctgcagcc actttgagga catcaccatg   2940

acagatttcc tggaggtcaa ccgccaggag ctggggcgct ggctgcagga ggagccgggg   3000

gccttcaact ggagcatgta cagccaacat gcctgcctca ttgagggcaa ggggtaagga   3060

ctggggggtg agggttgggg aggaggcttc ccatagagtg gctggttggg gcaacagagg   3120

cctgagcgta gaacagcctt gagccctgcc ttgtgcctcc tgcacaggga atgctggcag   3180

gataaggagc gccagctgcg agccagggtg aaacgggtcc tgcccatcga cgtgcaccag   3240

ccccagcccc tgggtgctgg gagcccagct cccctgcctg ctgacgccct ggtctctgcc   3300

ttctgcttgg aggctgtgag cccagatctt gccagctttc agcgggccct ggaccacatc   3360

accacgctgc tgaggcctgg ggggcacctc ctcctcatcg ggccctgga ggagtcgtgg   3420

tacctggctg gggaggccag gctgacggtg gtgccagtgt ctgaggagga ggtgagggag   3480

gccctggtgc gtagtggcta caaggtccgg gacctccgca cctatatcat gcctgcccac   3540

cttcagacag gcgtagatga tgtcaagggc gtcttcttcg cctgggctca gaaggttggg   3600

ctgtgagggc tgtacctggt gccctgtggc ccccacccac ctggattccc tgttctttga   3660

agtggcacct aataaagaaa taataccctg ccgctgcggt cagtgctgtg tgtggctctc   3720

ctgggaagca gcaagggccc agagatctga gtgtccgggt aggggagaca ttcaccctag   3780

gcttttttttc cagaagctt                                              3799
```

<210> SEQ ID NO 99
<211> LENGTH: 1550
<212> TYPE: DNA
<213> ORGANISM: Homo sapiens

<400> SEQUENCE: 99

```
tgccgccgtc ccgcccgcca gcgccccagc gaggaagcag cgcgcagccc gcggcccagc     60

gcacccgcag cagcgcccgc agctcgtccg cgccatgttc caggcggccg agcgccccca    120

ggagtgggcc atggagggcc cccgcgacgg gctgaagaag gagcggctac tggacgaccg    180

ccacgacagc ggcctggact ccatgaaaga cgaggagtac gagcagatgg tcaaggagct    240

gcaggagatc cgcctcgagc cgcaggaggt gccgcgcggc tcggagccct ggaagcagca    300

gctcaccgag gacggggact cgttcctgca cttggccatc atccatgaag aaaaggcact    360

gaccatggaa gtgatccgcc aggtgaaggg agacctggct ttcctcaact tccagaacaa    420

cctgcagcag actccactcc acttggctgt gatcaccaac cagccagaaa ttgctgaggc    480

acttctggga gctggctgtg atcctgagct ccgagacttt cgaggaaata ccccccctaca    540

ccttgcctgt gagcagggct gcctggccag cgtgggagtc ctgactcagt cctgcaccac    600

cccgcacctc cactccatcc tgaaggctac caactacaat ggccacacgt gtctacactt    660
```

-continued

```
agcctctatc catggctacc tgggcatcgt ggagcttttg gtgtccttgg gtgctgatgt    720

caatgctcag gagccctgta atggccggac tgcccttcac ctcgcagtgg acctgcaaaa    780

tcctgacctg gtgtcactcc tgttgaagtg tggggctgat gtcaacagag ttacctacca    840

gggctattct ccctaccagc tcacctgggg ccgcccaagc acccggatac agcagcagct    900

gggccagctg acactagaaa accttcagat gctgccagag agtgaggatg aggagagcta    960

tgacacagag tcagagttca cggagttcac agaggacgag ctgccctatg atgactgtgt   1020

gtttggaggc cagcgtctga cgttatgagt gcaaaggggc tgaaagaaca tggacttgta   1080

tatttgtaca aaaaaaaagt tttatttttc taaaaaaaga aaaaagaaga aaaaatttaa   1140

agggtgtact tatatccaca ctgcacactg cctagcccaa aacgtcttat tgtggtagga   1200

tcagccctca ttttgttgct tttgtgaact tttgtagggg gacgagaaag atcattgaaa   1260

ttctgagaaa acttctttta aacctcacct ttgtggggtt tttggagaag gttatcaaaa   1320

atttcatgga aggaccacat tttatattta ttgtgcttcg agtgactgac cccagtggta   1380

tcctgtgaca tgtaacagcc aggagtgtta agcgttcagt gatgtggggt gaaaagttac   1440

tacctgtcaa ggtttgtgtt accctcctgt aaatggtgta cataatgtat tgttggtaat   1500

tattttggta cttttatgat gtatatttat taaagagatt tttacaaatg              1550


<210> SEQ ID NO 100
<211> LENGTH: 4673
<212> TYPE: DNA
<213> ORGANISM: Homo sapiens

<400> SEQUENCE: 100

tttgctcctg ctcctccgct cctcctgcgc ggggtgctga aacagcccgg ggaagtagag     60

ccgcctccgg ggagcccaac cagccgaacg ccgccggcgt cagcagcctt gcgcggccac    120

agcatgaccg ctcgcggcct ggcccttggc ctcctcctgc tgctactgtg tccagcgcag    180

gtgttttcac agtcctgtgt ttggtatgga gagtgtggaa ttgcatatgg ggacaagagg    240

tacaattgcg aatattctgg cccaccaaaa ccattgccaa aggatggata tgacttagtg    300

caggaactct gtccaggatt cttctttggc aatgtcagtc tctgttgtga tgttcggcag    360

cttcagacac taaaagacaa cctgcagctg cctctacagt ttctgtccag atgtccatcc    420

tgtttttata acctactgaa cctgttttgt gagctgacat gtagccctcg acagagtcag    480

tttttgaatg ttacagctac tgaagattat gttgatcctg ttacaaacca gacgaaaaca    540

aatgtgaaag agttacaata ctacgtcgga cagagttttg ccaatgcaat gtacaatgcc    600

tgccgggatg tggaggcccc ctcaagtaat gacaaggccc tgggactcct gtgtgggaag    660

gacgctgacg cctgtaatgc caccaactgg attgaataca tgttcaataa ggacaatgga    720

caggcacctt ttaccatcac tcctgtgttt tcagattttc cagtccatgg gatggagccc    780

atgaacaatg ccaccaaagg ctgtgacgag tctgtggatg aggtcacagc accatgtagc    840

tgccaagact gctctattgt ctgtggcccc aagcccccagc ccccacctcc tcctgctccc    900

tggacgatcc ttggcttgga cgccatgtat gtcatcatgt ggatcaccta catggcgttt    960

ttgcttgtgt tttttggagc attttttgca gtgtggtgct acagaaaacg gtattttgtc   1020

tccgagtaca ctcccatcga tagcaatata gctttttctg ttaatgcaag tgacaaagga   1080

gaggcgtcct gctgtgaccc tgtcagcgca gcatttgagg gctgcttgag gcggctgttc   1140

acacgctggg ggtctttctg cgtccgaaac cctggctgtg tcattttctt ctcgctggtc   1200
```

-continued

```
ttcattactg cgtgttcgtc aggcctggtg tttgtccggg tcacaaccaa tccagttgac   1260
ctctggtcag cccccagcag ccaggctcgc ctggaaaaag agtactttga ccagcacttt   1320
gggcctttct tccggacgga gcagctcatc atccgggccc ctctcactga caaacacatt   1380
taccagccat acccttcggg agctgatgta ccctttggac ctccgcttga catacagata   1440
ctgcaccagg ttcttgactt acaaatagcc atcgaaaaca ttactgcctc ttatgacaat   1500
gagactgtga cacttcaaga catctgcttg gcccctcttt caccgtataa cacgaactgc   1560
accattttga gtgtgttaaa ttacttccag aacagccatt ccgtgctgga ccacaagaaa   1620
ggggacgact tctttgtgta tgccgattac cacacgcact ttctgtactg cgtacgggct   1680
cctgcctctc tgaatgatac aagtttgctc catgaccctt gtctgggtac gtttggtgga   1740
ccagtgttcc cgtggcttgt gttgggaggc tatgatgatc aaaactacaa taacgccact   1800
gcccttgtga ttaccttccc tgtcaataat tactataatg atacagagaa gctccagagg   1860
gcccaggcct gggaaaaaga gtttattaat tttgtgaaaa actacaagaa tcccaatctg   1920
accatttcct tcactgctga acgaagtatt gaagatgaac taaatcgtga aagtgacagt   1980
gatgtcttca ccgttgtaat tagctatgcc atcatgtttc tatatatttc cctagccttg   2040
gggcacatca aaagctgtcg caggcttctg gtggattcga aggtctcact aggcatcgcg   2100
ggcatcttga tcgtgctgag ctcggtggct tgctccttgg gtgtcttcag ctacattggg   2160
ttgcccttga ccctcattgt gattgaagtc atcccgttcc tggtgctggc tgttggagtg   2220
gacaacatct tcattctggt gcaggcctac cagagagatg aacgtcttca aggggaaacc   2280
ctggatcagc agctgggcag ggtcctagga gaagtggctc ccagtatgtt cctgtcatcc   2340
ttttctgaga ctgtagcatt tttcttagga gcattgtccg tgatgccagc cgtgcacacc   2400
ttctctctct ttgcgggatt ggcagtcttc attgactttc ttctgcagat tacctgtttc   2460
gtgagtctct tggggttaga cattaaacgt caagagaaaa atcggctaga catcttttgc   2520
tgtgtcagag gtgctgaaga tggaacaagc gtccaggcct cagagagctg tttgtttcgc   2580
ttcttcaaaa actcctattc tccacttctg ctaaaggact ggatgagacc aattgtgata   2640
gcaatatttg tgggtgttct gtcattcagc atcgcagtcc tgaacaaagt agatattgga   2700
ttggatcagt ctctttcgat gccagatgac tcctacatgg tggattattt caaatccatc   2760
agtcagtacc tgcatgcggg tccgcctgtg tactttgtcc tggaggaagg gcacgactac   2820
acttcttcca aggggcagaa catggtgtgc ggcggcatgg gctgcaacaa tgattccctg   2880
gtgcagcaga tatttaacgc ggcgcagctg gacaactata cccgaatagg cttcgccccc   2940
tcgtcctgga tcgacgatta tttcgactgg gtgaagccac agtcgtcttg ctgtcgagtg   3000
gacaatatca ctgaccagtt ctgcaatgct tcagtggttg accctgcctg cgttcgctgc   3060
aggcctctga ctccggaagg caaacagagg cctcaggggg gagacttcat gagattcctg   3120
cccatgttcc tttcggataa ccctaacccc aagtgtggca aaggggggaca tgctgcctat   3180
agttctgcag ttaacatcct ccttggccat ggcaccaggg tcggagccac gtacttcatg   3240
acctaccaca ccgtgctgca gacctctgct gactttattg acgctctgaa gaaagcccga   3300
cttatagcca gtaatgtcac cgaaaccatg ggcattaacg gcagtgccta ccgagtattt   3360
ccttacagtg tgttttatgt cttctacgaa cagtacctga ccatcattga cgacactatc   3420
ttcaacctcg gtgtgtccct gggcgcgata tttctggtga ccatggtcct cctgggctgt   3480
gagctctggt ctgcagtcat catgtgtgcc accatcgcca tggtcttggt caacatgttt   3540
ggagttatgt ggctctgggg catcagtctg aacgctgtat ccttggtcaa cctggtgatg   3600
```

-continued agctgtggca tctccgtgga gttctgcagc cacataacca gagcgttcac ggtgagcatg 3660
aaaggcagcc gcgtggagcg cgcggaagag gcacttgccc acatgggcag ctccgtgttc 3720
agtggaatca cacttacaaa atttggaggg attgtggtgt tggcttttgc caaatctcaa 3780
attttccaga tattctactt caggatgtat ttggccatgg tcttactggg agccactcac 3840
ggattaatat ttctccctgt cttactcagt tacatagggc catcagtaaa taaagccaaa 3900
agttgtgcca ctgaagagcg atacaaagga acagagcgcg aacggcttct aaatttctag 3960
ccctctcgca gggcatcctg actgaactgt gtctaagggt cggtcggttt accactggac 4020
gggtgctgca tcggcaaggc caagttgaac accggatggt gccaaccatc ggttgtttgg 4080
cagcagcttt gaacgtagcg cctgtgaact caggaatgca cagttgactt gggaagcagt 4140
attactagat ctggaggcaa ccacaggaca ctaaacttct cccagcctct tcaggaaaga 4200
aacctcattc tttggcaagc aggaggtgac actagatggc tgtgaatgtg atccgctcac 4260
tgacactctg taaaggccaa tcaatgcact gtctgtcctc tcctttttag gagtaagcca 4320
tcccacaagt tctataccat atttttagtg acagttgagg ttgtagatac actttataac 4380
attttatagt ttaaagagct ttattaatgc aataaattaa ctttgtacac atttttatat 4440
aaaaaaacag caagtgattt cagaatgttg taggcctcat tagagcttgg tctccaaaaa 4500
tctgtttgaa aaaagcaaca tgttcttcac agtgttcccc tagaaaggaa gagatttaat 4560
tgccagttag atgtggcatg aaatgaggga caaagaaagc atctcgtagg tgtgtctact 4620
gggttttaac ttatttttct ttaataaaat acattgtttt cctaaaaaaa aaa 4673

<210> SEQ ID NO 101
<211> LENGTH: 1362
<212> TYPE: DNA
<213> ORGANISM: Homo sapiens

<400> SEQUENCE: 101
catttgggga cgctctcagc tctcggcgca cggcccagct tccttcaaaa tgtctactgt 60
tcacgaaatc ctgtgcaagc tcagcttgga gggtgatcac tctacacccc caagtgcata 120
tgggtctgtc aaagcctata ctaactttga tgctgagcgg gatgctttga acattgaaac 180
agccatcaag accaaaggtg tggatgaggt caccattgtc aacattttga ccaaccgcag 240
caatgcacag agacaggata ttgccttcgc ctaccagaga aggaccaaaa aggaacttgc 300
atcagcactg aagtcagcct tatctggcca cctggagacg gtgattttgg gcctattgaa 360
gacacctgct cagtatgacg cttctgagct aaaagcttcc atgaaggggc tgggaaccga 420
cgaggactct ctcattgaga tcatctgctc cagaaccaac caggagctgc aggaaattaa 480
cagagtctac aaggaaatgt acaagactga tctggagaag gacattattt cggacacatc 540
tggtgacttc cgcaagctga tggttgccct ggcaaagggt agaagagcag aggatggctc 600
tgtcattgat tatgaactga ttgaccaaga tgctcgggat ctctatgacg ctggagtgaa 660
gaggaaagga actgatgttc ccaagtggat cagcatcatg accgagcgga gcgtgcccca 720
cctccagaaa gtatttgata ggtacaagag ttacagccct tatgacatgt tggaaagcat 780
caggaaagag gttaaaggag acctggaaaa tgctttcctg aacctggttc agtgcattca 840
gaacaagccc ctgtattttg ctgatcggct gtatgactcc atgaagggca aggggacgcg 900
agataaggtc ctgatcagaa tcatggtctc ccgcagtgaa gtggacatgt tgaaaattag 960
gtctgaattc aagagaaagt acggcaagtc cctgtactat tatatccagc aagacactaa 1020

-continued

```
gggcgactac cagaaagcgc tgctgtacct gtgtggtgga gatgactgaa gcccgacacg   1080

gcctgagcgt ccagaaatgg tgctcaccat gcttccagct aacaggtcta gaaaaccagc   1140

ttgcgaataa cagtccccgt ggccatccct gtgagggtga cgttagcatt acccccaacc   1200

tcattttagt tgcctaagca ttgcctggcc ttcctgtcta gtctctcctg taagccaaag   1260

aaatgaacat tccaaggagt tggaagtgaa gtctatgatg tgaaacactt tgcctcctgt   1320

gtactgtgtc ataaacagat gaataaactg aatttgtact tt                      1362
```

<210> SEQ ID NO 102
<211> LENGTH: 2591
<212> TYPE: DNA
<213> ORGANISM: Homo sapiens

<400> SEQUENCE: 102

```
cccggacgtg cggctcccct cggcctcctc gccatggacg cggacgactc ccgggccccc     60

aagggctcct tgcggaagtt cctggagcac ctctccgggg ccggcaaggc catcggcgtg    120

ctgaccagcg gcggggatgc tcaaggtatg aacgctgccg tccgtgccgt ggtgcgcatg    180

ggtatctacg tgggggccaa ggtgtacttc atctacgagg gctaccaggg catggtggac    240

ggaggctcaa acatcgcaga ggccgactgg gagagtgtct ccagcatcct gcaagtgggc    300

gggacgatca ttggcagtgc gcggtgccag gccttccgca cgcgggaagg ccgcctgaag    360

gctgcttgca acctgctgca gcgcggcatc accaacctgt gtgtgatcgg cggggacggg    420

agcctcaccg ggggccaacct cttccggaag gagtggagtg ggctgctgga ggagctggcc    480

aggaacggcc agatcgataa ggaggccgtg cagaagtacg cctacctcaa cgtggtgggc    540

atggtgggct ccatcgacaa tgatttctgc ggcaccgaca tgaccatcgg cacggactcc    600

gccctgcaca ggatcatcga ggtcgtcgac gccatcatga ccacggccca gagccaccag    660

aggaccttcg ttctggaggt gatgggacga cactgtgggt acctggccct ggtgagtgcc    720

ttggcctgcg gtgcggactg ggtgttcctt ccagaatctc caccagagga aggctgggag    780

gagcagatgt gtgtcaaact ctcggagaac cgtgcccgga aaaaaaggct gaatattatt    840

attgtggctg aaggagcaat tgatacccaa aataaaccca tcacctctga gaaaatcaaa    900

gagcttgtcg tcacgcagct gggctatgac acacgtgtga ccatcctcgg gcacgtgcag    960

agaggaggga ccccttcggc attcgacagg atcttggcca gccgcatggg agtggaggca   1020

gtcatcgcct tgctagaggc caccccggac accccagctt gcgtcgtgtc actgaacggg   1080

aaccacgccg tgcgcctgcc gctgatggag tgcgtgcaga tgactcagga tgtgcagaag   1140

gcgatggacg agaggagatt tcaagatgcg gttcgactcc gagggaggag ctttgcgggc   1200

aacctgaaca cctacaagcg acttgccatc aagctgccgg atgatcagat cccaaagacc   1260

aattgcaacg tagctgtcat caacgtgggg gcacccgcgg ctgggatgaa cgcggccgta   1320

cgctcagctg tgcgcgtggg cattgccgac ggccacagga tgctcgccat ctatgatggc   1380

tttgacggct tcgccaaggg ccagatcaaa gaaatcggct ggacagatgt cgggggctgg   1440

accggccaag gaggctccat tcttgggaca aaacgcgttc tcccggggaa gtacttggaa   1500

gagatcgcca cacagatgcg cacgcacagc atcaacgcgc tgctgatcat cggtggattc   1560

gaggcctacc tgggactcct ggagctgtca gccgcccggg agaagcacga ggagttctgt   1620

gtccccatgg tcatggttcc cgctactgtg tccaacaatg tgccgggttc cgatttcagc   1680

atcggggcag acaccgccct gaacactatc accgacacct gcgaccgcat caagcagtcc   1740

gccagcggaa ccaagcggcg cgtgttcatc atcgagacca tgggcggcta ctgtggctac   1800
```

-continued

```
ctggccaaca tggggggct cgcggccgga gctgatgccg catacatttt cgaagagccc   1860

ttcgacatca gggatctgca gtccaacgtg gagcacctga cggagaaaat gaagaccacc   1920

atccagagag gccttgtgct cagaaatgag agctgcagtg aaaactacac caccgacttc   1980

atttaccagc tgtattcaga agagggcaaa ggcgtgtttg actgcaggaa gaacgtgctg   2040

ggtcacatgc agcagggtgg ggcaccctct ccatttgata gaaactttgg aaccaaaatc   2100

tctgccagag ctatggagtg gatcactgca aaactcaagg aggcccgggg cagaggaaaa   2160

aaatttacca ccgatgattc catttgtgtg ctgggaataa gcaaaagaaa cgttattttt   2220

caacctgtgg cagagctgaa gaagcaaacg gattttgagc acaggattcc caaagaacag   2280

tggtggctca agctacggcc cctcatgaaa atcctggcca agtacaaggc cagctatgac   2340

gtgtcggact caggccagct ggaacatgtg cagccctgga gtgtctgacc cagtcccgcc   2400

tgcatgtgcc tgcagccacc gtggactgtc tgtttttgta acacttaagt tattttatca   2460

gcactttatg cacgtattat tgacattaat acctaatcgg cgagtgccca tctgccccac   2520

cagctccagt gcgtgctgtc tgtggagtgt gtctcatgct ttcagatgtg catatgagca   2580

gaattaatta a                                                       2591
```

```
<210> SEQ ID NO 103
<211> LENGTH: 865
<212> TYPE: DNA
<213> ORGANISM: Homo sapiens

<400> SEQUENCE: 103

gaattccgga gttccgggcg cgcgcgacgt cagtttgagt tctgtgttct ccccgcccgt     60

gtcccgcccg acccgcgccc gcgatgctgg cgctgcgctg cggctcccgc tggctcggcc    120

tgctctccgt cccgcgctcc gtgccgctgc gcctccccgc ggcccgcgcc tgcagcaagg    180

gctccggcga cccgtcctct tcctcctcct ccgggaaccc gctcgtgtac ctggacgtgg    240

acgccaacgg gaagccgctc ggccgcgtgg tgctggagct gaaggcagat gtcgtcccaa    300

agacagctga gaacttcaga gccctgtgca ctggtgagaa gggcttcggc tacaaaggct    360

ccaccttcca cagggtgatc ccttccttca tgtgccaggc gggcgacttc accaaccaca    420

atggcacagg cgggaagtcc atctacggaa gccgctttcc tgacgagaac tttacactga    480

agcacgtggg gccaggtgtc ctgtccatgg ctaatgctgg tcctaacacc aacggctccc    540

agttcttcat ctgcaccata aagacagact ggttggatgg caagcatgtt gtgttcggtc    600

acgtcaaaga gggcatggac gtcgtgaaga aaatagaatc tttcggctct aagagtggga    660

ggacatccaa gaagattgtc atcacagact gtggccagtt gagctaatct gtggccaggg    720

tgctggcatg gtggcagctg caaatgtcca tgcacccagg tggccgcgtt gggctgtcag    780

ccaaggtgcc tgaaacgata cgtgtgccca ctccactgtc acagtgtgcc tgaggaaggc    840

tgctagggat gttagacgga attcc                                          865
```

```
<210> SEQ ID NO 104
<211> LENGTH: 661
<212> TYPE: DNA
<213> ORGANISM: Homo sapiens

<400> SEQUENCE: 104

tcaaactgaa gctcgcactc tcgcctccag catgaaagtc tctgccgccc ttctgtgcct     60

gctgctcata gcagccacct tcattcccca agggctcgct cagccagatg caatcaatgc    120
```

-continued

```
cccagtcacc tgctgctata acttcaccaa taggaagatc tcagtgcaga ggctcgcgag    180

ctatagaaga atcaccagca gcaagtgtcc caaagaagct gtgatcttca agaccattgt    240

ggccaaggag atctgtgctg accccaagca gaagtgggtt caggattcca tggaccacct    300

ggacaagcaa acccaaactc cgaagacttg aacactcact ccacaaccca agaatctgca    360

gctaacttat tttcccctag ctttccccag acatcctgtt ttattttatt ataatgaatt    420

ttgtttgttg atgtgaaaca ttatgcctta agtaatgtta attcttattt aagttattga    480

tgttttaagt ttatctttca tggtactagt gttttttaga tacagagact tggggaaatt    540

gcttttcctc ttgaaccaca gttctacccc tgggatgttt tgagggtctt tgcaagaatc    600

atttttttaa cattccaatg catttaatac aaagaattgc taaaatatta ttgtggaaat    660

g                                                                    661


<210> SEQ ID NO 105
<211> LENGTH: 420
<212> TYPE: DNA
<213> ORGANISM: Homo sapiens

<400> SEQUENCE: 105

gggggctggc cgagcgccgt gcgcgcttgg gagaaggccg gaagcttacc agccgagaag     60

gaattcctag ctagcttcag agccggtgcc tccggagcca gcgtggtggc catagacaac    120

aagttcgaac aggccatgga tctggtgaag aatcatctga tgtatgctgt gagagaggag    180

gtggagatcc tgaaggagca gatccgagag ctggtggaga agaactccca gctagagcgt    240

gagaacaccc tgttgaagac cctggcaagc ccagagcagc tggagaagtt ccagtcctgt    300

ctgagccctg aagagccagc tcccgaatcc ccacaagtgc ccgaggcccc tggtggttct    360

gcggtgtaag tcgctctgtc ctcagggtgg gcagagccac taaacttgtt ttacctaggg    420


<210> SEQ ID NO 106
<211> LENGTH: 926
<212> TYPE: DNA
<213> ORGANISM: Homo sapiens

<400> SEQUENCE: 106

gaatctcttt ctctcccttc agaatcttat cttggctttg gatcttagaa gagaatcact     60

aaccagagac gagactcagt gagtgagcag gtgttttgga caatggactg gttgagccca    120

tccctattat aaaaatgtct cagagcaacc gggagctggt ggttgacttt ctctcctaca    180

agctttccca gaaaggatac agctggagtc agtttagtga tgtggaagag aacaggactg    240

aggccccaga agggactgaa tcggagatgg agacccccag tgccatcaat ggcaacccat    300

cctggcacct ggcagacagc cccgcggtga atggagccac tgcgcacagc agcagtttgg    360

atgcccggga ggtgatcccc atggcagcag taaagcaagc gctgagggag gcaggcgacg    420

agtttgaact gcggtaccgg cgggcattca gtgacctgac atcccagctc cacatcaccc    480

cagggacagc atatcagagc tttgaacagg tagtgaatga actcttccgg gatggggtaa    540

actggggtcg cattgtggcc tttttctcct tcggcggggc actgtgcgtg gaaagcgtag    600

acaaggagat gcaggtattg gtgagtcgga tcgcagcttg gatggccact tacctgaatg    660

accacctaga gccttggatc caggagaacg gcggctggga tacttttgtg gaactctatg    720

ggaacaatgc agcagccgag agccgaaagg gccaggaacg cttcaaccgc tggttcctga    780

cgggcatgac tgtggccggc gtggttctgc tgggctcact cttcagtcgg aaatgaccag    840

acactgacca tccactctac cctcccaccc ccttctctgc tccaccacat cctccgtcca    900
```

-continued gccgccattg ccaccaggag aacccg 926

<210> SEQ ID NO 107
<211> LENGTH: 1293
<212> TYPE: DNA
<213> ORGANISM: Homo sapiens

<400> SEQUENCE: 107
cacgtcagcc ggggctagaa aaggcggcgg ggctgggccc agcgaggtga cagcctcgct 60
tggacgcaga gcccggcccg acgccgccat gacggccgcg ctcttcagcc tggacggccc 120
ggccggcggc gcgccctggc ctgcggagcc tgcgcccttc tacgaaccgg gccgggcggg 180
caagccgggc cgcggggccg agccaggggc cctaggcgag ccaggcgccg ccgccccccgc 240 catgtacgac gacgagagcg ccatcgactt cagcgcctac atcgactcca tggccgccgt 300
gcccaccctg gagctgtgcc acgacgagct cttcgccgac ctcttcaaca gcaatcacaa 360
ggcgggcggc gcggggcccc tggagcttct tcccggcggc cccgcgcgcc ccttgggccc 420
gggccctgcc gctccccgcc tgctcaagcg cgagcccgac tggggcgacg gcgacgcgcc 480
cggctcgctg ttgcccgcgc aggtgggccc gtgcgcacag accgtggtga gcttggcggc 540
cgcagggcag cccaccccgc ccacgtcgcc ggagccgccg cgcagcagcc ccaggcagac 600
ccccgcgccc ggccccgccc gggagaagag cgccggcaag aggggcccgg accgcggcag 660
ccccgagtac cggcagcggc gcgagcgcaa caacatcgcc gtgcgcaaga gccgcgacaa 720
ggccaagcgg cgcaaccagg agatgcagca gaagttggtg gagctgtcgg ctgagaacga 780
gaagctgcac cagcgcgtgg agcagctcac gcgggacctg gccggcctcc ggcagttctt 840
caagcagctg cccagcccgc ccttcctgcc ggccgccggg acagcagact gccggtaacg 900
cgcggccggg gcgggagaga ctcagcaacg acccatacct cagacccgac ggcccggagc 960
ggacgccctg ctgccgacgc cagagccgcc gcgtgcccgc tgcagtttct tggacataga 1020
ccaaagaagc tacagcctgg acttaccacc actaaactgc gagagaagct aaacgtgttt 1080
attttccctt aaattatttt tgtaatggta gctttttcta catcttactc ctgttgatgc 1140
agctaaggta catttgtaaa aagaaaaaaa accagacttt tcagacaaac cctttgtatt 1200
gtagataaga ggaaaagact gagcatgctc actttttat attaattttt aggacagtat 1260
ttgtaagaat aaagcagcat ttgaaatgcc cct 1293

<210> SEQ ID NO 108
<211> LENGTH: 2529
<212> TYPE: DNA
<213> ORGANISM: Homo sapiens

<400> SEQUENCE: 108
cttcttcgtc ctcagggttg ccagcgcttc ctggaagtcc tgaagctctc gcagtgcagt 120
gagttcatgc accttcttgc caagcctcag tctttgggat ctggggaggc cgcctggttt 180
tcctccctcc ttctgcacgt ctgctggggt ctcttcctct ccaggccttg ccgtcccccct 240 ggcctctctt cccagctcac acatgaagat gcacttgcaa agggctctgg tggtcctggc 300
cctgctgaac tttgccacgg tcagcctctc tctgtccact tgcaccacct tggacttcgg 360
ccacatcaag aagaagaggg tggaagccat taggggacag atcttgagca agctcaggct 420
caccagcccc cctgagccaa cggtgatgac ccacgtcccc tatcaggtcc tggccctttta 480 caacagcacc cgggagctgc tggaggagat gcatggggag agggaggaag gctgcaccca 540

-continued

```
ggaaaacacc gagtcggaat actatgccaa agaaatccat aaattcgaca tgatccaggg    600
gctggcggag cacaacgaac tggctgtctg ccctaaagga attacctcca aggttttccg    660
cttcaatgtg tcctcagtgg agaaaaatag aaccaaccta ttccgagcag aattccgggt    720
cttgcgggtg cccaacccca gctctaagcg gaatgagcag aggatcgagc tcttccagat    780
ccttcggcca gatgagcaca ttgccaaaca gcgctatatc ggtggcaaga atctgcccac    840
acggggcact gccgagtggc tgtcctttga tgtcactgac actgtgcgtg agtggctgtt    900
gagaagagag tccaacttag gtctagaaat cagcattcac tgtccatgtc acacctttca    960
gcccaatgga gatatcctgg aaaacattca cgaggtgatg gaaatcaaat tcaaaggcgt   1020
ggacaatgag gatgaccatg gccgtggaga tctggggcgc ctcaagaagc agaaggatca   1080
ccacaaccct catctaatcc tcatgatgat tcccccacac cggctcgaca acccgggcca   1140
ggggggtcag aggaagaagc gggctttgga caccaattac tgcttccgca acttggagga   1200
gaactgctgt gtgcgccccc tctacattga cttccgacag gatctgggct ggaagtgggt   1260
ccatgaacct aagggctact atgccaactt ctgctcaggc ccttgcccat acctccgcag   1320
tgcagacaca acccacagca cggtgctggg actgtacaac actctgaacc ctgaagcatc   1380
tgcctcgcct tgctgcgtgc cccaggacct ggagcccctg accatcctgt actatgttgg   1440
gaggaccccc aaagtggagc agctctccaa catggtggtg aagtcttgta aatgtagctg   1500
agaccccacg tgcgacagag agaggggaga gagaaccacc actgcctgac tgcccgctcc   1560
tcgggaaaca cacaagcaac aaacctcact gagaggcctg gagcccacaa ccttcggctc   1620
cgggcaaatg gctgagatgg aggtttcctt ttggaacatt tctttcttgc tggctctgag   1680
aatcacggtg gtaaagaaag tgtgggtttg gttagaggaa ggctgaactc ttcagaacac   1740
acagactttc tgtgacgcag acagagggga tggggataga ggaaagggat ggtaagttga   1800
gatgttgtgt ggcaatggga tttgggctac cctaaaggga gaaggaaggg cagagaatgg   1860
ctgggtcagg gccagactgg aagacacttc agatctgagg ttggatttgc tcattgctgt   1920
accacatctg ctctagggaa tctggattat gttatacaag gcaagcattt tttttttttt   1980
ttaaagacag gttacgaaga caaagtccca gaattgtatc tcatactgtc tgggattaag   2040
ggcaaatcta ttacttttgc aaactgtcct ctacatcaat taacatcgtg ggtcactaca   2100
gggagaaaat ccaggtcatg cagttcctgg cccatcaact gtattgggcc ttttggatat   2160
gctgaacgca gaagaaaggg tggaaatcaa ccctctcctg tctgcctctg ggtccctcct   2220
ctcacctctc cctcgatcat atttcccctt ggacacttgg ttagacgcct tccaggtcag   2280
gatgcacatt tctggattgt ggttccatgc agggttgggg cattatgggt tcttccccca   2340
cttcccctcc aagaccctgt gttcatttgg tgttcctgga agcaggtgcg acaacatgtg   2400
aggcattcgg ggaagctcga catgtgccac acagtgactt ggccccagac gcatagactg   2460
aggtataaag acaagtatga atattactct caaaatcttt gtataaataa atatttttgg   2520
ggcatcctg                                                           2529
```

PROGESTERONE RECEPTOR-REGULATED GENE EXPRESSION AND METHODS RELATED THERETO

CROSS-REFERENCE TO RELATED APPLICATIONS

This application claims the benefit of priority under 35 U.S.C. § 119(e) from U.S. Provisional Application Serial No. 60/214,870, filed Jun. 28, 2000, entitled "Surrogate Gene Markers for Two Different Progesterone Receptor Isoforms in Breast Cancer, and Their Use to Screen for Isoform-Selective Progestational Ligands". The entire disclosure of U.S. Provisional Application Serial No. 60/214, 780 is incorporated herein by reference.

FIELD OF THE INVENTION

This invention generally relates to expression profiles of genes that are regulated by progesterone receptors, and particularly by progesterone receptor isoforms PR-A and PR-B, and to the use of such genes in methods for identifying progesterone receptor agonist and antagonist ligands, including progesterone receptor isoform-specific ligands and tissue-specific ligands. This invention also relates to methods for determining the profile of genes regulated by progesterone receptors in a tissue sample. In addition, pluralities of polynucleotides transcribed from genes that are regulated by progesterone receptors are disclosed, as are pluralities of antibodies that selectively bind to proteins encoded by such genes.

BACKGROUND OF THE INVENTION

Progesterone is a natural reproductive hormone that targets the breast, uterus, ovaries, brain, bone, blood vessels, immune system, etc. Progestational agents are widely used for oral contraception, menopausal hormone replacement therapy, and cancer treatments. Antiprogestins, which are synthetic ligands that antagonize the actions of progesterone, are in clinical trials for contraception, for induction of labor, and to treat endometriosis, breast cancers and meningiomas. The actions of progesterone are varied and tissue-specific. Even in the normal breast it can have diverse effects: depending on the physiological state of the woman, progesterone can be proliferative, antiproliferative, or differentiative. Additionally, progesterone promotes the development of breast cancers and accelerates the growth of established breast cancers. For example, when used for hormone replacement therapy at menopause, progestins, which are synthetic progestational agents, increase the risk of breast cancer. Paradoxically, they are protective in the uterus and prevent endometrial cancers.

Progesterone, synthetic progestins, and antiprogestins all initially work through the same molecular pathway. These are low molecular weight, lipid soluble "ligands ". They enter target cells passively, and pass into the nucleus where they bind to progesterone receptors (PRs). Ligand binding activates the PR proteins, which then dimerize, bind to DNA at the promoters of progesterone target genes, and either up- or down-regulate transcription of these genes.

There are two natural isoforms of PR, the A- and B-receptors, also referred to herein as PR-A and PR-B, respectively. The isoforms are derived from two distinct promoters in the single PR gene and are translated from separate translation initiation start sites. PR-B receptors are 933 amino acids in length, which is 164 amino acids longer at the N-terminus than PR-A, and contain a unique transcriptional activation function, AF-3 (Sartorius et al., *Mol. Endocrinol.* 8, 1347–1360 (1994)). Downstream of the additional 164 amino acids of PR-B, the two PRs have the identical primary amino acid content. However, despite this close amino acid composition, the two receptors have dramatically different abilities to activate transcription of progestin-responsive promoters in experimental model systems (Sartorius et al., *Mol. Endocrinol.* 8, 1347–1360 (1994); Meyer et al., *J. Biol. Chem.* 267, 10882–10887 (1992); Vegeto et al., *Mol. Endocrinol.* 7, 1244–1255 (1993); Tung et al., *Mol Endocrinol.* 7, 1256–1265 (1993); Sartorius et al., *J. Biol. Chem.* 268, 9262–9266 (1993)). Progestin agonist-liganded PR-B are stronger transactivators than PR-A, although there are cell-type and promoter-dependent exceptions. The antiprogestin RU486 has mixed agonist/antagonist activity on PR-B but not PR-A. Instead, agonist or antagonist-liganded PR-A can dominantly inhibit PR-B and other members of the steroid receptor family, including estrogen receptors (ERs). Thus, PR-A are more likely to be transcriptional repressors than PR-B. (Hovland et al., *J Biol Chem* 273, 5455–60(1998); Vegeto et al., *Mol. Endocrinol.* 7, 1244–1255 (1993); McDonnell et al., *J. Biol. Chem.* 269, 11945–11949 (1994)).

Indirect data suggest that the two PR isoforms have physiologically different functions. They are unequally expressed in different tissues and physiological states. For instance, increasing ratios of PR-A to PR-B in the chick oviduct in late winter, or in aged, nonlaying hens, resulted in measurable decreases in PR functional activity (Boyd-Leinen et al., *Endocrinology* 111,30–36 (1982); Spelsberg et al., *Endocrinology* 107, 1234–44 (1980)). There are stage-specific and region-specific variations in the PR-A:PR-B ratio in the developing rat brain (Kato et al., *J Steroid Biochem Mol Biol* 47, 173–82 (1993)) and studies in primates show that PR-B predominates in the estrogen treated hypothalamus, while expression of the PR-A isoform predominates in the pituitary (Baez et al., *J Biol Chem* 262, 6582–8 (1987); Bethea et al., *Endocrinology* 139, 677–87 (1998)). In the human endometrium, absolute levels and the ratio of PR-A to PR-B vary extensively during the menstrual cycle (Mote et al., *Hum Reprod* 15 Suppl 3, 48–56 (2000); Mote et al., *J Clin Endocrinol Metab* 84, 2963–71 (1999); Mangal et al., *J Steroid Biochem Mol Biol* 63, 195–202 (1997); Feil et al., *Endocrinology* 123, 2506–2513 (1988)). In addition, uncontrolled, or over-expressed PR-B levels are associated with a highly malignant phenotype in endometrial, cervical and ovarian cancers (Farr et al., *Mamm. Genome* 4, 577–584 (1993); Fujimoto et al., *J Steroid Biochem Mol Biol* 62, 449–54 (1997)).

In the normal breast, progesterone is both proliferative and differentiative [reviewed in\(Clarke et al., *Endocr. Rev.* 11, 266–301 (1990))]. Breast epithelium mitoses increase during the menstrual cycle and peak in the late luteal phase, coincident with high circulating levels of progesterone. Progesterone induces lobular-alveolar outgrowth during each menstrual cycle and during pregnancy induces further lobular-alveolar development in preparation for the terminal differentiative event of lactation. PR null mice exhibit incomplete mammary gland ductal branching and failure of lobulo-alveolar development, as well as failure to ovulate and to exhibit sexual behavior (Lydon et al., *Genes Develop.* 9, 2266–2278 (1995)).

Little is known about cyclic changes in PR-A and PR-B in the normal human breast. However, in the mouse mammary gland, evidence supports a critical and unique role for each of the two PR isoforms. It has been reported that a 3:1 overexpression of PR-A over PR-B results in extensive mammary gland epithelial cell hyperplasia, excessive ductal branching, and a disorganized basement membrane; all features associated with neoplasia (Shyamala et al., *Proc Natl Acad Sci USA* 95, 696–701 (1998)). In contrast, when PR-B is overexpressed, ductal growth prematurely arrests and inappropriate lobulo-alveolar formation is observed (Shyamala et al., *Proc Natl Acad Sci USA* 97, 3044–9 (2000)). However, when the PR-A isoform was selectively knocked out, leaving only PR-B, the mammary gland appeared to develop normally in response to estradiol and progesterone. In contrast, decidualization of the endometrium and the normal antiproliferative effect of progesterone in the uterus were absent (Mulac-Jericevic et al., *Science* 289, 1751–4 (2000)). Such data indicate that PR-A and PR-B have different tissue-specific effects.

In human breast cancers the presence of PR in estrogen receptor (ER) positive tumors indicates that responsiveness to endocrine therapies is likely, while absence of PR is associated with hormone resistance. thus, PR are routinely measured in breast cancers as a guide to treatment (Horwitz et al., *Recent Prog. Horm. Res.* 41, 249–316 (1985); Horwitz et al., *J Biol Chem* 253, 8185–91 (1978); McGuire, *Semin. Oncol.* 5, 428–433 (1978)). PR are also direct targets of second-line progestin therapies in patients whose tumors have developed antiestrogen resistance (Kimmick et al., *Cancer Treat Res* 94, 231–54 (1998); Howell et al., *Recent Results Cancer Res* 152, 227–44 (1998)). Nothing is known, however, about the role of PR-A vs. PR-B in breast cancers. The PR-A to PR-B ratio was measured in 202 PR-positive humanbreast tumors (Graham et al., *Cancer Res.* 55, 5063–5068 (1995)). The majority had PR-A to PR-B ratios greater than one, and 33% had 3.7 times or more PR-A than PR-B. The functional significance of this is unknown. In breast cancer cell lines, overexpression of PR-A results in marked changes in morphology and loss of adherent properties (McGowan et al., *Mol Endocrinol* 13, 1657–71 (1999)). Thus, overexpression of PR-A as seen in many breast tumors, may lead to suppression of PR-B, and may be associated with poor prognosis. However, there are no clinical data to support this conjecture.

Prior to the present invention, few, if any, endogenous genes differentially regulated by PR-A vs. PR-B were known in breast cancers or any other tissues. An excess of PR-A enhances the expression of SOX4 mRNA levels in breast cancer cells. Whether PR-B also regulates this gene is unknown. SOX4 induces DNA bending. PR-A enhance expression of the mouse multiple drug resistance (mdr) 1b gene, important for development of drug resistance in tumors. Whether this gene is regulated endogenously only by PR-A is unknown. To the present inventors' knowledge, no data on PR-B specific gene regulation in breast cancers (or any tissues) has been published prior to the present invention. Although certain of the genes listed in Table 8 below were previously known to be progesterone regulated, the PR isoform specificity of this regulation was not known.

Knowledge of the unique sets of genes that are selectively regulated by each PR isoform would serve as a surrogate marker for the presence and function of PR-A vs. PR-B in various tissue types and in various disease states. Furthermore, knowledge of such genes and their promoters, would serve as a tool for screening PR ligands, and particularly, PR-A vs. PR-B selective ligands. However, defining which sets of genes are uniquely regulated by one or the other PR isoform in breast cancers was impossible in progesterone target tissues because both PR-A and PR-B receptors are simultaneously present in those tissues, and are simultaneously activated by progesterone treatment.

SUMMARY OF THE INVENTION

One embodiment of the present invention relates to a method to identify agonist ligands of progesterone receptors. The method includes the steps of: (a) contacting a progesterone receptor with a putative agonist ligand, wherein the progesterone receptor is selected from the group consisting of progesterone receptor A (PR-A) and progesterone receptor B (PR-B), under conditions wherein, in the absence of the putative agonist ligand, the progesterone receptor is not activated; (b) detecting expression of at least one gene that is regulated by the progesterone receptor when the progesterone receptor is activated; and, (c) comparing the expression of the at least one gene in the presence and in the absence of the putative agonist ligand, wherein detection of regulation of the expression of the at least one gene in the manner associated with activation of the progesterone receptor as set forth in (b) indicates that the putative agonist ligand is a progesterone receptor agonist.

In one aspect, detection of upregulation of expression of at least one gene chosen from a gene in Table 1, or detection of downregulation of at least one gene chosen from a gene in Table 2, in the presence of the putative agonist ligand, indicates that the putative agonist ligand is a selective agonist of PR-A. In another aspect, detection of upregulation of expression of at least one gene chosen from a gene in Table 3, or detection of downregulation of at least one gene chosen from a gene in Table 4, in the presence of the putative agonist ligand, indicates that the putative agonist ligand is a selective agonist of PR-B.

Another embodiment of the present invention relates to a method to identify antagonists of progesterone receptors. This method includes the steps of: (a) contacting a progesterone receptor with a putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (b) detecting expression of at least one gene that is regulated by the progesterone receptor when the progesterone receptor is activated; and, (c) comparing the expression of the at least one gene in the presence and in the absence of the putative antagonist ligand, wherein detection of inhibition or reversal of the regulation of expression of the at least one gene as compared to the regulation of expression of the at least one gene in the manner associated with activation of the progesterone receptor as set forth in (b), indicates that the putative antagonist ligand is aprogesterone receptor antagonist. The progesterone receptor can be activated by contacting the receptor with a compound that activates the receptor, the step of contacting being performed prior to, simultaneously with, or after the step of contacting of (a).

In one aspect of this embodiment, detection of inhibition of expression or downregulated expression of at least one gene chosen from a gene in Table 1 in the presence of the putative antagonist ligand as compared to the expression of the at least one gene in the presence of the compound that activates the progesterone receptor, or detection of inhibition of expression or upregulation of expression of at least one gene chosen from a gene in Table 2 in the presence of the putative antagonist ligand as compared to the expression of the at least one gene in the presence of the compound that activates the progesterone receptor, indicates that the putative antagonist ligand is a selective antagonist of PR-A. In another aspect, detection of inhibition of expression or downregulation of expression of at least one gene chosen from a gene in Table 3 in the presence of the putative antagonist ligand as compared to the expression of the at least one gene in the presence of the compound that activates the progesterone receptor, or detection of inhibition of expression or upregulation of expression of at least one gene chosen from a gene in Table 4, in the presence of the putative antagonist ligand as compared to the expression of the at least one gene in the presence of the compound that activates the progesterone receptor, indicates that the putative antagonist ligand is a selective antagonist of PR-B.

In each of the above-described methods, the at least one gene is selected from the group consisting of: (i) at least one gene that is selectively upregulated by PR-A chosen from a gene in Table 1; (ii) at least one gene that is selectively downregulated by PR-A chosen from a gene in Table 2; (iii) at least one gene that is selectively upregulated by PR-B chosen from a gene in Table 3; (iv) at least one gene that is selectively downregulated by PR-B chosen from a gene in Table 4; (v) at least one gene that is upregulated or downregulated by both PR-A and PR-B chosen from a gene in Table 5; (vi) at least one gene that is reciprocally regulated by PR-A and PR-B chosen from a gene in Table 6; and, (vii) at least one gene that is regulated by one of the PR-A or the PR-B, wherein regulation of the gene is altered when the other of the PR-A or PR-B is expressed by the same cell, chosen from a gene in Table 7. In one embodiment, the method further includes a step of detecting expression of at least one gene chosen from the genes in Table 8.

In one aspect, step (b) includes detecting expression of: 11-beta-hydroxysteroid dehydrogenase type 2, tissue factor gene, PCI gene (plasminogen activator inhibitor 3), MAD-3 Ikβ-alpha, Niemann-Pick C disease (NPC1), platelet-type phosphofructokinase, phenylethanolamine n-methyltransferase (PNMT), transforming growth factor-beta 3 (TGF-beta3), Monocyte Chemotactic Protein 1, delta sleep inducing peptide (related to TSC-22), and estrogen receptor-related protein (hERRa1). In another aspect, step (b) includes detecting expression of: growth arrest-specific protein (gas6), tissue factor gene, NF-IL6-beta (C/EBPbeta), PCI gene (plasminogen activator inhibitor), Stat5A, calcium-binding protein S100P, MSX-2, lipocortin II (calpactin I), selenium-binding protein (hSBP), and bullous pemphigoid antigen (plakin family). In another aspect, step (b) includes detecting expression of phenylethanolamine n-methyltransferase (PNMT) adrenal medulla. In another aspect, step (b) includes detecting expression of proteasome-like subunit MECL-1. In another aspect, step (b) includes detecting expression of: growth arrest-specific protein and tissue factor gene.

In each of the above-described methods, the progesterone receptor can be PR-A, PR-B or both PR-A and PR-B.

In one aspect of the above-described methods, the step (b) of detecting comprises detecting expression of at least five genes from any one or more of the Tables 1–7. In another aspect, the step (b) of detecting comprises detecting expression of at least ten genes from any one or more of the Tables 1–7. In yet another aspect, the step (b) of detecting comprises detecting expression of at least 15 genes from any one or more of the Tables 1–7.

In one aspect of the above-described methods, the progesterone receptor is expressed by a cell. In this aspect, the progesterone receptor is endogenously expressed by the cell or recombinantly expressed by the cell. In one embodiment, cell is part of a tissue from a test animal. In this embodiment, the step of contacting is performed by administration of the putative agonist ligand to the test animal or to the tissue of the test animal.

In another aspect of the above-described methods, expression of the at least one gene is detected by measuring amounts of transcripts of the at least one gene before and after contact of the progesterone receptor with the putative agonist ligand. In one aspect, expression of the at least one gene is detected by detecting hybridization of at least a portion of the at least one gene or a transcript thereof to a nucleic acid molecule comprising a portion of the at least one gene or a transcript thereof in a nucleic acid array. In another aspect, expression of the at least one gene is detected by measuring expression of a reporter gene that is operatively linked to at least the regulatory region of the at least one gene. In another aspect, expression of the at least one gene is detected by detecting the production of a protein encoded by the at least one gene.

In yet another aspect of the above-described methods, the putative agonist ligand is a product of rational drug design.

Yet another embodiment of the present invention relates to a method to identify isoform-specific agonists of progesterone receptors. This method includes the steps of: (a) contacting a progesterone receptor with a putative agonist ligand, wherein the progesterone receptor is selected from the group consisting of progesterone receptor A (PR-A) and progesterone receptor B (PR-B), under conditions wherein in the absence of the putative agonist ligand, the progesterone receptor is not activated; (b) detecting expression of at least one gene that is regulated by the progesterone receptor when the progesterone receptor is activated; and, (c) comparing the expression of the at least one gene in the presence and in the absence of the putative agonist ligand, wherein detection of regulation of the expression of the at least one gene in the manner associated with activation of the progesterone receptor as set forth in (b)(i) but not (b)(ii), indicates that the putative agonist ligand is a PR-A-specific agonist, and wherein detection of regulation of the expression of the at least one gene in the manner associated with activation of the progesterone receptor as set forth in (b)(ii) but not (b)(i), indicates that the putative agonist ligand is a PR-B-specific agonist.

Another embodiment of the present invention relates to a method to identify isoform-specific antagonists of progesterone receptors. This method includes the steps of: (a) contacting a progesterone receptor with a putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (b) detecting expression of at least one gene that is regulated by the progesterone receptor when the progesterone receptor is activated; and, (c) comparing the expression of the at least one gene in the presence and in the absence of the putative antagonist ligand, wherein, in the presence of the putative antagonist ligand, detection of inhibition or reversal of the regulation of expression of the at least one gene as compared to the regulation of expression of the at least one gene in the manner associated with activation of the progesterone receptor as set forth in (b)(i) but not (b)(ii), indicates that the putative antagonist ligand is a PR-A-specific antagonist, and wherein, in the presence of the putative antagonist ligand, detection of inhibition or reversal of the regulation of expression of the at least one gene as compared to the regulation of the expression of the at least one gene in the manner associated with activation of the progesterone receptor as set forth in (b)(ii) but not (b)(i), indicates that the putative antagonist ligand is a PR-B-specific antagonist.

In each of the above-described methods of identifying a isoform-specific regulator of progesterone receptors, the progesterone receptor can include PR-A, PR-B, or both PR-A and PR-B. The at least one gene is selected from the group consisting of: (i) at least one gene that is exclusively upregulated or downregulated by PR-A, chosen from a Table selected from the group consisting of Table 1 and Table 2; and, (b) at least one gene that is exclusively upregulated or downregulated by PR-B chosen from a Table selected from the group consisting of Table 3 and Table 4. In one aspect, the step (b) of detecting comprises detecting expression of at least five genes from any one or more of the Tables 1–4. In another aspect, the step (b) of detecting comprises detecting expression of at least ten genes from any one or more of the Tables 1–4. In yet another aspect, the step (b) of detecting comprises detecting expression of at least 15 genes from any one or more of the Tables 1–4.

Another embodiment of the present invention relates to a method to identify a tissue-specific agonist of a progesterone receptor. This embodiment includes the steps of: (a) providing an expression profile for at least one gene that is known to be regulated by a progesterone receptor in both a first and second tissue type when the progesterone receptor is activated, wherein the at least one gene is chosen from the genes in any one or more of the genes in Tables 1–7; (b) contacting a progesterone receptor expressed by a first tissue type with a putative agonist ligand, wherein the progesterone receptor is selected from the group consisting of progesterone receptor A (PR-A) and progesterone receptor B (PR-B), under conditions wherein, in the absence of the putative agonist ligand, the progesterone receptor is not activated; (c) contacting a progesterone receptor expressed by a second tissue type with the putative agonist ligand under conditions wherein, in the absence of the putative agonist ligand, the progesterone receptor is not activated, wherein the progesterone receptor is the same isoform as the progesterone receptor contacted in (b); (d) detecting expression of the at least one gene from (a); (e) comparing the expression of the at least one gene in the presence and in the absence of the putative agonist ligand in each of the first and second tissue types, wherein detection of regulation of the expression of the at least one gene in one of the first or second tissue types in the manner associated with activation of the progesterone receptor as set forth in the expression profile of (a), and detection of inhibition of regulation or no regulation of the at least one gene in the other of the first or second tissue types, as compared to the expression of the at least one gene associated with activation of the progesterone receptor as set forth in the expression profile of (a), indicates that the putative agonist ligand is a tissue-specific progesterone receptor agonist.

Yet another embodiment relates to a method to identify a tissue-specific antagonist of a progesterone receptor. This method includes the steps of: (a) providing an expression profile for at least one gene that is known to be regulated by a progesterone receptor in both a first and second tissue type when the progesterone receptor is activated, wherein the at least one gene is chosen from the genes in any one or more of the genes in Tables 1–7; (b) contacting a progesterone receptor expressed by a first tissue type with a putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (c) contacting a progesterone receptor expressed by a second tissue type with the putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (d) detecting expression of the at least one gene from (a); and, (e) comparing the expression of the at least one gene in the presence and in the absence of the putative antagonist ligand in each of the first and second tissue types, wherein detection of regulation of the expression of the at least one gene in one of the first or second tissue types in the manner associated with activation of the progesterone receptor as set forth in the expression profile of (a) in the presence of the putative antagonist ligand, and detection of inhibition or reversal of regulation of expression of the at least one gene in the other of the first or second tissue types in the presence of the putative antagonist ligand, as compared to the expression of the at least one gene associated with activation of the progesterone receptor as set forth in the expression profile of (a), indicates that the putative antagonist ligand is a tissue-specific progesterone receptor antagonist.

Another embodiment of the present invention relates to a method to identify a tissue-specific agonist of a progesterone receptor. This method includes the steps of: (a) providing an expression profile for at least one gene that is known to be regulated by a progesterone receptor in a first tissue type but not a second tissue type when the progesterone receptor is activated, wherein the at least one gene is chosen from the genes in any one or more of the genes in Tables 1–7; (b) contacting a progesterone receptor expressed by the first tissue type with a putative agonist ligand, wherein the progesterone receptor is selected from the group consisting of progesterone receptor A (PR-A) and progesterone receptor B (PR-B), under conditions wherein, in the absence of the putative agonist ligand, the progesterone receptor is not activated; (c) detecting expression of the at least one gene from (a); (d) comparing the expression of the at least one gene in the presence and in the absence of the putative agonist ligand in the first tissue type, wherein detection of regulation of the expression of the at least one gene in the first tissue type in the manner associated with activation of the progesterone receptor as set forth in the expression profile of (a) indicates that the putative agonist ligand is a tissue-specific progesterone receptor agonist for the first tissue type.

Yet another embodiment of the present invention relates to a method to identify a tissue-specific antagonist of a progesterone receptor. This method includes the steps of: (a) providing an expression profile for at least one gene that is known to be regulated by a progesterone receptor in a first but not in a second tissue type when the progesterone receptor is activated, wherein the at least one gene is chosen from the genes in any one or more of the genes in Tables 1–7; (b) contacting a progesterone receptor expressed by a first tissue type with a putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (c) detecting expression of the at least one gene from (a); and, (d) comparing the expression of the at least one gene in the presence and in the absence of the putative antagonist ligand in the first tissue type, wherein detection of inhibition or reversal of regulation of expression of the at least one gene in the first tissue type in the presence of the putative antagonist ligand, as compared to the expression of the at least one gene associated with activation of the progesterone receptor as set forth in the expression profile of (a), indicates that the putative antagonist ligand is a tissue-specific progesterone receptor antagonist of the first tissue type.

In each of the above-described methods to identify a tissue-specific regulator of a progesterone receptor, in one aspect, the first tissue type is breast, and wherein the at least one gene is selected from the group consisting of: (i) at least one gene that is selectively upregulated by PR-A chosen from a gene in Table 1; (ii) at least one gene that is selectively downregulated by PR-A chosen from a gene in Table 2; (iii) at least one gene that is selectively upregulated by PR-B chosen from a gene in Table 3; (iv) at least one gene that is selectively downregulated by PR-B chosen from a gene in Table 4; (v) at least one gene that is upregulated or downregulated by both PR-A and PR-B chosen from a gene in Table 5; (vi) at least one gene that is reciprocally regulated by PR-A and PR-B chosen from a gene in Table 6; and, (vii) at least one gene that is regulated by one of the PR-A or the PR-B, wherein regulation of the gene is altered when the other of the PR-A or PR-B is expressed by the same cell, chosen from a gene in Table 7. In one aspect, the second tissue type is selected from the group consisting of breast, uterus, bone, cartilage, cardiovascular tissues, heart, lung, brain, meninges, pituitary, ovary, oocyte, corpus luteum, oviduct, fallopian tubes, T lymphocytes, B lymphocytes, thymocytes, salivary gland, placenta, skin, gut, pancreas, liver, testis, epididymis, bladder, urinary tract, eye, and teeth. In one aspect, the first tissue type is a non-malignant tissue and wherein the second tissue type is a malignant tissue from the same tissue source as the first tissue type. A preferred tissue source is breast tissue. In another aspect, the first tissue type is a normal tissue and wherein the second tissue type is a non-malignant, abnormal tissue.

In each of the above-described methods for identifying a tissue-specific regulator of a progesterone receptor, the expression profile of genes regulated by a progesterone receptor in the first or second tissue type can be provided by a method comprising: (a) providing a first cell of a selected tissue type that expresses a progesterone receptor A (PR-A) and not a progesterone receptor B (PR-B) and a second cell of the same tissue type that expresses PR-B and not PR-A; (b) stimulating the progesterone receptors in (a) by contacting the first and second cells with a progesterone receptor stimulatory ligand; (c) detecting expression of genes by the first and second cells in the presence of the stimulatory ligand and in the absence of the stimulatory ligand, wherein a difference in the expression of a gene in the presence of the stimulatory ligand as compared to in the absence of the stimulatory ligand, indicates that the gene is regulated by the progesterone receptor in the selected tissue type.

Another embodiment of the present invention relates to method to determine the profile of genes regulated by progesterone receptors in a breast tumor sample. This method includes the steps of: (a) obtaining from a patient a breast tumor sample; (b) detecting expression of at least one gene in the breast tumor sample that is regulated by a progesterone receptor when the progesterone receptor is activated; and, (c) producing a profile of genes for the tumor sample that are regulated selectively by PR-A, selectively by PR-B, or by both PR-A and PR-B. The at least one gene is selected from the group consisting of: (i) at least one gene that is selectively upregulated by PR-A chosen from a gene in Table 9; (ii) at least one gene that is selectively downregulated by PR-A chosen from a gene in Table 10; (iii) at least one gene that is selectively upregulated by PR-B chosen from a gene in Table 11; (iv) at least one gene that is selectively downregulated by PR-B chosen from a gene in Table 12; (v) at least one gene that is upregulated or downregulated by both PR-A and PR-B chosen from a gene in Table 13; (vi) at least one gene that is reciprocally regulated by PR-A and PR-B chosen from a gene in Table 14; and, (vii) at least one gene that is regulated by one of the PR-A or the PR-B, wherein regulation of the gene is altered when the other of the PR-A or PR-B is expressed by the same cell, chosen from a gene in Table 15.

Yet another embodiment of the present invention relates to a plurality of polynucleotides for the detection of the expression of genes regulated by progesterone receptors in breast tissue. The plurality of polynucleotides consists of polynucleotide probes that are complementary to RNA transcripts, or nucleotides derived therefrom, of genes that are regulated by progesterone receptors. The plurality of polynucleotides also comprises polynucleotide probes that are complementary to RNA transcripts, or nucleotides derived therefrom, of genes selected from the group consisting of: (a) at least one gene that is selectively upregulated by PR-A chosen from a gene in Table 1; (b) at least one gene that is selectively downregulated by PR-A chosen from a gene in Table 2; (c) at least one gene that is selectively upregulated by PR-B chosen from a gene in Table 3; (d) at least one gene that is selectively downregulated by PR-B chosen from a gene in Table 4; (e) at least one gene that is upregulated or downregulated by both PR-A and PR-B chosen from a gene in Table 5; (e) at least one gene that is reciprocally regulated by PR-A and PR-B chosen from a gene in Table 6; and, (f) at least one gene that is regulated by one of the PR-A or the PR-B, wherein regulation of the gene is altered when the other of the PR-A or PR-B is expressed by the same cell, chosen from a gene in Table 7.

In one aspect, the polynucleotide probes are immobilized on a substrate. In another aspect, the polynucleotide probes are hybridizable array elements in a microarray. In another aspect, the polynucleotide probes are conjugated to detectable markers. In yet another aspect, the plurality of polynucleotides further comprises at least one polynucleotide probe that is complementary to RNA transcripts, or nucleotides derived therefrom, of at least one gene chosen from the genes in Table 8.

Another embodiment of the present invention relates to a plurality of antibodies, or antigen binding fragments thereof, for the detection of the expression of genes regulated by progesterone receptors in breast tissue. The plurality of antibodies, or antigen binding fragments thereof, consists of antibodies, or antigen binding fragments thereof, that selectively bind to proteins encoded by genes that are regulated by progesterone receptors. The plurality of antibodies, or antigen binding fragments thereof, also comprises antibodies, or antigen binding fragments thereof, that selectively bind to proteins encoded by genes selected from the group consisting of: (a) at least one gene that is selectively upregulated by PR-A chosen from a gene in Table 1; (b) at least one gene that is selectively downregulated by PR-A chosen from a gene in Table 2; (c) at least one gene that is selectively upregulated by PR-B chosen from a gene in Table 3; (d) at least one gene that is selectively downregulated by PR-B chosen from a gene in Table 4; (e) at least one gene that is upregulated or downregulated by both PR-A and PR-B chosen from a gene in Table 5; (e) at least one gene that is reciprocally regulated by PR-A and PR-B chosen from a gene in Table 6; and, (f) at least one gene that is regulated by one of the PR-A or the PR-B, wherein regulation of the gene is altered when the other of the PR-A or PR-B is expressed by the same cell, chosen from a gene in Table 7.

In one aspect, the plurality of antibodies, or antigen binding fragments thereof, further comprises at least one antibody, or an antigen binding fragment thereof, that selectively binds to a protein encoded by a gene chosen from the genes in Table 8.

Another embodiment of the present invention relates to a method to identify genes that are regulated by a progesterone receptor in two or more tissue types. This method includes the steps of: (a) activating a progesterone receptor in two or more tissue types that express the progesterone receptor; (b) detecting expression of at least one gene the two or more tissue types, the at least one gene being chosen from a gene in any one or more of Tables 1–7, and, (c) identifying genes that are regulated by the progesterone receptor in each of the two or more tissue types. This method can further include the step of detecting whether the genes are regulated selectively by PR-A, selectively by PR-B, or by both PR-A and PR-B.

Another embodiment of the present invention relates to a method to regulate the expression of a gene selected from the group consisting of any one or more of the genes in Tables 1–7. The method includes administering to a cell that expresses a progesterone receptor a compound selected from the group consisting of: progesterone, a progestin, and an antiprogestin, wherein the compound is effective to regulate the expression of the gene. In one embodiment, the gene is selected from the group consisting of: growth arrest-specific protein (gas6), NF-IL6-beta (C/EBPbeta), calcium-binding protein S100P, MSX-2, selenium-binding protein (hSBP), and bullous pemphigoid antigen (plakin family). In another embodiment, the cell that expresses a progesterone receptor is in the breast tissue of a patient that has, or is at risk of developing, breast cancer.

DETAILED DESCRIPTION OF THE INVENTION

The present invention generally relates to the identification of a large number of genes that are regulated by progesterone receptors, and particularly, to the identification of how these genes are regulated by the progesterone receptor isoforms, PR-A and PR-B. Using the gene expression profiles disclosed herein, one can identify novel ligands of progesterone receptors (both progestin-like agonists and anti-progestin-like antagonists) that regulate progesterone receptors, including in an isoform-specific and/or tissue specific manner. In addition, these genes can be used to profile individuals that have been diagnosed with breast cancer to enhance the ability of the clinician to develop a prognosis and treatment protocols for the individual patient. The genes can also be used to profile the progesterone receptor regulated gene expression in tissue types other than breast tissue. Moreover, given the knowledge of these genes, one can produce novel combinations of polynucleotides and/or antibodies and/or peptides for use in progestational drug screening assays or expression profiling of patient samples.

The present inventors have generated model systems to study PRs in breast cancer cells, that are unique to the present inventors' laboratory. In most target tissues, including the breast and uterus, PRs are induced by estradiol. Thus, one can only study progestin actions in the background of an estrogenized system. This makes it virtually impossible to dissect out responses that are due to progesterone, from those that are due to estrogens. Furthermore, all these target tissues contain both PR-A and PR-B. This makes it impossible to dissect out the effects of each PR isoform independently. The T47Dco breast cancer cells are unique to the present inventors' laboratory. They have retained PR and express both PR-A and PR-B at equal levels (Horwitz et al., *Cell* 28, 633–42 (1982)). However, the PRs in these cells are constitutively regulated without estrogens. In order to study differential gene regulation by the two PR isoforms independently, the present inventors constructed a model system in which a PR-negative subline (termed T47D-Y), was derived from T47Dco breast cancer cells. T47D-4 cells were then engineered to stably express either PR-B (termed T47D-4B) or PR-A (termed T47D-4A) at equal levels to each other and to the parental T47Dco cells (Sartorius et al., *Cancer Res*. 54, 3668–3877 (1994)). The present inventors have now used these three new cell lines to analyze progesterone-responsive gene regulation via PR-B or PR-A (with PR negative T47D-Y cells serving as a control) using Affymetrix™ microarray HFL6800 gene expression chips and Atlas™ Human cDNA Expression Arrays. In addition to confirming the regulation of the few known progesterone-responsive genes, the present inventors have identified many genes not previously known to be regulated by PR. Importantly, the results described herein now allow discrimination of genes that are regulated uniquely by PR-B from genes that are uniquely regulated by PR-A. It was found that PR-B regulate more genes than PR-A in response to progesterone, but that a number of genes are uniquely regulated by PR-A. Many of these results have been confirmed by northern blot analysis or RT-PCR of the gene transcripts, or by western blot analyses of the protein products. The data presented herein demonstrate that the two PR isoforms do indeed have unique roles in gene regulation in breast cancer cells. Lastly, the present inventors have observed that the expression levels of a subset of genes are modified by the presence of PR in a ligand-independent fashion.

Genes Regulated by Progesterone Receptors:

Of the more than 6000 human genes screened, the present inventors have identified multiple genes, the expression of which is regulated by progesterone receptors. The genes can be grouped into categories based on the regulation of expression of the genes by the progesterone receptor isoforms, PR-A and PR-B. More particularly, the genes have been grouped into the following main categories: (1) Genes that are selectively (i.e., exclusively or uniquely) upregulated by PR-A (Tables 1 and 9); (2) genes that are selectively downregulated by PR-A (Tables 2 and 10); (3) genes that are selectively upregulated by PR-B (Tables 3 and 11); (4) genes that are selectively downregulated by PR-B (Tables 4 and 12); (5) genes that are upregulated or downregulated in the same direction by both PR-A and PR-B (Tables 5 and 13); (6) genes that are reciprocally regulated by PR-A and PR-B (Tables 6 and 14); and (7) genes that are regulated by one of the isoforms, wherein such regulation is altered when the other isoform is present (e.g., the expression of the gene is either up- or downregulated in the presence of both receptors relative to the expression level of the gene in the presence of only one receptor) (Tables 7 and 15). In this last category, the gene is characterized in that the regulation of expression of the gene by one isoform is altered or suppressed by the presence of the other isoform. It is noted that genes in this last category can also fall within one of the other 6 categories. Tables 1–7 include all genes that were newly discovered to be regulated by progesterone receptors by the present inventors. Tables 9–15 include all of the genes from Tables 1–7, respectively, and additionally include the genes that were identified by the present inventors that had previously been identified to be regulated generally by progesterone. This particular subset of genes (i.e., previously known to be regulated by progesterone) is also set forth separately in Table 8. It is noted that even though the genes in Table 8 were known to be regulated by progesterone, the isoform specificity of these genes was not previously known. Therefore, the identification of the PR isoform regulation of the genes in Table 8 is novel. Other categories of the genes identified in the present invention are as follows: Table 16 is a list of genes identified in the present invention which were previously known to be involved in breast cancer or in the development of mammary tissue. Table 17 is a list that categorizes the genes shown to be regulated by progesterone by the present inventors into functional categories based on GeneCard information as well as extensive literature reviews of each gene product. Table 18 (See Example 1) shows the cumulative results of the gene array analysis with regard to the PR-B-expressing cells described in the Examples. Table 19 (See Example 1) shows the cumulative results of the gene array analysis with regard to the PR-A-expressing cells described in the Examples.

Accordingly, in one embodiment of the present invention, the genes identified as being regulated by progesterone receptors by the present inventors can be used as endpoints or markers in a method to identify ligands that regulate progesterone receptor activity. According to the present invention, in general, the biological activity or biological action of a protein such as a progesterone receptor refers to any function(s) exhibited or performed by the protein that is ascribed to the naturally occurring form of the protein as measured or observed in vivo (i.e., in the natural physiological environment of the protein) or in vitro (i.e., under laboratory conditions). In particular, the biological activity of a progesterone receptor that is of interest herein includes the effect of the receptor, particularly when the receptor is activated, on the expression of the downstream genes identified in the present invention. According to the present invention, a "downstream gene" or "endpoint gene" is any gene, the expression of which is regulated (up or down) by a progesterone receptor (PR-A and/or PR-B). The expression of the gene is typically regulated by the progesterone receptor when it is activated, although the expression of the gene may be regulated by the progesterone receptor in the absence of a stimulatory compound (i.e., the regulation may be ligand independent, or constitutive). Pharmaceutical companies are keenly interested in screening their vast libraries of chemical compounds for ones that bind to (ligands), and either activate or inhibit, progesterone receptors. Selected sets of one, two, three, or more of the genes (up to the number equivalent to all of the genes) of this invention can be used as end-points for rapid through-put screening of ligands that specifically and selectively influence the activity of PR-A and/or PR-B. The ligands can be either agonists or antagonists of the progesterone receptor.

As used herein, the phrase "PR agonist ligand" or "PR agonist" refers to any compound that interacts with a PR and elicits an observable response. More particularly, a PR agonist can include, but is not limited to, steroidal or non-steroidal compounds; a protein, peptide, or nucleic acid that selectively binds to and activates or increases the activation of a progesterone receptor; and most commonly includes progesterone, progesterone analogs, and any suitable product of drug design (e.g., a mimetic of progesterone, or a synthetic progestin) which is characterized by its ability to agonize (e.g., stimulate, induce, increase, enhance) the biological activity of a naturally occurring progesterone receptor in a manner similar to the natural agonist, progesterone (e.g., by interaction/binding with and/or direct or indirect activation of a progesterone receptor). It is noted that the term "progestin" as used herein is generally intended to include progesterone as well as any progesterone analog, such as a synthetic progestin. Since the progesterone receptor is an intracellular receptor, a suitable agonist typically does not include an antibody or antigen binding fragment thereof, but to the extent that an antibody that selectively binds to and activates or increases the activation of a progesterone receptor can be designed and implemented as an agonist, such a compound is also contemplated. It is noted that the effect of the action of a given PR agonist on the expression of a downstream gene may be the downregulation of the gene or the suppression of the expression of a gene (e.g., when both isoforms of PR are present). Moreover, the action of the agonist on a PR may have undesirable consequences in one tissue type and beneficial consequences in another tissue type. However, the term agonist is intended to refer to the ability of the ligand to act on a progesterone receptor in a manner that is substantially similar to the action of the natural PR ligand, progesterone, on the progesterone receptor (described in more detail below). Typically, a PR agonist is identified under conditions wherein, in the absence of the agonist, the PR receptor is not activated, or is at least believed not to be in the presence of a compound that is known to activate the receptor, such as the natural ligand progesterone or a known progestin.

The phrase, "PR antagonist ligand" or "PR antagonist" refers to any compound which inhibits the effect of a PR agonist, as described above. More particularly, a PR antagonist is capable of associating with a progesterone receptor such that the biological activity of the receptor is decreased (e.g., reduced, inhibited, blocked, reversed, altered) in a manner that is antagonistic (e.g., against, a reversal of, contrary to) to the action of the natural agonist, progesterone, on the receptor. Such a compound can include, but is not limited to, steroidal or non-steroidal compounds; a protein, peptide, or nucleic acid that selectively binds to and blocks access to the receptor by a natural or synthetic agonist ligand or reduces or inhibits the activity of a progesterone receptor; or a product of drug design that blocks the receptor or alters the biological activity of the receptor (e.g., an antiprogestin, which antagonizes the actions of progesterone). Again, since the progesterone receptor is an intracellular receptor, antibody antagonists are typically not practical, although if appropriate and feasible, their use is contemplated herein. It is noted that the action of a given PR antagonist on a given downstream gene via a PR may be to actually upregulate the gene. Moreover, the action of the antagonist on a PR may have undesirable consequences in one tissue type and beneficial consequences in another tissue type. However, the term antagonist is intended to refer to the ability of the ligand to act on a progesterone receptor in a manner that is antagonistic to the action of the natural PR ligand, progesterone, or a synthetic PR agonist, on the progesterone receptor. Typically, an antagonist is identified under control conditions wherein, in the absence of the antagonist, the progesterone receptor is stimulated, such as by the natural ligand, progesterone, or by any suitable progestin. In one embodiment, a PR antagonist can be identified by its ability to alter the regulation of downstream genes by the receptor in the absence of a known stimulator of the receptor. In this embodiment, ligand-independent regulators of progesterone receptor function can be identified by detecting effects on genes that are constitutively regulated by PR in the ligand-unactivated state.

According to the present invention, agonists and antagonist ligands can include any regulatory ligand or compound that has the above-mentioned characteristics with regard to regulation of a progesterone receptor. For example, agonists and antagonists can include steroidal and non-steroidal compounds, proteins and peptides, nucleic acid molecules, antibodies, and/or mimetics (e.g., products of drug design or combinatorial chemistry).

Natural sex steroid hormone agonists are low molecular weight ringed cyclopentanophenanthrene compounds that in mammals include progesterone, estrogens and androgens. Steroid agonists can be extracted from a variety of natural sources, including the ovaries and testes. With the aim of enhancing the properties of natural steroid compounds, researchers have modified the cyclopentanophenanthrene structures and/or altered the substituent side-chains to generate semi-synthetic and synthetic steroidal and non-steroidal compounds. Non-steroidal compounds lack the classical cyclopentanophenanthrene structure. Nevertheless, all of these compounds—natural, semi-synthetic and synthetic, steroidal and non-steroidal compounds, bind to their respective nuclear receptors. Modified compounds can be either agonists or antagonists.

Progesterone is the natural "progestin" produced by the ovaries and adrenal glands of mammals. Semi-synthetic or synthetic analogs that have progesterone-like effects, can be either steroidal or non-steroidal. They are also included in the generic category called "progestins." Natural, semi-synthetic or synthetic progestins bind to intracellular, usually intranuclear, progesterone receptors. Such progestins can be either "agonists" or "antagonists" (antiprogestins). Both agonists and antagonists can have variable levels of activity of the receptors. An agonist can be strong or weak with many levels in between. An antagonist can also be strong or weak. Some antagonists may have "mixed" agonist/antagonist properties. The present invention can screen for all of these types of progestins.

Other compounds in addition to steroidal and non-steroidal compounds can bind progesterone receptors. These include proteins and peptides, and nucleic acids and fragments thereof. Any compound that binds a receptor can be classified as a "ligand" of the receptor. If the ligand influences the activity of the progesterone receptor, the present invention can be used to screen for such ligand(s).

An isolated protein, according to the present invention, is a protein (including a peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. An isolated protein useful as an antagonist or agonist according to the present invention can be isolated from its natural source, produced recombinantly or produced synthetically. Smaller peptides useful as regulatory ligands are typically produced synthetically by methods well known to those of skill in the art. Regulatory ligands of the present invention can also include an antibody or antigen binding fragment that selectively binds to a progesterone receptor.

According to the present invention, the phrase "selectively binds to" refers to the ability of an antibody, antigen binding fragment or other binding partner (protein, peptide, nucleic acid) to preferentially bind to specified proteins. More specifically, the phrase "selectively binds" refers to the specific binding of one protein to another, wherein the level of binding, as measured by any standard assay, is statistically significantly higher than the background control for the assay.

Agonists and antagonists that are products of drug design can be produced using various methods known in the art. Various methods of drug design, useful to design mimetics or other regulatory compounds useful in the present invention are disclosed in Maulik et al., 1997, *Molecular Biotechnology: Therapeutic Applications and Strategies*, Wiley-Liss, Inc., which is incorporated herein by reference in its entirety. A PR agonist or antagonist can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, natural or synthetic steroidal compounds, carbohydrates and/or natural or synthetic organic and non-steroidal molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

As used herein, the term "mimetic" is used to refer to any natural or synthetic steroidal compound, peptide, oligonucleotide, carbohydrate and/or natural or synthetic organic and non-steroidal molecule that is able to mimic the biological action of a naturally occurring or known synthetic progestin.

Methods and Products of the Present Invention:

One embodiment of the present invention relates to a method to identify agonist ligands of progesterone receptors. This method includes the steps of: (a) contacting a progesterone receptor with a putative agonist ligand, wherein the progesterone receptor is selected from the group consisting of progesterone receptor A (PR-A) and progesterone receptor B (PR-B), under conditions wherein, in the absence of the putative agonist ligand, the progesterone receptor is not activated; (b) detecting expression of at least one gene that is regulated by the progesterone receptor when the progesterone receptor is activated and, (c) comparing the expression of the at least one gene in the presence and in the absence of the putative agonist ligand, wherein detection of regulation of the expression of the at least one gene in the manner associated with activation of the progesterone receptor as set forth in (b) indicates that the putative agonist ligand is a progesterone receptor agonist. The gene can include any one or more of any of the following genes: (i) one or more of the genes that are selectively upregulated by PR-A chosen from a gene in Table 1; (ii) one or more of the genes that are selectively downregulated by PR-A chosen from a gene in Table 2; (iii) one or more of the genes that are selectively upregulated by PR-B chosen from a gene in Table 3; (iv) one or more of the genes that are selectively downregulated by PR-B chosen from a gene in Table 4; (v) one or more of the genes that are upregulated or downregulated in the same direction by both PR-A and PR-B chosen from a gene in Table 5; (vi) one or more of the genes that are reciprocally regulated by PR-A and PR-B chosen from a gene in Table 6; and, (vii) one or more of the genes that are regulated by one of either PR-A or PR-B, wherein the regulation of the gene is altered when the other of the PR-A or PR-B is present, such a gene being chosen from a gene in Table 7.

Another embodiment of the present invention relates to a method to identify antagonists of progesterone receptor. This method includes the steps of: (a) contacting a progesterone receptor with a putative antagonist ligand, wherein the progesterone receptor is selected from the group consisting of progesterone receptor A (PR-A) and progesterone receptor B (PR-B), under conditions wherein, in the absence of said putative antagonist ligand, said progesterone receptor is activated (i.e., before, simultaneously with or after the contact of the receptor with the putative regulatory ligand); (b) detecting expression of at least one gene that is regulated by the progesterone receptor when the progesterone receptor is activated; and, (c) comparing the expression of the at least one gene in the presence and in the absence of the putative antagonist ligand. Detection of inhibition or reversal of the regulation of expression of the at least one gene as compared to the regulation of expression of the at least one gene in the manner associated with activation of the progesterone receptor as set forth in (b), indicates that the putative antagonist ligand is a progesterone receptor antagonist. The gene(s) to be detected in step (b) are chosen from one or more of the following genes: (i) one or more of the genes that are selectively upregulated by PR-A chosen from a gene in Table 1; (ii) one or more of the genes that are selectively downregulated by PR-A chosen from a gene in Table 2; (iii) one or more of the genes that are selectively upregulated by PR-B chosen from a gene in Table 3; (iv) one or more of the genes that are selectively downregulated by PR-B chosen from a gene in Table 4; (v) one or more of the genes that are upregulated or downregulated by both PR-A and PR-B chosen from a gene in Table 5; (vi) one or more of the genes that are reciprocally regulated by PR-A and PR-B chosen from a gene in Table 6; and, (vii) one or more of the genes that are regulated by one of the PR-A or the PR-B, wherein regulation of the gene is altered when the other of the PR-A or PR-B is expressed by the same cell, chosen from a gene in Table 7. In one embodiment, the progesterone receptor is activated by contacting the receptor with a compound that activates the receptor, the step of contacting being performed prior to, simultaneously with, or after the step of contacting of (a).

The steps of the method of the present invention will now be described in some detail for these embodiments of the invention; however, this discussion generally applies to other methods of identifying various ligands of progesterone receptors as described below.

As used herein, the term "putative regulatory compound" or "putative regulatory ligand" refers to compounds having an unknown regulatory activity, at least with respect to the ability of such compounds to regulate progesterone receptors as described herein.

In the method of identifying a regulatory ligand (i.e., an agonist or an antagonist) according to the present invention, the method can be a cell-based assay, or non-cell-based assay. In one embodiment, the progesterone receptor is expressed by a cell (i.e., a cell-based assay). In another embodiment the progesterone receptor is in a cell lysate, is in isolated cell nuclei, or is purified or produced free of cells. The progesterone receptor can be a PR-A, a PR-B, or a combination of PR-A and PR-B. One advantage of the present invention is that, given the knowledge of the isoform regulation of the various downstream genes disclosed herein, one can screen for ligands of the progesterone receptor, including screening for isoform specific ligands, using cells that express both receptors. Prior to the present invention, it was impossible to distinguish between the effects of one isoform or the other, because most cells express both isoforms.

In one embodiment, the conditions under which a receptor according to the present invention is contacted with a putative regulatory ligand, such as by mixing, are conditions in which the receptor is not stimulated (activated) if essentially no regulatory ligand is present. For example, such conditions include normal culture conditions in the absence of a known stimulatory compound (a stimulatory compound being, for example, the natural ligand for the receptor (progesterone), a stimulatory peptide, or other equivalent stimulus, such as a synthetic progestin). The putative regulatory ligand is then contacted with the receptor. In this embodiment, the step of detecting is designed to indicate whether the putative regulatory ligand alters the biological activity of the receptor as compared to in the absence of the putative regulatory ligand (i.e., the background level), as determined by the effects of the contact between the ligand and the receptor on the expression of downstream genes as described herein.

In an alternate embodiment, the conditions under which a progesterone receptor according to the present invention is contacted with a putative regulatory ligand, such as by mixing, are conditions in which the receptor is normally stimulated (activated) if essentially no regulatory ligand is present. Such conditions can include, for example, contact of said receptor with a stimulator molecule (a stimulatory compound being, e.g., the natural ligand for the receptor (progesterone), a stimulatory peptide, or other equivalent stimulus, such as a synthetic progestin) which binds to the receptor and causes the receptor to become activated. In this embodiment, the putative regulatory ligand can be contacted with the receptor prior to, or simultaneously with, the contact of the receptor with the stimulatory compound (e.g., to determine whether the putative regulatory ligand blocks or otherwise inhibits the stimulation of the progesterone receptor by the stimulatory compound), or after contact of the receptor with the stimulatory compound (e.g., to determine whether the putative regulatory ligand downregulates, or reduces the activation of the receptor).

The present methods involve contacting the progesterone receptor with the ligand being tested for a sufficient time to allow for interaction, activation or inhibition of the receptor by the ligand. The period of contact with the ligand being tested can be varied depending on the result being measured, and can be determined by one of skill in the art. For example, for binding assays, a shorter time of contact with the compound being tested is typically suitable, than when activation is assessed, and particularly, when the expression of downstream genes is assessed. The methods of the present invention detect the expression of downstream genes and therefore, the time of incubation is dependent upon the time required to achieve expression of the downstream genes. Such a time period is typically at least 2 hours, and more preferably at least 4 hours, and more preferably at least 6 hours, although the time can be extended, if necessary to detect expression of a selected downstream gene. As used herein, the term "contact period" refers to the time period during which the progesterone receptor is in contact with the ligand being tested. The term "incubation period" refers to the entire time during which the cells expressing the receptor, for example, are allowed to grow prior to evaluation, or the time during which genes affected by activation of the progesterone receptor are allowed to be expressed, and such time period can be inclusive of the contact period. Thus, the incubation period includes all of the contact period and may include a further time period during which the compound being tested is not present, or is no longer being supplied to the receptor, but during which gene expression is continuing (in the case of a cell based assay) prior to scoring. The incubation time for growth of cells can vary but is sufficient to allow for the binding of the progesterone receptor, the activation or inhibition of the receptor, and the effect on the expression of the downstream genes regulated by the receptor. It will be recognized that shorter incubation times are preferable because compounds can be more rapidly screened.

In accordance with the present invention, a cell-based assay is conducted under conditions which are effective to screen for regulatory compounds useful in the method of the present invention. Effective conditions include, but are not limited to, appropriate media, temperature, pH and oxygen conditions that permit the growth of the cell that expresses the receptor. An appropriate, or effective, medium refers to any medium in which a cell that naturally or recombinantly expresses a progesterone receptor, when cultured, is capable of cell growth and expression of the progesterone receptor. Such a medium is typically a solid or liquid medium comprising growth factors and assimilable carbon, nitrogen and phosphate sources, as well as appropriate salts, minerals, metals and other nutrients, such as vitamins. Culturing is carried out at a temperature, pH and oxygen content appropriate for the cell. Such culturing conditions are within the expertise of one of ordinary skill in the art. Exemplary cells expressing progesterone receptors are described in the Examples, and in detail in (Sartorius et al., *Cancer Res.* 54, 3668–3877 (1994)).

Cells that are useful in the cell-based assays of the present invention include any cell that expresses a progesterone receptor of the isoform A, isoform B, or a combination of PR-A and PR-B. Such cells include cells that naturally express progesterone receptors, or cells that express progesterone receptors by recombinant technology. Such cells preferably include, but are not limited to mammalian cells, which can originate from the breast or any other tissue. For example, tissues containing cells that are known to express the progesterone receptor naturally include, but are not limited to, breast, uterus, bone, cartilage, cardiovascular tissues, heart, lung, brain, meninges, pituitary, ovary, oocyte, corpus luteum, oviduct, fallopian tubes, T lymphocytes, B lymphocytes, thymocytes, salivary gland, placenta, skin, gut, pancreas, liver, testis, epididymis, bladder, urinary tract, eye, and teeth. Cells suitable for use in a cell-based assay include normal or malignant cells, as well as cells that are not malignant, but which are abnormal, such as cells from a non-malignant tissue that is otherwise diseased (e.g., tissues from endometriosis and leiomyoma of the uterus, fibrocystic disease of the breast, polycystic ovary). Other suitable cells are cells that express PR-A, PR-B, or both isoforms, as a result of recombinant technology. Such cells were used to discover the PR downstream genes of the present invention and are described in detail in Sartorius et al. (Sartorius et al., *Cancer Res.* 54, 3668–3877 (1994)). Other suitable cells are cells that express a PR-A and/or a PR-B transgene (i.e., cells isolated from a transgenic animal), or cells that have a germline deletion of one of the PR isoforms, but not the other (i.e., cells from a PR-A or PR-B knockout animal).

According to the present invention, the method includes the step of detecting the expression of at least one, and preferably more than one, of the downstream genes that have now been shown to be regulated by progesterone receptors by the present inventors. As used herein, the term "expression", when used in connection with detecting the expression of a downstream gene of the present invention, can refer to detecting transcription of the gene and/or to detecting translation of the gene. To detect expression of a downstream gene refers to the act of actively determining whether a gene is expressed or not. This can include determining whether the gene expression is upregulated as compared to a control, downregulated as compared to a control, or unchanged as compared to a control. Therefore, the step of detecting expression does not require that expression of the gene actually is upregulated or downregulated, but rather, can also include detecting that the expression of the gene has not changed (i.e., detecting no expression of the gene or no change in expression of the gene).

The present method includes the step of detecting the expression of at least one gene that is regulated by a progesterone receptor when the receptor is activated, as set forth in detail above. In a preferred embodiment, the step of detecting includes detecting the expression of at least 2 genes, and preferably at least 3 genes, and more preferably at least 4 genes, and more preferably at least 5 genes, and more preferably at least 6 genes, and more preferably at least 7 genes, and more preferably at least 8 genes, and more preferably at least 9 genes, and more preferably at least 10 genes, and more preferably at least 11 genes, and more preferably at least 12 genes, and more preferably at least 13 genes, and more preferably at least 14 genes, and more preferably at least 15 genes, and so on, in increments of one, up to detecting expression of all of the downstream genes disclosed herein. Analysis of a number of genes greater than 1 can be accomplished simultaneously, sequentially, or cumulatively.

In the method of identifying an agonist or an antagonist of a progesterone receptor of the present invention, the gene(s) to be detected are preferably selected from the genes described in any one or more of Tables 1–7. These tables disclose genes that are regulated by progesterone receptors, and particularly, these tables disclose the manner in which the genes are regulated by the PR isoforms when the progesterone receptor is activated (i.e., by a stimulator of the receptor). The genes to be detected can include one or more of: (1) genes that are selectively (i.e., exclusively or uniquely) upregulated by PR-A (Table 1); (2) genes that are selectively downregulated by PR-A (Table 2); (3) genes that are selectively upregulated by PR-B (Table 3); (4) genes that are selectively downregulated by PR-B (Table 4); (5) genes that are upregulated or downregulated in the same direction by both PR-A and PR-B (Table 5); (6) genes that are reciprocally regulated by PR-A and PR-B (Table 6); and (7) genes that are regulated by one of the PR isoforms, wherein such regulation is altered when the other PR isoform is present (e.g., the expression of the gene is either up- or downregulated in the presence of both receptors relative to the expression level of the gene in the presence of only one receptor) (Table 7). In one embodiment, the method further includes the additional detection of the expression of one or more genes that were previously known to be regulated by progesterone, but for which the PR isoform regulation was not known until the present invention. Such genes are disclosed in Table 8.

It is to be understood that the organization of various genes into the present tables is for purposes of clarity and identification of various genes on the basis of the manner in which the gene is regulated by a progesterone receptor isoform. The selection of genes to be detected in any given method can include any one or more of the genes in any one or more of the Tables, and can include the detection of any combination of two or more of the genes in any one or more of the Tables. It is not mandatory that a given assay be restricted to the detection of all of the various genes in a single table, or to one gene in each table. In addition, with regard to Tables 1–7, it is believed that these tables encompass genes that have been identified by the present inventors to be regulated by progesterone receptors, but which have not previously been described as being regulated by progesterone. However, in the event that one or more of the genes in Tables 1–7 is found to have previously been known to be regulated by progesterone, the removal of such gene from these tables and the placement of such gene into Table 8, is explicitly contemplated. This rationale also applies to the genes of Table 16, which are believed to include all of those genes identified by the inventors that were previously known to be involved in breast cancer or mammary development. It is expressly contemplated that other genes from Tables 1–7 or 9–15 can be added to Table 16, if required for accuracy. Tables 9–15 include all of the genes identified by the present inventors as being regulated by progesterone receptors (organized by isoform regulation, as for Tables 1–7), and, as discussed previously herein, include genes that were previously known to be regulated by progesterone.

Given the knowledge of the genes regulated by progesterone receptors according to the present invention, one of skill in the art will be able to select one or more genes to detect in a method of the present invention, and the selection of the one or more genes can be determined by different factors. For example, certain subsets of the genes are useful for detecting genes regulated by PR-A exclusively (i.e., genes in Tables 1, 2, 9 and 10). Other subsets of genes are useful for detecting genes regulated by PR-B exclusively (i.e., genes in Tables 3, 4, 11 and 12). One of skill in the art may wish to detect genes disclosed herein that are related to a particular function, to a particular tissue-type, or that are associated (or likely to be associated) with a particular disease or condition. One of skill in the art may also wish to select genes on the basis of the change in expression level in the presence of progesterone (i.e., and therefore activation of the PR) as compared to in the absence of progesterone.

In one aspect of the methods of the present invention, the method of the present invention includes detecting genes of the present invention that are related by function. For example, Table 17 provides a listing of the various genes identified by the present inventors, categorized by function. Therefore, one could screen functional sets of genes to make a specific determination about a given cell or tissue that expresses a progesterone receptor, or to identify a ligand that has an action that might be correlated with a functional gene. For example, one could use subsets of the disclosed genes to screen a tumor for the likelihood that it will metastasize by screening the genes in the “cell adhesion or cytoskeletal interaction” group of Table 17. Other uses for screening functional groups will be apparent to those of skill in the art.

In another aspect, one could detect genes that are of interest in a particular tissue type. Examples of such genes are disclosed below in the discussion regarding the identification of tissue-specific ligands of progesterone receptors.

In another aspect, one could detect those genes that are associated with a particular disease, such as breast cancer. An exemplary grouping of genes that are regulated by progesterone receptors (as disclosed herein) and that were previously known to be involved in breast cancer or mammary gland development, are shown in Table 16. In one embodiment, one may be interested in detecting those genes listed in Table 16 which are not also listed in Table 8.

In another aspect, it may be desirable to select those genes for detection that are particularly highly regulated by progesterone receptors in that they display the largest increases or decreases in expression levels in the presence of progesterone as compared to in the absence of progesterone. The detection of such genes can be advantageous because the endpoint may be more clear and require less quantitation. The relative expression levels of the genes identified in the present invention are listed in the tables. In these tables, the fold increase or decrease in expression of the gene upon treatment of the progesterone receptor with progesterone for 6 hours is indicated. The fold increase or decrease was made with respect to the background level of expression of the gene, which in some cases, was undetectable (i.e., the gene was not detected at all in the absence of progesterone, but was detected in the presence of progesterone). Therefore, in one embodiment, one of skill in the art might choose to detect genes that exhibited a fold increase above background of at least 2. In another embodiment, one of skill in the art might choose to detect genes that exhibited a fold increase or decrease above background of at least 3, and in another embodiment at least 4, and in another embodiment at least 5, and in another embodiment at least 6, and in another embodiment at least 7, and in another embodiment at least 8, and in another embodiment at least 9, and in another embodiment at least 10 or higher fold changes. It is noted that fold increases or decreases are not typically compared from one gene to another, but with reference to the background level for that particular gene.

In order to determine whether a putative regulatory compound is an agonist or antagonist of PR as defined herein, it is necessary to know how a given gene is regulated by the PR so that one can compare the results in the presence and absence of the putative regulatory ligand to the gene expression profile produced by an activated receptor. This allows the investigator to thereby detect whether the contact of the receptor with the putative ligand results in a profile of gene expression that is substantially similar to the profile of gene expression of an activated PR (i.e., agonist action), or whether contact of the receptor with the putative ligand results in a profile of gene expression that is an inhibition, or reversal, of the profile of gene expression of an activated PR (i.e., antagonist action).

In one aspect of the method of the present invention, the step of detecting can include the detection of one or more reporter genes that are linked to promoters of one or more downstream genes according to the present invention. In this embodiment, the transcriptional read-out can use one, two or more promoters of any of the genes of this invention, linked to any of several reporter constructs, which are introduced into cells by any of several established transfection or infection methods, including, but not limited to, calcium phosphate transfection, transformation, electroporation, microinjection, lipofection, adsorption, infection (e.g., by a viral vector) and protoplast fusion. The cells can be naturally PR-positive (containing both PRs), or they can stably or transiently express either one or both of the two PR-isoforms. The cells can be exposed to the test ligands (i.e., the putative regulatory ligands) for different times and/or concentrations, and transcription of the PR-responsive promoter(s) of the downstream genes disclosed in this invention can be quantified.

In another aspect of this method of the present invention, cells expressing a PR as described above are exposed to the unknown test ligands at various concentrations and for various periods of time. The transcriptional read-out can be expression of one, two or more of the genes of this invention, which are endogenously regulated in the cells. Expression of their transcripts and/or proteins is measured by any of a variety of known methods in the art several of which are exemplified in the Examples section. For RNA expression, methods include but are not limited to: extraction of cellular mRNA and northern blotting using labeled probes that hybridize to transcripts encoding all or part of one or more of the genes of this invention; amplification of mRNA expressed from one or more of the genes of this invention using gene-specific primers and reverse transcriptase—polymerase chain reaction, followed by quantitative detection of the product by any of a variety of means; extraction of total RNA from the cells, which is then labeled and used to probe cDNAs or oligonucleotides encoding all or part of the PR-responsive genes of this invention, arrayed on any of a variety of surfaces.

Methods to measure protein expression levels of selected genes of this invention, include, but are not limited to: western blotting, immunocytochemistry, flow cytometry or other immunologic-based assays; assays based on a property of the protein including but not limited to DNA binding, ligand binding, or interaction with other protein partners.

Nucleic acid arrays are particularly useful for detecting the expression of the downstream genes of the present invention. The production and application of high-density arrays in gene expression monitoring have been disclosed previously in, for example, WO 97/10365; WO 92/10588; U.S. Pat. No. 6,040,138; U.S. 5,445,934; or WO95/35505, all of which are incorporated herein by reference in their entireties. Also for examples of arrays, see Hacia et al. (1996) *Nature Genetics* 14:441–447; Lockhart et al. (1996) Nature Biotechnol. 14:1675–1680; and De Risi et al. (1996) *Nature Genetics* 14:457–460. In general, in an array, an oligonucleotide, a cDNA, or genomic DNA, that is a portion of a known gene occupies a known location on a substrate. A nucleic acid target sample is hybridized with an array of such oligonucleotides and then the amount of target nucleic acids hybridized to each probe in the array is quantified. One preferred quantifying method is to use confocal microscope and fluorescent labels. The Affymetrix GeneChip™ Array system (Affymetrix, Santa Clara, Calif.) and the Atlas™ Human cDNA Expression Array system are particularly suitable for quantifying the hybridization; however, it will be apparent to those of skill in the art that any similar systems or other effectively equivalent detection methods can also be used. The Examples section describes the use of these two different array systems. In a particularly preferred embodiment, one can use the knowledge of the genes described herein to design novel arrays of polynucleotides, cDNAs or genomic DNAs for screening methods described herein. Such novel pluralities of polynucleotides are contemplated to be a part of the present invention and are described in detail below.

Suitable nucleic acid samples for screening on an array contain transcripts of interest or nucleic acids derived from the transcripts of interest (i.e., transcripts derived from the PR-regulated genes of the present invention). As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Preferably, the nucleic acids for screening are obtained from a homogenate of cells or tissues or other biological samples. Preferably, such sample is a total RNA preparation of a biological sample. More preferably in some embodiments, such a nucleic acid sample is the total mRNA isolated from a biological sample. Biological samples may be of any biological tissue or fluid or cells from any organism. Frequently the sample will be a "clinical sample" which is a sample derived from a patient, such as a breast tumor sample from a patient. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

In one embodiment, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high-density array may then include probes specific to the internal standard for quantification of the amplified nucleic acid. Other suitable amplification methods include, but are not limited to polymerase chain reaction (PCR) Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al, Proc. Nat. Acad. Sci. USA, 87: 1874 (1990)).

Nucleic acid hybridization simply involves contacting a probe and target nucleic acid under conditions where the probe and its complementary target can form stable hybrid duplexes through complementary base pairing. As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety. Nucleic acids that do not form hybrid duplexes are washed away from the hybridized nucleic acids and the hybridized nucleic acids can then be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

High stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). One of skill in the art can use the formulae in Meinkoth et al., 1984, *Anal. Biochem.* 138, 267–284 (incorporated herein by reference in its entirety) to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6× SSC (0.9 M $Na^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6× SSC (0.9 M $Na^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62.

The hybridized nucleic acids are detected by detecting one or more labels attached to the sample nucleic acids. The labels may be incorporated by any of a number of means well known to those of skill in the art. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads.TM.), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

In one aspect of the present method, in vitro cell based assays may be designed to screen for compounds that affect the regulation of genes by a progesterone receptor at either the transcriptional or translational level. One, two or more promoters of the genes of this invention can be used to screen unknown ligands for their ability to selectively regulate transcription in vitro via PR-A or PR-B. Promoters of the selected genes can be linked to any of several reporters (including but not limited to chloramphenicol acetyl transferase, or luciferase) that measure transcriptional readout. The promoters can be tested as pure DNA, or as DNA bound to chromatin proteins. Ligands at different concentrations and under different assay conditions can be screened for their ability to either up- or downregulate transcription of the selected genes, under the control of either PR-A, PR-B or both. In this embodiment, cells expressing progesterone receptors or cell lysates comprising progesterone receptors are contacted with a putative regulatory ligand for a time sufficient to act on the receptor. The cells or cell lysates contain one, two or more promoters of the selected genes that are linked to any of several reporters, and the transcription or translation of the reporter genes is measured. Appropriate cells are preferably prepared from any cell type that naturally expresses the progesterone receptor or that recombinantly expresses the progesterone receptor, thereby ensuring that the cells contain the transcription factors required for transcription. The screen can be used to identify ligands that modulate the expression of the reporter construct. In such screens, the level of reporter gene expression is determined in the presence of the test ligand and compared to the level of expression in the absence of the test ligand, or the test ligand is compared to a known ligand, such as progesterone.

In one aspect of the present method, the step of detecting can include detecting the expression of one or more downstream genes of the invention in intact animals or tissues obtained from such animals. Mammalian (i.e. mouse, rat, monkey) or non-mammalian (i.e. chicken) species that express PRs in their tissues and elaborate progesterone, can be the test animals. The unknown test ligand is introduced into intact or castrated animals by any of a variety of oral, intravenous, intramuscular, subdermal or other routes, for a variety of treatment times or concentrations. The tissues to be surveyed can be either normal or malignant progesterone targets (including but not limited to the mammary glands, mammary cancers, uterus, or endometrial cancers). The presence and quantity of endogenous mRNA or protein expression of one, two or more of the genes of this invention can be measured in those progesterone target tissues. The gene markers can be measured in tissues that are fresh, frozen, fixed or otherwise preserved. They can be measured in cytoplasmic or nuclear organ-, tissue- or cell-extracts; or in cell membranes including but not limited to plasma, cytoplasmic, mitochondrial, golgi or nuclear membranes; in the nuclear matrix; or in cellular organelles and their extracts including but not limited to ribosomes, nuclei, nucleoli, mitochondria, or golgi. Assays for endogenous expression of mRNAs or proteins encoded by the genes of this invention can be performed as described above. Alternatively, intact transgenic animals can be generated for ligand screening. Animals can be genetically manipulated to express the promoters of one, two or more of the genes of this invention linked to one or more reporters such as X-gal. After treatment of the animals with the test unknown ligands, expression of galactosidase can be measured calorimetrically in normal or malignant progesterone target organs, or tissues containing PRs, or in organs or tissues during development. Ligands that activate through either PR-A or PR-B can be identified by their ability to regulate the appropriate selective gene promoter.

The method of the present invention includes a step of comparing the results of detecting the expression of the one or more downstream genes in the presence and in the absence of the putative regulatory ligand, in order to determine whether any observed change in expression is due to the presence of the putative regulatory compound. The step of comparing further includes comparing the expression of the one or more downstream genes detected in the presence of the ligand to the manner of expression of the genes that is associated with the activation of the progesterone receptor when the receptor is activated (described in detail below). As discussed above, the present inventors have identified the expression profile of multiple genes that are regulated by PR, including the manner in which the genes are regulated (i.e., by which PR isoform, and in which direction by such isoform). Therefore, one can determine whether the contact of the receptor with the putative ligand results in a profile of gene expression that is substantially similar to the profile of gene expression of an activated PR (i.e., agonist action), or whether contact of the receptor with the putative ligand results in a profile of gene expression that is an inhibition, or reversal, of the profile of gene expression of an activated PR (i.e., antagonist action). According to the present invention, a putative test ligand is determined to be a regulator of PR if the expression of the gene or genes detected after contact of the PR with the ligand is statistically significantly altered (i.e., up or down) from the expression detected in the profile of a PR that has been activated by progesterone, or an equivalent agonist. The expression profiles for the genes in Tables 1–19 were determined by evaluating PR that had been activated by progesterone after 6 hours.

A PR agonist is identified by detecting an expression profile in the presence of the agonist that, at a minimum, regulates the expression of the gene in the same direction (i.e, upregulation or downregulation) as it is regulated by an activated progesterone receptor (e.g., the manner of expression of the gene as indicated in Tables 1–7, 9–15 or 18 and 19). More specifically, and by way of example, detection of the regulation of the expression of the gene in the "manner" associated with the activation of the PR (i.e., the natural activation of the PR), at a minimum, refers to the detection of the upregulation of a gene that has now been shown by the present inventors to be selectively upregula3ted by PR-A (genes in Tables 1 and 9) when the receptor is in the presence of the putative agonist, as compared to in the absence of the putative agonist. Similarly, an agonist is identified when the expression of a gene from Tables 2 or 10 is detected to be downregulated in the presence of the putative agonist as compared to in the absence of the agonist. Such downregulation also indicates that, at a minimum, the agonist regulated the PR-A isoform. In a preferred embodiment, the agonist regulates the expression of the gene in the same direction and to at least about 10%, and more preferably at least 20%, and more preferably at least 25%, and more preferably at least 30%, and more preferably at least 35%, and more preferably at least 40%, and more preferably at least 45%, and more preferably at least 50%, and preferably at least 55%, and more preferably at least 60%, and more preferably at least 65%, and more preferably at least 70%, and more preferably at least 75%, and more preferably at least 80%, and more preferably at least 85%, and more preferably at least 90%, and more preferably at least 95%, of the level of expression that is induced by a progesterone receptor that has been activated by progesterone. In a particularly preferred embodiment, an agonist regulates the expression of the gene in the same direction and to a level of expression that is substantially equal to or greater than the level of expression that is induced by a progesterone receptor that has been activated by progesterone. The level of expression is determined with reference to the expression of the gene in the absence of the putative regulatory compound, or in the absence of progesterone, in the case of the control. The level of expression is then compared to the level of expression of the control, or the level of expression that is expected from the control.

A PR antagonist is identified by detecting an expression profile in the presence of the antagonist that, at a minimum, regulates the expression of the gene in the opposite direction (i.e, upregulation instead of downregulation) than the gene is regulated by an activated progesterone receptor (e.g., the manner of expression of the gene as indicated in Tables 1–7, 9–15 or 18 and 19), or causes a statistically significant reduction in the expression level of the gene as compared to the expression level of the gene when it is activated by progesterone, or prevents the regulation of the gene as compared to the regulation of the gene when the receptor is activated by progesterone. In the antagonist screening embodiments, the putative antagonists are screened against a PR that is activated, and so in the absence of the putative antagonist, the expression profile of the genes should be substantially the same as the expression profile set forth in Tables 1–7, 9–15 and 18–19). Therefore, any statistically significant decrease (inhibition) in the expression level of the gene or a reversal of the direction of expression of the gene in the presence of the putative antagonist as compared to in the absence of the antagonist, indicates that the putative ligand is an antagonist. In a preferred embodiment, the antagonist inhibits the expression of the detected gene by at least 5%, and more preferably at least 10%, and more preferably at least 15%, and more preferably at least 20%, and more preferably at least 25%, and more preferably at least 30%, and more preferably at least 40%, and more preferably at least 50%, and more preferably at least 60%, and more preferably at least 70%, and more preferably at least 80%, and more preferably at least 90%, as compared to the level of expression that is induced by the activated progesterone receptor in the absence of the putative antagonist. In one embodiment, an antagonist regulates the expression of the gene in the opposite direction (i.e., reverses the expression) as compared to the expression of the gene induced by the activated progesterone receptor in the absence of the putative antagonist.

It will be appreciated by those of skill in the art that differences between the expression of genes regulated by the putative ligand (via the PR) and the expression of genes regulated by the natural ligand (via the PR) may be small or large. Some small differences may be very reproducible and therefore the ligand identified by the method can be useful. For other purposes, large differences may be desirable for ease of detection of the regulatory activity. It will be therefore appreciated that the exact boundary between what is called an agonist and what is called an antagonist can shift, depending on the goal of the screening assay. For some assays it may be useful to set threshold levels of change. For other purposes the putative antagonist ligand may simply have a lower level of activity than an agonist ligand (e.g. a test ligand having 10% of the activity of an agonist can be an antagonist of that agonist). This may depend on the technique being used for detection as well as on the number of genes which are being tested. One of skill in the art can readily determine the criteria for selection of suitable antagonists.

Given the knowledge of the gene expression profiles of the present invention as set forth in Tables 1–7, 9–15 and 18–19, one of skill in the art can, for the first time, identify isoform-specific regulators of progesterone receptors. Therefore, one embodiment of the present invention relates to a method to identify isoform-specific agonists of progesterone receptors. This method includes the steps of: (a) contacting a progesterone receptor with a putative agonist ligand, wherein the progesterone receptor is selected from the group consisting of progesterone receptor A (PR-A) and progesterone receptor B (PR-B), under conditions wherein in the absence of the putative agonist ligand, the progesterone receptor is not activated; (b) detecting expression of at least one gene that is selectively regulated by the progesterone receptor when the progesterone receptor is activated, and (c) comparing the expression of the at least one gene in the presence and in the absence of the putative agonist ligand. In this embodiment, the at least one gene is selected from the group consisting of: (i) at least one gene that is exclusively upregulated or downregulated by PR-A, chosen from a Table selected from the group consisting of Table 1 and Table 2; and, (ii) at least one gene that is exclusively upregulated or downregulated by PR-B chosen from a Table selected from the group consisting of Table 3 and Table 4. Detection of regulation of the expression of the at least one gene in the manner associated with activation of the progesterone receptor as set forth in (i) but not (ii), indicates that the putative agonist ligand is a PR-A-specific agonist, and wherein detection of regulation of the expression of the at least one gene in the manner associated with activation of the progesterone receptor as set forth in (ii) but not (i), indicates that the putative agonist ligand is a PR-B-specific agonist.

Another embodiment of the present invention relates to a method to identify isoform-specific antagonists of progesterone receptors, comprising: (a) contacting a progesterone receptor with a putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (b) detecting expression of at least one gene that is regulated by the progesterone receptor when the progesterone receptor is activated; and (c) comparing the expression of the at least one gene in the presence and in the absence of the putative antagonist ligand. In this embodiment, the at least one gene is selected from the group consisting of: (i) at least one gene that is exclusively upregulated or downregulated by PR-A, chosen from a Table selected from the group consisting of Table 1 and Table 2; and, (ii) at least one gene that is exclusively upregulated or downregulated by PR-B chosen from a Table selected from the group consisting of Table 3 and Table 4. In the presence of the putative antagonist ligand, detection of inhibition or reversal of the regulation of expression of the at least one gene as compared to the regulation of expression of the at least one gene in the manner associated with activation of the progesterone receptor as set forth in (i) but not (ii), indicates that the putative antagonist ligand is a PR-A-specific antagonist, and wherein, in the presence of the putative antagonist ligand, detection of inhibition or reversal of the regulation of expression of the at least one gene as compared to the regulation of the expression of the at least one gene in the manner associated with activation of the progesterone receptor as set forth in (ii) but not (i), indicates that the putative antagonist ligand is a PR-B-specific antagonist.

Given the knowledge of the genes regulated exclusively by progesterone receptor isoforms according to the present invention, one of skill in the art will be able to select one or more genes to detect in a method of the present invention, and the selection of the one or more genes can be determined by different factors. For example, one of skill in the art may wish to further select genes to be detected on the basis of the function of the gene or gene product, on the basis of tissue-type in which a PR is expressed, on the basis of association with a particular condition or disease, or on the basis of the change in the level of expression of the gene when in the presence of progesterone. Such embodiments have generally been described above.

Antiprogestins that selectively inhibit progestin effects on only one of the two PRs, would be highly desirable, but do not exist at present. Such antagonist ligands would be useful not only for breast cancer treatment, but to treat a variety of reproductive disorders, and for contraception. Antagonists that can inhibit only PR-A without affecting PR-B (and vice-versa) would be highly desirable. The current invention allows for rapid and direct screening for such ligands. For example, the invention identifies clusters of genes that are upregulated only by PR-A or PR-B in the presence of the agonist, progesterone. These gene clusters are perfect targets for antiprogestin (antagonist) and progestin (agonist) screening by the cell-free in vitro, intact cell in vitro, or whole animal endogenous or transgenic methods described above. For the embodiment related to antagonists, a selected cluster of one, two or more of the genes of this invention that are exclusively regulated by PR-A or PR-B would first be activated by progesterone or another progestin. Putative antiprogestins would be screened and selected on the basis of their ability to reverse or inhibit the effects of the agonist, progesterone, by comparing the expression profiles of the genes in the presence of the putative antiprogestin to the expression profile of the genes as a result of activation of the receptor with a progestin. Isoform-specific agonists of PRs can be similarly selected by choosing ligands on the basis of their ability to mimic the effects of the agonist, progesterone, on the PR isoforms.

These two embodiments of the present invention take advantage of the knowledge provided herein of the isoform-specific regulation of genes by progesterone receptors. Prior to the present invention, such assays were impossible, because the specific regulation of a gene by one PR isoform, and not the other, was not known. By way of example, if a gene in Table 1 is detected (i.e., a gene that is known to be upregulated selectively (i.e., exclusively, uniquely) by PR-A) when the PR to be tested (at least PR-A or a combination of PR-A and PR-B) is in the presence of a putative regulatory ligand, and the expression of that gene is determined to be in the manner associated with activation of the progesterone receptor (i.e., the gene is upregulated), then it can be concluded that the putative regulatory compound is a PR-A-specific agonist, because the present inventors have shown that the gene is exclusively upregulated by PR-A. Similarly, if a gene in Table 4 is detected (i.e., a gene that is known to be downregulated selectively (i.e., exclusively, uniquely) by PR-B) when the PR to be tested (at least PR-B or a combination of PR-A and PR-B) is in the presence of a putative regulatory ligand, and the expression of that gene is determined to be in the manner associated with activation of the progesterone receptor (i.e., the gene is downregulated), then it can be concluded that the putative regulatory compound is a PR-B-specific agonist, because the present inventors have shown that this particular gene is exclusively downregulated by PR-B. For a putative antagonist, if the same gene in Table 4 is detected when the PR to be tested is or will be activated and is in the presence of the putative antagonist, and the expression of that gene is determined to be inhibited or reversed (i.e., the gene is upregulated or is statistically significantly less downregulated) as compared to the expression of the gene in the manner associated with activation of the progesterone receptor, then it can be concluded that the putative regulatory compound is a PR-B-specific antagonist, because the present inventors have shown that this particular gene is exclusively downregulated by PR-B.

The particular details relating to the contacting, detecting and comparing steps of the above-described methods for identification of PR isoform-specific ligands are substantially the same as those described above for the broader methods of identifying PR regulatory ligands and will not be repeated here.

Agonists and antagonists of progesterone receptors identified by the above methods or any other suitable method are useful in a variety of therapeutic methods as described herein.

Yet another embodiment of the present invention relates to a method to identify a tissue-specific agonist of a progesterone receptor. This method includes the steps of: (a) providing an expression profile for at least one gene that is known to be regulated by a progesterone receptor in both a first and second tissue type when the progesterone receptor is activated, wherein the at least one gene is chosen from the genes in any one or more of the genes in Tables 1–7; (b) contacting a progesterone receptor expressed by a first tissue type with a putative agonist ligand, wherein the progesterone receptor is selected from the group consisting of progesterone receptor A (PR-A) and progesterone receptor B (PR-B), under conditions wherein, in the absence of the putative agonist ligand, the progesterone receptor is not activated; (c) contacting a progesterone receptor expressed by a second tissue type with the putative agonist ligand under conditions wherein, in the absence of the putative agonist ligand, the progesterone receptor is not activated, wherein the progesterone receptor is the same isoform as the progesterone receptor contacted in (b); (d) detecting expression of the at least one gene from (a); and, (e) comparing the expression of the at least one gene in the presence and in the absence of the putative agonist ligand in each of the first and second tissue types. Detection of regulation of the expression of the at least one gene in one of the first or second tissue types in the manner associated with activation of the progesterone receptor as set forth in the expression profile of (a), and detection of inhibition of regulation or no regulation of the at least one gene in the other of the first or second tissue types, as compared to the expression of the at least one gene associated with activation of the progesterone receptor as set forth in the expression profile of (a), indicates that the putative agonist ligand is a tissue-specific progesterone receptor agonist.

Similarly, another embodiment of the present invention relates to a method to identify a tissue-specific agonist of a progesterone receptor, such method comprising: (a) providing an expression profile for at least one gene that is known to be regulated by a progesterone receptor in a first tissue type but not a second tissue type when the progesterone receptor is activated, wherein the at least one gene is chosen from the genes in any one or more of the genes in Tables 1–7; (b) contacting a progesterone receptor expressed by the first tissue type with a putative agonist ligand, wherein the progesterone receptor is selected from the group consisting of progesterone receptor A (PR-A) and progesterone receptor B (PR-B), under conditions wherein, in the absence of the putative agonist ligand, the progesterone receptor is not activated; (c) detecting expression of the at least one gene from (a); (d) comparing the expression of the at least one gene in the presence and in the absence of the putative agonist ligand in the first tissue type, wherein detection of regulation of the expression of the at least one gene in the first tissue type in the manner associated with activation of the progesterone receptor as set forth in the expression profile of (a) indicates that the putative agonist ligand is a tissue-specific progesterone receptor agonist for the first tissue type. In this embodiment, it is desirable to include additional controls or the detection of multiple genes that confirm that the regulation of the PR by the putative regulatory ligand is tissue-specific.

Another embodiment of the present invention relates to a method to identify a tissue-specific antagonist of a progesterone receptor. This method includes the steps of: (a) providing an expression profile for at least one gene that is known to be regulated by a progesterone receptor in both a first and second tissue type when the progesterone receptor is activated, wherein the at least one gene is chosen from the genes in any one or more of the genes in Tables 1–7; (b) contacting a progesterone receptor expressed by a first tissue type with a putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (c) contacting a progesterone receptor expressed by a second tissue type with the putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (d) detecting expression of the at least one gene from (a); and, (e) comparing the expression of the at least one gene in the presence and in the absence of the putative antagonist ligand in each of the first and second tissue types, wherein detection of regulation of the expression of the at least one gene in one of the first or second tissue types in the manner associated with activation of the progesterone receptor as set forth in the expression profile of (a) in the presence of the putative antagonist ligand, and detection of inhibition or reversal of regulation of expression of the at least one gene in the other of the first or second tissue types in the presence of the putative antagonist ligand, as compared to the expression of the at least one gene associated with activation of the progesterone receptor as set forth in the expression profile of (a), indicates that the putative antagonist ligand is a tissue-specific progesterone receptor antagonist.

Similarly, another embodiment of the present invention relates to a method to identify a tissue-specific antagonist of a progesterone receptor, such method including the steps of: (a) providing an expression profile for at least one gene that is known to be regulated by a progesterone receptor in a first but not in a second tissue type when the progesterone receptor is activated, wherein the at least one gene is chosen from the genes in any one or more of the genes in Tables 1–7; (b) contacting a progesterone receptor expressed by a first tissue type with a putative antagonist ligand, wherein the progesterone receptor is selected from the group consisting of progesterone receptor A (PR-A) and progesterone receptor B (PR-B), under conditions wherein, in the absence of the putative antagonist ligand, the progesterone receptor is activated; (c) detecting expression of the at least one gene from (a); and, (d) comparing the expression of the at least one gene in the presence and in the absence of the putative antagonist ligand in the first tissue type, wherein detection of inhibition or reversal of regulation of expression of the at least one gene in the first tissue type in the presence of the putative antagonist ligand, as compared to the expression of the at least one gene associated with activation of the progesterone receptor as set forth in the expression profile of (a), indicates that the putative antagonist ligand is a tissue-specific progesterone receptor antagonist of the first tissue type. In this embodiment, it is desirable to include additional controls or the detection of multiple genes that confirm that the regulation of the PR by the putative regulatory ligand is tissue-specific.

In one aspect of any of the above-described embodiments for identifying a tissue-specific regulator of PR activity, the first tissue type is breast, and at least one gene is selected from the group consisting of any one or more of the genes in Tables 1–7. In general, the first or second tissue type can be any tissue type, including any cell type, that expresses a progesterone receptor. For example, tissues that are known to express progesterone receptors include, but are not limited to, breast, uterus, bone, cartilage, cardiovascular tissues, heart, lung, brain, meninges, pituitary, ovary, oocyte, corpus luteum, oviduct, fallopian tubes, T lymphocytes, B lymphocytes, thymocytes, salivary gland, placenta, skin, gut, pancreas, liver, testis, epididymis, bladder, urinary tract, eye, and teeth.

In another aspect, the first tissue type is a non-malignant tissue and wherein the second tissue type is a malignant tissue from the same tissue source as the first tissue type. A preferred tissue source for screening for regulators of malignant tissue but not non-malignant tissue is breast tissue.

In another aspect, the first tissue type is a normal tissue and wherein the second tissue type is a non-malignant, abnormal tissue. Such tissues include, but are not limited to, tissues from endometriosis and leiomyoma of the uterus, fibrocystic disease of the breast, or polycystic ovary.

In one aspect of the tissue-specific methods of the present invention, the method includes the detection of the any one or more of the following genes: 11-beta-hydroxysteroid dehydrogenase type 2, tissue factor gene, PCI gene (plasminogen activator inhibitor 3), MAD-3 Ikβ-alpha, Niemann-Pick C disease (NPC1), platelet-type phosphofructokinase, phenylethanolamine n-methyltransferase (PNMT), transforming growth factor-beta 3 (TGF-beta3), Monocyte Chemotactic Protein 1, delta sleep inducing peptide (related to TSC-22), estrogen receptor-related protein (hERRa1). These genes are of particular interest when one of the tissue types is the endometrium.

In another aspect of the tissue-specific methods of the present invention, the method includes the detection of the any one or more of the following genes: growth arrest-specific protein (gas6), tissue factor gene, NF-IL6-beta (C/EBPbeta), PCI gene (plasminogen activator inhibitor), Stat5A, calcium-binding protein S100P, MSX-2, lipocortin II (calpactin I), selenium-binding protein (hSBP), and bullous pemphigoid antigen (plakin family). These genes are of particular interest when one of the tissue types is the breast.

In another aspect of the tissue-specific methods of the present invention, the method includes the detection of phenylethanolamine n-methyltransferase (PNMT) adrenal medulla. This gene is of particular interest when one of the tissue types is brain tissue.

In another aspect of the tissue-specific methods of the present invention, the method includes the detection of proteasome-like subunit MECL-1. This gene is of particular interest when one of the tissue types is thymus tissue.

In yet another aspect of these methods, the expression profile of genes regulated by a progesterone receptor in the first or second tissue type is provided by a method comprising: (a) providing a first cell of a selected tissue type that expresses a progesterone receptor A (PR-A) and not a progesterone receptor B (PR-B) and a second cell of the same tissue type that expresses PR-B and not PR-A; (b) stimulating the progesterone receptors in (a) by contacting the first and second cells with a progesterone receptor stimulatory ligand; (c) detecting expression of genes by the first and second cells in the presence of the stimulatory ligand and in the absence of the stimulatory ligand, wherein a difference in the expression of a gene in the presence of the stimulatory ligand as compared to in the absence of the stimulatory ligand, indicates that the gene is regulated by the progesterone receptor in the selected tissue type.

The present invention defines genes that are regulated by PR-A vs. PR-B in breast cancer cells. It is believed that many, if not most of these genes, will also be regulated by progesterone receptors in other tissues. Similar data can be generated for other tissues, including the uterus, bone, cardiovascular tissues, etc., or malignant vs. normal tissues. Progestin regulated genes in other tissues, which differ from the genes in breast cancer cells of this invention, can be identified, and be used to screen for ligands that regulate candidate genes only in the desired tissue. For example, using the appropriate gene clusters, one could identify a ligand that activates PR-A in the uterus but not the breast. Similarly one could screen out ligands that have undesirable organ or tissue effects. For example, ligands that are inadvertently bioactive in the liver, where they might induce liver toxicity, could be discarded. Alternatively, when a gene is regulated in both tissue types, one can screen for ligands that regulate the expression of the gene in one tissue type, but not the other tissue type. For example, by using tissue specific methods described above, it is also possible to screen for antagonists that block the actions of progestins in one organ or tissue and through one PR isoform, but not another organ or tissue and the other PR isoform. For example, if PR-A are "good" receptors in the uterus but not the breast, a selective "antiprogestin-A" might be found that is only inhibitory in the breast.

Given the guidance provided herein, it is within the ability of those of skill in the art to screen other tissue types for the presence or absence of the genes regulated by PR in breast tissue, and/or to perform a de novo screening assay for the identification of genes regulated by PR in another tissue, to develop gene expression profiles for use in screening for tissue specific ligands. One of skill in the art can now look to see if a given gene that is regulated by PR in breast is also regulated by PR in another tissue type, thereby providing a gene profile for use in the tissue-specific ligand identification methods of the present invention.

The particular details relating to the contacting, detecting and comparing steps of the above-described methods for identification of PR isoform-specific ligands are substantially the same as those described above for the broader methods of identifying PR regulatory ligands and will not be repeated here.

Another method of the present invention relates to a method to identify genes that are regulated by a progesterone receptor in two or more tissue types. The method includes the steps of: (a) activating a progesterone receptor in two or more tissue types that express the progesterone receptor; (b) detecting expression of at least one gene in the two or more tissue types, the at least one gene being chosen from a gene in any one or more of Tables 1–7, and, (c) identifying genes that are regulated by the progesterone receptor in each of the two or more tissue types. In one embodiment, the method further includes detecting whether the genes are regulated selectively by PR-A, selectively by PR-B, or by both PR-A and PR-B. This method can generally be used to provide a profile of genes in a tissue type other than breast. Such a profile can then be used in a method for the identification of tissue-specific progesterone receptor ligands as described above, or in a method of determining a profile of genes for a given tissue sample as described below.

Yet another embodiment of the present invention relates to a method to determine the profile of genes regulated by progesterone receptors in a tissue sample. In a preferred embodiment, the sample is a breast tumor sample. This method includes the steps of: (a) obtaining from a patient a breast tumor sample; (b) detecting expression of at least one gene in the breast tumor sample that is regulated by a progesterone receptor when the progesterone receptor is activated; and, (c) producing a profile of genes for the tumor sample that are regulated selectively by PR-A, selectively by PR-B, or by both PR-A and PR-B. In this embodiment, the gene(s) to be profiled are being selected from the group consisting of: (i) at least one gene that is selectively upregulated by PR-A chosen from a gene in Table 9; (ii) at least one gene that is selectively downregulated by PR-A chosen from a gene in Table 10; (iii) at least one gene that is selectively upregulated by PR-B chosen from a gene in Table 11; (iv) at least one gene that is selectively downregulated by PR-B chosen from a gene in Table 12; (v) at least one gene that is upregulated or downregulated by both PR-A and PR-B chosen from a gene in Table 13; (vi) at least one gene that is reciprocally regulated by PR-A and PR-B chosen from a gene in Table 14; and, (vii) at least one gene that is regulated by one of the PR-A or the PR-B, wherein regulation of the gene is altered when the other of the PR-A or PR-B is expressed by the same cell, chosen from a gene in Table 15.

Because of their physiological importance in the breast, PRs are routinely measured in all breast cancers when the disease is first diagnosed. Presence of PRs, especially if the levels are high, informs the oncologist that the tumor is likely to be “hormone-dependent” and will respond to endocrine treatments. This spares the woman from much harsher treatments involving chemotherapies. Additionally, the number of PRs allows the oncologist to predict how aggressive the tumor is likely to be. High PR levels in her tumor indicates that a woman’s prognosis is good. Thus measurement of total PRs levels plays a key role in the management of breast cancers.

Both PR-A and PR-B are present in PR-positive breast cancers. The PR-A:PR-B ratio varies widely from tumor to tumor, and some tumors express only one or the other isoform. However, the clinical consequences of this heterogeneity are unknown. Because the transcriptional effects of the two PRs are believed to be so different, fluctuations in their ratio are expected to critically influence the biology of the tumors. However, at present, how that biology is affected is unknown. Whether in fact, PR-A are “bad” and PR-B are “good” in breast cancers, is also unknown. Since most breast cancer cell lines lose their PRs, and both isoforms are co-expressed in cell lines that retain their PRs, one way to determine the biological consequences of varying A:B ratios is to define the endogenous genes that each of the two PRs regulates independently. Knowledge of the unique sets of genes that are selectively regulated by each PR isoform as disclosed herein allows the genes to serve as surrogate markers for the presence and function of PR-A vs. PR-B. Furthermore, knowledge of such genes and their promoters, allows the genes to serve as a tool for screening PR-A vs. PR-B selective ligands. However, prior to the present invention, defining which sets of genes were uniquely regulated by one or the other PR in breast cancers was impossible because both receptors are simultaneously activated by progesterone treatment. The present invention has provided a solution to this problem.

As discussed above, total PRs are routinely measured in all primary breast cancers as a guide to therapy. Their presence and levels are used to predict whether the tumor is likely to respond to hormone treatments, and to estimate disease prognosis. Tumors that lack PRs have less than 10% chance of responding to hormone treatments; tumors that contain PRs have on average a 70% chance of responding to hormone treatments depending on the receptor levels. These numbers are statistical only, and therefore are not specifically informative for any individual patient. The present invention has led to the development of assays that profile the tumor of an individual patient for “good” and “bad” surrogate markers of PR-A and PR-B. Thus it is now possible to measure not only the presence of PRs in a tumor, but the function of the PRs in that tumor.

In this embodiment, one or more of the genes set forth in Tables 9–15 are selected to be screened in a tissue sample from a patient. Preferably, the tissue sample is a breast tumor sample. The expression of the genes in the tissue sample can be detected using techniques described above for the various other methods of the present invention. For example, transcript expression levels of the selected genes can be measured in the tumor of a patient, by any of a number of known methods. For mRNA expression, methods include but are not limited to: northern blotting; reverse transcriptase—polymerase chain reaction and detection of the product; use of labeled mRNA from the tumor to probe cDNAs or oligonucleotides encoding all or part of the PR-responsive genes of interest, arrayed on any of a variety of surfaces, as described above. For detection of protein expression levels of the selected genes, methods include but are not limited to: western blotting, immunocytochemistry, flow cytometry or other immunologic-based assays; assays based on a property of the protein including but not limited to DNA binding, ligand binding, or interaction with other protein partners, as described above. The presence and quantity of each gene marker can be measured in primary tumors, metastatic tumors, locally recurring tumors, ductal carcinomas in situ, or other tumors of breast cell origin. The markers can be measured in solid tumors that are fresh, frozen, fixed or otherwise preserved. They can be measured in cytoplasmic or nuclear tumor extracts; or in tumor membranes including but not limited to plasma, mitochondrial, golgi or nuclear membranes; in the nuclear matrix; or in tumor cell organelles and their extracts including but not limited to ribosomes, nuclei, mitochondria, golgi.

A profile of individual gene markers, including a matrix of two or more markers, can be generated by one or more of the methods described above. According to the present invention, a profile of the genes regulated by progesterone receptors in a tissue sample refers to a reporting of the expression level of a given gene from Tables 9–15, wherein, based on the knowledge of the regulation of the genes provided by Tables 9–15, includes a classification of the gene with regard to how the gene is regulated by the PR isoforms. For example, if the gene, estrogen receptor-related protein, is identified as being expressed by a tumor sample, the profile for the tumor will include the reporting of the expression of at least one gene that is exclusively regulated by PR-A. The data can be reported as raw data, and/or statistically analyzed by any of a variety of methods, and/or combined with any other prognostic marker(s) including but not limited to ER, % S-phase, other proliferation markers, markers of ER expression, tumor suppressor genes, etc. Prior to the present invention, one of skill in the art would not have known to screen breast tumors for the genes in Tables 1–7, 9–10 or 18–19, (excepting genes in Table 16), and one of skill in the art would not have been able to classify any of these genes on the basis of the PR isoform regulation.

Given the knowledge of the genes regulated by progesterone receptor isoforms according to the present invention, one of skill in the art will be able to select one or more genes to detect in this method of the present invention, and the selection of the one or more genes can be determined by different factors. For example, one of skill in the art may wish to further select genes to be detected on the basis of the function of the gene or gene product, on the basis of PR isoform-specificity, on the basis of association with a particular condition or disease, or on the basis of the change in the level of expression of the gene when in the presence of progesterone. Such embodiments have generally been described above.

In one aspect of this method of the present invention, the method preferably includes the detection of the any one or more of the following genes: growth arrest-specific protein (gas6), tissue factor gene, NF-IL6-beta (C/EBPbeta), PCI gene (plasminogen activator inhibitor), Stat5A, calcium-binding protein S100P, MSX-2, lipocortin II (calpactin I), selenium-binding protein (hSBP), and bullous pemphigoid antigen (plakin family). These genes are of particular interest when one of the tissue types is the breast.

In another aspect of this method of the present invention, the method preferably includes the detection of the any one of more of the following genes: growth arrest-specific protein (gas6), NF-IL6-beta (C/EBPbeta), calcium-binding protein S100P, MSX-2, selenium-binding protein (hSBP), and bullous pemphigoid antigen (plakin family).

The profile of genes provided as a result of the screening of the tissue can be used by the patient or physician for decision-making regarding the usefulness of endocrine therapies in general (i.e. oophorectomy, antiestrogens or other SERMs, aromatase inhibitors, or others), or progestational therapy in particular (high dose progestins, anti-progestins or others). The profile can be used to estimate how the disease is likely to respond and progress in any individual patient. Clinical trials can be developed to correlate the relationship between PR-A vs. PR-B regulated genes, and the biological behavior of the tumor.

In addition, if it is determined that one PR isoform is harmful, and the other beneficial, the gene clusters of this invention can be measured or quantified in normal breast or other normal tissues, either frozen or preserved, or in tissue or organelle extracts as described above, either alone or together with other markers (for example BRCA1), and used for genetic counseling.

In addition, one of the key questions that the present invention can address, is whether breast tumors that overexpress PR-B or PR-A represent phenotypically different tumor subsets. For example, breast tumors that are identified as "PR-B rich" based on their expression of PR-B specific genes, can be further assessed in terms of usual clinical parameters—tumor staging, pathological staging, size, nodal status, metastasis, responsiveness to hormonal and chemotherapies—and compared to parallel tumors that are "PR-A rich". Without being bound by theory, the present inventors predict that PR-B rich tumors may be larger and more aggressive than PR-A rich tumors. One reason for this is that this invention demonstrates that PR-B strongly and uniquely upregulate two important genes that support angiogenesis: L13720, growth arrest-specific protein (gas 6) is increased 23.1 fold; M27436, tissue factor gene is increased 18.1 fold. Increased angiogenesis, by increasing their blood (and nutrient) supply, promotes tumor growth. This is one example of the hypotheses that can be raised and tested, based on the new information revealed by this invention.

In one aspect of this embodiment of the invention, the profiling of genes can be extended to other tissue types and/or other genes. For example, as discussed above, using the guidance provided herein, it is within the ability of those of skill in the art to screen other tissue types for the presence or absence of the genes regulated by PR in breast tissue, and/or to perform a de novo screening assay for the identification of genes regulated by PR in another tissue, to develop gene expression profiles for use in screening for tissue specific ligands. One of skill in the art can now look to see if a given gene that is regulated by PR in breast is also regulated by PR in another tissue type. Moreover, the 4 breast cancer cell lines described in Example 1, can be used to screen other gene arrays, including arrays of expressed tag sequences, to discover additional novel, PR-A vs. PR-B regulated genes. The procedure used to produce these cells can be extended to cells from other tissue sources (e.g., the uterus), and new PR-A and PR-B regulated genes can be identified for these tissue sources. Additional applications of the present invention include screening for genes that are regulated by PRs in a ligand-independent manner. The extension of the gene profiles to other tissue types will allow for the development of a variety of diagnostic assays in other tissues and for diseases related to such other tissues, as well as the identification of additional targets for therapeutic strategies.

Another embodiment of the present invention relates to a plurality of polynucleotides for the detection of the expression of genes regulated by progesterone receptors in breast tissue. The plurality of polynucleotides consists of polynucleotide probes that are complementary to RNA transcripts, or nucleotides derived therefrom, of genes that are regulated by progesterone receptors, and is therefore distinguished from previously known nucleic acid arrays and primer sets. The plurality of polynucleotides within the above-limitation includes at least one or more, but is not limited to one or more, polynucleotide probes that are complementary to RNA transcripts, or nucleotides derived therefrom, of genes identified by the present inventors. Such genes are selected from: (a) at least one gene that is selectively upregulated by PR-A chosen from a gene in Table 1; (b) at least one gene that is selectively downregulated by PR-A chosen from a gene in Table 2; (c) at least one gene that is selectively upregulated by PR-B chosen from a gene in Table 3; (d) at least one gene that is selectively downregulated by PR-B chosen from a gene in Table 4; (e) at least one gene that is upregulated or downregulated by both PR-A and PR-B chosen from a gene in Table 5; (f) at least one gene that is reciprocally regulated by PR-A and PR-B chosen from a gene in Table 6; and, (g) at least one gene that is regulated by one of the PR-A or the PR-B, wherein regulation of the gene is altered when the other of the PR-A or PR-B is expressed by the same cell, chosen from a gene in Table 7.

In one embodiment, it is contemplated that additional genes that are not regulated by progesterone receptors can be added to the plurality of polynucleotides. Such genes would not be random genes, or large groups of unselected human genes, as are commercially available now, but rather, would be specifically selected to complement the sets of progesterone receptor-regulated genes identified by the present invention. For example, one of skill in the art may wish to add to the above-described plurality of genes one or more genes that are of relevance because they are expressed by a particular tissue of interest (e.g., breast tissue), are associated with a particular disease or condition of interest (e.g., breast cancer), or are associated with a particular cell, tissue or body function (e.g., angiogenesis). The development of additional pluralities of polynucleotides (and antibodies, as disclosed below), which include both the above-described plurality and such additional selected polynucleotides, are explicitly contemplated by the present invention.

In one embodiment, the plurality of polynucleotides further comprises at least one polynucleotide probe that is complementary to RNA transcripts, or nucleotides derived therefrom, of at least one gene chosen from the genes in Table 8. In another embodiment, the plurality of polynucleotides comprises polynucleotide probes that are complementary to RNA transcripts, or nucleotides derived therefrom, of particular subsets of the genes disclosed in the present invention. For example, one of skill in the art may wish to design pluralities of polynucleotides on the basis of the function of the gene or gene product, on the basis of a tissue-type that expresses a PR, on the basis of PR isoform specificity, on the basis of association with a particular condition or disease, or on the basis of the change in the level of expression of the gene when in the presence of progesterone. Such embodiments have generally been described above.

According to the present invention, a plurality of polynucleotides refers to at least 2, and more preferably at least 3, and more preferably at least 4, and more preferably at least 5, and more preferably at least 6, and more preferably at least 7, and more preferably at least 8, and more preferably at least 9, and more preferably at least 10, and so on, in increments of one, up to any suitable number of polynucleotides, including at least 100, 500, 1000, $10^4$, $10^5$, or at least $10^6$ or more polynucleotides.

In accordance with the present invention, an isolated polynucleotide, or an isolated nucleic acid molecule, is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. The polynucleotides useful in the plurality of polynucleotides of the present invention are typically a portion of a gene of the present invention that is suitable for use as a hybridization probe or PCR primer for the identification of a full-length gene (or portion thereof) in a given sample (e.g., a cell sample). An isolated nucleic acid molecules can include a gene or a portion of a gene (e.g., the regulatory region or promoter), for example, to produce a reporter construct according to the present invention. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis. If the polynucleotide is an oligonucleotide probe, the probe preferably ranges from about 5 to about 50 or about 500 nucleotides, more preferably from about 10 to about 40 nucleotides, and most preferably from about 15 to about 40 nucleotides in length.

In one embodiment, the polynucleotide probes are conjugated to detectable markers. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads.TM.), fluorescent dyes (e.g., fluorescein, texas red, rhodamine, green fluorescent protein, and the like), radiolabels (e.g., $^{3}H$, $^{125}I$, $^{35}S$, $^{14}C$ or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Preferably, the polynucleotide probes are immobilized on a substrate.

In one embodiment, the polynucleotide probes are hybridizable array elements in a microarray or high density array. Nucleic acid arrays are well known in the art and are described for use in comparing expression levels of particular genes of interest, for example, in U.S. Pat. No. 6,177,248, which is incorporated herein by reference in its entirety. Nucleic acid arrays are suitable for quantifying a small variations in expression levels of a gene in the presence of a large population of heterogeneous nucleic acids. Knowing the identity of the downstream genes of the present invention, nucleic acid arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. It is noted that all of the genes identified by the present invention have been previously sequenced, at least in part, such that oligonucleotides suitable for the identification of such nucleic acids can be produced. The database accession number for each of the genes identified by the present inventors is provided in the tables of the invention. Suitable nucleic acids are also produced by amplification of template, such as by polymerase chain reaction or in vitro transcription.

Synthesized oligonucleotide arrays are particularly preferred for this aspect of the invention. Oligonucleotide arrays have numerous advantages, as opposed to other methods, such as efficiency of production, reduced intra- and inter array variability, increased information content and high signal-to-noise ratio.

One of skill in the art will appreciate that an enormous number of array designs are suitable for the practice of this invention. An array will typically include a number of probes that specifically hybridize to the sequences of interest. In addition, in a preferred embodiment, the array will include one or more control probes. The high-density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiments, test probes are double or single strand DNA sequences. DNA sequences are isolated or cloned from natural sources or amplified from natural sources using natural nucleic acids as templates, or produced synthetically. These probes have sequences complementary to particular subsequences of the genes whose expression they are designed to detect. Thus, the test probes are capable of specifically hybridizing to the target nucleic acid they are to detect.

Another embodiment of the present invention relates to a plurality of antibodies, or antigen binding fragments thereof, for the detection of the expression of genes regulated by progesterone receptors in breast tissue. The plurality of antibodies, or antigen binding fragments thereof, consists of antibodies, or antigen binding fragments thereof, that selectively bind to proteins encoded by genes that are regulated by progesterone receptors. In addition, the plurality of antibodies, or antigen binding fragments thereof, comprises antibodies, or antigen binding fragments thereof, that selectively bind to proteins encoded by genes selected from the group consisting of: (a) genes that are selectively upregulated by PR-A chosen from genes in Table 1; (b) genes that are selectively downregulated by PR-A chosen from genes in Table 2; (c) genes that are selectively upregulated by PR-B chosen from genes in Table 3; (d) genes that are selectively downregulated by PR-B chosen from genes in Table 4; (e) genes that are upregulated or downregulated by both PR-A and PR-B chosen from genes in Table 5; (f) genes that are reciprocally regulated by PR-A and PR-B chosen from genes in Table 6; and, (g) genes that are regulated by one of the PR-A or the PR-B, wherein regulation of the gene is altered when the other of the PR-A or PR-B is expressed by the same cell, chosen from genes in Table 7.

In one aspect, the plurality of antibodies, or antigen binding fragments thereof, further comprises at least one antibody, or an antigen binding fragment thereof, that selectively binds to a protein encoded by a gene chosen from the genes in Table 8.

The plurality of antibodies, or antigen binding fragments thereof, further comprises at least one antibody, or an antigen binding fragment thereof, that selectively binds to a protein encoded by a one or more of a particular subset of the genes disclosed in the present invention. For example, one of skill in the art may wish to design pluralities of antibodies on the basis of the function of the gene product, on the basis of tissue-type, on the basis of PR isoform specificity, on the basis of association with a particular condition or disease, or on the basis of the change in the level of expression of the gene when in the presence of progesterone. Such embodiments have generally been described above.

According to the present invention, a plurality of antibodies, or antigen binding fragments thereof, refers to at least 2, and more preferably at least 3, and more preferably at least 4, and more preferably at least 5, and more preferably at least 6, and more preferably at least 7, and more preferably at least 8, and more preferably at least 9, and more preferably at least 10, and so on, in increments of one, up to any suitable number of antibodies, or antigen binding fragments thereof, including at least 100, 500, or at least 1000 antibodies, or antigen binding fragments thereof.

According to the present invention, the phrase "selectively binds to" refers to the ability of an antibody, antigen binding fragment or binding partner of the present invention to preferentially bind to specified proteins (e.g., a protein encoded by a PR regulated gene according to the present invention). The phrase "selectively binds" with regard to antibodies and antigen binding fragments thereof, has been defined previously herein.

Limited digestion of an immunoglobulin with a protease may produce two fragments. An antigen binding fragment is referred to as an Fab, an Fab', or an $F(ab')_2$ fragment. A fragment lacking the ability to bind to antigen is referred to as an Fc fragment. An Fab fragment comprises one arm of an immunoglobulin molecule containing a L chain ($V_L$+$C_L$ domains) paired with the $V_H$ region and a portion of the $C_H$ region (CH1 domain). An Fab' fragment corresponds to an Fab fragment with part of the hinge region attached to the CH1 domain. An $F(ab')_2$ fragment corresponds to two Fab' fragments that are normally covalently linked to each other through a di-sulfide bond, typically in the hinge regions.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or $F(ab)_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies maybe produced according to the methodology of Kohler and Milstein (*Nature* 256:495–497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

Finally, PR-regulated genes of this invention, or their RNA or protein products, can serve as targets for therapeutic strategies. For example, neutralizing antibodies could be directed against one of the protein products of a selected gene, expressed on the surface of a tumor cell.

One embodiment of this aspect of the invention relates to a method to regulate the expression of a gene selected from the group consisting of any one or more of the genes in Tables 1–7. The method includes administering to a cell that expresses a progesterone receptor a compound selected from the group consisting of: progesterone, a progestin, and an antiprogestin, wherein the compound is effective to regulate the expression of the gene(s) in Table 1–7. In a preferred embodiment, the gene is selected from the group consisting of genes that are listed in Table 16 (known to be involved in breast cancer or mammary gland development), but not in Table 8 (known to be regulated by progesterone). Such genes include, e.g., growth arrest-specific protein (gas6), NF-IL6-beta (C/EBPbeta), calcium-binding protein S100P, MSX-2, selenium-binding protein (hSBP), and bullous pemphigoid antigen (plakin family). In this aspect of the invention, the cell that expresses a progesterone receptor is in the breast tissue of a patient that has, or is at risk of developing, breast cancer. In addition to administering a progestin to the cell, these genes can serve as targets for the development of other therapeutic methods.

Once a suitable therapeutic compound, including a progesterone receptor agonist or antagonist, is identified using the methods and genes of the present invention, a composition can be formulated. A composition, and particularly a therapeutic composition, of the present invention generally includes the therapeutic compound (e.g., the progesterone receptor regulatory ligand) and a carrier, and preferably, a pharmaceutically acceptable carrier. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably a cell that expresses a progesterone receptor. In some embodiments, a suitable site for delivery is a site of inflammation, a site of a tumor, a site of a transplanted graft, or a site of any other disease or condition in which progesterone receptor regulation, or modulation of genes regulated by a PR, can be beneficial, particularly given the knowledge of the genes regulated by PR according to the invention. Preferred pharmaceutically acceptable carriers are capable of maintaining a steroidal or non-steroidal compound, a protein, a peptide, nucleic acid molecule or mimetic (drug) according to the present invention in a form that, upon arrival of the steroidal or non-steroidal compound, protein, peptide, nucleic acid molecule or mimetic at the cell target in a culture or in patient, the steroidal or non-steroidal compound, protein, peptide, nucleic acid molecule or mimetic is capable of interacting with its target (e.g., a naturally occurring PR or a nucleic acid or protein product of a PR-regulated gene).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), a drug, an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other carriers of the present invention include liquids that, upon administration to a patient, form a solid or a gel in situ. Preferred carriers are also biodegradable (i.e., bioerodible). When the compound is a recombinant nucleic acid molecule, suitable delivery vehicles include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of a compound of the present invention at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is herein referred to as a "delivery vehicle." Delivery vehicles of the present invention are capable of delivering a composition of the present invention to a target site in a patient. A "target site" refers to a site in a patient to which one desires to deliver a composition. For example, a target site can be any cell which is targeted by direct injection or delivery using liposomes, viral vectors or other delivery vehicles, including ribozymes and antibodies. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a compound of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One preferred delivery vehicle of the present invention is a liposome. A liposome is capable of remaining stable in an animal for a sufficient amount of time to deliver a nucleic acid molecule (e.g., an anti-sense nucleic acid molecule that hybridizes to a nucleic acid sequence in a gene for which inhibition is desired) to a preferred site in the animal. A liposome, according to the present invention, comprises a lipid composition that is capable of delivering a nucleic acid molecule described in the present invention to a particular, or selected, site in a patient. A liposome according to the present invention comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule of the present invention can be achieved using methods standard in the art.

A liposome delivery vehicle is preferably capable of remaining stable in a patient for a sufficient amount of time to deliver a nucleic acid molecule or other compound of the present invention to a preferred site in the patient (i.e., a target cell). A liposome delivery vehicle of the present invention is preferably stable in the patient into which it has been administered for at least about 30 minutes, more preferably for at least about 1 hour and even more preferably for at least about 24 hours. A preferred liposome delivery vehicle of the present invention is from about 0.01 microns to about 1 microns in size.

Another preferred delivery vehicle comprises a viral vector. A viral vector includes an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

A composition which includes an agonist or antagonist of a progesterone receptor can be delivered to a cell culture or patient by any suitable method. Selection of such a method will vary with the type of compound being administered or delivered (i.e., steroidal or non-steroidal compound, protein, peptide, nucleic acid molecule, or mimetic), the mode of delivery (i.e., in vitro, in vivo, ex vivo) and the goal to be achieved by administration/delivery of the compound or composition. According to the present invention, an effective administration protocol (i.e., administering a composition in an effective manner) comprises suitable dose parameters and modes of administration that result in delivery of a composition to a desired site (i.e., to a desired cell) and/or in the desired regulatory event (e.g., regulation of the PR receptor biological activity or of the biological activity of a gene that is regulated by PR).

Administration routes include in vivo, in vitro and ex vivo routes. In vivo routes include, but are not limited to, oral, nasal, intratracheal injection, inhaled, transdermal, rectal, and parenteral routes. Preferred parenteral routes can include, but are not limited to, subcutaneous, intradermal, intravenous, intramuscular and intraperitoneal routes. Intravenous, intraperitoneal, intradermal, subcutaneous and intramuscular administrations can be performed using methods standard in the art. Aerosol (inhalation) delivery can also be performed using methods standard in the art (see, for example, Stribling et al., *Proc. Natl. Acad. Sci. USA* 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Direct injection techniques are particularly useful for suppressing graft rejection by, for example, injecting the composition into the transplanted tissue, or for site-specific administration of a compound, such as at the site of a tumor. Ex vivo refers to performing part of the regulatory step outside of the patient, such as by transfecting a population of cells removed from a patient with a recombinant molecule comprising a nucleic acid sequence encoding a protein according to the present invention under conditions such that the recombinant molecule is subsequently expressed by the transfected cell, and returning the transfected cells to the patient. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell.

In the method of the present invention, a therapeutic compound, including agonists and antagonists of progesterone receptors, as well as compositions comprising such compounds, can be administered to any organism, and particularly, to any member of the Vertebrate class, Mammalia, including, without limitation, primates, rodents, livestock and domestic pets. Livestock include mammals to be consumed or that produce useful products (e.g., sheep for wool production). Preferred mammals to protect include humans. Typically, it is desirable to modulate (e.g., regulate (up or down)) progesterone receptor biological activity or the biological activity of a gene regulated by a PR, to obtain a therapeutic benefit in a patient. A therapeutic benefit is not necessarily a cure for a particular disease or condition, but rather, preferably encompasses a result which can include alleviation of the disease or condition, elimination of the disease or condition, reduction of a symptom associated with the disease or condition, prevention or alleviation of a secondary disease or condition resulting from the occurrence of a primary disease or condition, and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment) to reduce the symptoms of the disease. A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

The following examples are provided for the purpose of illustration and are not intended to limit the scope of the present invention.

EXAMPLES

Example 1

The following example describes the identification of genes regulated by progesterone receptors.

Materials and Methods

Cell Culture

Wild-type PR-positive T47Dco breast cancer cell line and its clonal derivatives T47D-Y, T47D-YA and T47D-YB, have been described (Horwitz et al., *Cell* 28, 633–42 (1982); Sartorius et al., *Cancer Res.* 54, 3668–3877 (1994)). Briefly, cells are routinely cultured in 75 $cm^2$ plastic flasks and incubated in 5% $CO_2$ at 37° C. in a humidified environment. The stock medium consists of Eagle's Minimum Essential Medium with Earle's salts (MEM), containing L-glutamine (292 mg/liter) buffered with sodium bicarbonate (2.2 g/liter), insulin (6 ng/ml) and 5% fetal bovine serum (Hyclone, Logan, Utah) with G418.

Arrays

Atlas™ Human cDNA Expression Array.

T47D-YA and T47D-YB breast cancer cells were grown to mid-confluence in Minimal Essential Medium containing 5% Fetal Calf Serum, then either treated with 10 nM progesterone dissolved in ethanol for 6 or 12 hours, or in ethanol alone. This yielded 4 treatment types. Total RNA was prepared from the 4 sets of cells using guanidinium isothiocyanate, poly$A^+$ RNA was purified with the Oligotex mRNA Kit (Qiagen, Valencia, Calif.), and $^{32}P$-labeled cDNA was synthesized from 1 ug of each sample using SuperScriptII reverse transcriptase (Gibco BRL Life Technologies, Gaithersburg, Md.). Labeled probes were separately hybridized to Atlas™ Human cDNA Expression Arrays (Clontech, Palo Alto, Calif.) consisting of nylon membranes onto which 588 cDNA fragments encoding known proteins were spotted in duplicate. After a high stringency wash, hybridization was detected by autoradiography and phosphoimaging on a Molecular DynamicsPhosphoImager™ (Molecular Dynamics, Sunnyvale, Calif.). Data were analyzed using Atlas™ Image 1.0, and normalized to signals from control housekeeping genes on the same filter. For selected genes, progesterone inducibility and PR-isoform specificity were confirmed by northern blotting, reverse transcriptase-polymerase chain reaction (RT-PCR), and/or western blotting.

Affymetrix GeneChip™ Array.

T47D-Y, T47D-YA and T47D-YB breast cancer cells were grown to mid-confluence in Minimal Essential Medium containing 5% Fetal Calf Serum, then either treated with 10 nM progesterone dissolved in ethanol for 6 hours, or in ethanol alone. This yielded 6 treatment types. Total RNA and poly$A^+$ RNA were prepared from the 6 sets, as described above. First strand cDNA was synthesized from 2 ug of poly$A^+$ RNA using SSII Reverse Transcriptase, the T7dT 24mer, and other components of the Superscript Choice system (Gibco BRL Life Technologies, Gaithersburg, Md.). Following second strand synthesis, the DNA was purified by phenol/chloroform extraction and precipitation, and resuspended in 12 ul DEPC-treated RNase water. 5 ul were used in an in vitro transcription reaction using the EnZo BioArray™ High Yield transcript Labeling Kit (Affymetrix, Inc., Santa Clara, Calif.), to synthesize RNA transcripts and incorporate biotin labeled ribonucleotides. Unincorporated nucleotides were removed with RNeasy affinity columns (Qiagen, Valencia, Calif.). Purified, biotinylated cRNAs were quantified, and 20 ug were subjected to a fragmentation reaction by incubation at 94C for 35 min (Affymetrix™ protocol 700218) to randomly generate fragments ranging from 35 to 200 bases. HuGeneFL Array™ chips consisting of 5,600 full-length human genes from Unigene, Genebank and TIGR databases were used for hybridization. Thirty $\mu l$ of fragmented cRNA were added to a hybridization mixture (100 mM MES, 1M NaCl, 20mMEDTA, and 0.01% Tween 20) and control oligonucleotide B2 and control cRNA cocktail, as described in the Affymetrix™ protocol. Hybridizations and subsequent washes were done in the GeneChip Hybridization Oven and Fluidics Station 400. After overnight hybridization, the solutions were removed, the chips were washed and stained with streptavidin-phycoerythrin. DNA chips were read at a resolution of 6 um with a Hewlett-Packard GeneArray Scanner.

Each gene on the chip is represented by perfectly matched (PM) and mismatched (MM) oligonucleotides from 16–20 regions of each gene. The mismatched probes act as specificity controls, which allow direct subtraction of background and cross-hybridization signals. The number of instances in which the PM hybridization signal is larger that the MM signal is computed along with the average of the logarithm of the PM:MM ratio (after background subtraction) for each probe set. These values were used to arrive at a matrix-based decision concerning the presence or absence of an RNA transcript. Detailed protocols for data analyses of Affymetrix microarrays and extensive documentation of the sensitivity and quantitative aspects of the method have been described. Briefly, the first level of analysis including the "present" or "absent" call, and pairwise comparisons, were done using GeneChip 3.1 Expression Analysis Program™ (Affymetrix, Inc., Santa Clara, Calif.). A second level of analysis to identify clusters of genes regulated by progesterone via PR-A, PR-B or both was performed using GeneSpring™ version 3.0 (Silicon Genetics, San Carlos, Calif.). The present inventors used customized software capable of comparing multiple experimental pairwise comparisons (minus versus plus progesterone) and multiple control comparisons (all minus hormone samples and all plus hormone samples) to compare fold change minus versus plus hormone as compared to the fold change between controls. This served as a measure of the variability between samples. As a third level of analysis, k-means clustering was performed using GeneSpring™ version 3.2.12 (Silicon Genetics, San Carlos, Calif.) to identify patterns of gene regulation in PR-A, PR-B, or PR-negative cells treated with or without progesterone.

Selected genes, i.e., ones that were substantially regulated or are of particular biological interest, have been confirmed by northern and/or RT-PCR, and/or by western blotting. Additionally, the promoters of several genes of interest have been cloned, linked upstream of a luciferase reporter, and tested for their ability to be transcriptionally regulated by PR-A vs. PR-B after transfection into HeLa cervicocarcinoma cells, followed by progesterone treatment of the cells. In the examples tested, regulation by PR-A vs. PR-B using the synthetic promoter/reporter constructs, mimicked the regulation of the endogenous genes in the breast cancer cells, supporting the use of these approaches for drug discovery.

RT-PCR and Northern Blot Analysis

RT-PCR amplifications of target sequences were performed with co-amplification of an internal control sequence (p2MG or GAPDH) using: β2MG forward primer: 5'-ATCCAGCGTACTCCAAAGATTC-3' (SEQ ID NO:1); β2MG reverse primer: 5'-TCCTTGCTGAAAGACAAGTCTG-3' (SEQ ID NO:2); resulting in a product of 178 bp. GAPDH primers yielded a product of 485 bp. GAPDH, Integrin α6, and bc1-x cDNA primer sequences were obtained from Clontech. Total RNA was prepared from T47DY-A or -B cells as described above. One μg of RNA was mixed with 0.4 μM random hexamers and heated to 65° C. for five min. (Perkin Elmer). 1× PCR buffer (5 mM $MgCl_2$), 20 U RNAse inhibitor, 4 mM dNTPs, and 125 U MMLV reverse transcriptase were added and tubes were incubated at 42° C. for 1 hour. Five μl of the cDNA synthesis reactions were added to 1×PCR buffer, 1.8 mM $MgCl_2$, 100 mM dNTP blend, and 60 pmoles of specific primers were incubated with 5 U AmpliTaq DNA polymerase at 94° C. for 30 s, 65 C for 45 s, and 68° C. for 1 min for 16–18 cycles (cycle number was chosen to be in the linear range of amplification for each product). All PCR reagents were purchased from Perkin Elmer, Foster City, Calif. Five μl of samples were resolved on a 2% agarose gel, and Southern blots were performed in 0.4M. Blots were prehybridized in Rapid-hyb (Amersham) for 1 h at 65° C. cDNA probes were generated by RT-PCR and radioactively labeled using MegaPrime DNA labeling system (Amersham) and $^{32}$P-αdCTP. Blots were probed for 2 h to overnight at 65° C. Blots were washed and exposed to autoradiography film or phosphoimaging screen and then quantified using ImageQuant, Molecular Dynamics. In some cases the RT-PCR products could be visualized on an ethidium bromide stained gel when amplified in the linear range of production and in these cases Southern blotting and hybridizing with a labeled probe was unnecessary and products were instead directly quantitated. In some cases Northern blot analysis was used to detect transcripts. In these cases 25 μg of total RNA was electrophoresed in a formaldehyde agarose gel and transferred to a Hybond nylon membrane (Amersham) and hybridized sequentially with cDNA inserts for specific genes generated by random priming PCR products generate as above with $^{32}$P-dCTP using Mega-Prime DNA Labeling Kit (Amersham). Membranes were then probed with fragments of housekeeping genes (either B2MG or GAPDH).

Transcriptional Assay:

HeLa cells plated at $4\times10^5$ cells per 10 cm dish in MEM supplemented with 5% fetal bovine serum were then transiently transfected with 100 ng of HPR1 (PR-B in pSG5) or HPR2 (PR-A in pSG5) and 1.2 μg of the integrin a6 promoter (-740) in pGL3-Basic vector plasmid (gift from Dr. Sohei Kitazawa, Kobe University School of Medicine, Department of Pathology), 1.2 μg of β-galactosidase expression plasmid pCH110, and 5.5 μg BSM. treated with 10 nM progesterone or ethanol vehicle for 24 hours.

Immunoblots:

For time course treatments with progesterone, cells were plated at 2 million cells per large plates in MEM with supplements described above and were treated with 10 nM progesterone (Sigma). Cells were harvested in RIPA buffer (10 mM sodium phosphate, pH 7.0, 150 mM NaCl, 2 mM EDTA, 1% deoxycholic acid, 1% Nonedet P-40, 0.1% SDS, 0.1% β-mercaptoethanol, 1 mM PMSF, 50 mM sodium fluoride, 200 μM $Va_3VO_4$, and one Complete Protease Inhibitor Mixture tablet (Boehringer Mannheim, GmbH Germany) per 50 mls of RIPA buffer made fresh for each use. Protein extracts were equalized to 150 μg by Bradford assay (Bio-Rad), resolved by SDS-PAGE, and transferred to nitrocellulose. Equivalent protein loading was confirmed by Ponceau S staining. Following incubation with the appropriate antibodies, and HRP-conjugated secondary antibodies, protein bands were detected by enhanced chemiluminescence (Amersham, Arlington Heights, Ill.).

Results

Gene expression data from Affymetrix HuGeneFL Array™ chips were analyzed using Microarray Suite 4.0 Expression Analysis Program (Affymetrix™). Experimental data from independent triplicate experiments for T47D-YA and T47D-YB cells and duplicate T47D-Y cells treated with or without 10 nM progesterone were analyzed and pairwise comparisons were performed to identify genes that had increased or decreased with addition of hormone. These data were imported into Microsoft Excel and custom formulas were written to identify genes that had repeatedly increased or decreased with hormone in three out of three experiments by at least 1.8 fold, but did not vary more than two fold between control groups. Genes that met these criteria and were up- or downregulated by progesterone by in PR-B containing cells are shown in Table 18, while those up- or downregulated by progesterone in PR-A containing cells are shown in Table 19. In both tables fold increases and decreases (negative numbers) upon treatment with progesterone for 6 hrs are indicated. Genes which were at below detectable levels and called absent in one sample, but which were detectable and called as present in the other are denoted with a tilde beside the fold changes. The fold changes indicated with a tilde cannot be compared to those that are not marked with a tilde (indicating they were present in both minus and plus hormone samples) as the fold change was calculated by setting the undetectable gene to background level. Genes in bold in Table 18 are uniquely regulated by progesterone only via PR-B, while those in bold in Table 19 are uniquely regulated by PR-A; those not bolded were regulated in both PR-B and PR-A containing cells. Only genes that were regulated in 3 out of 3 experiments are shown and average fold inductions are given. Genes marked with an asterisk were identified from Atlas™ Human cDNA Expression Arrays (Clonetech, Palo Alto, Calif.) and those marked by an & symbol were identified as being progesterone regulated on using both Atlas™ Human cDNA Expression Arrays and Affymetrix HuGeneFL Array™ chips (Affymetrix, Inc., Santa Clara, Calif.), all others were identified using Affymetrix HuGeneFL Array™ chips (Affymetrix, Inc., Santa Clara, Calif.). The present inventors have categorized genes regulated by progesterone in this study into functional categories based on GeneCard information as well as extensive literature reviews of each gene product (Table 17). Ten of the genes found to be regulated by progesterone in the present study have previously been reported by other groups to be progesterone responsive in either breast cancer cells or other hormone responsive cell types or tissues (Table 8). However, the PR-A and/or PR-B isoform specificity of these genes was unknown prior to the present invention. The independent identification of genes that have previously been reported to be progesterone-regulated serves as an internal control and also demonstrates the sensitivity of this assay, as even genes induced by progesterone as little as 1.9 fold were detected on the arrays. Additionally, 8 of the genes found to be regulated by progesterone in the present study have previously been reported to be involved in either breast cancer or mammary gland development (Table 16).

The average differences indicating relative intensities obtained from triplicate experiments from T47D-YA and T47D-YB cell lines and duplicate experiments in the PR-negative T47D-Y cells were entered into GeneSpring™ 3.2.12 (Silicon Genetics, San Carlos, Calif.). To normalize for variation among chips each gene intensity value was normalized to 1 (intensity of gene A on chip X divided by the median of all intensities measured on chip X). To identify patterns of gene expression among cell lines and hormone treatments, k-means clustering was performed. Clustergrams of various patterns of gene regulation were generated. Within these clusters, any one gene can be viewed individually and standard error bars generated from replicate experiments are shown for gene expression levels in cell lines containing either PR-A, PR-B, or no PR, with or without progesterone treatment. A cluster of genes was shown to be upregulated by progesterone in both PR-A and PR-B containing cells, but not in the PR-negative cell line. While most of these genes were upregulated by progesterone treatment more strongly via PR-B, some, such as S100P calcium binding protein, and Grb10 are upregulated equally well via PR-A and PR-B. Upregulation of IkappaBalpha via both receptors was confirmed at the protein level as early as 6 hours, and remained elevated for up to 48 hours in the presence of progesterone (data not shown). Additionally, the gene encoding Ezrin, identified as being progesterone regulated using Atlas™ Human cDNA Expression Arrays probed with RNA from T47D-YA and YB cells left untreated or treated with progesterone for 12 hrs was confirmed to be equally well upregulated by both PR-A and PR-B at 12, 24 and 48 hrs by northern blot analysis (data not shown).

The present inventors have demonstrated that although some genes (and their protein products) are regulated by progesterone through both PR isoforms, many genes are uniquely regulated by either PR-A or PR-B. In the T47D breast cancer cell lines used for the present invention, many more genes were regulated by progesterone through PR-B than through PR-A. However, it remains to be determined whether this situation is reversed in other types of cells or tissues; the endometrium for instance. Data from knock-out mice show that PR-A, but not PR-B, plays an important role in opposing the proliferative effect of estrogen on the endometrium. This is one example of tissue and PR isoform specificity (Mulac-Jericevic et al., *Science* 289, 1751–4 (2000)).

Many progesterone regulated genes require PR-B as illustrated by Tables 3, 4, 11, 12 and 18. Two examples are Stat5a and C/EBP beta. Their differential upregulation only by PR-B was confirmed by immunoblot at several time-points after progesterone treatment (data not shown). In contrast, the same western blot probed for two control proteins, p21 and cyclin D 1, previously reported to be progesterone regulated (Musgrove et al., *Mol. Cell. Biol.* 13, 3577–3587 (1993); Musgrove et al., *Mol. Endocrinol.* 11, 54–66 (1997); Groshong et al., *Mol Endocrinol* 11, 1593–607 (1997)), showed them to be equally well regulated by either PR-A or PR-B. The gene encoding tissue factor is also uniquely regulated by PR-B. This too was confirmed by RT-PCR. Similarly, RT-PCR confirmed that integrin alpha 6 is uniquely regulated by PR-B at 6, 12, and 24 hours after progesterone treatment. To demonstrate the differential regulation of this gene by PR-B in a different cell line and by different methods, the present inventors transfected the integrin alpha 6 promoter linked to luciferase into progesterone treated PR-negative HeLa cells that were cotransfected with either PR-B or PR-A. Transcription of the integrin alpha 6 promoter was induced 4.4 fold by PR-B, but was not regulated at all by PR-A, or by cells lacking PR (not shown).

Fewer genes were uniquely regulated by PR-A (Table 19) and they tended to be expressed at relatively low levels. The gene encoding the docking protein enhancer of filamentation was significantly upregulated only by PR-A. The gene encoding the estrogen related receptor (ERR), which can heterodimerize with ERα and Erβ is also PR-A dependent. The preferential upregulation of ERR by PR-A was confirmed by RT-PCR at both 6 and 12 hrs of progesterone treatment. The anti-apoptosis inducing protein BC1-XL, is another gene uniquely regulated by PR-A as confirmed by RT-PCR (not shown).

In general, fewer genes were downregulated by progesterone treatment than were upregulated (Tables 18 and 19). Analysis of pairwise comparisons using MicroArray Suite 4.0 Expression Analysis Program™ was used to demonstrate the statistical significance of the downregulation (in 3 out of 3 experiments). Similarly, gene filtering using GeneSpring™ generated a clustergram of downregulated genes (data not shown) confirming the accuracy of the assignments. Of the downregulated genes, three were downregulated by both PR-A and PR-B; eleven were uniquely downregulated by PR-B; and two were uniquely downregulated by PR-A. Downregulation of three of these genes, monocyte chemotactic protein, bullous pemphigoid antigen, and transforming growth factor-beta 3 (TGF-beta 3) was confirmed by RT-PCR (data not shown).

Several genes that were identified by the present inventors as being regulated by progesterone, were previously known to be important in breast cancers. Based on the present invention they may now be targeted for specific progestin therapies. (1) For instance, S100P calcium-binding protein overexpression is associated with immortalization of human breast epithelial cells in vitro and with early stages of breast cancer development in vivo (Guerreiro da Silva et al., *Int J Oncol* 16, 231–40 (2000)). (2) The gene encoding tissue factor, a cell surface glycoprotein, is associated with metastasis in breast and other types of cancers (Ueno et al., *Br J Cancer* 83, 164–70 (2000); Lwaleed et al., *J Pathol* 187(3):291–4 (1999)). Tis factor was previously known to be regulated by progesterone in the endometrium (Krikun et al., *Mol Endocrinol* 14, 393–400 (2000); Lockwood et al., *J Clin Endocrinol Metab* 85, 297–301 (2000); Krikun et al., *J Clin Endocrinol Metab* 83, 926–30 (1998)), but not in the breast or in breast cancers. (3) The gene encoding Gas6, a ligand for the tyrosine kinase receptor Ax1 receptor tyrosine kinase (RTK) and other members of the RTK family, was recently reported to be mitogenic in breast cancer cells (Goruppi et al., *Mol Cell Biol* 21, 902–915 (2001)) and it promotes angiogenesis (Fridell et al., *J. Biol Chem* 273, 7123–6. (1998)). (4) The HEF1 gene is highly related to BCAR1/p130Cas, which has been found to be upregulated in tamoxifen resistant tumors (van der Flier et al., *Int J Cancer* 89, 465–8 (2000); van der Flier et al, *J Natl Cancer Inst* 92, 120–7 (2000)). The present invention provides the rationale for measuring the expression levels of these genes in breast cancers. It may be that tumors that overexpress these genes good candidates for suppressive therapy with progesterone antagonists.

Additionally the inventors now demonstrate the progesterone regulation of several genes previously known to be preferentially expressed in normal breast epithelium compared to breast cancers. For instance, the gene encoding bullous pemphigoid antigen, a protein associated with hemidesmosomes, is overexpressed 12-fold in normal breast cells compared to breast tumors (Nacht et al., *Cancer Res* 59, 5464–70 (1999)). Such desmosomes are important in maintaining the normal differentiated architecture of the breast. The present inventors have found that bullous pemphigoid antigen is downregulated by progesterone through both PR isoforms. This down regulation may be harmful, and/or it may disrupt important cell-cell interactions. It is possible that antiprogestin therapy would prevent this downregulation.

Some of the genes that were discovered by the present inventors to be progesterone regulated are involved in particular functional pathways. Groups of temporally regulated genes are often involved in the same pathway. For example, it was previously known that progesterone regulates genes involved in the steroid biosynthesis and trafficking pathways (Watari et al., *Exp Cell Res* 259, 247–56 (2000); Damel et al., *J Steroid Biochem Mol Biol* 70:203–10 (1999); Arcuri et al., *Endocrinology* 137:595–600 (1996)), and the present investigators identify a cluster of such genes. However, less is known about the role of progesterone in regulating signaling pathways controlled by growth factors and cytokines. The present inventors' data demonstrate for the first time, that progesterone plays an important role in regulating many genes involved in these signaling pathways. In addition, the present inventors' demonstrate that progesterone regulates expression of genes for proteins previously known to interact with PR. Examples are FKB54 (Kester et al., *J Biol Chem* 272, 16637–43 (1997)), Stat5 (Richer et al., *J Biol Chem* 273,31317–26 (1998)), IκBα and cytoplasmic dynein light chain 1 (Crepieux et al, *Mol Cell Biol* 17:7375–85 (1997)).

TABLE 1

Genes selectively upregulated by PR-A

| Accession No. | Fold Increase | Gene Name |
|---|---|---|
| L43821 | 4.7 | enhancer of filamentation (HEF1) |
| L38487 | 2.3 | estrogen receptor-related protein (hERRa1) |

TABLE 2

Genes selectively downregulated by PR-A

| Accession No. | Fold Decrease | Gene Name |
|---|---|---|
| U44103 (SEQ ID NO:5) | −2.8 | small GTP binding protein Rab9 |

TABLE 3

Genes selectively upregulated by PR-B.

| Accession No. | Fold Increase | Gene Name |
|---|---|---|
| L13720 (SEQ ID NO:6) | ~23.1 | growth arrest-specific protein (gas6) |
| D79990 (SEQ ID NO:8) | 10.2 | KIAA0168 Ras association (RaIGDS/AF-6) domain family 2 (RASSF2) |
| U01120 (SEQ ID NO:9) | ~9.8 | glucose-6-phosphatase |
| D25539 (SEQ ID NO:10) | ~8 | KIAA0040 gene |
| U37546 (SEQ ID NO:11) | ~7.2 | IAP homolog C (MIHC) |
| D87953 (SEQ ID NO:12) | 6.8 | RTP, DRG1, CAP43 |
| M76180 (SEQ ID NO:13) | ~6.5 | aromatic amino acid decarboxylase (ddc) |
| M77140 (SEQ ID NO:14) | ~6 | pro-galanin |
| D50840 (SEQ ID NO:15) | ~5.6 | ceramide glucosyltransferase |
| HG2743-HT2846 (SEQ ID NO:16) | ~5.1 | Caldesmon 1 Non-Muscle |
| U76421 (SEQ ID NO:17) | ~4.7 | dsRNA adenosine deaminase DRADA2b |
| U40572 (SEQ ID NO:18) | 4.6 | beta2-syntrophin (SNT B2) |
| S69189 (SEQ ID NO:19) | ~4.5 | peroxisomal acyl-coenzyme A oxidase |
| U44754 (SEQ ID NO:20) | 4.4 | PSE-binding factor PTF gamma subunit |
| U02081 (SEQ ID NO:21) | 4.1 | guanine nucleotide regulatory protein (NET1) oncogene[1] |
| D16227 (SEQ ID NO:22) | ~4 | BDP-1 (member of the recoverin family) |
| D17793 (SEQ ID NO:23) | ~4 | 3-alpha hydroxysteroid dehydrogenase type IIb |
| U83461 (SEQ ID NO:24) | 3.7 | putative copper uptake protein (hCTR2) |
| M23254 (SEQ ID NO:25) | 3.6 | Ca2+-activated neutral protease (CANP) |
| D15050 (SEQ ID NO:26) | 3.6 | transcription factor AREB6 |
| HG2167-HT2237 (SEQ ID NO:27) | ~3.5 | Protein Kinase Ht31, Camp-Dependent |
| D10040 (SEQ ID NO:28) | 3.5 | long-chain acyl-CoA synthetase |
| D31887 (SEQ ID NO:29) | 3.5 | KIAA0062 gene |
| X60673 (SEQ ID NO:30) | 3.4 | adenylate kinase 3 |
| U45878 (SEQ ID NO:31) | ~3.3 | inhibitor of apoptosis protein 1 |
| L09229 (SEQ ID NO:32) | 3.3 | long-chain acyl-coenzyme A synthetase (FACL1) |
| U09646 (SEQ ID NO:33) | 3.2 | carnitine palmitoyltransferase II precursor (CPT1) |
| D31716 (SEQ ID NO:34) | 3.2 | GC box bindig protein |
| M37400 (SEQ ID NO:35) | 3.1 | cytosolic aspartate aminotransferase |
| X59834 (SEQ ID NO:36) | 3.1 | glutamine synthase |
| D78335 (SEQ ID NO:37) | 3.1 | uridine monophosphate kinase (UMPK) |
| U41387 (SEQ ID NO:38) | 3 | RNA helicase II/Gu) |
| U07919 (SEQ ID NO:39) | 3 | aldehyde dehydrogenase 6 |
| M69013 (SEQ ID NO:40) | 2.9 | guanine nucleotide-binding regulatory protein (G-y-alpha)[1] |
| HG2530-HT2626 (SEQ ID NO:41) | 2.9 | Adenylyl Cyclase-Associated Protein 2 |
| U79288 (SEQ ID NO:42) | 2.8 | clone 23682 |
| D10704 (SEQ ID NO:43) | 2.6 | choline kinase |
| Y08134 (SEQ ID NO:44) | 2.6 | ASM-like phosphodiesterase 3b |
| U33632 (SEQ ID NO:45) | 2.6 | two P-domain K+ channel TWIK-1 |
| M21154 (SEQ ID NO:46) | 2.5 | S-adenosylmethionine decarboxylase |

TABLE 3-continued

Genes selectively upregulated by PR-B.

| Accession No. | Fold Increase | Gene Name |
|---|---|---|
| U77949 (SEQ ID NO:47) | 2.5 | Cdc6-related protein (HsCDC6) |
| M95767 (SEQ ID NO:48) | ~2.5 | di-N-acetylchitobiase |
| D83781 (SEQ ID NO:49) | 2.5 | KIAA0197 gene |
| X98534 (SEQ ID NO:50) | 2.5 | vasodilator-stimulated phosphoprotein (VASP) |
| X53586 (SEQ ID NO:51) | 2.5 | Integrin α 6* |
| D80001 (SEQ ID NO:52) | 2.4 | KIAA0179 gene |
| L18960 (SEQ ID NO:53) | 2.4 | protein synthesis factor (eIF-4C) |
| D23673 (SEQ ID NO:54) | 2.3 | insulin receptor substrate-1 (IRS-1) |
| J02888 (SEQ ID NO:55) | 2.3 | quinone oxidoreductase (NQO2) |
| D63487 (SEQ ID NO:56) | 2.3 | KIAA0153 gene |
| U14603 (SEQ ID NO:57) | 2.3 | protein-tyrosine phosphatase (HU-PP-1) |
| L41887 (SEQ ID NO:58) | 2.3 | splicing factor, arginine/serine-rich 7 (SFRS7) |
| M92287 (SEQ ID NO:59) | 2.2 | cyclin D3 (CCND3) |
| X61123 (SEQ ID NO:60) | 2.2 | BTG1 |
| M95929 (SEQ ID NO:61) | 2.1 | homeobox protein (PHOX1) |
| U32944 (SEQ ID NO:62) | 2.1 | cytoplasmic dynein light chain 1 (hdlc1) |
| D79994 (SEQ ID NO:63) | 2.1 | KIAA0172 gene (similar to ankyrin) |
| D89377 (SEQ ID NO:64) | 2 | MSX-2 |
| U90878 (SEQ ID NO:65) | 2 | LIM domain protein CLP-36 |
| U97105 (SEQ ID NO:66) | 2 | N2A3 dihydropyrimidinase related protein-2 |
| L40379 (SEQ ID NO:67) | 2 | thyroid receptor interactor (TRIP10) |
| J05459 (SEQ ID NO:68) | 1.9 | glutathione transferase M3 (GSTM3) |
| L42542 (SEQ ID NO:69) | 1.8 | RLIP76 (raIA binding protein 1) |
| D42047 (SEQ ID NO:70) | 1.7 | KIAA0089 similar to glycerol-3-phosphate dehydrogenase 1 |
| M84349 (SEQ ID NO:71) | 1.7 | transmembrane protein (CD59) |
| D43950 (SEQ ID NO:72) | 1.6 | KIAA0098 T-COMPLEX PROTEIN 1 (TCP-1-EPSILON) |
| M15796 (SEQ ID NO:73) | 1.6 | proliferating cell nuclear antigen (PCNA) |

TABLE 4

Genes selectively downregulated by PR-B

| Accession No. | Fold Decrease | Gene Name |
|---|---|---|
| U07225 (SEQ ID NO:74) | ~−4.3 | P2U nucleotide receptor |
| M27492 (SEQ ID NO:75) | ~−3.4 | interleukin 1 receptor mRNA |
| Y08682 (SEQ ID NO:76) | −3.1 | carnitine palmitoyltransferase I type I |
| U29091 (SEQ ID NO:77) | ~−2.9 | selenium-binding protein (hSBP) |
| X79683 (SEQ ID NO:78) | −2.6 | beta2 laminin. |
| AB000220 (SEQ ID NO:79) | −2.6 | semaphorin E[1] |
| HG2197-HT2267 (SEQ ID NO:80) | ~−2.5 | Collagen, Type Vii, Alpha 1 |
| U65011 (SEQ ID NO:81) | ~−2.5 | preferentially expressed antigen of melanoma (PRAME) |
| M18391 (SEQ ID NO:82) | ~−2.3 | tyrosine kinase receptor (eph) |
| X71874 (SEQ ID NO:83) | −1.9 | proteasome-like subunit MECL-1 |

TABLE 5

Genes up or downregulated by both PR-A and PR-B

| Accession No. | Fold | Gene Name |
|---|---|---|
| X51521 (SEQ ID NO:84) | ~22.6 | Ezrin* |
| U70663 (SEQ ID NO:85) | ~7.5 | zinc finger transcription factor EZF |
| U16799 (SEQ ID NO:86) | 6.1 | Na, K-ATPase beta-1 subunit |
| X65614 (SEQ ID NO:87) | 3.6 | calcium-binding protein S100P |
| D86962 (SEQ ID NO:88) | 2.9 | Grb10 |
| S81914 (SEQ ID NO:89) | 2.6 | IEX-1 = radiation-inducible immediate-early |
| U00115 (SEQ ID NO:90) | 2.4 | bcl-6 |
| M69225 (SEQ ID NO:91) | ~−3.5 | bullous pemphigoid antigen (plakin family) |
| U90907 (SEQ ID NO:92) | −3.2 | clone 23907 |
| M92357 (SEQ ID NO:93) | −2.1 | tumor necrosis factor alpha-induced protein 2 (B94) |

TABLE 6

Gene that is reciprocally regulated (upregulated by PR-B, downregulated by PR-A)

| Accession No. | Fold | Gene Name |
|---|---|---|
| X53586 (SEQ ID NO:51) | 2.5 | Integrin α 6* |

TABLE 7

Group of genes for which the expression level is different depending on which isoform is present.

| Accession No. | Fold | Gene Name |
|---|---|---|
| L13720 (SEQ ID NO:6) | ~23.1 | growth arrest-specific protein (gas6) |
| D79990 (SEQ ID NO:8) | 10.2 | KIAA0168 Ras association (RaIGDS/AF-6) domain family 2 (RASSF2) |
| U01120 (SEQ ID NO:9) | ~9.8 | glucose-6-phosphatase |
| U37546 (SEQ ID NO:11) | ~7.2 | IAP homolog C (MIHC) |
| D87953 (SEQ ID NO:12) | 6.8 | RTP, DRG1, CAP43 |

TABLE 7-continued

Group of genes for which the expression level is different depending on which isoform is present.

| Accession No. | Fold | Gene Name |
|---|---|---|
| M76180 (SEQ ID NO:13) | ~6.5 | aromatic amino acid decarboxylase (ddc) |
| M77140 (SEQ ID NO:14) | ~6 | pro-galanin |
| D50840 (SEQ ID NO:15) | ~5.6 | ceramide glucosyltransferase |
| HG2743-HT2846 (SEQ ID NO:16) | ~5.1 | Caldesmon 1 Non-Muscle |
| U76421 (SEQ ID NO:17) | ~4.7 | dsRNA adenosine deaminase DRADA2b |
| U40572 (SEQ ID NO:18) | 4.6 | beta2-syntrophin (SNT B2) |
| S69189 (SEQ ID NO:19) | ~4.5 | peroxisomal acyl-coenzyme A oxidase |
| U44754 (SEQ ID NO:20) | 4.4 | PSE-binding factor PTF gamma subunit |
| U02081 (SEQ ID NO:21) | 4.1 | guanine nucleotide regulatory protein (NET1) oncogene |
| D16227 (SEQ ID NO:22) | ~4 | BDP-1 (member of the recoverin family) |
| D17793 (SEQ ID NO:23) | ~4 | 3-alpha hydroxysteroid dehydrogenase type IIb |
| U83461 (SEQ ID NO:24) | 3.7 | putative copper uptake protein (hCTR2) |
| M23254 (SEQ ID NO:25) | 3.6 | Ca2+-activated neutral protease (CANP) |
| D15050 (SEQ ID NO:26) | 3.6 | transcription factor AREB6 |
| HG2167-HT2237 (SEQ ID NO:27) | ~3.5 | Protein Kinase Ht31, Camp-Dependent |
| D10040 (SEQ ID NO:28) | 3.5 | long-chain acyl-CoA synthetase |
| D31887 (SEQ ID NO:29) | 3.5 | KIAA0062 gene |
| X60673 (SEQ ID NO:30) | 3.4 | adenylate kinase 3 |
| U45878 (SEQ ID NO:31) | ~3.3 | inhibitor of apoptosis protein 1 |
| L09229 (SEQ ID NO:32) | 3.3 | long-chain acyl-coenzyme A synthetase (FACL1) |
| U09646 (SEQ ID NO:33) | 3.2 | carnitine palmitoyltransferase II precursor (CPT1) |
| D31716 (SEQ ID NO:34) | 3.2 | GC box bindig protein |
| M37400 (SEQ ID NO:35) | 3.1 | cytosolic aspartate aminotransferase |
| X59834 (SEQ ID NO:36) | 3.1 | glutamine synthase |
| D78335 (SEQ ID NO:37) | 3.1 | uridine monophosphate kinase (UMPK) |
| U41387 (SEQ ID NO:38) | 3 | RNA helicase II/Gu) |
| U07919 (SEQ ID NO:39) | 3 | aldehyde dehydrogenase 6 |
| M69013 (SEQ ID NO:40) | 2.9 | guanine nucleotide-binding regulatory protein (G-y-alpha) |
| HG2530-HT2626 (SEQ ID NO:41) | 2.9 | Adenylyl Cyclase-Associated Protein 2 |
| U79288 (SEQ ID NO:42) | 2.8 | clone 23682 |
| D10704 (SEQ ID NO:43) | 2.6 | choline kinase |
| Y08134 (SEQ ID NO:44) | 2.6 | ASM-like phosphodiesterase 3b |
| U33632 (SEQ ID NO:45) | 2.6 | two P-domain K+ channel TWIK-1 |
| M21154 (SEQ ID NO:46) | 2.5 | S-adenosylmethionine decarboxylase |
| U77949 (SEQ ID NO:47) | 2.5 | Cdc6-related protein (HsCDC6) |
| M95767 (SEQ ID NO:48) | ~2.5 | di-N-acetylchitobiase |
| D83781 (SEQ ID NO:49) | 2.5 | KIAA0197 gene |

TABLE 7-continued

Group of genes for which the expression level is different depending on which isoform is present.

| Accession No. | Fold | Gene Name |
|---|---|---|
| X98534 (SEQ ID NO:50) | 2.5 | vasodilator-stimulated phosphoprotein (VASP) |
| D80001 (SEQ ID NO:52) | 2.4 | KIAA0179 gene |
| L18960 (SEQ ID NO:53) | 2.4 | protein synthesis factor (eIF-4C) |
| D23673 (SEQ ID NO:54) | 2.3 | insulin receptor substrate-1 (IRS-1) |
| J02888 (SEQ ID NO:55) | 2.3 | quinone oxidoreductase (NQO2) |
| D63487 (SEQ ID NO:56) | 2.3 | KIAA0153 gene |
| U14603 (SEQ ID NO:57) | 2.3 | protein-tyrosine phosphatase (HU-PP-1) |
| L41887 (SEQ ID NO:58) | 2.3 | splicing factor, arginine/serine-rich 7 (SFRS7) |
| M92287 (SEQ ID NO:59) | 2.2 | cyclin D3 (CCND3) |
| X61123 (SEQ ID NO:60) | 2.2 | BTG1 |
| M95929 (SEQ ID NO:61) | 2.1 | homeobox protein (PHOX1) |
| U32944 (SEQ ID NO:62) | 2.1 | cytoplasmic dynein light chain 1 (hdlc1) |
| D79994 (SEQ ID NO:63) | 2.1 | KIAA0172 gene (similar to ankyrin) |
| D89377 (SEQ ID NO:64) | 2 | MSX-2 |
| U90878 (SEQ ID NO:65) | 2 | LIM domain protein CLP-36 |
| U97105 (SEQ ID NO:66) | 2 | N2A3 dihydropyrimidinase related protein-2 |
| L40379 (SEQ ID NO:67) | 2 | thyroid receptor interactor (TRIP10) |
| J05459 (SEQ ID NO:68) | 1.9 | glutathione transferase M3 (GSTM3) |
| L42542 (SEQ ID NO:69) | 1.8 | RLIP76 (raIA binding protein 1) |
| D42047 (SEQ ID NO:70) | 1.7 | KIAA0089 similar to glycerol-3-phosphate dehydrogenase 1 |
| M84349 (SEQ ID NO:71) | 1.7 | transmembrane protein (CD59) |
| D43950 (SEQ ID NO:72 | 1.6 | KIAA0098 T-COMPLEX PROTEIN 1 (TCP-1-EPSILON) |
| M15796 (SEQ ID NO:73) | 1.6 | proliferating cell nuclear antigen (PCNA) |
| U07225 (SEQ ID NO:74) | ~-4.3 | P2U nucleotide receptor |
| M27492 (SEQ ID NO:75) | ~-3.4 | interleukin 1 receptor mRNA |
| Y08682 (SEQ ID NO:76) | -3.1 | carnitine palmitoyltransferase I type I |
| U29091 (SEQ ID NO:77) | ~-2.9 | selenium-binding protein (hSBP) |
| X79683 (SEQ ID NO:78) | -2.6 | beta2 laminin. |
| AB000220 (SEQ ID NO:79) | -2.6 | semaphorin E |
| HG2197-HT2267 (SEQ ID NO:80) | ~-2.5 | Collagen, Type Vii, Alpha 1 |
| U65011 (SEQ ID NO:81) | ~-2.5 | preferentially expressed antigen of melanoma (PRAME) |
| M18391 (SEQ ID NO:82) | ~-2.3 | tyrosine kinase receptor (eph) |
| X71874 (SEQ ID NO:83) | -1.9 | proteasome-like subunit MECL-1 |
| L43821 (SEQ ID NO:3) | 4.7 | enhancer of filamentation (HEF1) |
| L38487 (SEQ ID NO:4) | 2.3 | estrogen receptor-related protein (hERRa1) |
| D25539 (SEQ ID NO:10) | ~8 | KIAA0040 gene |

TABLE 8

Genes encoding products previously reported to be regulated by progesterone

| Accession no. | Gene Name | Cell or tissue type | Isoform |
|---|---|---|---|
| U26726 (SEQ ID NO:94) | 11-beta-hydroxysteroid dehydrogenase type 2 | endometrial stromal cells, endometrial cancer cells, | Both[1] |
| M27436 (SEQ ID NO:7) | tissue factor gene | endometrium | PR-B only[2] |
| U42031 (SEQ ID NO:95) | progesterone receptor-associated FKBP54 | breast cancer cells | Both[3] |
| M68516 (SEQ ID NO:96) | PCI gene (plasminogen activator inhibitor) | endometrial stromal cells | PR-B only[4] |
| U43185 (SEQ ID NO:97) | Stat5A | breast cancer cells | PR-B only[5] |
| X52730 (SEQ ID NO:98) | phenylethanolamine n-methyltransferase (PNMT) | adrenal medulla | PR-B only[6] |
| M69043 (SEQ ID NO:99) | MAD-3 encoding lkB-alpha | macrophage cells and endometrium | Both[7] |
| AF002020 (SEQ ID NO:100) | Niemann-Pick C disease (NPC1) | granulosa cells | PR-B only[8] |
| D00017 (SEQ ID NO:101) | lipocortin II (calpactin I) | endometrial cancer cells | PR-B only[9] |
| D25328 (SEQ ID NO:102) | platelet-type phosphofructokinase | breast cancer cells, intestinal epithelium, granulosa cells | PR-B only[10] |
| M80254 (SEQ ID NO:103) | cyclophilin isoform (hCyP3) | liver | PR-B only[11] |
| HG4069-HT4339_s_at (SEQ ID NO:104) | Monocyte Chemotactic Protein 1 | endometrial cells and breast cancer cells | PR-A only[12] |
| Z50781 (SEQ ID NO:105) | delta sleep inducing peptide (related to TSC-22) | breast cancer cells | PR-A only[13] |

References
[1]Arcuri et al., Endocrinology, 137: 595–600 (1996); Darnel et al., J. Steroid Biochem Mol Biol 70: 203–10 (1999)
[2]Krikun et al., Mol Endocrinol, 14: 393–400 (2000); Lockwood et al., J Clin Endocrinol Metab, 85: 297–301 (2000); Krikun et al., J. Clin Endocrinol Metab 83: 926–30 (1998)
[3]Kester et al., J Biol Chem, 272: 16637–43 (1997)
[4]Lockwood et al., Ann NY Acad Sci, 734: 57–79 (1994)
[5]Richer et al., J Biol Chem, 273: 31317–26 (1998)
[6]Fernandez-Ruiz et al., Life Sci, 42(9): 1019–28 (1988)
[7]King et al., Mol Hum Reprod, 7(2): 175–183 (2001); Miller et al., J Immunol, 160(10): 5098–104 (1998)
[8]Watari et al., Exp Cell Res, 259: 247–56 (2000)
[9]Croxtall et al., J Steroid Biochem Mol Biol, 42(2): 121–9 (1992)
[10]Hamilton et al., Mol Endocrinol, 11(4): 490–502 (1997); Khoja et al., Biochim Biophys Acta, 1074(3): 357–62 (1991); Malik et al., Exp Cell Biol, 56(5): 264–9 (1988)
[11]Ourlin et al., Arch Biochem Biophys, 373(2): 375–84 (2000)
[12]Kelly et al., Biochem Biophys Res Commun, 239(2): 557–61 (1997)
[13]Kester et al., J Biol Chem, 272: 16637–43 (1997)

TABLE 9

Genes selectively upregulated by PR-A

| Accession No. | Fold Increase | Gene Name |
|---|---|---|
| L43821 (SEQ ID NO:3) | 4.7 | enhancer of filamentation (HEF1) |
| Z23115 (SEQ ID NO:106) | 3.2 | Bcl-x* |
| Z50781 (SEQ ID NO:105) | 2.5 | delta sleep inducing peptide (higly related to TSC-22) |
| L38487 (SEQ ID NO:4) | 2.3 | estrogen receptor-related protein (hERRa1) |

TABLE 10

Genes selectively downregulated by PR-A

| Accession No. | Fold Decrease | Gene Name |
|---|---|---|
| HG4069-HT4339 (SEQ ID NO:105) | ~−7.4 | Monocyte Chemotactic Protein 1 |
| U44103 (SEQ ID NO:5) | −2.8 | small GTP binding protein Rab9 |

TABLE 11

Genes selectively upregulated by PR-B

| Accession No. | Fold Increase | Gene Name |
|---|---|---|
| L13720 (SEQ ID NO:6) | ~23.1 | growth arrest-specific protein (gas6) |
| M27436 (SEQ ID NO:7) | ~18.1 | tissue factor gene |
| D79990 (SEQ ID NO:8) | 10.2 | KIAA0168 Ras association (RaIGDS/AF-6) domain family 2 (RASSF2) |
| U01120 (SEQ ID NO:9) | ~9.8 | glucose-6-phosphatase |
| D25539 (SEQ ID NO:10) | ~8 | KIAA0040 gene |
| U37546 (SEQ ID NO:11) | ~7.2 | IAP homolog C (MIHC) |
| D87953 (SEQ ID NO:12) | 6.8 | RTP, DRG1, CAP43 |
| M76180 (SEQ ID NO:13) | ~6.5 | aromatic amino acid decarboxylase (ddc) |
| M83667 (SEQ ID NO:107) | 6.4 | NF-IL6 (C/EBPbeta) |
| M68516 (SEQ ID NO:96) | ~6.2 | PCI gene (plasminogen activator inhibitor 3) |
| U43185 (SEQ ID NO:97) | ~6.1 | Stat5A |

TABLE 11-continued

Genes selectively upregulated by PR-B

| Accession No. | Fold Increase | Gene Name |
|---|---|---|
| M77140 (SEQ ID NO:14) | ~6 | pro-galanin |
| D50840 (SEQ ID NO:15) | ~5.6 | ceramide glucosyltransferase |
| HG2743-HT2846 (SEQ ID NO:16) | ~5.1 | Caldesmon 1 Non-Muscle |
| U76421 (SEQ ID NO:17) | ~4.7 | dsRNA adenosine deaminase DRADA2b |
| U40572 (SEQ ID NO:18) | 4.6 | beta2-syntrophin (SNT B2) |
| S69189 (SEQ ID NO:19) | ~4.5 | peroxisomal acyl-coenzyme A oxidase |
| U44754 (SEQ ID NO:20) | 4.4 | PSE-binding factor PTF gamma subunit |
| X52730 (SEQ ID NO:98) | 4.4 | phenylethanolamine n-methyltransferase (PNMT) |
| U02081 (SEQ ID NO:21) | 4.1 | guanine nucleotide regulatory protein (NET1) oncogene[1] |
| D16227 (SEQ ID NO:22) | ~4 | BDP-1 (member of the recoverin family) |
| D17793 (SEQ ID NO:23) | ~4 | 3-alpha hydroxysteroid dehydrogenase type IIb |
| U83461 (SEQ ID NO:24) | 3.7 | putative copper uptake protein (hCTR2) |
| M23254 (SEQ ID NO:25) | 3.6 | Ca2+-activated neutral protease (CANP) |
| D15050 (SEQ ID NO:26) | 3.6 | transcription factor AREB6 |
| HG2167-HT2237 (SEQ ID NO:27) | ~3.5 | Protein Kinase Ht31, Camp-Dependent |
| D10040 (SEQ ID NO:28) | 3.5 | long-chain acyl-CoA synthetase |
| D31887 (SEQ ID NO:29) | 3.5 | KIAA0062 gene |
| X60673 (SEQ ID NO:30) | 3.4 | adenylate kinase 3 |
| U45878 (SEQ ID NO:31) | ~3.3 | inhibitor of apoptosis protein I |
| L09229 (SEQ ID NO:32) | 3.3 | long-chain acyl-coenzyme A synthetase (FACL1) |
| U09646 (SEQ ID NO:33) | 3.2 | carnitine palmitoyltransferase II precursor (CPT1) |
| D31716 (SEQ ID NO:34) | 3.2 | GC box bindig protein |
| M37400 (SEQ ID NO:35) | 3.1 | cytosolic aspartate aminotransferase |
| X59834 (SEQ ID NO:36) | 3.1 | glutamine synthase |
| D78335 (SEQ ID NO:37) | 3.1 | uridine monophosphate kinase (UMPK) |
| U41387 (SEQ ID NO:38) | 3 | RNA helicase II/Gu) |
| U07919 (SEQ ID NO:39) | 3 | aldehyde dehydrogenase 6 |
| M69013 (SEQ ID NO:40) | 2.9 | guanine nucleotide-binding regulatory protein (G-y-alpha)[1] |
| HG2530-HT2626 (SEQ ID NO:41) | 2.9 | Adenylyl Cyclase-Associated Protein 2 |
| U79288 (SEQ ID NO:42) | 2.8 | clone 23682 |
| D10704 (SEQ ID NO:43) | 2.6 | choline kinase |
| Y08134 (SEQ ID NO:44) | 2.6 | ASM-like phosphodiesterase 3b |
| U33632 (SEQ ID NO:45) | 2.6 | two P-domain K+ channel TWIK-1 |
| M21154 (SEQ ID NO:46) | 2.5 | S-adenosylmethionine decarboxylase |
| U77949 (SEQ ID NO:47) | 2.5 | Cdc6-related protein (HsCDC6) |
| M95767 (SEQ ID NO:48) | ~2.5 | di-N-acetylchitobiase |
| D83781 (SEQ ID NO:49) | 2.5 | KIAA0197 gene |
| X98534 (SEQ ID NO:50) | 2.5 | vasodilator-stimulated phosphoprotein (VASP) |
| X53586 (SEQ ID NO:51) | 2.5 | Integrin α 6* |
| D80001 (SEQ ID NO:52) | 2.4 | KIAA0179 gene |
| L18960 (SEQ ID NO:53) | 2.4 | protein synthesis factor (eIF-4C) |
| D23673 (SEQ ID NO:54) | 2.3 | insulin receptor substrate-1 (IRS-1) |
| J02888 (SEQ ID NO:55) | 2.3 | quinone oxidoreductase (NQO2) |
| D63487 (SEQ ID NO:56) | 2.3 | KIAA0153 gene |
| U14603 (SEQ ID NO:57) | 2.3 | protein-tyrosine phosphatase (HU-PP-1) |
| L41887 (SEQ ID NO:58) | 2.3 | splicing factor, arginine/serine-rich 7 (SFRS7) |
| M92287 (SEQ ID NO:59) | 2.2 | cyclin D3 (CCND3) |
| X61123 (SEQ ID NO:60) | 2.2 | BTG1 |
| AF002020 (SEQ ID NO:100) | 2.1 | Niemann-Pick C disease (NPC1) |
| M95929 (SEQ ID NO:61) | 2.1 | homeobox protein (PHOX1) |
| U32944 (SEQ ID NO:62) | 2.1 | cytoplasmic dynein light chain 1 (hdlc1) |
| D79994 (SEQ ID NO:63) | 2.1 | KIAA0172 gene (similar to ankyrin) |
| D89377 (SEQ ID NO:64) | 2 | MSX-2 |
| U90878 (SEQ ID NO:65) | 2 | LIM domain protein CLP-36 |
| U97105 (SEQ ID NO:66) | 2 | N2A3 dihydropyrimidinase related protein-2 |
| L40379 (SEQ ID NO:67) | 2 | thyroid receptor interactor (TRIP10) |
| D00017 (SEQ ID NO:101) | 1.9 | lipocortin II |
| J05459 (SEQ ID NO:68) | 1.9 | glutathione transferase M3 (GSTM3) |
| D25328 (SEQ ID NO:102) | 1.9 | platelet-type phosphofructokinase |
| M80254 (SEQ ID NO:103) | 1.9 | cyclophilin isoform (hCyP3) |
| L42542 (SEQ ID NO:69) | 1.8 | RLIP76 (ralA binding protein 1) |
| D42047 (SEQ ID NO:70) | 1.7 | KIAA0089 similar to glycerol-3-phosphate dehydrogenase 1 |
| M84349 (SEQ ID NO:71) | 1.7 | transmembrane protein (CD59) |
| D43950 (SEQ ID NO:72) | 1.6 | KIAA0098 T-COMPLEX PROTEIN 1 (TCP-1-EPSILON) |
| M15796 (SEQ ID NO:73) | 1.6 | proliferating cell nuclear antigen (PCNA) |

TABLE 12

Genes selectively downregulated by PR-B

| Accession No. | Fold Decrease | Gene Name |
|---|---|---|
| U07225 (SEQ ID NO:74) | ~−4.3 | P2U nucleotide receptor |
| M27492 (SEQ ID NO:75) | ~−3.4 | interleukin 1 receptor mRNA |
| Y08682 (SEQ ID NO:76) | −3.1 | carnitine palmitoyltransferase I type I |
| U29091 (SEQ ID NO:77) | ~−2.9 | selenium-binding protein (hSBP) |
| X79683 (SEQ ID NO:78) | −2.6 | beta2 laminin. |
| AB000220 (SEQ ID NO:79) | −2.6 | semaphorin E[1] |
| HG2197–HT2267 (SEQ ID NO:80) | ~−2.5 | Collagen, Type Vii, Alpha 1 |
| U65011 (SEQ ID NO:81) | ~−2.5 | preferentially expressed antigen of melanoma (PRAME) |
| M18391 (SEQ ID NO:82) | ~−2.3 | tyrosine kinase receptor (eph) |
| X71874 (SEQ ID NO:83) | −1.9 | proteasome-like subunit MECL-1 |

TABLE 13

Genes up or downregulated by progesterone via both PR-A and PR-B

| Accession No. | Fold | Gene Name |
|---|---|---|
| U26726 (SEQ ID NO:94) | ~22.6 | 11-beta-hydroxysteroid dehydrogenase type 2 |
| X51521 (SEQ ID NO:84) | 12.7 | Ezrin* |

TABLE 13-continued

Genes up or downregulated by progesterone via both PR-A and PR-B

| Accession No. | Fold | Gene Name |
|---|---|---|
| U42031 (SEQ ID NO:95) | 9.4 | progesterone receptor-associated FKBP54[1] |
| U70663 (SEQ ID NO:85) | ~7.5 | zinc finger transcription factor EZF |
| U16799 (SEQ ID NO:86) | 6.1 | Na, K-ATPase beta-1 subunit |
| M69043 (SEQ ID NO:99) | 4.2 | MAD-3 (IkB-alpha) |
| X65614 (SEQ ID NO:87) | 3.6 | calcium-binding protein S100P |
| D86962 (SEQ ID NO:88) | 2.9 | Grb10 |
| S81914 (SEQ ID NO:89) | 2.6 | IEX-1 = radiation-inducible immediate-early |
| U00115 (SEQ ID NO:90) | 2.4 | bcl-6 |
| M69225 (SEQ ID NO:91) | ~−3.5 | bullous pemphigoid antigen (plakin family) |
| U90907 (SEQ ID NO:92) | −3.2 | clone 23907 |
| J03241 (SEQ ID NO:108) | ~−3 | transforming growth factor-beta 3 (TGF-beta3) |
| M92357 (SEQ ID NO:93) | −2.1 | tumor necrosis factor alpha-induced protein 2 (B94) |

TABLE 14

Gene that is reciprocally regulated (upregulated by PR-B, downregulated by PR-A)

| Accession No. | Fold | Gene Name |
|---|---|---|
| X53586 (SEQ ID NO:51) | 2.5 | Integrin α 6* |

TABLE 15

Group of genes for which the expression level is different depending on which isoform is present.

| Accession No. | Fold | Gene Name |
|---|---|---|
| L13720 (SEQ ID NO:6) | ~23.1 | growth arrest-specific protein (gas6) |
| M27436 (SEQ ID NO:7) | ~18.1 | tissue factor gene |
| D79990 (SEQ ID NO:8) | 10.2 | KIAA0168 Ras association (RaIGDS/AF-6) domain family 2 (RASSF2) |
| U01120 (SEQ ID NO:9) | ~9.8 | glucose-6-phosphatase |
| U37546 (SEQ ID NO:11) | ~7.2 | IAP homolog C (MIHC) |
| D87953 (SEQ ID NO:12) | 6.8 | RTP, DRG1, CAP43 |
| M76180 (SEQ ID NO:13) | ~6.5 | aromatic amino acid decarboxylase (ddc) |
| M77140 (SEQ ID NO:14) | ~6 | pro-galanin |
| D50840 (SEQ ID NO:15) | ~5.6 | ceramide glucosyltransferase |
| HG2743-HT2846 (SEQ ID NO:16) | ~5.1 | Caldesmon 1 Non-Muscle |
| U76421 (SEQ ID NO:17) | ~4.7 | dsRNA adenosine deaminase DRADA2b |
| U40572 (SEQ ID NO:18) | 4.6 | beta2-syntrophin (SNT B2) |
| S69189 (SEQ ID NO:19) | ~4.5 | peroxisomal acyl-coenzyme A oxidase |
| U44754 (SEQ ID NO:20) | 4.4 | PSE-binding factor PTF gamma subunit |
| U02081 (SEQ ID NO:21) | 4.1 | guanine nucleotide regulatory protein (NET1) oncogene |
| D16227 (SEQ ID NO:22) | ~4 | BDP-1 (member of the recoverin family) |
| D17793 (SEQ ID NO:23) | ~4 | 3-alpha hydroxysteroid dehydrogenase type IIb |
| U83461 (SEQ ID NO:24) | 3.7 | putative copper uptake protein (hCTR2) |
| M23254 (SEQ ID NO:25) | 3.6 | Ca2+-activated neutral protease (CANP) |
| D15050 (SEQ ID NO:26) | 3.6 | transcription factor AREB6 |
| HG2167-HT2237 (SEQ ID NO:27) | ~3.5 | Protein Kinase Ht31, Camp-Dependent |
| D10040 (SEQ ID NO:28) | 3.5 | long-chain acyl-CoA synthetase |
| D31887 (SEQ ID NO:29) | 3.5 | KIAA0062 gene |
| X60673 (SEQ ID NO:30) | 3.4 | adenylate kinase 3 |
| U45878 (SEQ ID NO:31) | ~3.3 | inhibitor of apoptosis protein I |
| L09229 (SEQ ID NO:32) | 3.3 | long-chain acyl-coenzyme A synthetase (FACL1) |
| U09646 (SEQ ID NO:33) | 3.2 | carnitine palmitoyltransferase II precursor (CPT1) |

TABLE 15-continued

Group of genes for which the expression level is different depending on which isoform is present.

| Accession No. | Fold | Gene Name |
|---|---|---|
| D31716 (SEQ ID NO:34) | 3.2 | GC box bindig protein |
| M37400 (SEQ ID NO:35) | 3.1 | cytosolic aspartate aminotransferase |
| X59834 (SEQ ID NO:36) | 3.1 | glutamine synthase |
| D78335 (SEQ ID NO:37) | 3.1 | uridine monophosphate kinase (UMPK) |
| U41387 (SEQ ID NO:38) | 3 | RNA helicase II/Gu) |
| U07919 (SEQ ID NO:39) | 3 | aldehyde dehydrogenase 6 |
| M69013 (SEQ ID NO:40) | 2.9 | guanine nucleotide-binding regulatory protein (G-y-alpha) |
| HG2530-HT2626 (SEQ ID NO:41) | 2.9 | Adenylyl Cyclase-Associated Protein 2 |
| U79288 (SEQ ID NO:42) | 2.8 | clone 23682 |
| D10704 (SEQ ID NO:43) | 2.6 | choline kinase |
| Y08134 (SEQ ID NO:44) | 2.6 | ASM-like phosphodiesterase 3b |
| U33632 (SEQ ID NO:45) | 2.6 | two P-domain K+ channel TWIK-1 |
| M21154 (SEQ ID NO:46) | 2.5 | 5-adenosylmethionine decarboxylase |
| U77949 (SEQ ID NO:47) | 2.5 | Cdc6-related protein (HsCDC6) |
| M95767 (SEQ ID NO:48) | ~2.5 | di-N-acetylchitobiase |
| D83781 (SEQ ID NO:49) | 2.5 | KIAA0197 gene |
| X98534 (SEQ ID NO:50) | 2.5 | vasodilator-stimulated phosphoprotein (VASP) |
| D80001 (SEQ ID NO:51) | 2.4 | KIAA0179 gene |
| L18960 (SEQ ID NO:52) | 2.4 | protein synthesis factor (elF-4C) |
| D23673 (SEQ ID NO:53) | 2.3 | insulin receptor substrate-1 (IRS-1) |
| J02888 (SEQ ID NO:55) | 2.3 | quinone oxidoreductase (NQO2) |
| D63487 (SEQ ID NO:56) | 2.3 | KIAA0153 gene |
| U14603 (SEQ ID NO:57) | 2.3 | protein-tyrosine phosphatase (HU-PP-1) |
| L41887 (SEQ ID NO:58) | 2.3 | splicing factor, arginine/serine-rich 7 (SFRS7) |
| M92287 (SEQ ID NO:59) | 2.2 | cyclin D3 (CCND3) |
| X61123 (SEQ ID NO:60) | 2.2 | BTG1 |
| M95929 (SEQ ID NO:61) | 2.1 | homeobox protein (PHOX1) |
| U32944 (SEQ ID NO:62) | 2.1 | cytoplasmic dynein light chain 1 (hdlc1) |
| D79994 (SEQ ID NO:63) | 2.1 | KIAA0172 gene (similar to ankyrin) |
| D89377 (SEQ ID NO:64) | 2 | MSX-2 |
| U90878 (SEQ ID NO:65) | 2 | LIM domain protein CLP-36 |
| U97105 (SEQ ID NO:66) | 2 | N2A3 dihydropyrimidinase related protein-2 |
| L40379 (SEQ ID NO:67) | 2 | thyroid receptor interactor (TRIP10) |
| J05459 (SEQ ID NO:68) | 1.9 | glutathione transferase M3 (GSTM3) |
| L42542 (SEQ ID NO:69) | 1.8 | RLIP76 (ralA binding protein 1) |
| D42047 (SEQ ID NO:70) | 1.7 | KIAA0089 similar to glycerol-3-phosphate dehydrogenase 1 |
| M84349 (SEQ ID NO:71) | 1.7 | transmembrane protein (CD59) |
| D43950 (SEQ ID NO:72) | 1.6 | KIAA0098 T-COMPLEX PROTEIN 1 (TCP-1-EPSILON) |
| M15796 (SEQ ID NO:73) | 1.6 | proliferating cell nuclear antigen (PCNA) |
| U07225 (SEQ ID NO:74) | ~-4.3 | P2U nucleotide receptor |
| M27492 (SEQ ID NO:75) | ~-3.4 | interleukin 1 receptor mRNA |
| Y08682 (SEQ ID NO:76) | -3.1 | carnitine palmitoyltransferase I type I |
| U29091 (SEQ ID NO:77) | ~-2.9 | selenium-binding protein (hSBP) |
| X79683 (SEQ ID NO:78) | -2.6 | beta2 laminin. |
| AB000220 (SEQ ID NO:79) | -2.6 | semaphorin E |
| HG2197-HT2267 (SEQ ID NO:80) | ~-2.5 | Collagen, Type Vii, Alpha 1 |
| U65011 (SEQ ID NO:81) | ~-2.5 | preferentially expressed antigen of melanoma (PRAME) |
| M18391 (SEQ ID NO:82) | ~-2.3 | tyrosine kinase receptor (eph) |
| X71874 (SEQ ID NO:83) | -1.9 | proteasome-like subunit MECL-1 |
| L43821 (SEQ ID NO:3) | 4.7 | enhancer of filamentation (HEF1) |
| L38487 (SEQ ID NO:4) | 2.3 | estrogen receptor-related protein (hERRa1) |
| D25539 (SEQ ID NO:10) | ~8 | KIAA0040 gene |
| HG4069-HT4339 (SEQ ID NO:104) | ~-7.4 | Monocyte Chemotactic Protein 1 |

TABLE 16

Genes encoding products involved in breast cancer or mammary gland development*.

| Accession no. | Fold | Gene Name |
|---|---|---|
| L13720 (SEQ ID NO:6) | ~23.1 | growth arrest-specific protein (gas6) |
| M27436 (SEQ ID NO:7) | ~18.1 | tissue factor gene |
| M83667 (SEQ ID NO:107) | 6.4 | NF-IL6-beta (C/EBPbeta)* |

TABLE 16-continued

Genes encoding products involved in breast cancer or mammary gland development*.

| Accession no. | Fold | Gene Name |
|---|---|---|
| M68516 (SEQ ID NO:96) | ~6.2 | PCI gene (plasminogen activator inhibitor) |
| U43185 (SEQ ID NO:97) | ~6.1 | Stat5A* |
| X65614 (SEQ ID NO:87) | 3.6 | calcium-binding protein S100P |

TABLE 16-continued

Genes encoding products involved in breast cancer or mammary gland development*.

| Accession no. | Fold | Gene Name |
|---|---|---|
| X53586 (SEQ ID NO:51) | 2.5 | Integrin α 6* |
| D89377 (SEQ ID NO:64) | 2 | MSX-2* |
| D00017 (SEQ ID NO:101) | 1.9 | lipocortin II (calpactin I) |
| U29091 (SEQ ID NO:77) | ~-2.9 | selenium-binding protein (hSBP) |
| M69225 (SEQ ID NO:91) | ~-3.5 | bullous pemphigoid antigen (plakin family) |

References
1. Goruppi et al., Mol Cell Biol, 21: 902–915 (2001)

TABLE 16-continued

Genes encoding products involved in breast cancer or mammary gland development*.

| Accession no. | Fold | Gene Name |
|---|---|---|

2. Ueno et al., Br J Cancer, 83: 164–70 (2000); Lwaleed et al., J Pathol, 187: 291–4 (1999); Lwaleed et al., J Pathol, 188(1): 3–8 (1999)
3. Seagroves et al., Mol Endocrinol, 14(3): 359–68 (2000); Robinson et al., Genes Dev, 12(12): 1907–16 (1998); Seagroves et al., Genes Dev, 12(12): 1917–1928 (1998)
4. Nelson et al., J Natl Cancer Inst, 92(11): 866–8 (2000)
5. Liu et al., Genes Dev, 11(2): 179–86 (1997); Watson et al., Br J Cancer, 71(4): 840–844 (1995)
6. Guerreiro de Silva et al., Int J Oncol, 16: 231–40 (2000)
7. Wewer et al., Am J Pathol, 151 (5): 1191–8 (1997); Tagliabue et al., Eur J Cancer, 34(12): 1982–3 (1998)
8. Phippard et al., Development, 122(9): 2729–37 (1996); Friedmann et al., Dev Biol, 177(1): 347–55 (1996)
9. Mai et al., Biochim Biophys Acta, 1477(1–2): 215–30 (2000)
10. Vinceti et al., Tumori 86(2): 105–18 (2000); Jiang et al., Mol Carcinog, 26(4): 213–25 (1999)
11. Nacht et al., Cancer Res, 59: 5464–70 (1999)

TABLE 17

Genes regulated by progesterone organized by primary function of gene product.

| Accession no. | Fold | Gene Name | Regulation Pattern |
|---|---|---|---|
| Transcription factors | | | |
| U70663 | ~7.5 | zinc finger transcription factor EZF | Up by Both |
| M83667 | 6.4 | NF-IL6 (C/EBPbeta) | Up by PR-B |
| U43185 | ~6.1 | Stat5A | Up by PR-B |
| D15050 | 3.6 | transcription factor AREB6 | Up by PR-B |
| D31716 | 3.2 | GC box bindig protein | Up by PR-B |
| U00115 | 2.4 | bcl-6 | Up by Both |
| U44754 | 4.4 | PSE-binding factor PTF gamma subunit | Up by PR-B |
| M95929 | 2.1 | homeobox protein (PHOX1) | Up by PR-B |
| S81914 | 2.6 | IEX-1 = radiation-inducible DIF2 | Up by Both |
| D89377 | 2 | MSX-2 | Up by PR-B |
| Z50781 | 2.5 | delta sleep inducing peptide (higly related to TSC-22) | Up by PR-A |
| L38487 | 2.3 | estrogen receptor-related protein (hERRa1) | Up by PR-A |
| Cell adhesion or cytoskeleton interaction | | | |
| HG2743-HT2846 | ~5.1 | Caldesmon 1 Non-Muscle | Up by PR-B |
| L43821 | 4.7 | enhancer of filamentation (HEF1) | Up by PR-A |
| U40572 | 4.6 | beta2-syntrophin (SNT B2) | Up by PR-B |
| X98534 | 2.5 | vasodilator-stimulated phosphoprotein (VASP) | Up by PR-B |
| U32944 | 2.1 | cytoplasmic dynein light chain 1 (hdlc1) | Up by PR-B |
| U90878 | 2 | LIM domain protein CLP-36 | Up by PR-B |
| X79683 | ~2.6 | beta2 laminin. | Down by PR-B |
| L43821 | 4.7 | enhancer of filamentation (HEF1) | Up by PR-A |
| Calcium binding proteins | | | |
| D16227 | ~4 | BDP-1 (member of the recoverin family) | Up by PR-B |
| X65614 | 3.6 | calcium-binding protein S100P | Up by Both |
| D00017 | 1.9 | lipocortin II (calpactin I) | Up by PR-B |
| Cholesterol or steroid metabolism and trafficking | | | |
| U26726 | ~22.6 | 11-beta-hydroxysteroid dehydrogenase type 2 | Up by Both |
| D17793 | ~4 | 3-alpha hydroxysteroid dehydrogenase type IIb | Up by PR-B |
| AF002020 | 2.1 | Niemann-Pick C disease (NPC1) | Up by PR-B |
| Fatty acid/lipid metabolism | | | |
| M76180 | ~6.5 | aromatic amino acid decarboxylase (ddc) | Up by PR-B |
| D50840 | ~5.6 | ceramide glucosyltransferase (phospholipid synthesis) | Up by PR-B |

TABLE 17-continued

Genes regulated by progesterone organized by primary function of gene product.

| Accession no. | Fold | Gene Name | Regulation Pattern |
|---|---|---|---|
| S69189 | ~4.5 | peroxisomal acyl-coenzyme A oxidase | Up by PR-B |
| X52730 | 4.4 | phenylethanolamine n-methyltransferase (PNMT) | Up by PR-B |
| L09229 | 3.3 | long-chain acyl-coenzyme A synthetase (FACL1) | Up by PR-B |
| U09646 | 3.2 | carnitine palmitoyltransferase II precursor (CPT1) | Up by PR-B |
| X59834 | 3.1 | glutamine synthase | Up by PR-B |
| D78335 | 3.1 | uridine monophosphate kinase (UMPK) | Up by PR-B |
| Y08134 | 2.6 | ASM-like phosphodiesterase 3b | Up by PR-B |
| J02888 | 2.3 | quinone oxidoreductase (NQO2) | Up by PR-B |
| Y08682 | −3.1 | carnitine palmitoyltransferase I type I | down by PR-B |
| Nucleotide or amino acid metabolism | | | |
| M37400 | 3.1 | cytosolic aspartate aminotransferase (amino acid metabolism) | Up by PR-B |
| U97105 | 2 | N2A3 dihydropyrimidinase related protein-2 | Up by PR-B |
| U07225 | ~−4.3 | P2U nucleotide receptor | down by PR-B |
| General metabolic/synthetic | | | |
| U01120 | ~9.8 | glucose-6-phosphatase (gluconeogenesis) | Up by PR-B |
| U07919 | 3 | aldehyde dehydrogenase 6 (alcohol metabolism) | Up by PR-B |
| M21154 | 2.5 | 5-adenosylmethionine decarboxylase (polyamine biosynthesis) | Up by PR-B |
| M95767 | ~2.5 | di-N-acetylchitobiase (glycoprotein synthesis) | Up by PR-B |
| D42047 | 1.7 | KIAA0089 gene (similar to glycerol-3-phosphate dehydrogenase 1) | Up by PR-B |
| J05459 | 1.9 | glutathione transferase M3 (GSTM3) | Up by PR-B |
| D25328 | 1.9 | platelet-type phosphofructokinase | Up by PR-B |
| U29091 | ~−2.9 | selenium-binding protein (hSBP) | down by PR-B |
| DNA-replication/transcription/translation and protein processing | | | |
| U76421 | ~4.7 | dsRNA adenosine deaminase DRADA2b | Up by PR-B |
| U41387 | 3 | RNA helicase II/Gu | Up by PR-B |
| L18960 | 2.4 | protein synthesis factor (elF-4C) | Up by PR-B |
| L41887 | 2.3 | splicing factor, arginine/serine-rich 7 (SFRS7) | Up by PR-B |
| U77949 | 2.5 | Cdc6-related protein (HsCDC6) | Up by PR-B |
| X71874 | −1.9 | proteasome-like subunit MECL-1 | Down by PR-B |
| Secreted molecules | | | |
| L13720 | ~23.1 | growth arrest-specific protein (gas6) | Up by PR-B |
| M27436 | ~18.1 | tissue factor gene | Up by PR-B |
| M68516 | ~6.2 | PCI gene (plasminogen activator inhibitor 3) | Up by PR-B |
| M77140 | ~6 | pro-galanin | Up by PR-B |
| M23254 | 3.6 | Ca2+-activated neutral protease (CANP) | Up by PR-B |
| AB000220 | −2.6 | semaphorin E | Down by PR-B |
| Signal transduction | | | |
| D79990 | 10.2 | KIAA0168 Ras association (RaIGDS/AF-6) domain family 2 (RASSF2) | |
| M69043 | 4.2 | MAD-3 encoding lkB-alpha | Up by Both |
| U02081 | 4.1 | guanine nucleotide regulatory protein (NET1) oncogene | Up by PR-B |
| HG2167-HT2237 | ~3.5 | Protein Kinase Ht31, cAMP-Dependent | Up by PR-B |
| X60673 | 3.4 | adenylate kinase 3 | Up by PR-B |
| HG2530-HT2626 | 2.9 | Adenylyl Cyclase-Associated Protein 2 | Up by PR-B |
| D86962 | 2.9 | Grb10 | Up by Both |
| M69013 | 2.9 | guanine nucleotide-binding regulatory protein (G-y-alpha) | Up by PR-B |
| D10704 | 2.6 | choline kinase | Up by PR-B |
| U14603 | 2.3 | protein-tyrosine phosphatase (HU-PP-1) | Up by PR-B |
| L40379 | 2 | thyroid receptor interactor (TRIP10) | Up by PR-B |
| M18391 | ~−2.3 | tyrosine kinase receptor (eph) | Down by PR-B |
| U44103_at | −2.8 | small GTP binding protein Rab9 | Down by PR-A |
| Cytokines/Cytokine Receptors and Chemokines | | | |
| M27492 | ~−3.4 | interleukin 1 receptor mRNA | Down by PR-B |
| J03241 | ~−3 | transforming growth factor-beta 3 (TGF-beta3) | Down by Both |
| HG4069-HT4339_s_at | ~−7.4 | Monocyte Chemotactic Protein 1 | Down by PR-A |
| Membrane bound molecules | | | |
| U16799 | 6.1 | Na, K-ATPase beta-1 subunit | Up by Both |
| U83461 | 3.7 | putative copper uptake protein (hCTR2) | Up by PR-B |
| U33632 | 2.6 | two P-domain K+ channel TWIK-1 | Up by PR-B |
| M84349 | 1.7 | transmembrane protein (CD59) | Up by PR-B |
| M69225 | ~−3.5 | bullous pemphigoid antigen (plakin family) | Down by Both |
| U65011 | ~−2.5 | preferentially expressed antigen of melanoma (PRAME) | Down by PR-B |
| Chaperones/Protein folding | | | |
| U42031 | 9.4 | progesterone receptor-associated FKBP54 | Up by Both |
| M80254 | 1.9 | cyclophilin isoform (hCyP3) | Up by PR-B |

TABLE 17-continued

Genes regulated by progesterone organized by primary function of gene product.

| Accession no. | Fold | Gene Name | Regulation Pattern |
|---|---|---|---|
| Apoptosis | | | |
| U37546 | ~7.2 | IAP homolog C (binds TNF receptor-associated factors) | Up by PR-B |
| U45878 | ~3.3 | inhibitor of apoptosis protein 1 mRNA | Up by PR-B |
| Cell cycle | | | |
| D87953 | 6.8 | RTP | Up by PR-B |
| M92287 | 2.2 | cyclin D3 (CCND3) | Up by PR-B |
| M15796 | 1.6 | proliferating cell nuclear antigen (PCNA) | Up by PR-B |
| X61123 | 2.2 | BTG1 | Up by PR-B |
| Unknown Function | | | |
| D25539 | ~8 | KIAA0040 gene | Up by PR-B |
| D31887 | 3.5 | KIAA0062 gene | Up by PR-B |
| U79288 | 2.8 | clone 23682 | Up by PR-B |
| D83781 | 2.5 | KIAA0197 gene | Up by PR-B |
| D80001 | 2.4 | KIAA0179 gene | Up by PR-B |
| D63487 | 2.3 | KIAA0153 gene | Up by PR-B |
| D79994 | 2.1 | KIAA0172 gene (similar to ankyrin) | Up by PR-B |
| M92357 | −2.1 | tumor necrosis factor, alpha-induced protein 2 B94 | Down by PR-B |
| U90907 | −2.1 | clone 23907 (similar to mouse p55PIK) | Down by Both |

TABLE 18

Transcripts regulated in T47D-YB cells after 6 hrs progesterone treatment

| Accession no. | | Gene Name |
|---|---|---|
| | Fold Increase | |
| L13720 | ~23.1 | growth arrest-specific protein (gas6) |
| U26726 | ~22.6 | 11-beta-hydroxysteroid dehydrogenase type 2 |
| M27436 | ~18.1 | tissue factor gene |
| D79990 | 10.2 | KIAA0168 Ras association (RaIGDS/AF-6) domain family 2 (RASSF2) |
| U01120 | ~9.8 | glucose-6-phosphatase |
| U42031 | 9.4 | progesterone receptor-associated FKBP54* |
| D25539 | ~8 | KIAA0040 gene |
| U70663 | ~7.5 | zinc finger transcription factor EZF |
| U37546 | ~7.2 | IAP homolog C (MIHC) |
| D87953 | 6.8 | RTP, DRG1, CAP43 |
| M76180 | ~6.5 | aromatic amino acid decarboxylase (ddc) |
| M83667 | 6.4 | NF-IL6 (C/EBPbeta) |
| M68516 | ~6.2 | PCI gene (plasminogen activator inhibitor 3) |
| U43185 | ~6.1 | Stat5A |
| U16799 | 6.1 | Na, K-ATPase beta-1 subunit |
| M77140 | ~6 | pro-galanin |
| D50840 | ~5.6 | ceramide glucosyltransferase |
| HG2743-HT2846 | ~5.1 | Caldesmon 1 Non-Muscle |
| U76421 | ~4.7 | dsRNA adenosine deaminase DRADA2b |
| U40572 | 4.6 | beta2-syntrophin (SNT B2) |
| S69189 | ~4.5 | peroxisomal acyl-coenzyme A oxidase |
| U44754 | 4.4 | PSE-binding factor PTF gamma subunit |
| X52730 | 4.4 | phenylethanolamine n-methyltransferase (PNMT) |
| M69043 | 4.2 | MAD-3 (lkB-alpha) |
| U02081 | 4.1 | guanine nucleotide regulatory protein (NET1) oncogene* |
| D16227 | ~4 | BDP-1 (member of the recoverin family) |
| D17793 | ~4 | 3-alpha hydroxysteroid dehydrogenase type IIb |
| U83461 | 3.7 | putative copper uptake protein (hCTR2) |
| X65614 | 3.6 | calcium-binding protein S100P |
| M23254 | 3.6 | Ca2+-activated neutral protease (CANP) |
| D15050 | 3.6 | transcription factor AREB6 |
| HG2167-HT2237 | ~3.5 | Protein Kinase Ht31, Camp-Dependent |
| D10040 | 3.5 | long-chain acyl-CoA synthetase |
| D31887 | 3.5 | KIAA0062 gene |
| X60673 | 3.4 | adenylate kinase 3 |
| U45878 | ~3.3 | inhibitor of apoptosis protein 1 |
| L09229 | 3.3 | long-chain acyl-coenzyme A synthetase (FACL1) |
| U09646 | 3.2 | camitine palmitoyltransferase II precursor (CPT1) |
| D31716 | 3.2 | GC box bindig protein |
| M37400 | 3.1 | cytosolic aspartate aminotransferase |
| X59834 | 3.1 | glutamine synthase |

TABLE 18-continued

| Transcripts regulated in T47D-YB cells after 6 hrs progesterone treatment | | |
|---|---|---|
| Accession no. | | Gene Name |
| D78335 | 3.1 | uridine monophosphate kinase (UMPK) |
| U41387 | 3 | RNA helicase II/Gu) |
| U07919 | 3 | aldehyde dehydrogenase 6 |
| D86962 | 2.9 | Grb10 |
| M69013 | 2.9 | guanine nucleotide-binding regulatory protein (G-y-alpha)* |
| HG2530-HT2626 | 2.9 | Adenylyl Cyclase-Associated Protein 2 |
| U79288 | 2.8 | clone 23682 |
| D10704 | 2.6 | choline kinase |
| Y08134 | 2.6 | ASM-like phosphodiesterase 3b |
| U33632 | 2.6 | two P-domain K+ channel TWIK-1 |
| S81914 | 2.6 | IEX-1 = radiation-inducible immediate-early |
| M21154 | 2.5 | S-adenosylmethionine decarboxylase |
| U77949 | 2.5 | Cdc6-related protein (HsCDC6) |
| M95767 | ~2.5 | di-N-acetylchitobiase |
| D83781 | 2.5 | KIAA0197 gene |
| X98534 | 2.5 | vasodilator-stimulated phosphoprotein (VASP) |
| D80001 | 2.4 | KIAA0179 gene |
| L18960 | 2.4 | protein synthesis factor (elF-4C) |
| U00115 | 2.4 | bcl-6 |
| J02888 | 2.3 | quinone oxidoreductase (NQO2) |
| D63487 | 2.3 | KIAA0153 gene |
| U14603 | 2.3 | protein-tyrosine phosphatase (HU-PP-1) |
| L41887 | 2.3 | splicing factor, arginine/serine-rich 7 (SFRS7) |
| M92287 | 2.2 | cyclin D3 (CCND3) |
| X61123 | 2.2 | BTG1 |
| AF002020 | 2.1 | Niemann-Pick C disease (NPC1) |
| M95929 | 2.1 | homeobox protein (PHOX1) |
| U32944 | 2.1 | cytoplasmic dynein light chain 1 (hdlc1) |
| D79994 | 2.1 | KIAA0172 gene (similar to ankyrin) |
| D89377 | 2 | MSX-2 |
| U90878 | 2 | LIM domain protein CLP-36 |
| U97105 | 2 | N2A3 dihydropyrimidinase related protein-2 |
| L40379 | 2 | thyroid receptor interactor (TRIP10) |
| D00017 | 1.9 | lipocortin II |
| J05459 | 1.9 | glutathione transferase M3 (GSTM3) |
| D25328 | 1.9 | platelet-type phosphofructokinase |
| M80254 | 1.9 | cyclophilin isoform (hCyP3) |
| L42542 | 1.8 | RLIP76 (ralA binding protein 1) |
| D42047 | 1.7 | KIAA0089 similar to glycerol-3-phosphate dehydrogenase 1 |
| M84349 | 1.7 | transmembrane protein (CD59) |
| D43950 | 1.6 | KIAA0098 T-COMPLEX PROTEIN 1 (TCP-1-EPSILON) |
| M15796 | 1.6 | proliferating cell nuclear antigen (PCNA) |
| | Fold Decrease | |
| U07225 | ~-4.3 | P2U nucleotide receptor |
| M69225 | ~-3.5 | bullous pemphigoid antigen (plakin family) |
| M27492 | ~-3.4 | interleukin 1 receptor mRNA |
| U90907 | -3.2 | clone 23907 |
| Y08682 | -3.1 | carnitine palmitoyltransferase I type I |
| J03241 | ~-3 | transforming growth factor-beta 3 (TGF-beta3) |
| U29091 | ~-2.9 | selenium-binding protein (hSBP) |
| X79683 | -2.6 | beta2 laminin. |
| AB000220 | -2.6 | semaphorin E* |
| HG2197-HT2267 | ~-2.5 | Collagen, Type Vii, Alpha 1 |
| U65011 | ~-2.5 | preferentially expressed antigen of melanoma (PRAME) |
| M18391 | ~-2.3 | tyrosine kinase receptor (eph) |
| M92357 | -2.1 | tumor necrosis factor, alpha-induced protein 2 B94 |
| X71874 | -1.9 | proteasome-like subunit MECL-1 |

TABLE 19

| Transcripts regulated in T47D-YA cells after 6 hrs progesterone treatment | | |
|---|---|---|
| Accession no. | | Gene Name |
| | Fold Increase | |
| U26726 | 6.5 | 11-beta-hydroxysteroid dehydrogenase type 2 |
| L43821 | 4.7 | enhancer of filamentation (HEF1) |

TABLE 19-continued

| Transcripts regulated in T47D-YA cells after 6 hrs progesterone treatment | | |
|---|---|---|
| Accession no. | | Gene Name |
| U70663 | ~7.5 | zinc finger transcription factor EZF |
| U16799 | 3.9 | Na, K-ATPase beta-1 subunit |
| U42031 | 3.3 | progesterone receptor-associated FKBP54 |

TABLE 19-continued

| Accession no. | Transcripts regulated in T47D-YA cells after 6 hrs progesterone treatment | Gene Name |
|---|---|---|
| Z50781 | 2.5 | delta sleep inducing peptide (higly related to TSC-22) |
| L38487 | 2.3 | estrogen receptor-related protein (hERRa1) |
| U00115 | 2.3 | bcl-6 |
| X65614 | 2.2 | calcium-binding protein S100P |
| S81914 | 2.1 | IEX-1 = radiation-inducible immediate-early |
| M69043 | 2.0 | MAD-3 mRNA (IkB-alpha) |
| D86962 | 2.0 | Grb10 |
| | Fold Decrease | |
| HG4069-HT4339 | ~−7.4 | Monocyte Chemotactic Protein 1 |
| M69225 | ~−4.3 | bullous pemphigoid antigen (BPAG1) |
| J03241 | −3.3 | transforming growth factor-beta 3 (TGF-beta3) |

TABLE 19-continued

| Accession no. | Transcripts regulated in T47D-YA cells after 6 hrs progesterone treatment | Gene Name |
|---|---|---|
| M92357 | −3.0 | tumor necrosis factor, alpha-induced protein 2 B94 |
| U44103 | −2.8 | small GTP binding protein Rab9 |
| U90907 | −2.1 | clone 23907 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to identify agonist ligands of progesterone receptors, comprising:

a. contacting a progesterone receptor with a putative agonist ligand, wherein said progesterone receptor is selected from the group consisting of progesterone receptor A (PR-A) and progesterone receptor B (PR-B), under conditions wherein, in the absence of said putative agonist ligand, said progesterone receptor is not activated;

b. detecting expression of at least one gene that is regulated by said progesterone receptor when said progesterone receptor is activated, said at least one gene being selected from the group consisting of:

i. at least one gene that is selectively upregulated by PR-A chosen from a gene comprising a nucleic acid sequence selected from the group consisting of: SEQ ID NO:3 and SEQ ID NO:4;

ii. a gene that is selectively downregulated by PR-A comprising a nucleic acid sequence represented by SEQ ID NO:5;

iii. at least one gene that is selectively upregulated by PR-B chosen from a gene comprising a nucleic acid sequence selected from the group consisting of: SEQ ID NO:6, SEQ ID NO:8 and SEQ ID NO:9;

iv. a gene that is selectively downregulated by PR-B comprising a nucleic acid sequence represented by SEQ ID NO:74 and v. at least one gene that is upregulated or downregulated by both PR-A and PR-B chosen from a gene comprising a nucleic acid sequence selected from the group consisting of: SEQ ID NO:84, SEQ ID NO:85, and SEQ ID NO:87; and, c. comparing the expression of said at least one gene in the presence and in the absence of said putative agonist ligand, wherein detection of regulation of the expression of said at least one gene in the manner associated with activation of said progesterone receptor as set forth in (b) indicates that said putative agonist ligand is a progesterone receptor agonist.

2. The method of claim 1, wherein said progesterone receptor is PR-A.

3. The method of claim 1, wherein said progesterone receptor is PR-B.

4. The method of claim 1, wherein said progesterone receptor comprises both PR-A and PR-B.

5. The method of claim 1, wherein detection of upregulation of expression of at least one gene chosen from a gene comprising a nucleic acid sequence selected from the group consisting of: SEQ ID NO:3 and SEQ ID NO:4, or detection of downregulation of at least one gene chosen from a gene comprising a nucleic acid sequence represented by SEQ ID NO:5, in the presence of said putative agonist ligand, indicates that said putative agonist ligand is a selective agonist of PR-A.

6. The method of claim 1, wherein detection of upregulation of expression of at least one gene chosen from a gene comprising a nucleic acid sequence selected from the group consisting of SEQ ID NO:6, SEQ ID NO:8 and SEQ ID NO:9, or detection of downregulation of a gene comprising a nucleic acid sequence represented by SEQ ID NO:74, in the presence of said putative agonist ligand, indicates that said putative agonist ligand is a selective agonist of PR-B.

7. The method of claim 1, wherein said step (b) of detecting comprises detecting expression of at least five genes from any one or more of said genes in (b)(i)-(b)(v).

8. The method of claim 1, wherein said step (b) of detecting comprises detecting expression of at least ten genes from any one or more of said genes in (b)(i)-(b)(v).

9. The method of claim 1, further comprising a step of detecting expression of at least one gene chosen from the genes comprising a nucleic acid sequence selected from the group consisting of: SEQ ID NO:94, SEQ ID NO:7, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, and SEQ ID NO:104.

10. The method of claim 1, wherein said progesterone receptor is expressed by a cell.

11. The method of claim 10, wherein said progesterone receptor is endogenously expressed by said cell.

12. The method of claim 10, wherein said progesterone receptor is recombinantly expressed by said cell.

13. The method of claim 10, wherein said cell is part of a tissue isolated from a test animal.

14. The method of claim 13, wherein said step of contacting is performed by administration of said putative agonist ligand to said test animal or to said tissue of said test animal, followed by removing the tissue from the rest animal and detecting the expression of said at least one gene in step (b).

15. The method of claim 1, wherein expression of said at least one gene is detected by measuring amounts of transcripts of said at least one gene before and after contact of said progesterone receptor with said putative agonist ligand.

16. The method of claim 1, wherein expression of said at least one gene is detected by detecting hybridization of at least a portion of said at least one gene or a transcript thereof to a nucleic acid molecule comprising a portion of said at least one gene or a transcript thereof in a nucleic acid array.

17. The method of claim 1, wherein expression of said at least one gene is detected by measuring expression of a reporter gene that is operatively linked to at least the regulatory region of said at least one gene.

18. The method of claim 1, wherein expression of said at least one gene is detected by detecting the production of a protein encoded by said at least one gene.

19. The method of claim 1, wherein said putative agonist ligand is a product of rational drug design.

20. the method of claim 1, comprising, in step (b), detecting expression of: 11-beta-hydroxysteroid dehydrogenase type 2 (represented by SEQ ID NO:94), tissue factor gene (represented by SEQ ID NO:7), PCI gene (plasminogen activator inhibitor 3) (represented by SEQ ID NO:96), MAD-3 Ikβ-alpha (represented by SEQ ID NO:99), Niemann-Pick C disease (NPC1) (represented by SEQ ID NO:100), platelet-type phosphofructokinase (represented by SEQ ID NO:102), phenylethanolamine n-methyltransferase (PNMT) (represented by SEQ ID NO:98), transforming growth factor-beta 3 (TGF-beta3) (represented by SEQ ID NO:108), Monocyte Chemotactic Protein 1 (represented by SEQ ID NO:104), delta sleep inducing peptide (related to TSC-22) (represented by SEQ ID NO:105), and estrogen receptor-related protein (hERRa1) (represented by SEQ ID NO:4).

21. The method of claim 1, comprising, in step (b), detecting expression of: growth arrest-specific protein (gas6) (represented by SEQ ID NO:6), tissue factor gene (represented by SEQ ID NO:7), NF-IL6-beta (C/EBPbeta) (represented by SEQ ID NO:107), PCI gene (plasminogen activator inhibitor) (represented by SEQ ID NO:96), Stat5A (represented by SEQ ID NO:97), calcium-binding protein S100P (represented by SEQ ID NO:87), MSX-2 (represented by SEQ ID NQ:64), lipocortin II (calpactin I) (represented by SEQ ID NO:101), selenium-binding protein (hSBP) (represented by SEQ ID NO:77), and bullous pemphigoid antigen (plakin family) (represented by SEQ ID NO:91).

22. The method of claim 1, further comprising, in step (b), detecting expression of phenylethanolamine n-methyltransferase (PNMT) adrenal medulla (represented by SEQ ID NO:98).

23. The method of claim 1, further comprising, in step (b), detecting expression of proteasome-like subunit MECL-1 (represented by SEQ ID NO:83).

24. The method of claim 1, comprising, in step (b), detecting expression of: growth arrest-specific protein (represented by SEQ ID NO: 6) and tissue factor gene (represented by SEQ ID NO: 7).

25. The method of claim 1, further comprising a step of detecting expression of Bcl-x (represented by SEQ ID NO:106).

26. The method of claim 1, further comprising a step of detecting expression of NF-IL6 (C/EBPbeta) (represented by SEQ ID NO:107).

27. The method of claim 1, further comprising a step of detecting expression of transforming growth factor-beta 3 (represented by SEQ ID NO:108).

28. The method of claim 1, further comprising in step (b), detecting expression of at least one additional gene diet is regulated by said progesterone receptor when said progesterone receptor is activated, said at least one gene being selected from the group consisting of:

(1) at least one gene tat is selectively upregulated by PR-A chosen from a gene comprising a nucleic acid sequence selected from the group consisting of: SEQ ID NO:105 and SEQ ID NO:106;

(2) a gene that is selectively downregulated by PR-A comprising a nucleic acid sequence represented by SEQ ID NO:104;

(3) at least one gene that is selectively upregulated by PR-B chosen from a gene comprising a nucleic acid sequence selected from the group consisting of: SEQ ID NO:7, any of SEQ ID NOs:10 –73, SEQ ID NO:96, SEQ ID NO:97, SEQ ID NO:98, SEQ ID NO:100, SEQ ID NO:101, SEQ ID NO:102, SEQ ID NO:103 and SEQ ID NO:107;

(4) at least one gene that is selectively downregulated by PR-B chosen from a gene comprising a nucleic acid sequence selected from the group consisting of SEQ ID NO:75, SEQ ID NO:76, SEQ ID NO:77, SEQ ID NO:78, SEQ ID NO:79, SEQ ID NO:80, SEQ ID NO:81, SEQ ID NO:82, and SEQ ID NO:83;

(5) at least one gene that is upregulated or downregulated by both PR-A and PR-B chosen from a gene comprising a nucleic acid sequence selected from the group consisting of: SEQ ID NO:86, SEQ ID NO:88, SEQ ID NO:89, SEQ ID NO:90, SEQ ID NO:91, SEQ ID NO:92, SEQ ID NO:93, SEQ ID NO:94, SEQ ID NO;95, SEQ ID NO:99 and SEQ ID NO:108;

(6) at least one gene that is reciprocally regulated by PR-A and PR-B chosen from a gene comprising a nucleic acid sequence represented by SEQ ID NO:51; and, (7) at least one gene that is regulated by one of said PR-A or said PR-B, wherein regulation of said gene is altered when the other of said PR-A or PR-B is expressed by the same call, chosen from a gene comprising a nucleic acid sequence selected from the group consisting of: SEQ ID NO:3, SEQ ID NO:4, any of SEQ ID NOs:6–50, any of SEQ ID NOs:52–83, and SEQ ID NO:104;

wherein detection of regulation of the expression of said at least one gene in the manner associated with activation of said progesterone receptor as set forth in (b) indicates that said putative agonist ligand is a progesterone receptor agonist.

29. The method of claim 28, wherein said step of detecting further comprises detecting expression of at least ten genes from any one or more of said genes in (1)–(7).

30. The method of claim 28, wherein said step of detecting further comprises detecting expression of at least ten genes from any one or more of said genes in (1)–(7).

31. The method of claim 28, wherein said step of detecting further comprises detecting expression of at least 15 genes from any one or more of said genes in (1)–(7).

* * * * *